(12) United States Patent
Adami et al.

(10) Patent No.: US 12,319,643 B2
(45) Date of Patent: *Jun. 3, 2025

(54) IONIZABLE COMPOUNDS AND COMPOSITIONS AND USES THEREOF

(71) Applicant: Nitto Denko Corporation, Osaka (JP)

(72) Inventors: Roger Adami, Carlsbad, CA (US); Hao Bai, San Diego, CA (US); John Gaudette, Poway, CA (US); Bharat Majeti, San Diego, CA (US); Seiji Nukui, San Diego, CA (US); Kwok Yin Tsang, Irvine, CA (US); Hai Wang, San Diego, CA (US); Haiqing Yin, San Marcos, CA (US); Wenbin Ying, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 357 days.

This patent is subject to a terminal disclaimer.

(21) Appl. No.: 17/658,075

(22) Filed: Apr. 5, 2022

(65) Prior Publication Data

US 2022/0242820 A1 Aug. 4, 2022

Related U.S. Application Data

(63) Continuation of application No. 16/228,054, filed on Dec. 20, 2018, now Pat. No. 11,384,051, which is a continuation of application No. 15/191,511, filed on Jun. 23, 2016, now Pat. No. 10,167,253.

(60) Provisional application No. 62/184,188, filed on Jun. 24, 2015.

(51) Int. Cl.

| | | |
|---|---|---|
| C07C 271/16 | (2006.01) | |
| A61K 9/127 | (2006.01) | |
| A61K 9/51 | (2006.01) | |
| A61K 31/7105 | (2006.01) | |
| A61K 31/713 | (2006.01) | |
| A61K 47/16 | (2006.01) | |
| A61K 47/22 | (2006.01) | |
| A61K 47/24 | (2006.01) | |
| C07C 237/08 | (2006.01) | |
| C07C 237/16 | (2006.01) | |
| C07C 237/50 | (2006.01) | |
| C07D 205/04 | (2006.01) | |
| C07D 207/09 | (2006.01) | |
| C07D 207/12 | (2006.01) | |
| C07D 211/74 | (2006.01) | |
| C07D 211/82 | (2006.01) | |
| C07D 211/86 | (2006.01) | |
| C07F 9/06 | (2006.01) | |
| C07F 9/10 | (2006.01) | |

(52) U.S. Cl.
CPC .............. *C07C 271/16* (2013.01); *A61K 9/127* (2013.01); *A61K 9/5123* (2013.01); *A61K 31/7105* (2013.01); *A61K 31/713* (2013.01); *A61K 47/16* (2013.01); *A61K 47/22* (2013.01); *A61K 47/24* (2013.01); *C07C 237/08* (2013.01); *C07C 237/16* (2013.01); *C07C 237/50* (2013.01); *C07D 205/04* (2013.01); *C07D 207/09* (2013.01); *C07D 207/12* (2013.01); *C07D 211/74* (2013.01); *C07D 211/82* (2013.01); *C07D 211/86* (2013.01); *C07F 9/06* (2013.01); *C07F 9/106* (2013.01)

(58) Field of Classification Search
CPC ...... A61K 31/713; A61K 47/16; A61K 47/22; A61K 2300/00; C12N 15/113; C12N 15/111; C12N 19/34; C12N 2310/14; C12N 2320/30
USPC ...................... 435/6.1, 91.1, 91.31, 455, 458; 514/44 A, 44 R; 536/23.1, 24.5
See application file for complete search history.

(56) References Cited

U.S. PATENT DOCUMENTS

| | | |
|---|---|---|
| 4,115,548 A | 9/1978 | Marsch et al. |
| 4,554,100 A | 11/1985 | Kasafirek et al. |
| 5,082,683 A | 1/1992 | Yarger et al. |
| 5,314,786 A | 5/1994 | Roeschert et al. |
| 5,370,877 A | 12/1994 | Rosenberg et al. |
| 5,958,894 A | 9/1999 | Heath et al. |
| 6,218,410 B1 | 4/2001 | Uehata et al. |
| 6,291,423 B1 | 9/2001 | Bischoff |
| 6,372,254 B1 | 4/2002 | Ting |
| 6,399,629 B1 | 6/2002 | Chamberland |
| 6,458,381 B1 | 10/2002 | Sourovoi |
| 8,916,576 B2 | 12/2014 | Bartolozzi |

(Continued)

FOREIGN PATENT DOCUMENTS

| | | |
|---|---|---|
| CN | 101648121 | 2/2010 |
| CN | 103857654 A | 6/2014 |

(Continued)

OTHER PUBLICATIONS

Office Action dated May 19, 2023 for Korean Application No. 10-2018-7002177, filed Jan. 23, 2018.

(Continued)

*Primary Examiner* — Jane J Zara
(74) *Attorney, Agent, or Firm* — Knobbe, Martens, Olson & Bear, LLP

(57) ABSTRACT

Ionizable compounds, and compositions and methods of use thereof. The ionizable compounds can be used for making nanoparticle compositions for use in biopharmaceuticals and therapeutics. More particularly, the compounds, compositions and methods are to provide nanoparticles to encapsulate active agents, such as nucleic acid agents, and to deliver and distribute the active agents to cells, tissues, organs, and subjects.

12 Claims, 32 Drawing Sheets

(56) References Cited

U.S. PATENT DOCUMENTS

| | | | |
|---|---|---|---|
| 9,408,914 | B2 | 8/2016 | Kuboyama et al. |
| 10,167,253 | B2 * | 1/2019 | Adami ............... A61K 31/7105 |
| 10,441,659 | B2 | 10/2019 | Payne et al. |
| 11,384,051 | B2 * | 7/2022 | Adami ................ C07D 211/74 |
| 2002/0187915 | A1 | 12/2002 | Sakai et al. |
| 2008/0132500 | A1 | 6/2008 | Liu et al. |
| 2009/0023215 | A1 | 1/2009 | Jessee et al. |
| 2010/0105899 | A1 | 4/2010 | Neumann et al. |
| 2011/0052673 | A1 | 3/2011 | Tzianabos et al. |
| 2013/0108685 | A1 | 5/2013 | Kuboyama et al. |
| 2013/0171127 | A1 | 7/2013 | Niitsu et al. |
| 2013/0280305 | A1 | 10/2013 | Kuboyama et al. |
| 2013/0330401 | A1 | 12/2013 | Payne et al. |
| 2014/0294934 | A1 | 10/2014 | Niitsu et al. |
| 2014/0364642 | A1 | 12/2014 | Hayashi et al. |
| 2015/0112051 | A1 | 4/2015 | Panzner |

FOREIGN PATENT DOCUMENTS

| | | |
|---|---|---|
| EP | 0597488 | 5/1994 |
| EP | 2774912 A1 | 9/2014 |
| EP | 16815348 | 10/2018 |
| JP | H04-315042 | 11/1992 |
| JP | H06-200478 | 7/1994 |
| JP | H06-336466 | 12/1994 |
| JP | H07-018569 | 1/1995 |
| JP | H07-018570 | 1/1995 |
| JP | H08-295657 | 11/1996 |
| JP | 2001-500162 | 1/2001 |
| JP | 2001-247532 | 9/2001 |
| JP | 2004-250343 | 9/2004 |
| JP | 2006-254877 A | 9/2006 |
| JP | 2009-288403 | 5/2009 |
| JP | 2010-235450 | 10/2010 |
| JP | 2014-529328 | 11/2014 |
| KR | 10-2013-0060210 | 6/2013 |
| KR | 10-2014-0033492 | 3/2014 |
| KR | 10-2015-0000465 A | 1/2015 |
| KR | 10-2015-0021566 | 3/2015 |
| RU | 2206321 C2 | 6/2003 |
| WO | WO 1991/003512 | 3/1991 |
| WO | WO 1998/011082 | 3/1998 |
| WO | WO 2002/028438 | 4/2002 |
| WO | WO 2002/030922 | 4/2002 |
| WO | WO 2005/054486 A1 | 6/2005 |
| WO | WO 2007/130073 | 11/2007 |
| WO | WO 2009/050483 | 4/2009 |
| WO | WO 2010/054384 | 5/2010 |
| WO | WO 2012/099755 | 7/2012 |
| WO | WO 2012/132022 | 10/2012 |
| WO | WO 2012/142622 | 10/2012 |
| WO | WO 2012/162210 | 11/2012 |
| WO | WO 2012/170952 A1 | 12/2012 |
| WO | WO 2012/170952 A2 | 12/2012 |
| WO | WO 2013/155493 | 10/2013 |
| WO | WO 2013/158127 | 10/2013 |
| WO | WO 2013/185116 | 12/2013 |
| WO | WO 2016/106405 | 6/2016 |
| WO | WO 2016/134146 | 8/2016 |

OTHER PUBLICATIONS

Notice of Decision of Refusal in Chinese Application No. 201680037092.8, issued on Apr. 25, 2022.
Office Action dated Jan. 12, 2023 for Brazilian Application No. BR112017027458.2, filed Jun. 23, 2016.
Arthur, JC et al. Microbial genomic analysis reveals the essential role of inflammation in bacteria-induced colorectal cancer. Nature Communications, vol. 5, 2014, article No. 4724, pp. 1-24.
V.G. Belikov, "Pharmaceutical Chemistry, study guide, 2007, Moscow," MEDpress-inform, p. 27-29.
Burke, B et al. Macrophages in gene therapy: cellular delivery vehicles and in vivo targets. urnal of Leukocyte Biology, vol. 72, Sep. 2002, pp. 417-428.
Chen et al., Novel Cationic Lipid Thal Delivers siRNA and Enhances Therapeutic Effect in Lung Cancer Cells, Molecular Pharmaceutics, 2009, vol. 6, No. 3, pp. 696-705.
Jayaraman et al., Maximizing the Potency of siRNA Lipid Nanoparticles for Hepatic Gene Silencing In Vivo, Angew. Chem. Int. Ed., 2012, vol. 51, pp. 8529—8533.
Jie et al., Fullerene Lipids: Synthesis of C60 Fullerene Derivatives Bearing a Long-Chain Saturated or Unsaturated Triester System, Lipids, vol. 34, No. 11, pp. 1223-1230 (1999).
D.A. Kharkevich, Pharmacology, $10^{th}$ ed. M: GEOTAR-Media, 2010, p. 73-74.
Mukherjee et al., Common co-lipids, in synergy, impart high gene transfer properties to transfection-incompetenl cationic lipids, FEBS Letters, 2005, vol. 579, pp. 1291-1300.
Roth et al., Synthesis of Thiol-Reactive Lipopeptide Adjuvants. Incorporation into Liposomes and Study of Their Mitogenic Effect on Mouse Splenocytes, Bioconjugate Chem., 2004, 15 (3), pp. 541-553, and correction Bioconjugate Chem., 2005, 16 (4), pp. 1049.
Schulze, U et al. Synthesis of Novel Cationic Poly{Ethylene Glycol) Containing Lipids. Bioconjugate Chemistry, vol. 10, 1999, pp. 548-552.
V.N. Zhulenko, G.I. Gorshkov. Pharmacology. M.: KolosS, 2008, p. 34-35.
Extended European Search Report issued on Oct. 10, 2018 for the European Patent Application No. 16815348.4.
Extended European Search Report issued in EP 20163284.1, dated Jul. 28, 2020.
Office Action dated Oct. 23, 2018 in Japan Application No. 2017-566796.
Office Action and Search Report received in Russian Patent Application No. 2018102536 dated Nov. 8, 2019.
Office action issued in corresponding Chinese application 201680037092.8, dated Dec. 11, 2020.
Office Action in Russian Application No. 2018102536, dated Feb. 17, 2021.
Office Action issued in Russian Application No. 2018102536, dated Nov. 8, 2019.
Office Action issued in Taiwanese Application No. 105120027, dated Mar. 13, 2020.
Office Action issued in Brazilian Application No. BR112017027458. 2, dated Aug. 3, 2020.
Decision of Refusal in Taiwanese Application No. 105120027, dated Sep. 29, 2020.
Office Action issued in Chinese Application No. 201680037092.8, dated Dec. 11, 2020.
Office Action issued in Indian Application No. 201717046890, dated Feb. 25, 2021.
Office Action in Chinese Application No. 201680037092.8, Issued on Nov. 2, 2021.
Search Report issued in EP application No. 20163284.1, dated May 12, 2020.
Office Action dated Mar. 31, 2023 for Canadian Patent Application No. 2,990,668, filed Dec. 21, 2017.
Burke, B et al. Macrophages in gene therapy: cellular delivery vehicles and in vivo targets. Journal of Leukocyte Biology, vol. 72, Sep. 2002, pp. 417-428.
Communication pursuant to Article 94(3) issued in European Application No. 20163284.1, dated Feb. 15, 2022.
Office Action issued in Canadian Application No. 2990668, dated Aug. 29, 2022.

* cited by examiner

Intermediate 5

Compound A9

Intermediate 3

Compound A5

Intermediate 3

Compound A1

Intermediate 14

Compound E4

Intermediate 15

Compound D1

Intermediate 15

Compound D7

Intermediate 27

Compound D17

Intermediate 27

Compound D18

Intermediate 28

Intermediate 29

Intermediate 30

Compound D20

Compound D21

IONIZABLE COMPOUNDS AND COMPOSITIONS AND USES THEREOF

BACKGROUND OF THE INVENTION

Therapeutic agents such as drug compounds, nucleic acid molecules and other active agents operate by uptake into cells, tissues, and organs of a subject. Transfection of agents and molecules into cells is often a limiting step in therapeutic action.

When the active agent molecules are sensitive to attack or degradation in serum or other biological settings, it becomes necessary to protect the molecules in order to achieve their medicinal effect.

For example, one way to carry out transfection of nucleic acids is to encapsulate the active molecules in a lipid nanoparticle. Drawbacks of this methodology include potential toxicity in various modalities of delivery, such as intravenous injection, and low rates of cell penetration.

There is a long-standing need for molecules to provide nanoparticles that have favorable transfection properties to deliver active agents to cells.

What is needed are compositions and compounds for forming nanoparticles for active agents. There is a continuing need for lipid-like molecules and compositions for efficient transfection and distribution of nucleic acid molecules and other agents to cells and subjects.

BRIEF SUMMARY

This invention relates to molecules and compositions thereof for use in biopharmaceuticals and therapeutics. More particularly, this invention relates to compounds, compositions and methods for providing nanoparticles to deliver and distribute active agents or drug compounds to cells, tissues, organs, and subjects.

This invention provides a range of ionizable compounds. The ionizable compounds of this invention can be used to form nanoparticles to deliver and distribute active agents.

Embodiments of this invention include a broad range of compounds having lipid-like or liposome-forming properties.

In some embodiments, a compound may have the structure shown in Formula I

*Formula I* wherein $R^1$ and $R^2$ are $R^1 = CH_2(CH_2)_n OC(=O)R^4$ $R^2 = CH_2(CH_2)_m OC(=O)R^5$ wherein n and m are each independently from 1 to 2; and $R^4$ and $R^5$ are independently for each occurrence a C(12-20) alkyl group, or a C(12-20) alkenyl group;

wherein $R^3$ is selected from wherein each $R^6$ is independently selected from H, alkyl, hydroxyl, hydroxyalkyl, alkoxy, alkoxyalkoxy, and aminoalkyl;

each $R^7$ is independently selected from H, alkyl, and hydroxyalkyl;

each $R^8$ is independently selected from H, alkyl, hydroxyalkyl, and aminoalkyl, and any two $R^8$ may form a ring;

q is from zero to four;

Q is O or NR;

p is from 1 to 4.

In further embodiments, a compound can have the structure shown in Formula II

*Formula II* wherein $R^1$ and $R^2$ are $R^1 = CH_2(CH_2)_n OC(=O)R^4$ $R^2 = CH_2(CH_2)_m OC(=O)R^5$ wherein n and m are each independently from 1 to 2; and $R^4$ and $R^5$ are independently for each occurrence a C(12-20) alkyl group, or a C(12-20) alkenyl group;

wherein $R^3$ is a C(12-20) alkyl group or a C(12-20) alkenyl group that is substituted with a carboxylic acid or ester group.

In additional embodiments, a compound may have the structure shown in Formula III

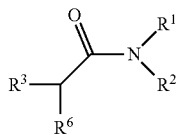

Formula III wherein $R^1$ and $R^2$ are

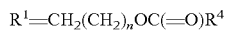

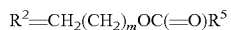

wherein n and m are each independently from 1 to 2; and $R^4$ and $R^5$ are independently for each occurrence a C(12-20) alkyl group, or a C(12-20) alkenyl group;

wherein $R^3$ is selected from alkyl, hydroxyalkyl, alkoxyalkoxy, and carboxyalkyl;

wherein $R^6$ is selected from $NR^7_2$, $N^+HR^7_2$ and $N^+R^7_3$;

wherein $R^7$ is selected from H, alkyl, hydroxyalkyl.

A compound of this invention may have the structure shown in Formula IV

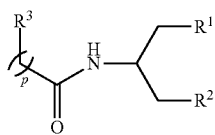

Formula IV wherein $R^1$ and $R^2$ are

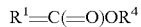

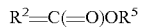

wherein $R^4$ and $R^5$ are independently for each occurrence a C(12-20) alkyl group, or a C(12-20) alkenyl group;

wherein $R^3$ is selected from

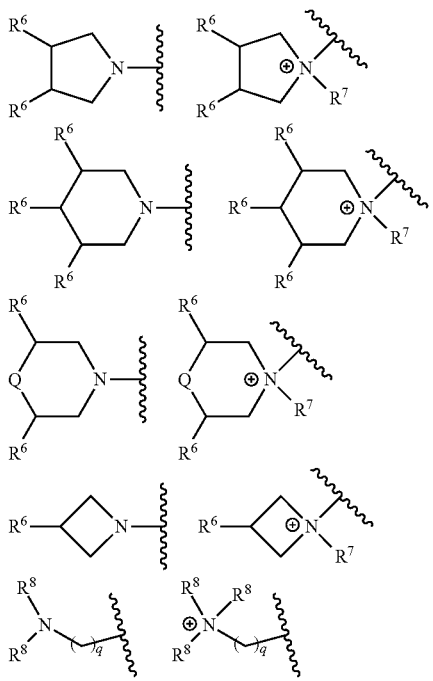

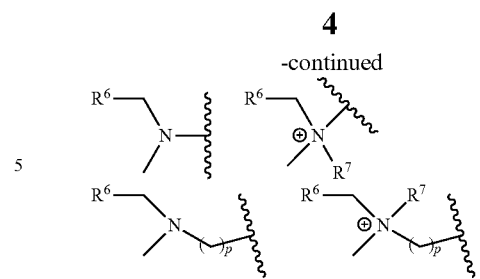

-continued wherein each $R^6$ is independently selected from H, alkyl, hydroxyl, hydroxyalkyl, alkoxy, alkoxyalkoxy, aminoalkyl;

each $R^7$ is independently selected from H, alkyl, hydroxyalkyl;

each $R^8$ is independently selected from H, alkyl, hydroxyalkyl, and aminoalkyl, and any two $R^8$ may form a ring;

q is from zero to four;

Q is O or $NR^7$;

p is from 1 to 4.

In further embodiments, a compound can have the structure shown in Formula IV-B

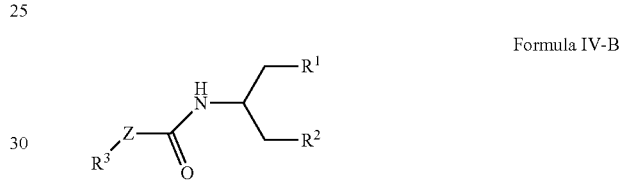

Formula IV-B wherein $R^1$ and $R^2$ are

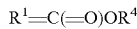

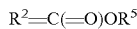

wherein $R^4$ and $R^5$ are independently for each occurrence a C(12-20) alkyl group, or a C(12-20) alkenyl group;

wherein Z is S or O;

wherein $R^3$ is selected from

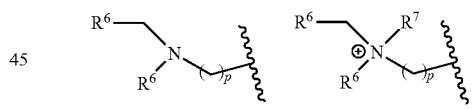

wherein each $R^6$ is independently selected from H, alkyl, hydroxyl, hydroxyalkyl, alkoxy, alkoxyalkoxy, aminoalkyl;

each $R^7$ is independently selected from H, alkyl, hydroxyalkyl;

p is from 1 to 4.

In further aspects, a compound may have the structure shown in Formula V

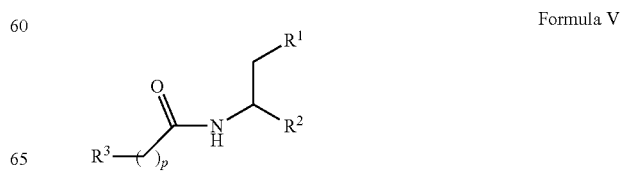

Formula V wherein R¹ and R² are $R^1=NHC(=O)R^4$ $R^2=C(=O)OR^5$ wherein R⁴ and R⁵ are independently for each occurrence a C(12-20) alkyl group, or a C(12-20) alkenyl group;
wherein p is from 1 to 4;
wherein R³ is selected from

[chemical structures showing various cyclic amine substituents including pyrrolidine, piperidine, morpholine, azetidine variants with R⁶, R⁷, R⁸ substituents]

wherein
each R⁶ is independently selected from H, alkyl, hydroxyl, hydroxyalkyl, alkoxy, alkoxyalkoxy, aminoalkyl;
each R⁷ is independently selected from H, alkyl, hydroxyalkyl;
each R⁸ is independently selected from H, alkyl, hydroxyalkyl, and aminoalkyl, and any two R⁸ may form a ring;
q is from zero to four;
Q is O or NR⁷.

A compound of this invention can have the structure shown in Formula VI

Formula VI

[structure showing R¹, R², R³ on NC(=O)R² framework]

wherein R¹ is $R^1=OC(=O)R^4$ wherein R² and R⁴ are independently for each occurrence a C(12-20) alkyl group, or a C(12-20) alkenyl group;
wherein R³ is selected from aminoalkyl, quaternary aminoalkyl.

In certain embodiments, a compound of this invention can have the structure shown in Formula VII Formula VII

[phosphate structure R³—O—P(=O)(O—R³)—O—CH₂—CH(R¹)—R²]

wherein R¹ and R² are $R^1=OC(=O)R^4$ $R^2=OC(=O)R^5$ wherein n and m are each independently from 1 to 2; and R⁴ and R⁵ are independently for each occurrence a C(12-20) alkyl group, or a C(12-20) alkenyl group;
wherein R³ is selected from H, alkyl, aminoalkyl, quaternary aminoalkyl, hydroxyalkyl, alkoxyalkyl, alkoxyalkoxyalkyl.

In further aspects, a compound may have the structure shown in Formula VIII

Formula VIII

[structure showing R¹, R², R³ substituents]

wherein R¹ and R² are $R^1=OC(=O)R^4$ $R^2=C(=O)ZR^5$ wherein Z is NH or O,
wherein R⁴ and R⁵ are independently for each occurrence a C(12-20) alkyl group, or a C(12-20) alkenyl group;
wherein R³ is selected from
amino;
quaternary amino;
aminoalkyl;
quaternary aminoalkyl;

[morpholine structures with R⁷]

$NHC(=O)(CH_2)_pR^{10}$;
$NHC(=O)SR^9$;
wherein R¹⁰ is selected from

[pyrrolidine structures with R⁶, R⁷]

-continued

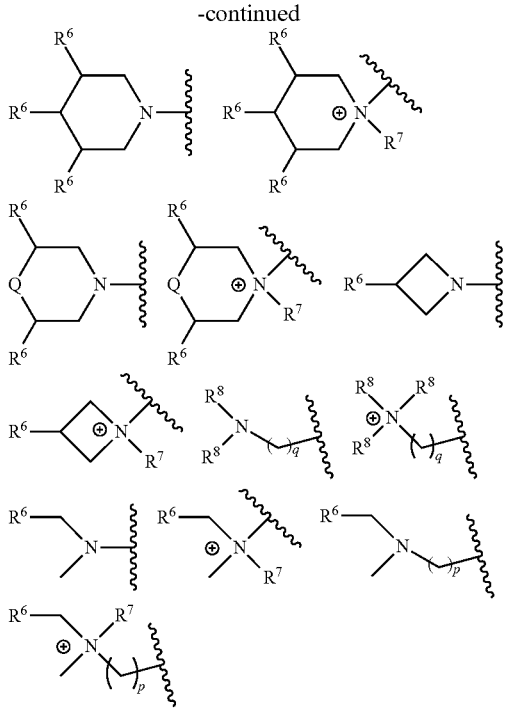

carboxyalkyl;
aminoalkyl;

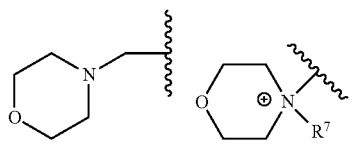

wherein R$^9$ is selected from
alkyl, hydroxyalkyl, alkoxy, alkoxyalkoxy, aminoalkyl;
and wherein
each R$^6$ is independently selected from H, alkyl, hydroxyl, hydroxyalkyl, alkoxy, alkoxyalkoxy, aminoalkyl;
each R$^7$ is independently selected from H, alkyl, hydroxyalkyl;
each R$^8$ is independently selected from H, alkyl, hydroxyalkyl, and aminoalkyl, and any two R$^8$ may form a ring;
q is from zero to four;
Q is O or NR$^7$.

In certain aspects, a compound may have the structure shown in Formula VIII-B

Formula VIII-B

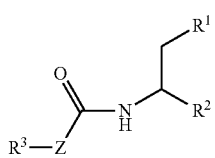

wherein R$^1$ and R$^2$ are

R$^1$=CH$_2$(CH$_2$)$_n$OC(=O)R$^4$

R$^2$=CH$_2$(CH$_2$)$_m$OC(=O)R$^5$ wherein n and m are each independently from 1 to 2;
R$^4$ and R$^5$ are independently for each occurrence a C(12-20) alkyl group, or a C(12-20) alkenyl group;
wherein Z is N, O;
wherein R$^3$ is selected from
alkyl, hydroxyalkyl, alkoxy, alkoxyalkoxy, aminoalkyl:

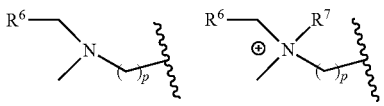

wherein
each R$^6$ is independently selected from H, alkyl, hydroxyl, hydroxyalkyl, alkoxy, alkoxyalkoxy, aminoalkyl;
each R$^7$ is independently selected from H, alkyl, hydroxyalkyl;
p is from 1 to 4.

In additional embodiments, a compound can have the structure shown in Formula IX Formula IX

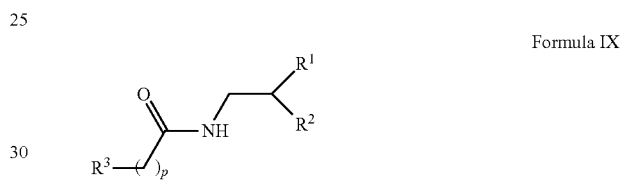

wherein R$^1$ and R$^2$ are

R$^1$=C(=O)OR$^4$

R$^2$=NHC(=O)R$^5$ wherein R$^4$ and R$^5$ are independently for each occurrence a C(12-20) alkyl group, or a C(12-20) alkenyl group;
wherein p is from 1 to 4;
wherein R$^3$ is selected from -continued

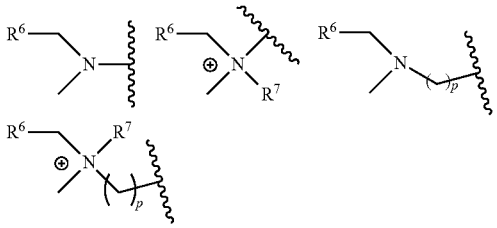

wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl;
each $R^8$ is independently selected from H, alkyl, hydroxyalkyl, and aminoalkyl, and any two $R^8$ may form a ring;
q is from zero to four;
Q is O or $NR^7$.

A compound of this disclosure can have the structure shown in Formula X

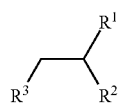

Formula X wherein $R^1$ and $R^2$ are $R^1 = C(=O)OR^4$ $R^2 = NHC(=O)R^5$ wherein $R^4$ and $R^5$ are independently for each occurrence a C(12-20) alkyl group, or a C(12-20) alkenyl group;
wherein $R^3$ is selected from
amino;
quaternary amino;
aminoalkyl;
quaternary aminoalkyl;
hydroxyalkylamino.

In further embodiments, a compound may have the structure shown in Formula XI

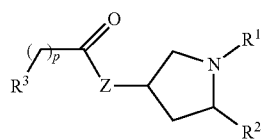

Formula XI wherein $R^1$ and $R^2$ are $R^1 = C(=O)R^4$ $R^2 = C(=O)OR^5$ wherein $R^4$ and $R^5$ are independently for each occurrence a C(12-20) alkyl group, or a C(12-20) alkenyl group;
wherein Z is O or NH;
wherein p is from 1 to 4;

wherein $R^3$ is selected from

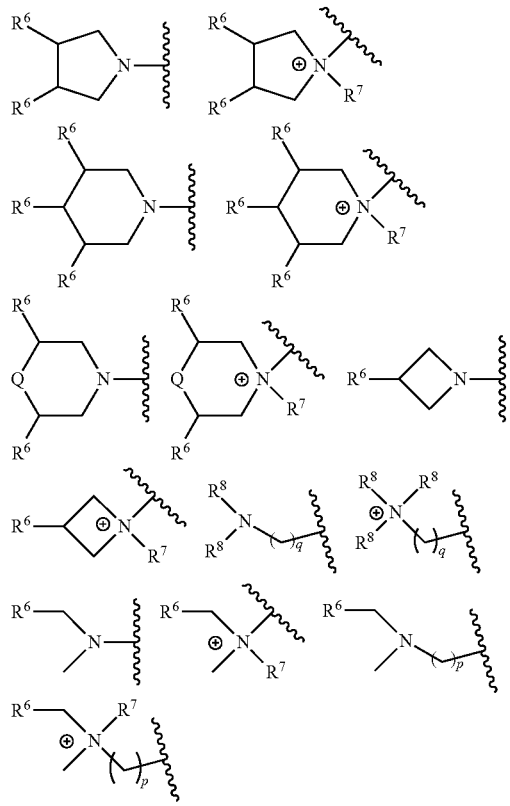

wherein
each $R^6$ is independently selected from H, alkyl, hydroxyl, hydroxyalkyl, alkoxy, alkoxyalkoxy, aminoalkyl;
each $R^7$ is independently selected from H, alkyl;
each $R^8$ is independently selected from H, alkyl, hydroxyalkyl, and aminoalkyl, and any two $R^8$ may form a ring;
q is from zero to four;
Q is O or $NR^7$.

This invention further contemplates compositions containing an ionizable compound above and a pharmaceutically acceptable carrier. In some embodiments, the composition may contain nanoparticles. This disclosure includes pharmaceutical compositions comprising an ionizable compound above, an active agent, and a pharmaceutically acceptable carrier. The ionizable compound may be from 15 mol % to 40 mol % of the lipids of the composition. In some embodiments, the composition may comprise nanoparticles.

An active agent of this disclosure may be one or more RNAi molecules. An active agent may be one or more RNAi molecules selected from small interfering RNAs (siRNA), double stranded RNAs (dsRNA) that are Dicer substrates, microRNAs (miRNA), short hairpin RNAs (shRNA), DNA-directed RNAs (ddRNA), Piwi-interacting RNAs (piRNA), repeat associated siRNAs (rasiRNA), and modified forms thereof.

An active agent of this disclosure may be one or more active pharmaceutical ingredients.

In certain embodiments, this invention includes compositions for use in distributing an active agent for treating a condition or disease in a subject, the composition comprising an ionizable compound above, a structural lipid, a stabilizer lipid, and a lipid for reducing immunogenicity of the composition. The active agent can be one or more RNAi molecules and the composition may comprise nanoparticles that encapsulate the RNAi molecules.

This invention further contemplates compositions containing an ionizable compound, and one or more pharmaceutically acceptable excipients. In some embodiments, a composition of this invention can be a nanoparticle composed, at least in part, of an ionizable compound.

Compounds of this invention can be used to make compositions for use in distributing an active agent in a subject, where the composition includes an ionizable compound.

A composition of this invention can be used in distributing an active agent for treating a condition or disease in a subject.

A composition for use in distributing an active agent for treating a condition or disease in a subject can include an ionizable compound, a structural lipid, and a lipid for reducing immunogenicity of the composition.

DETAILED DESCRIPTION OF THE INVENTION

Figure 1:
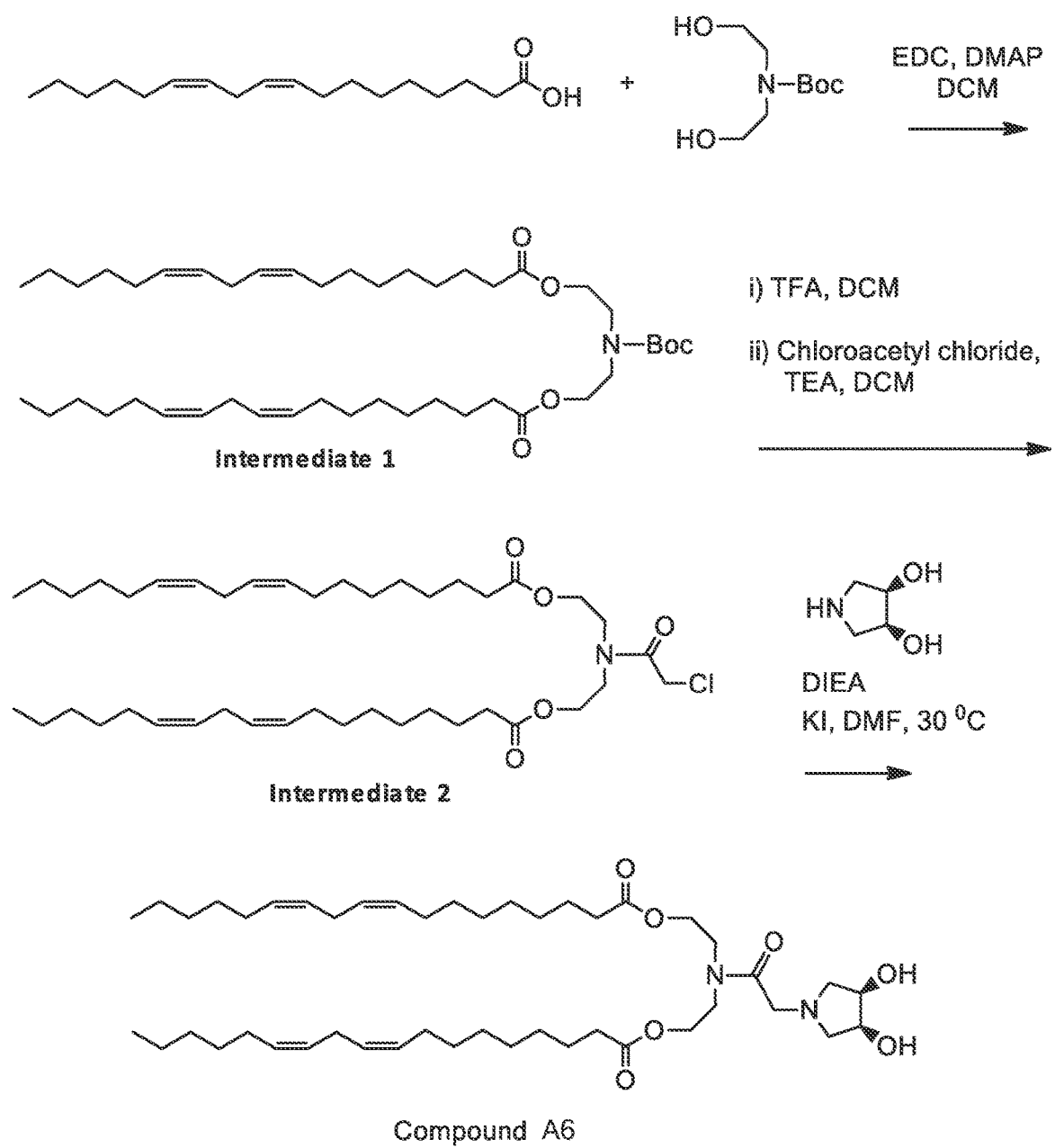
FIG. 1 shows a scheme for the preparation of Compound A6.

This invention provides a range of ionizable molecules that are amphiphiles with lipid-like properties. The ionizable compounds of this invention can be used in delivering therapeutic agents to cells, tissues or organs, organisms, and subjects.

In some aspects, this invention provides compounds for forming lipid nanoparticles for encapsulating and delivering active agents such as nucleic acid molecules to cells and subjects.

This invention can provide a composition for use in distributing an active agent in cells, tissues or organs, organisms, and subjects, where the composition includes one or more of the ionizable molecules of this invention.

Compositions of this invention may include one or more of the ionizable molecules, along with a structural lipid, and one or more lipids for reducing immunogenicity of the composition.

An ionizable molecule of this invention can be any mol % of a composition of this invention.

Compositions of this invention may include one or more of the ionizable molecules, along with a structural lipid, and one or more lipids for reducing immunogenicity of the composition.

Compositions of this invention may include one or more of the ionizable molecules, along with a structural lipid, one or more stabilizer lipids, and one or more lipids for reducing immunogenicity of the composition.

This invention includes compositions containing one or more ionizable compounds and a pharmaceutically acceptable carrier. The composition may comprise nanoparticles.

This invention further contemplates pharmaceutical compositions containing one or more ionizable compounds, an active agent, and a pharmaceutically acceptable carrier.

A composition may contain an ionizable compound in a quantity from 15 mol % to 40 mol % of the lipids of the composition.

An active agent can be one or more RNAi molecules. An active agent can be one or more RNAi molecules selected from small interfering RNAs (siRNA), double stranded RNAs (dsRNA) that are Dicer substrates, microRNAs (miRNA), short hairpin RNAs (shRNA), DNA-directed RNAs (ddRNA), Piwi-interacting RNAs (piRNA), repeat associated siRNAs (rasiRNA), and modified forms thereof.

In further aspects, this invention includes compositions for use in distributing an active agent for treating a condition or disease in a subject, where the composition contains one or more ionizable compounds, a structural lipid, a stabilizer lipid, and a lipid for reducing immunogenicity of the composition. The active agent can be one or more RNAi molecules, and the composition may comprise nanoparticles that encapsulate the RNAi molecules.

Compositions with Three Components

As used herein, a component of a formulation, such as a "lipid," can be a single compound, or can be a combination of one or more suitable lipid compounds. For example, "a stabilizer lipid" can refer to a single stabilizer lipid, or to a combination of one or more suitable stabilizer lipids. One skilled in the art can readily appreciate that certain combinations of the compounds described herein can be used without undue experimentation, and that various combinations of compounds are encompassed by the description of a component of a formulation.

The ionizable compounds of a composition of this invention can be from 50 mol % to 80 mol % of the lipid components of the composition. In certain embodiments, the ionizable molecules of a composition can be from 55 mol % to 65 mol % of the lipid components of the composition. In further embodiments, the ionizable molecules of a composition can be about 60 mol % of the lipid components of the composition.

The structural lipid of a composition of this invention can be from 20 mol % to 50 mol % of the lipid components of the composition. In certain embodiments, the structural lipid of a composition can be from 35 mol % to 45 mol % of the lipid components of the composition.

The one or more lipids for reducing immunogenicity of the composition can be from a total of 1 mol % to 8 mol % of the lipid components of the composition. In certain embodiments, the one or more lipids for reducing immunogenicity of the composition can be from a total of 1 mol % to 5 mol % of the lipid components of the composition.

In additional aspects, a composition of this invention can further include a cationic lipid, which can be from 5 mol % to 25 mol % of the lipid components of the composition. In certain embodiments, a composition of this invention can further include a cationic lipid, which can be from 5 mol % to 15 mol % of the lipid components of the composition. In these aspects, the molar ratio of the concentrations of the cationic lipid to the ionizable molecules of a composition of this invention can be from 5:80 to 25:50.

In compositions of this invention, the entirety of the lipid components may include one or more of the ionizable compound molecular components, a structural lipid, and one or more lipids for reducing immunogenicity of the composition.

Compositions with Four Components

The ionizable molecules of a composition of this invention can be from 15 mol % to 40 mol % of the lipid components of the composition. In certain embodiments, the ionizable molecules of a composition can be from 20 mol % to 35 mol % of the lipid components of the composition. In further embodiments, the ionizable molecules of a composition can be from 25 mol % to 30 mol % of the lipid components of the composition.

The structural lipid of a composition of this invention can be from 25 mol % to 40 mol % of the lipid components of the composition. In certain embodiments, the structural lipid of a composition can be from 30 mol % to 35 mol % of the lipid components of the composition.

The sum of the stabilizer lipids of a composition of this invention can be from 25 mol % to 40% mol % of the lipid components of the composition. In certain embodiments, the sum of the stabilizer lipids of a composition can be from 30 mol % to 40 mol % of the lipid components of the composition.

In some embodiments, a composition of this invention can include two or more stabilizer lipids, where each of the stabilizer lipids individually can be from 5 mol % to 35 mol % of the lipid components of the composition. In certain embodiments, a composition of this invention can include two or more stabilizer lipids, where each of the stabilizer lipids individually can be from 10 mol % to 30 mol % of the lipid components of the composition.

In certain embodiments, the sum of the one or more stabilizer lipids can be from 25 mol % to 40 mol % of the lipids of the composition, wherein each of the stabilizer lipids individually can be from 5 mol % to 35% mol %.

In certain embodiments, the sum of the one or more stabilizer lipids can be from 30 mol % to 40 mol % of the lipids of the composition, wherein each of the stabilizer lipids individually can be from 10 mol % to 30% mol %.

The one or more lipids for reducing immunogenicity of the composition can be from a total of 1 mol % to 8 mol % of the lipid components of the composition. In certain embodiments, the one or more lipids for reducing immunogenicity of the composition can be from a total of 1 mol % to 5 mol % of the lipid components of the composition.

In additional aspects, a composition of this invention can further include a cationic lipid, which can be from 5 mol % to 25 mol % of the lipid components of the composition. In certain embodiments, a composition of this invention can further include a cationic lipid, which can be from 5 mol % to 15 mol % of the lipid components of the composition. In these aspects, the molar ratio of the concentrations of the cationic lipid to the ionizable molecules of a composition of this invention can be from 5:35 to 25:15.

In certain embodiments, the entirety of the lipid components of a composition may include one or more of the ionizable compound molecular components, a structural lipid, one or more lipids for reducing immunogenicity of the composition, and one or more stabilizer lipids.

Examples of Lipid Compositions

In some embodiments, three lipid-like components, i.e. one or more ionizable molecules, a structural lipid, and one or more lipids for reducing immunogenicity of the composition can be 100% of the lipid components of the composition. In certain embodiments, a cationic lipid can be included.

Examples of compositions of this invention are shown in Table 1.

TABLE 1

Compositions of lipid components (each in mol % of total)

| Ionizable | Cationic | Structural | Reduce immun. |
|---|---|---|---|
| 60 | 0 | 32 | 8 |
| 60 | 0 | 35 | 5 |
| 55 | 0 | 44 | 1 |
| 65 | 0 | 32 | 3 |
| 60 | 0 | 36 | 4 |
| 65 | 0 | 32 | 3 |
| 70 | 0 | 25 | 5 |
| 74 | 0 | 20 | 6 |
| 78 | 0 | 20 | 2 |
| 50 | 10 | 35 | 5 |
| 55 | 15 | 25 | 5 |
| 55 | 20 | 20 | 5 |

In certain embodiments, four lipid-like components, i.e. one or more ionizable molecules, a structural lipid, and one or more lipids for reducing immunogenicity of the composition, and one or more stabilizer lipids can be 100% of the lipid components of the composition.

Examples of compositions of this invention are shown in Table 2.

TABLE 2

Compositions of lipid components (each in mol % of total)

| Ionizable | Cationic | Structural | Stabilizer | Reduce immun. |
|---|---|---|---|---|
| 17 | 0 | 35 | 40 | 8 |
| 20 | 0 | 35 | 40 | 5 |
| 25 | 0 | 35 | 39 | 1 |
| 25 | 0 | 35 | 35 | 5 |
| 25 | 0 | 30 | 40 | 5 |
| 25 | 0 | 40 | 30 | 5 |
| 30 | 0 | 25 | 40 | 5 |
| 35 | 0 | 25 | 35 | 5 |
| 40 | 0 | 30 | 25 | 5 |
| 25 | 5 | 30 | 35 | 5 |
| 25 | 10 | 30 | 30 | 5 |
| 25 | 15 | 25 | 30 | 5 |

Compositions for Selective Biodistribution

Aspects of this invention can provide a range of compositions for use in distributing an active agent to various organs or tissues of a subject.

For example, compositions of this invention can contain an ionizable lipid, a structural lipid, and a lipid for reducing immunogenicity of the composition.

In some embodiments, compositions of this invention can contain an ionizable lipid, a structural lipid, one or more stabilizer lipids, and a lipid for reducing immunogenicity of the composition.

Compositions of this invention may provide a surprisingly selective biodistribution of the active agent to a particular organ or tissue.

In some embodiments, a composition of this invention can provide a surprisingly selective biodistribution of the active agent to the lung of a subject.

In further embodiments, a composition of this invention can provide a surprisingly selective biodistribution of the active agent to the liver of a subject.

In some embodiments, a composition of this invention can provide a surprisingly selective biodistribution of the active agent to the colon of a subject.

In some embodiments, a composition of this invention can provide a surprisingly selective biodistribution of the active agent to the pancreas of a subject.

In certain embodiments, the ratio of the distribution of the active agent to the lung over the distribution of the active agent to the subject's liver can be at least 1.5.

In further embodiments, the ratio of the distribution of the active agent to the lung to the distribution of the active agent to the subject's liver can be at least 5.

Ionizable Compounds

The ionizable compounds of this invention can have lipid-like properties, for example, as amphiphiles.

Examples of an ionizable molecule include compounds having the structure shown in Formula I

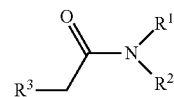

Formula I wherein $R^1$ and $R^2$ are

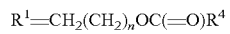

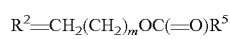

wherein n and m are each independently from 1 to 2; and $R^4$ and $R^5$ are independently for each occurrence a C(12-20) alkyl group, or a C(12-20) alkenyl group;

wherein $R^3$ is selected from 1-azetidines, 1-pyrrolidines, 1-piperidines, 4-morpholines, and 1,4-piperazines wherein the rings can be substituted at any carbon atom position,

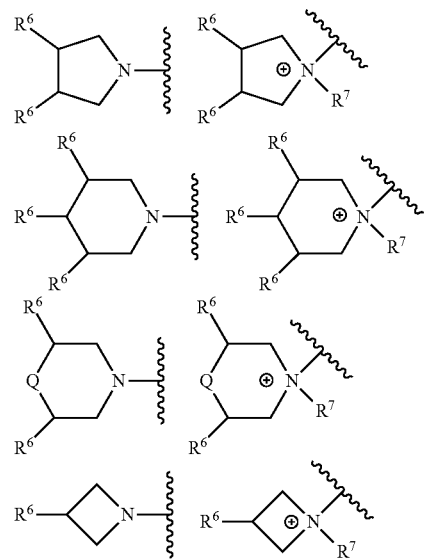

and can also be selected from amino and aminoalkyl groups, which may be substituted,

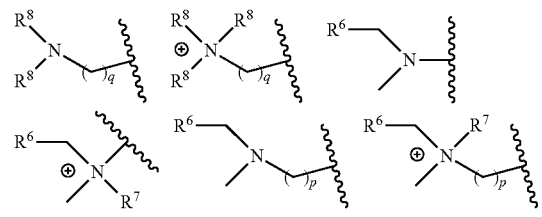

wherein each $R^6$ is independently selected from H, alkyl, hydroxyl, hydroxyalkyl, alkoxy, alkoxyalkoxy, and aminoalkyl;

each $R^7$ is independently selected from H, alkyl, hydroxyalkyl, and aminoalkyl;

each $R^8$ is independently selected from H, alkyl, hydroxyalkyl, and aminoalkyl, and any two $R^8$ may form a ring;

q is from zero to four;

Q is O or $NR^7$;

p is from 1 to 4.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, $R^4$ and $R^5$ are independently for each occurrence a C(16-18) alkyl group, or a C(16-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, p is 1, 2, 3 or 4.

In some embodiments, q is 0, 1, 2, 3 or 4.

In some embodiments, examples of an ionizable molecule include compounds having the structure shown in Formula I

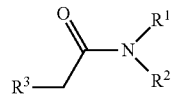

Formula I wherein $R^1$ and $R^2$ are

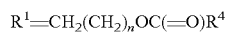

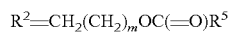

wherein n and m are each independently from 1 to 2; and $R^4$ and $R^5$ are independently for each occurrence a C(12-20) alkyl group, or a C(12-20) alkenyl group; wherein $R^3$ is selected from

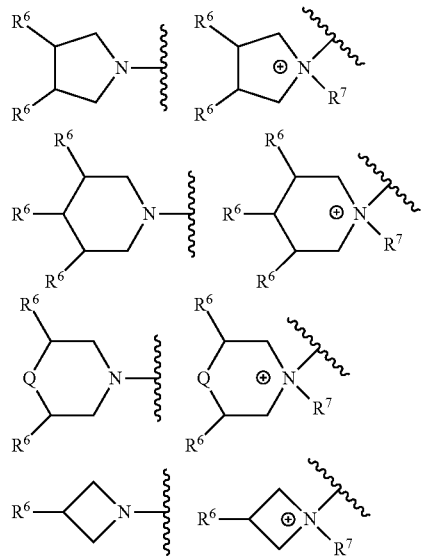

wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl;
Q is O or $NR^7$.

In some embodiments, each of the alkenyl groups can have from one to two double bonds.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, examples of an ionizable molecule include compounds having the structure shown in Formula I

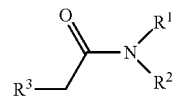

Formula I wherein $R^1$ and $R^2$ are

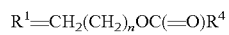

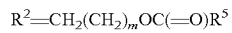

wherein n and m are each independently from 1 to 2; and $R^4$ and $R^5$ are independently for each occurrence a C(12-20) alkyl group, or a C(12-20) alkenyl group; wherein $R^3$ is selected from

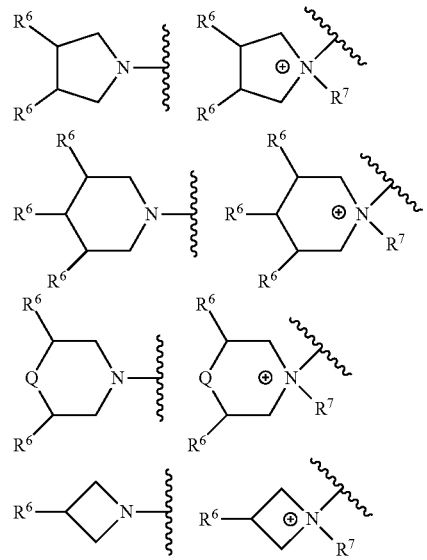

wherein
each $R^6$ is independently selected from H, alkyl, hydroxyl, hydroxyalkyl, alkoxy, alkoxyalkoxy, aminoalkyl;
each $R^7$ is independently selected from H, alkyl;
Q is O or $NR^7$.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, $R^4$ and $R^5$ are independently for each occurrence a C(16-18) alkyl group, or a C(16-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, n and m can be each independently from 3 to 6.

In some embodiments, examples of an ionizable molecule include compounds having the structure shown in Formula I

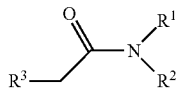

Formula I wherein $R^1$ and $R^2$ are

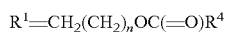

$R^1 = CH_2(CH_2)_n OC(=O)R^4$

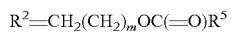

$R^2 = CH_2(CH_2)_m OC(=O)R^5$ wherein n and m are each independently from 1 to 2; and $R^4$ and $R^5$ are independently for each occurrence a C(12-20) alkyl group, or a C(12-20) alkenyl group;

wherein $R^3$ is selected from

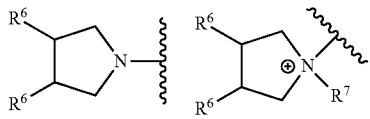

wherein
each $R^6$ is independently selected from H, alkyl, hydroxyl, hydroxyalkyl, alkoxy, alkoxyalkoxy, aminoalkyl;
each $R^7$ is independently selected from H, alkyl.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, examples of an ionizable molecule include compounds having the structure shown in Formula I

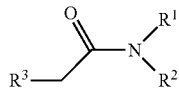

Formula I wherein $R^1$ and $R^2$ are

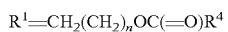

$R^1 = CH_2(CH_2)_n OC(=O)R^4$

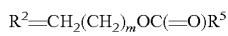

$R^2 = CH_2(CH_2)_m OC(=O)R^5$ wherein n and m are each independently from 1 to 2; and $R^4$ and $R^5$ are independently for each occurrence a C(12-20) alkyl group, or a C(12-20) alkenyl group;

wherein $R^3$ is selected from

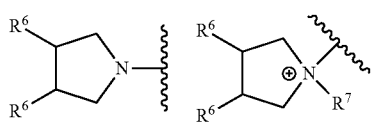

wherein
each $R^6$ is independently hydroxyl;
each $R^7$ is independently selected from H, alkyl.

In some embodiments, each of the alkenyl groups can have from one to two double bonds.

In some embodiments, $R^4$ and $R^5$ are independently for each occurrence a C(14-18) alkyl group, or a C(14-18) alkenyl group.

Examples of an ionizable compound include the following compound A1:

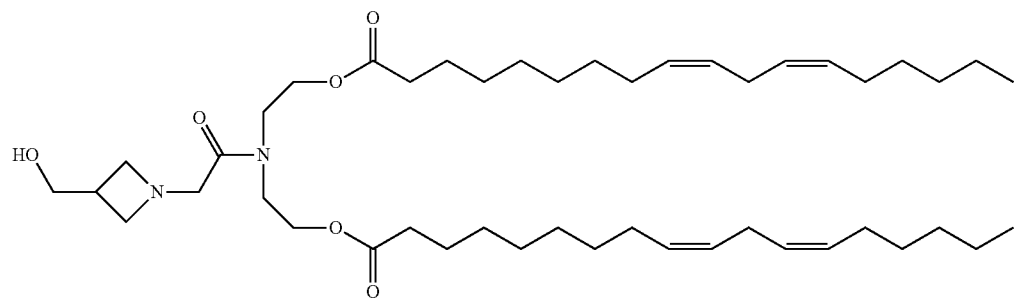 [SMILES: CCCCC/C=C\C/C=C\CCCCCCCC(=O)OCCN(CCOC(=O)CCCCCCC/C=C\C/C=C\CCCCC)C(=O)CN1CC(CO)C1]

which is ((2-(3-(hydroxymethyl)azetidin-1-yl)acetyl)azanediyl)bis(ethane-2,1-diyl) (9Z,9'Z,12Z,12'Z)-bis(octadeca-9,12-dienoate).

Examples of an ionizable compound include the following compound A2:

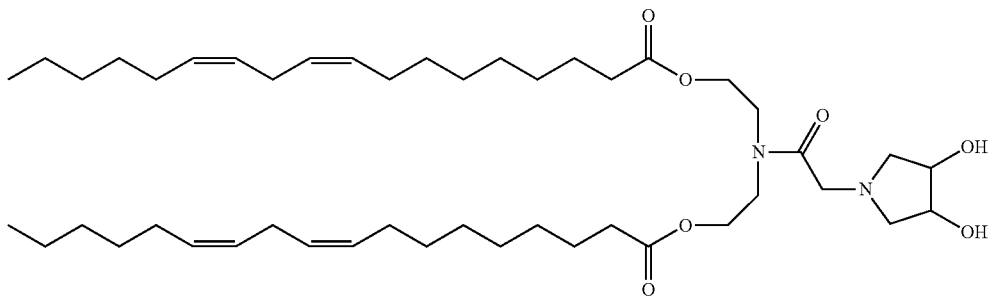 [SMILES: CCCCC/C=C\C/C=C\CCCCCCCC(=O)OCCN(CCOC(=O)CCCCCCC/C=C\C/C=C\CCCCC)C(=O)CN1CC(O)C(O)C1]

Examples of an ionizable compound include the following compound A3:

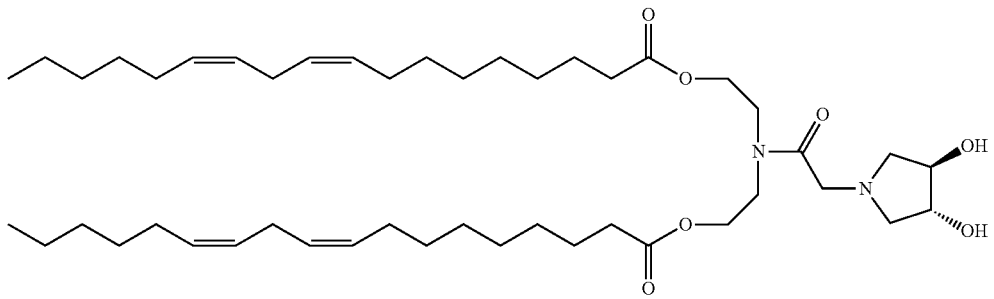 [SMILES: CCCCC/C=C\C/C=C\CCCCCCCC(=O)OCCN(CCOC(=O)CCCCCCC/C=C\C/C=C\CCCCC)C(=O)CN1C[C@@H](O)[C@H](O)C1]

Examples of an ionizable compound include the following compound A4:

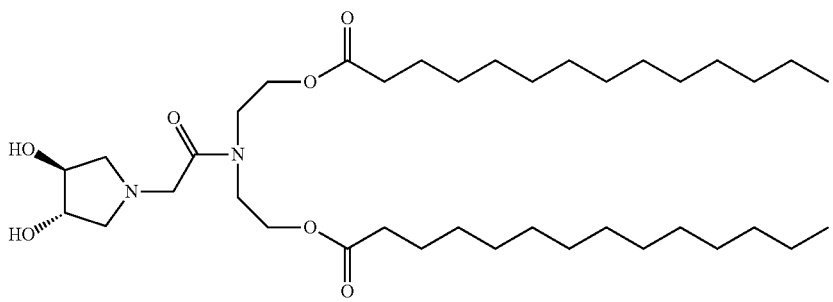 [SMILES: CCCCCCCCCCCCCC(=O)OCCN(CCOC(=O)CCCCCCCCCCCCC)C(=O)CN1C[C@H](O)[C@@H](O)C1]

which is ((2-((3S,4S)-3,4-dihydroxypyrrolidin-1-yl)acetyl)azanediyl)bis(ethane-2,1-diyl) ditetradecanoate.

Examples of an ionizable compound include the following compound A5:

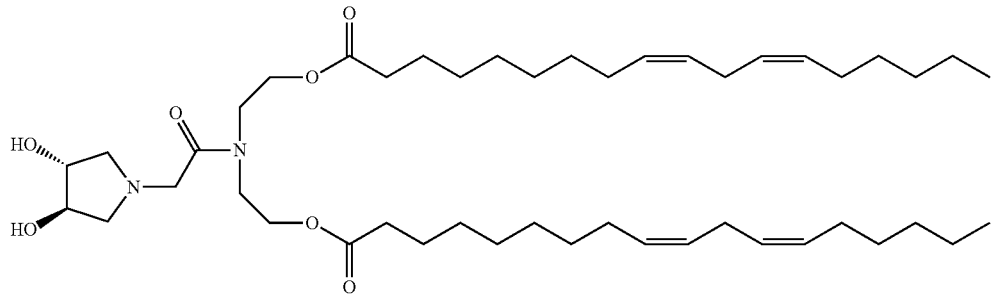 [SMILES: CCCCC/C=C\C/C=C\CCCCCCCC(=O)OCCN(CCOC(=O)CCCCCCC/C=C\C/C=C\CCCCC)C(=O)CN1C[C@@H](O)[C@H](O)C1]

which is ((2-((3R,4R)-3,4-dihydroxypyrrolidin-1-yl)acetyl)azanediyl)bis(ethane-2,1-diyl) (9Z,9'Z,12Z,12'Z)-bis(octadeca-9,12-dienoate).

Examples of an ionizable compound include the following compound A6:

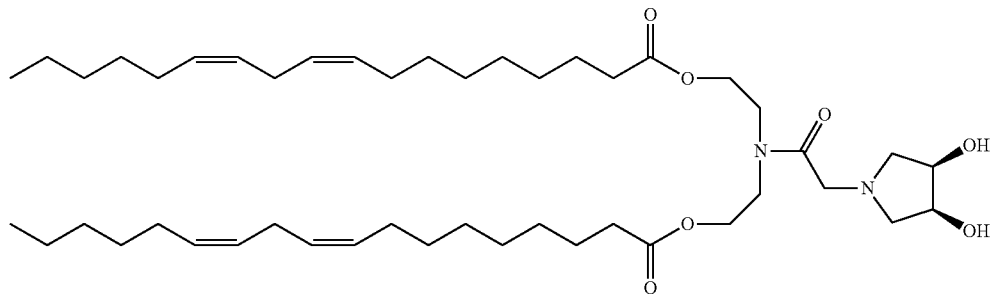 [SMILES: CCCCC/C=C\C/C=C\CCCCCCCC(=O)OCCN(CCOC(=O)CCCCCCC/C=C\C/C=C\CCCCC)C(=O)CN1C[C@@H](O)[C@@H](O)C1]

which is ((2-((3S,4R)-3,4-dihydroxypyrrolidin-1-yl)acetyl)azanediyl)bis(ethane-2,1-diyl) (9Z,9'Z,12Z,12'Z)-bis(octadeca-9,12-dienoate).

Examples of an ionizable compound include the following compound A7:

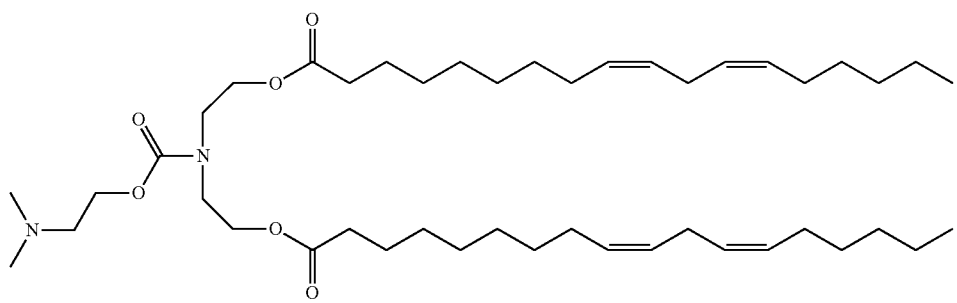 [SMILES: CCCCC/C=C\C/C=C\CCCCCCCC(=O)OCCN(CCOC(=O)CCCCCCC/C=C\C/C=C\CCCCC)C(=O)OCCN(C)C]

which is (((2-(dimethylamino)ethoxy)carbonyl)azanediyl)bis(ethane-2,1-diyl) (9Z,9'Z,12Z,12'Z)-bis(octadeca-9,12-dienoate).

Examples of an ionizable compound include the following compound A8:

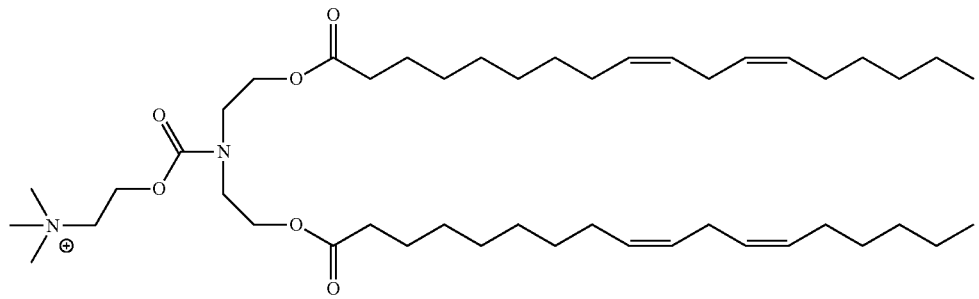 [SMILES: CCCCC/C=C\C/C=C\CCCCCCCC(=O)OCCN(CCOC(=O)CCCCCCC/C=C\C/C=C\CCCCC)C(=O)OCC[N+](C)(C)C]

which is 2-((bis(2-(((9Z,12Z)-octadeca-9,12-dienoyl)oxy)ethyl)carbamoyl)oxy)-N,N,N-trimethylethan-1-aminium.

Examples of an ionizable compound include the following compound A9:

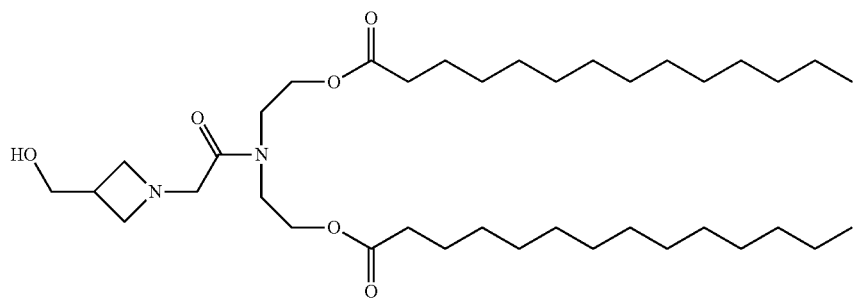 [SMILES: CCCCCCCCCCCCCC(=O)OCCN(CCOC(=O)CCCCCCCCCCCCC)C(=O)CN1CC(CO)C1]

which is ((2-(3-(hydroxymethyl)azetidin-1-yl)acetyl)azanediyl)bis(ethane-2,1-diyl) ditetradecanoate.

Examples of an ionizable compound include the following compound AA:

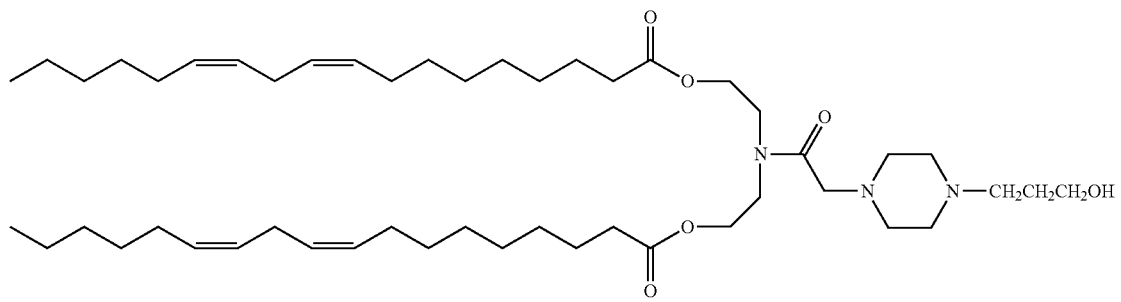

which is ((2-(4-(2-hydroxyethyl)piperazin-1-yl)acetyl)azanediyl)bis(ethane-2,1-diyl) (9Z,9'Z,12Z,12'Z)-bis(octadeca-9,12-dienoate).

Examples of an ionizable compound include the following compound AB:
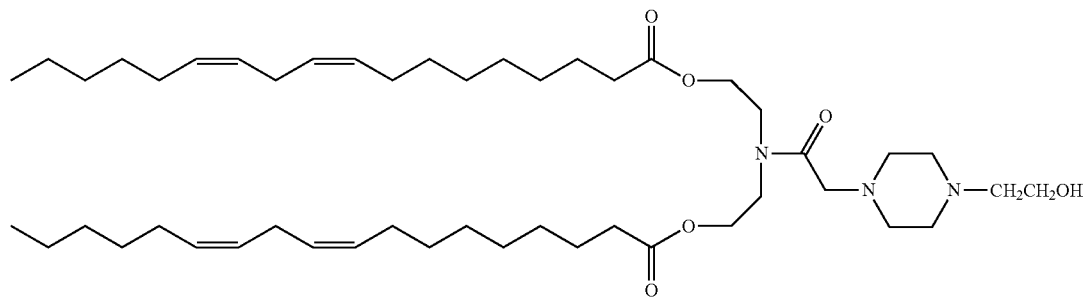
20
which is ((2-(4-(2-hydroxyethyl)piperazin-1-yl)acetyl)azanediyl)bis(ethane-2,1-diyl) (9Z,9'Z,12Z,12'Z)-bis(octadeca-9,12-dienoate).
Examples of an ionizable compound include the following compound AC:
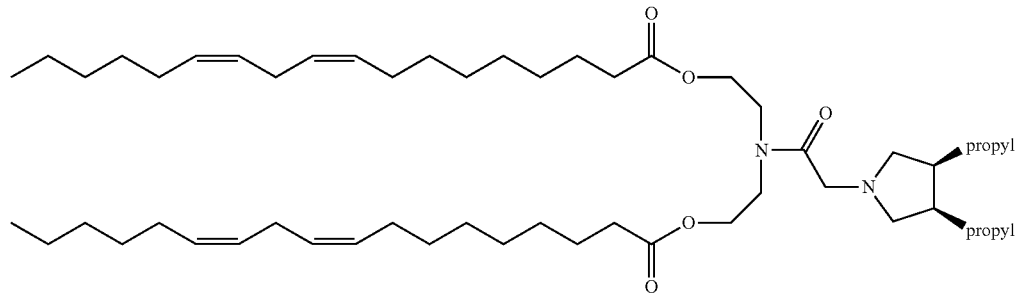
Examples of an ionizable compound include the following compound AD:
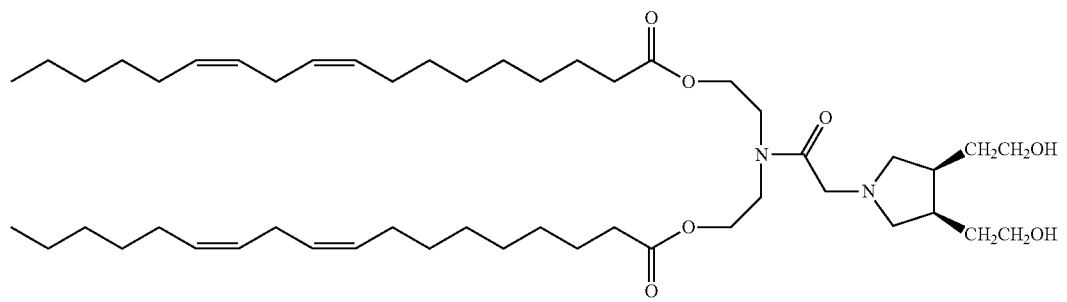

Examples of an ionizable compound include the following compound AE:
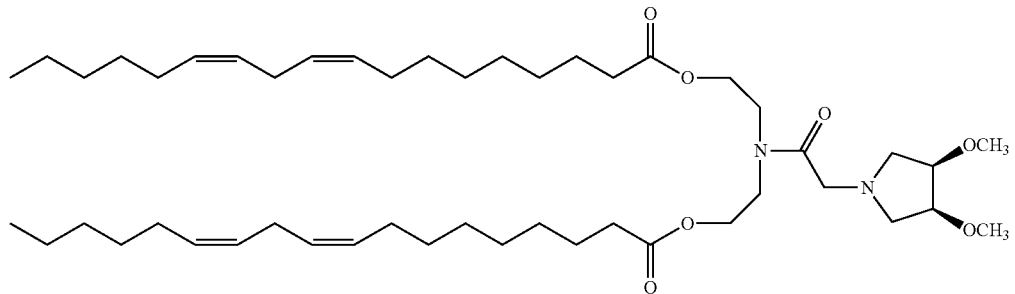 [SMILES: CCCCC/C=C\C/C=C\CCCCCCCC(=O)OCCN(CCOC(=O)CCCCCCC/C=C\C/C=C\CCCCC)C(=O)CN1C[C@H](OC)[C@H](OC)C1]
Examples of an ionizable compound include the following compound AF:
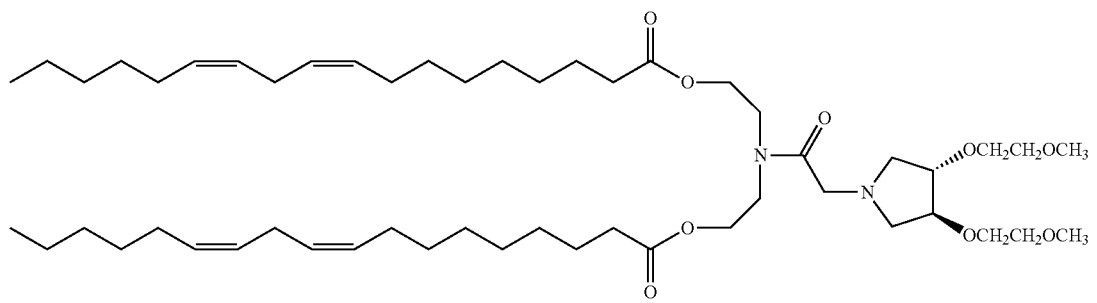
Examples of an ionizable compound include the following compound B1:
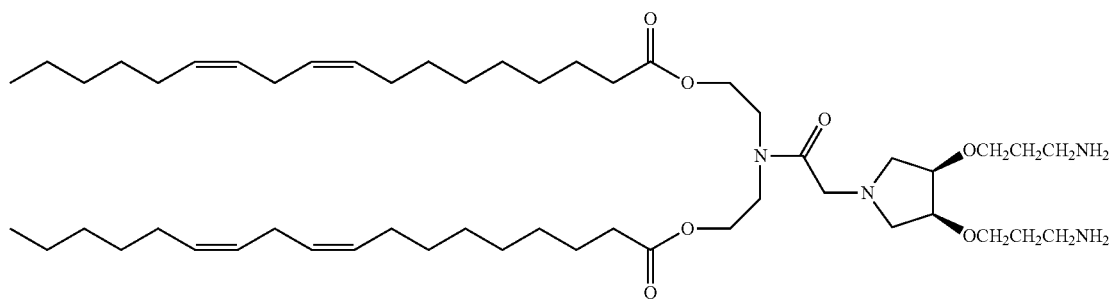

Examples of an ionizable compound include the following compound B2:
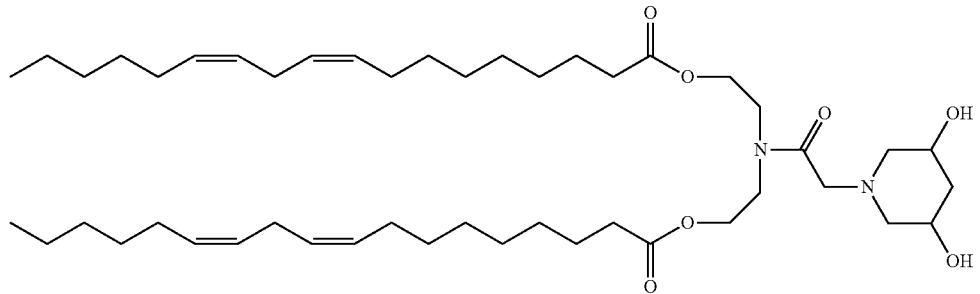 [SMILES: CCCCC/C=C\C/C=C\CCCCCCCC(=O)OCCN(CCOC(=O)CCCCCCC/C=C\C/C=C\CCCCC)C(=O)CN1CC(O)CC(O)C1]
Examples of an ionizable compound include the following compound B3:
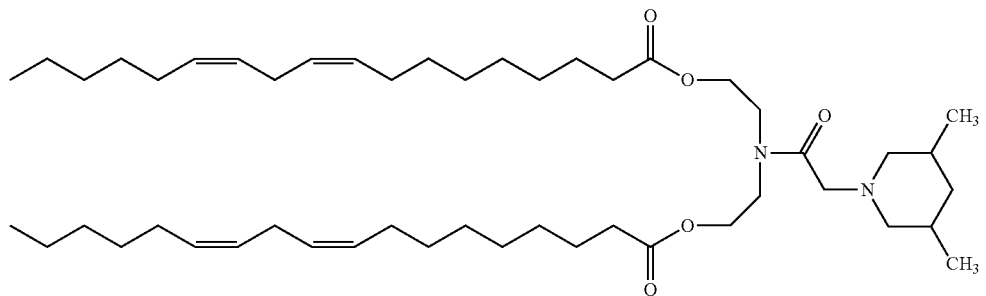 [SMILES: CCCCC/C=C\C/C=C\CCCCCCCC(=O)OCCN(CCOC(=O)CCCCCCC/C=C\C/C=C\CCCCC)C(=O)CN1CC(C)CC(C)C1]
Examples of an ionizable compound include the following compound B4:
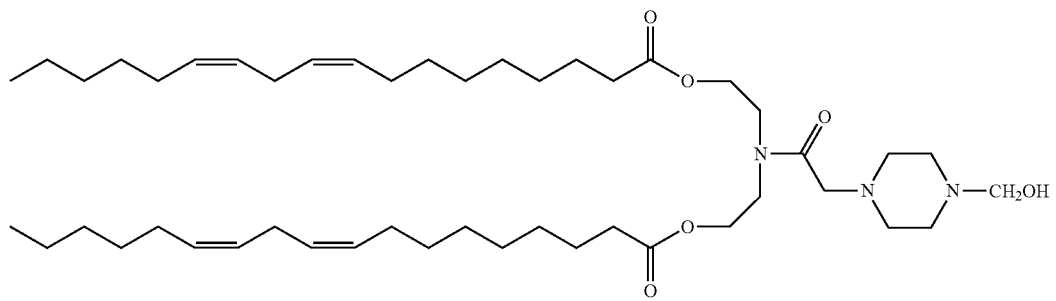 [SMILES: CCCCC/C=C\C/C=C\CCCCCCCC(=O)OCCN(CCOC(=O)CCCCCCC/C=C\C/C=C\CCCCC)C(=O)CN1CCN(CO)CC1]
Examples of an ionizable compound include the following compound B5:
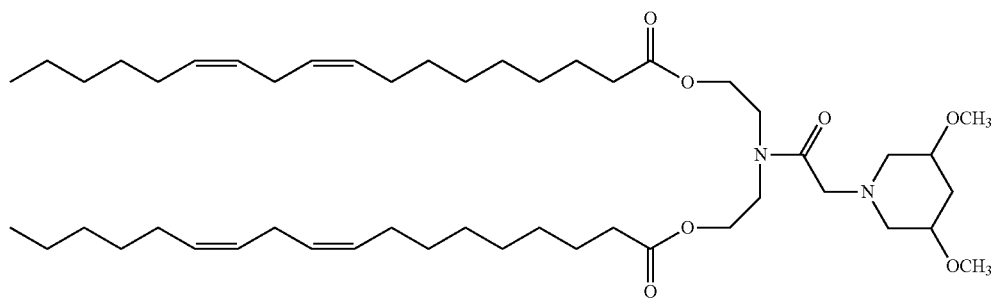 [SMILES: CCCCC/C=C\C/C=C\CCCCCCCC(=O)OCCN(CCOC(=O)CCCCCCC/C=C\C/C=C\CCCCC)C(=O)CN1CC(OC)CC(OC)C1]

Examples of an ionizable compound include the following compound B6:

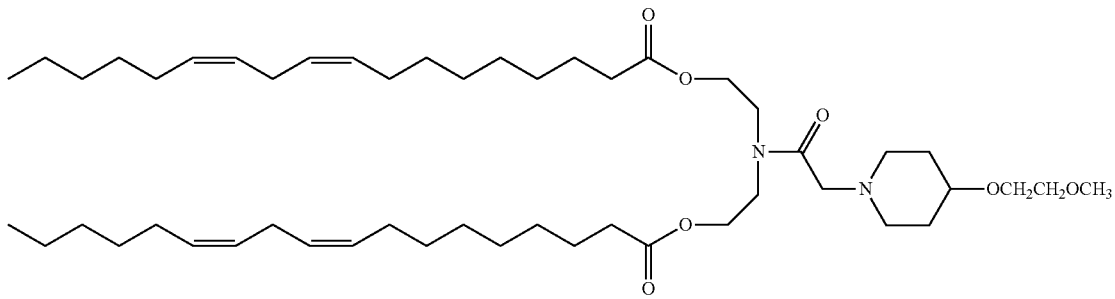

Examples of an ionizable compound include the following compound B7:

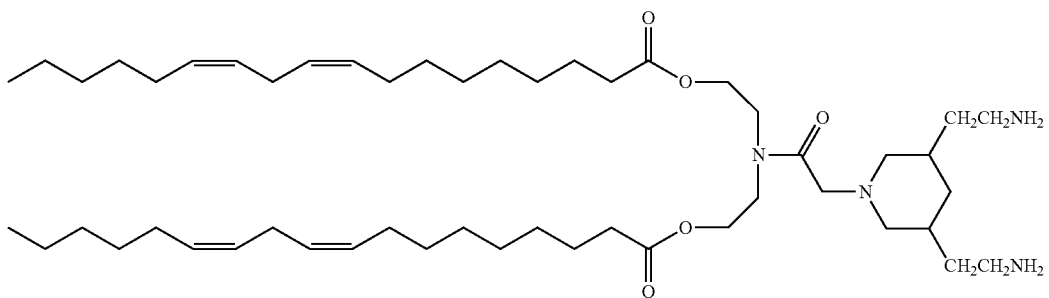

Examples of an ionizable molecule include compounds having the structure shown in Formula II

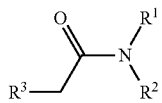

Formula II wherein $R^1$ and $R^2$ are

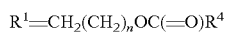
$R^1=CH_2(CH_2)_nOC(=O)R^4$

$R^2=CH_2(CH_2)_mOC(=O)R^5$ wherein n and m are each independently from 1 to 2; and $R^4$ and $R^5$ are independently for each occurrence a C(12-20) alkyl group, or a C(12-20) alkenyl group;

wherein $R^3$ is a C(12-20) alkyl group or a C(12-20) alkenyl group that is substituted with a carboxylic acid or ester group.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, $R^3$ is a C(14-18) alkyl group, or a C(14-18) alkenyl group that is substituted with a carboxylic acid or ester group.

Examples of an ionizable compound include the following compound B8:

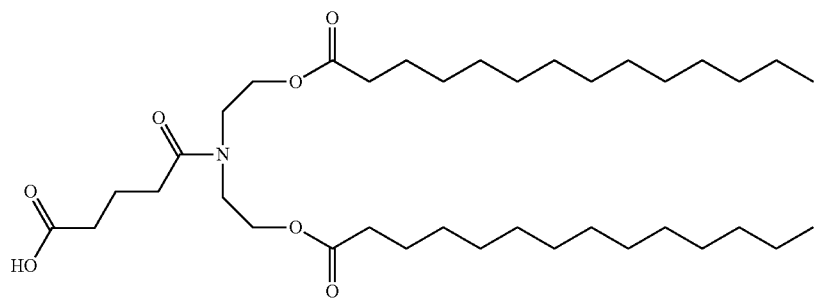 [SMILES: CCCCCCCCCCCCCC(=O)OCCN(CCOC(=O)CCCCCCCCCCCCC)C(=O)CCCC(=O)O]

Examples of an ionizable compound include the following compound B9:

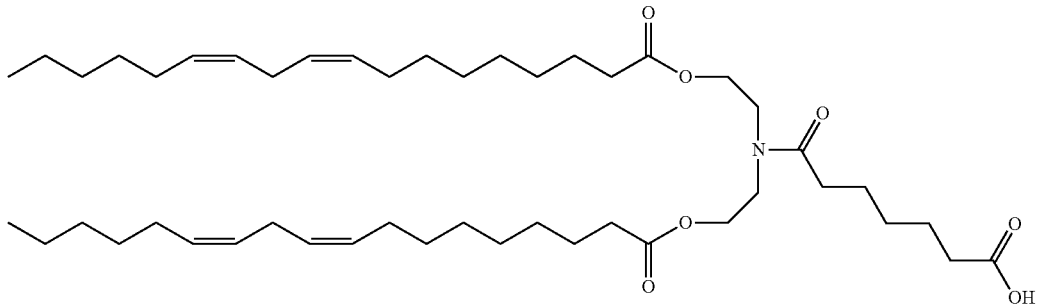 [SMILES: CCCCC/C=C\C/C=C\CCCCCCCC(=O)OCCN(CCOC(=O)CCCCCCC/C=C\C/C=C\CCCCC)C(=O)CCCCCC(=O)O]

Examples of an ionizable compound include the following compound BA:

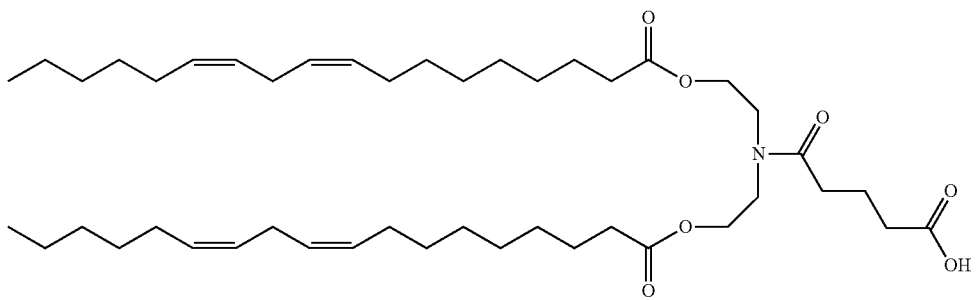 [SMILES: CCCCC/C=C\C/C=C\CCCCCCCC(=O)OCCN(CCOC(=O)CCCCCCC/C=C\C/C=C\CCCCC)C(=O)CCCC(=O)O]

Examples of an ionizable compound include the following compound BB:

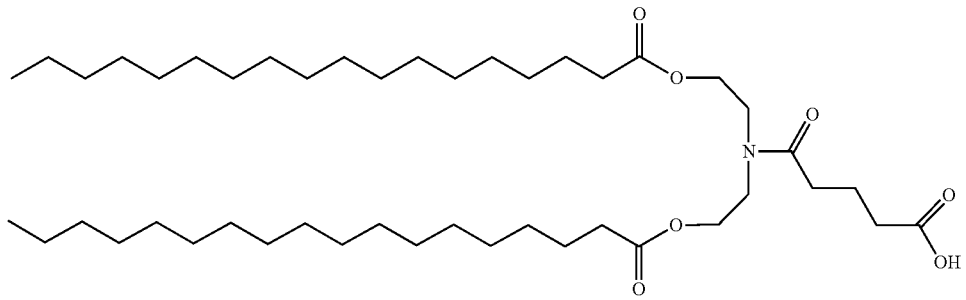 [SMILES: CCCCCCCCCCCCCCCCCC(=O)OCCN(CCOC(=O)CCCCCCCCCCCCCCCCC)C(=O)CCCC(=O)O]

In certain embodiments, examples of an ionizable compound include compounds having the structure shown in Formula III

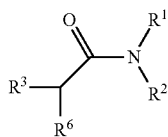

Formula III wherein $R^1$ and $R^2$ are

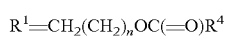

$R^1$=CH$_2$(CH$_2$)$_n$OC(=O)R$^4$

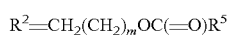

$R^2$=CH$_2$(CH$_2$)$_m$OC(=O)R$^5$ wherein n and m are each independently from 1 to 2; and
$R^4$ and $R^5$ are independently for each occurrence a C(12-20) alkyl group, or a C(12-20) alkenyl group;
wherein $R^3$ is selected from alkyl, hydroxyalkyl, alkoxyalkoxy, and carboxyalkyl;
wherein $R^6$ is selected from NR$^7$$_2$, N$^+$HR$^7$$_2$ and N$^+$R$^7$$_3$;
wherein $R^7$ is selected from H, alkyl, hydroxyalkyl, and aminoalkyl.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, each of the alkenyl groups can have from one to two double bonds.

In some embodiments, $R^4$ and $R^5$ are independently for each occurrence a C(16-18) alkyl group, or a C(16-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include the following compound BC:

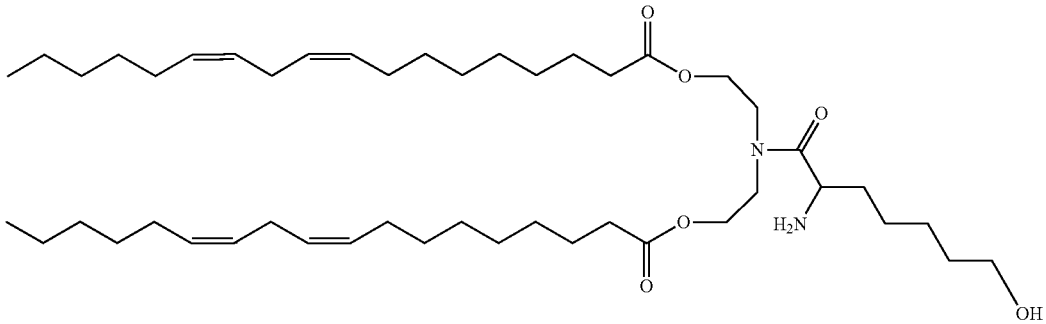 [SMILES: CCCCC/C=C\C/C=C\CCCCCCCC(=O)OCCN(CCOC(=O)CCCCCCC/C=C\C/C(C)=C\CCCCC)C(=O)C(N)CCCCCO]

Examples of an ionizable compound include the following compound BD:

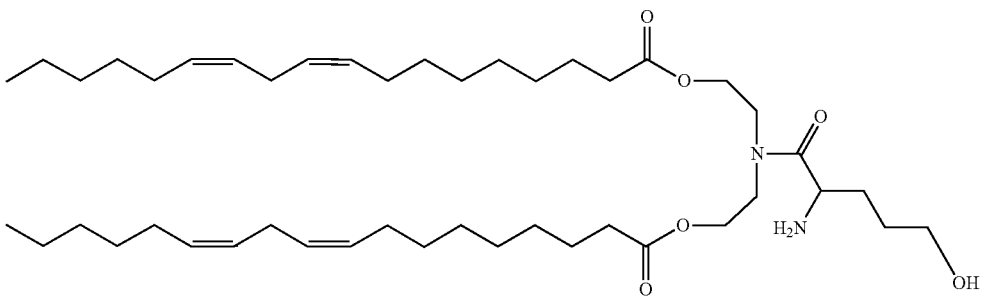 [SMILES: CCCCC/C=C\C/C=C\CCCCCCCC(=O)OCCN(CCOC(=O)CCCCCCC/C=C\C/C(C)=C\CCCCC)C(=O)C(N)CCCO]

Examples of an ionizable compound include the following compound BE:

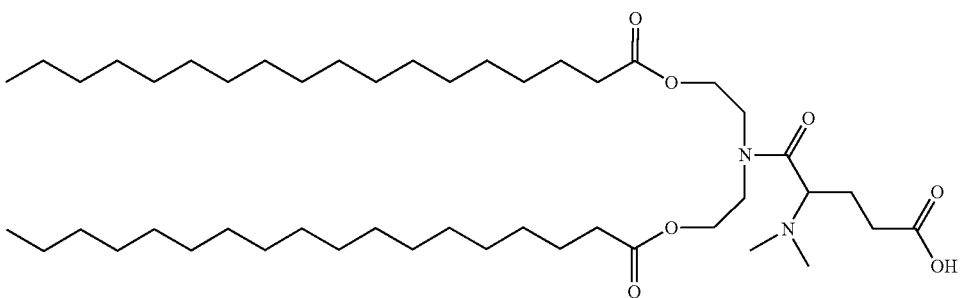 [SMILES: CCCCCCCCCCCCCCCCCC(=O)OCCN(CCOC(=O)CCCCCCCCCCCCCCCCC)C(=O)C(CCC(=O)O)N(C)C]

In some embodiments, each of the alkenyl groups can have from one to two double bonds.

Examples of an ionizable compound include compounds having the structure shown in Formula IV

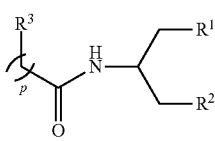

Formula IV wherein $R^1$ and $R^2$ are $R^1 = C(=O)OR^4$ $R^2 = C(=O)OR^5$ wherein $R^4$ and $R^5$ are independently for each occurrence a C(12-20) alkyl group, or a C(12-20) alkenyl group;

wherein $R^3$ is selected from 1-azetidines, 1-pyrrolidines, 1-piperidines, 4-morpholines, and 1,4-piperazines wherein the rings can be substituted at any carbon atom position,

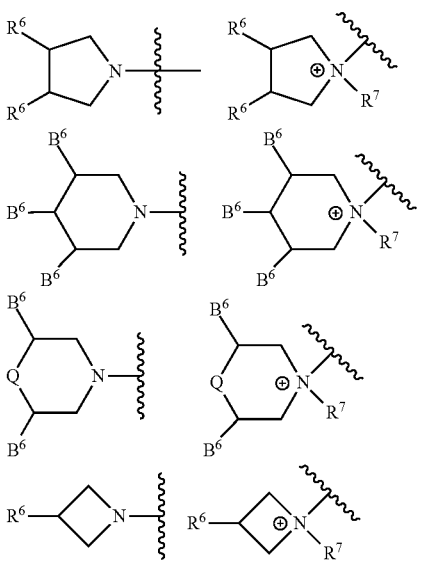

and can also be selected from amino and aminoalkyl groups which can be further substituted,

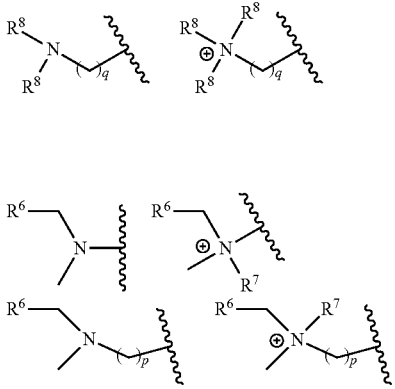

wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl, and aminoalkyl;
each $R^8$ is independently selected from H, alkyl, hydroxyalkyl, and aminoalkyl, and any two $R^8$ may form a ring;
q is from zero to four;
Q is O or $NR^7$;
p is from 1 to 4.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, $R^4$ and $R^5$ are independently for each occurrence a C(16-18) alkyl group, or a C(16-18) alkenyl group.

In some embodiments, p is 1, 2, 3 or 4.
In some embodiments, q is 0, 1, 2, 3 or 4.
Examples of an ionizable compound include compounds having the structure shown in Formula IV Formula IV

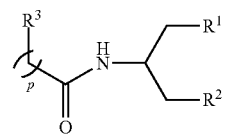

wherein $R^1$ and $R^2$ are
$R^1$=C(=O)O$R^4$
$R^2$=C(=O)O$R^5$ wherein $R^4$ and $R^5$ are independently for each occurrence a C(12-20) alkyl group, or a C(12-20) alkenyl group;
wherein $R^3$ is selected from

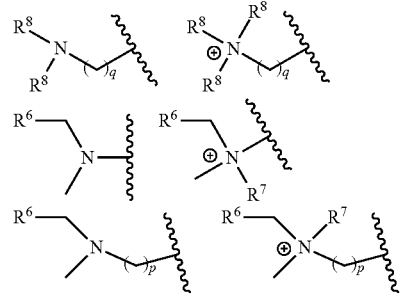

wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl;
each $R^8$ is independently selected from H, alkyl, hydroxyalkyl, and aminoalkyl, and any two $R^8$ may form a ring;
q is from zero to four;
p is from 1 to 4.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, $R^4$ and $R^5$ are independently for each occurrence a C(16-18) alkyl group, or a C(16-18) alkenyl group.

In some embodiments, p is 1, 2, 3 or 4.
In some embodiments, q is 0, 1, 2, 3 or 4.
Examples of an ionizable compound include compounds having the structure shown in Formula IV Formula IV

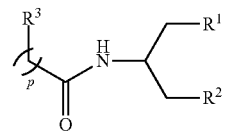

wherein $R^1$ and $R^2$ are

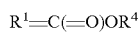

wherein $R^4$ and $R^5$ are independently for each occurrence a C(12-20) alkyl group, or a C(12-20) alkenyl group;

wherein $R^3$ is selected from

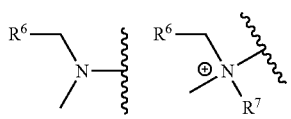

wherein each $R^6$ is independently selected from H, alkyl, hydroxyl, hydroxyalkyl, alkoxy, alkoxyalkoxy, aminoalkyl;

each $R^7$ is independently selected from H, alkyl, hydroxyalkyl;

p is from 1 to 4.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include compounds having the structure shown in Formula IV

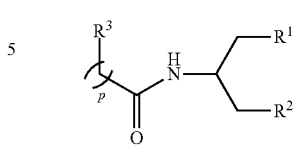

Formula IV wherein $R^1$ and $R^2$ are

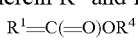

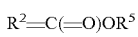

wherein $R^4$ and $R^5$ are independently for each occurrence a C(12-20) alkyl group, or a C(12-20) alkenyl group;

wherein $R^3$ is selected from

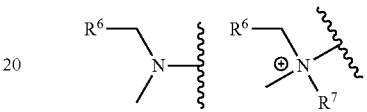

wherein each $R^6$ is independently selected from H, hydroxyl, hydroxyalkyl, aminoalkyl;

each $R^7$ is independently selected from H, alkyl;

p is from 1 to 4.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include the following compound BF:

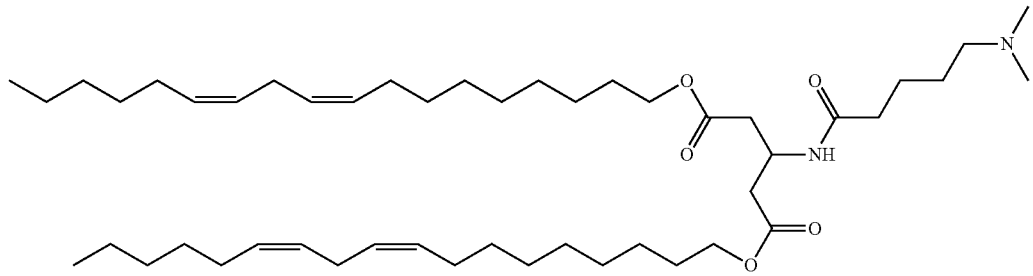 [SMILES: CCCCC/C=C\C/C=C\CCCCCCCCOC(=O)CC(CC(=O)OCCCCCCCC/C=C\C/C=C\CCCCC)NC(=O)CCCCN(C)C]

Examples of an ionizable compound include the following compound C1:

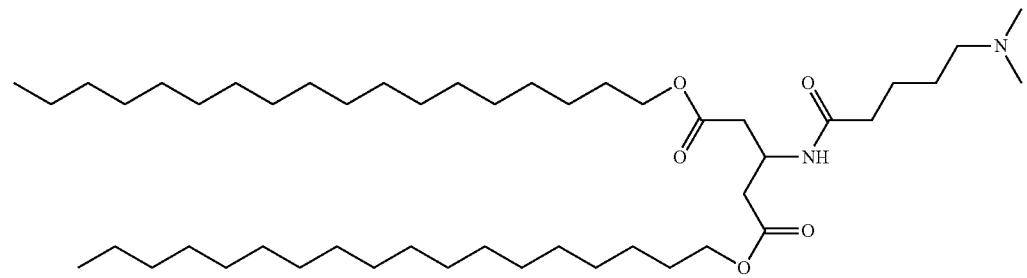 [SMILES: CCCCCCCCCCCCCCCCCCOC(=O)CC(CC(=O)OCCCCCCCCCCCCCCCCCC)NC(=O)CCCCN(C)C]

Examples of an ionizable compound include the following compound C2:

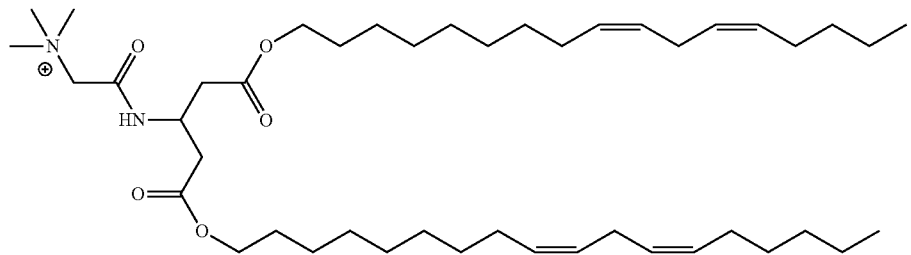 [SMILES: CCCC/C=C\C/C=C\CCCCCCCCOC(=O)CC(CC(=O)OCCCCCCCC/C=C\C/C=C\CCCCC)NC(=O)C[N+](C)(C)C]

which is 2-((1-(((9Z,12Z)-heptadeca-9,12-dien-1-yl)oxy)-5-(((9Z,12Z)-octadeca-9,12-dien-1-yl)oxy)-1,5-dioxopentan-3-yl)amino)-N,N,N-trimethyl-2-oxo-ethan-1-aminium.

Examples of an ionizable compound include the following compound C3:

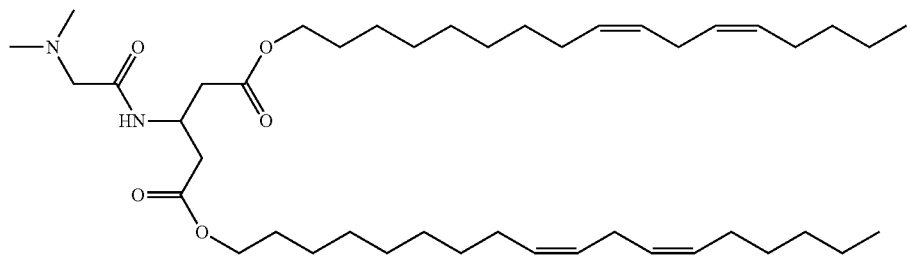 [SMILES: CCCC/C=C\C/C=C\CCCCCCCCOC(=O)CC(CC(=O)OCCCCCCCC/C=C\C/C=C\CCCCC)NC(=O)CN(C)C]

which is 1-((9Z,12Z)-heptadeca-9,12-dien-1-yl) 5-((9Z,12Z)-octadeca-9,12-dien-1-yl) 3-(2-(dimethylamino)acetamido)pentanedioate.

Examples of an ionizable compound include the following compound C4;

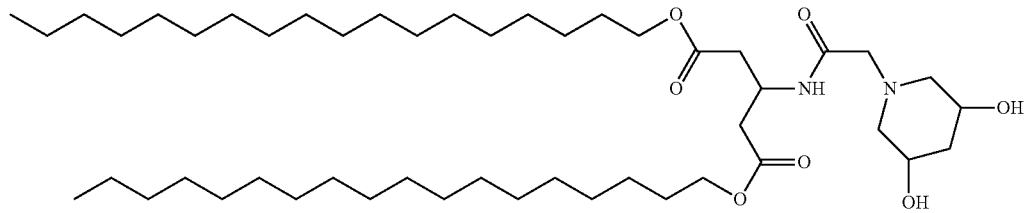 [SMILES: CCCCCCCCCCCCCCCCCCOC(=O)CC(CC(=O)OCCCCCCCCCCCCCCCCCC)NC(=O)CN1CC(O)CC(O)C1]

Examples of an ionizable compound include the following compound C5:

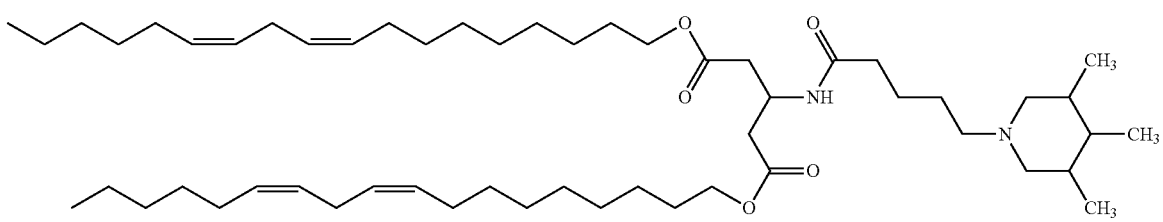 [SMILES: CCCCC/C=C\C/C=C\CCCCCCCCOC(=O)CC(CC(=O)OCCCCCCCC/C=C\C/C=C\CCCCC)NC(=O)CCCCN1CC(C)C(C)C(C)C1]

Examples of an ionizable compound include the following compound C6;
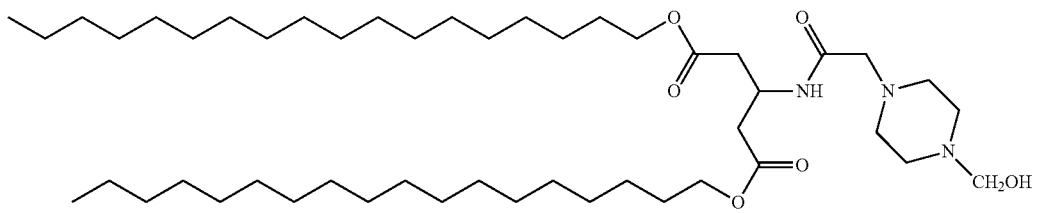 [SMILES: CCCCCCCCCCCCCCCCCCOC(=O)CC(CC(=O)OCCCCCCCCCCCCCCCCCC)NC(=O)CN1CCN(CO)CC1]
Examples of an ionizable compound include the following compound C7:
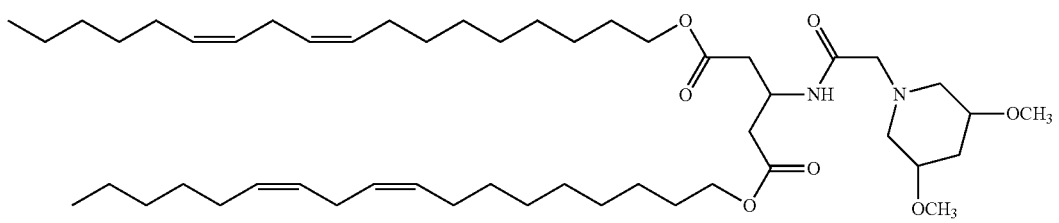 [SMILES: CCCCC/C=C\C/C=C\CCCCCCCCOC(=O)CC(CC(=O)OCCCCCCCC/C=C\C/C=C\CCCCC)NC(=O)CN1CC(OC)CC(OC)C1]
Examples of an ionizable compound include the following compound C8:
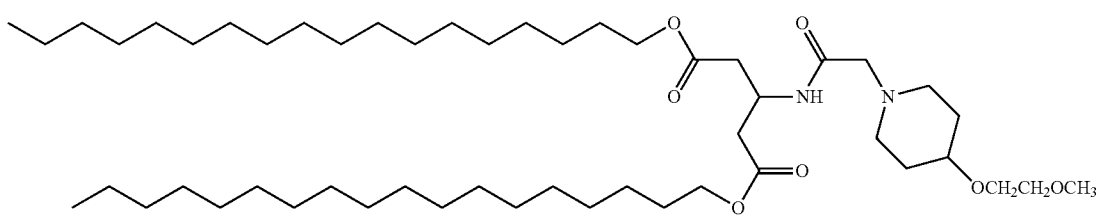
Examples of an ionizable compound include the following compound C9:
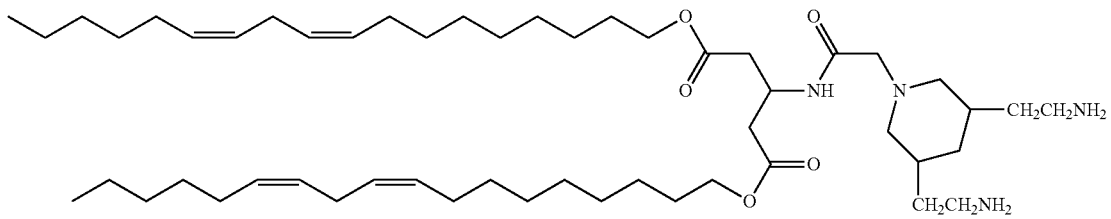
Examples of an ionizable compound include the following compound CA:
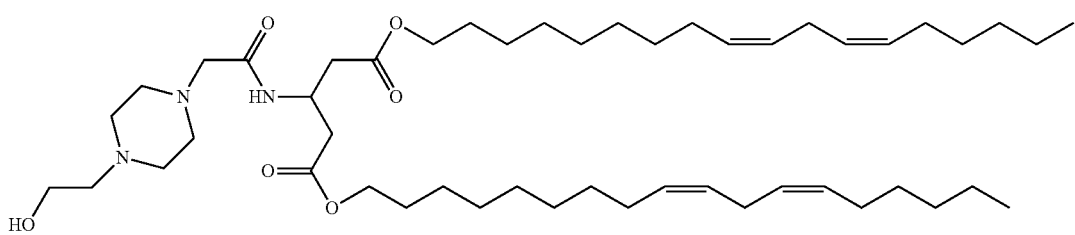 [SMILES: CCCCC/C=C\C/C=C\CCCCCCCCOC(=O)CC(CC(=O)OCCCCCCCC/C=C\C/C=C\CCCCC)NC(=O)CN1CCN(CCO)CC1]

which is di((9Z,12Z)-octadeca-9,12-dien-1-yl) 3-(2-(4-(2-hydroxyethyl)piperazin-1-yl)acetamido)pentanedioate.

Examples of an ionizable compound include the following compound CB:

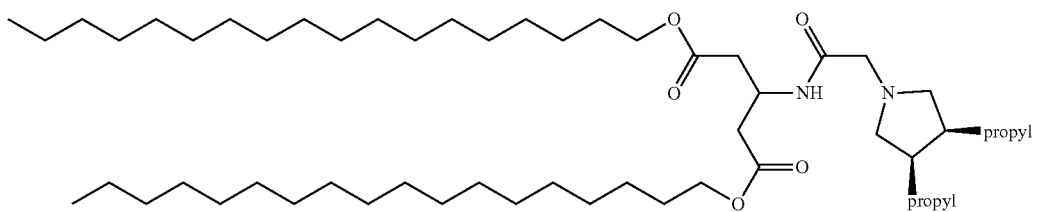

Examples of an ionizable compound include the following compound CC:

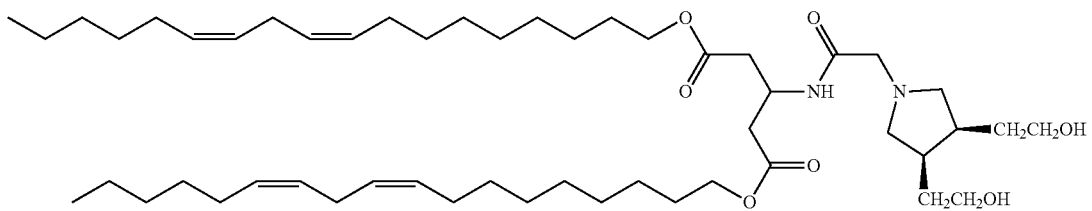

Examples of an ionizable compound include the following compound CD:

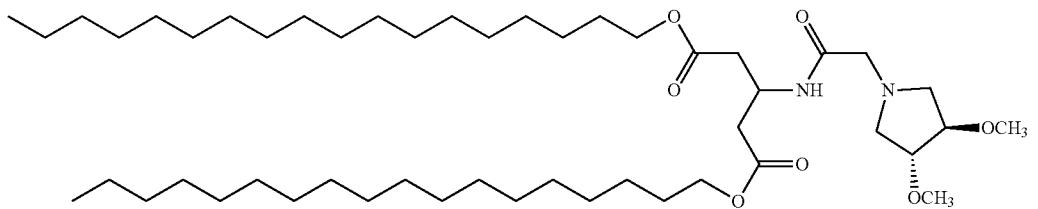 [SMILES: CCCCCCCCCCCCCCCCCCOC(=O)CC(CC(=O)OCCCCCCCCCCCCCCCCCC)NC(=O)CN1C[C@@H](OC)[C@H](OC)C1]

Examples of an ionizable compound include the following compound CE:

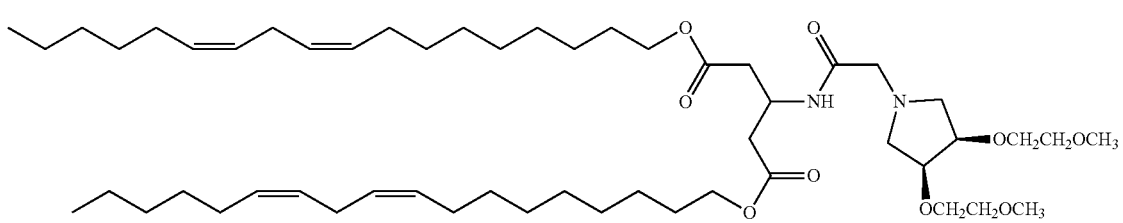

Examples of an ionizable compound include the following compound CF:

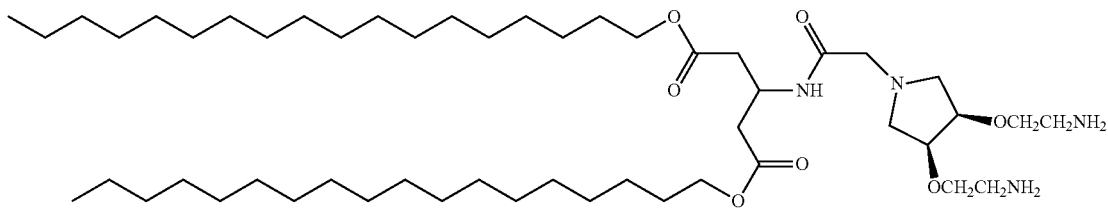

Examples of an ionizable compound include the following compound D1:

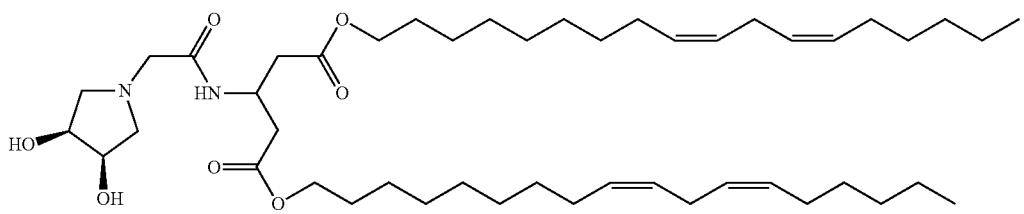 [SMILES: CCCCC/C=C\C/C=C\CCCCCCCCOC(=O)CC(CC(=O)OCCCCCCCC/C=C\C/C=C\CCCCC)NC(=O)CN1C[C@@H](O)[C@@H](O)C1]

which is di((9Z,12Z)-octadeca-9,12-dien-1-yl) 3-(2-((3S, 4R)-3,4-dihydroxypyrrolidin-1-yl)acetamido)pentanedioate.

Examples of an ionizable compound include the following compound D2:

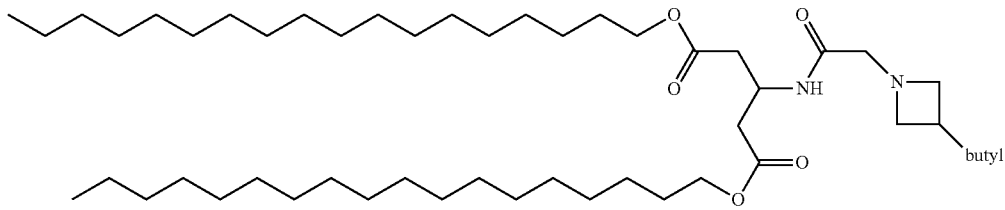

Examples of an ionizable compound include the following compound D3:

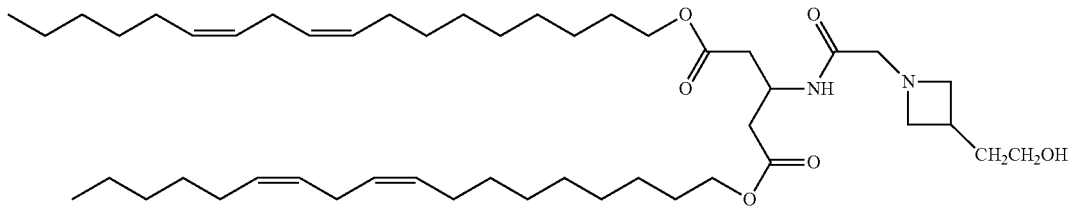

Examples of an ionizable compound include the following compound D4:

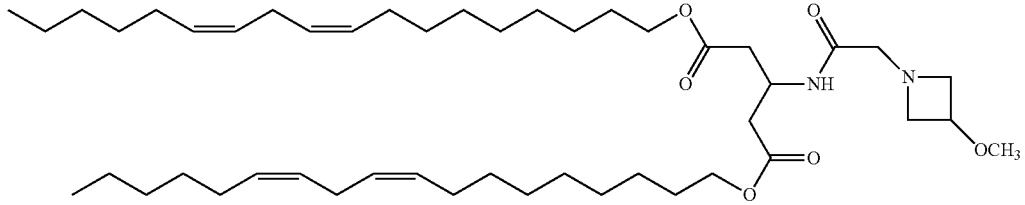 [SMILES: CCCCC/C=C\C/C=C\CCCCCCCCOC(=O)CC(CC(=O)OCCCCCCCC/C=C\C/C=C\CCCCC)NC(=O)CN1CC(OC)C1]

Examples of an ionizable compound include the following compound D5:

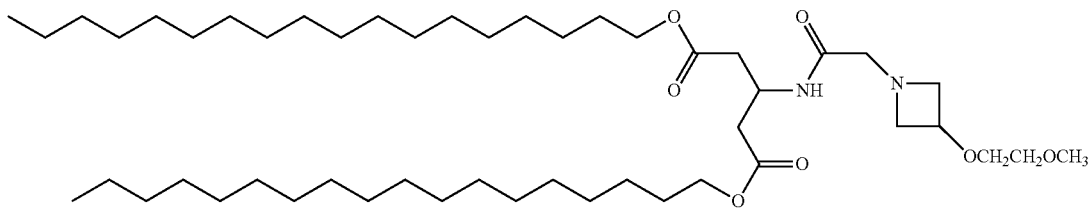

Examples of an ionizable compound include the following compound D6:

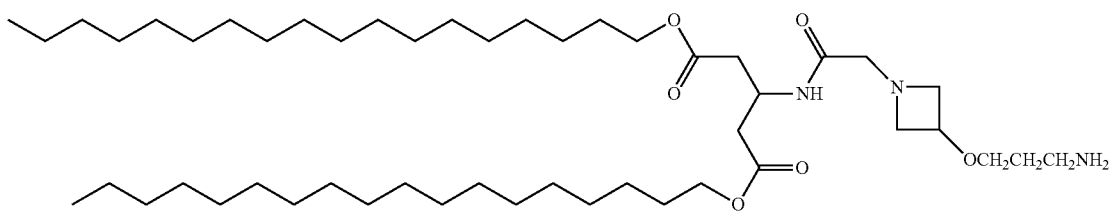

Examples of an ionizable compound include the following compound D7:

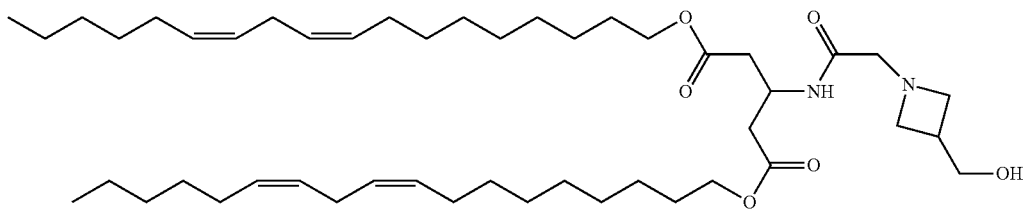 [SMILES: CCCCC/C=C\C/C=C\CCCCCCCCOC(=O)CC(CC(=O)OCCCCCCCC/C=C\C/C=C\CCCCC)NC(=O)CN1CC(CO)C1]

Examples of an ionizable compound include compounds having the structure shown in Formula IV-B

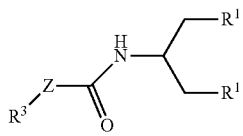

Formula IV-B wherein $R^1$ and $R^2$ are
$R^1 = C(=O)OR^4$
$R^2 = C(=O)OR^5$
wherein $R^4$ and $R^5$ are independently for each occurrence a C(12-20) alkyl group, or a C(12-20) alkenyl group;
wherein Z is S or O;
wherein $R^3$ is selected from

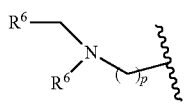 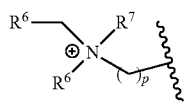

wherein each $R^6$ is independently selected from H, alkyl, hydroxyl, hydroxyalkyl, alkoxy, alkoxyalkoxy, aminoalkyl;

each $R^7$ is independently selected from H, alkyl, hydroxyalkyl, and aminoalkyl;

p is from 1 to 4.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, $R^4$ and $R^5$ are independently for each occurrence a C(16-18) alkyl group, or a C(16-18) alkenyl group.

In some embodiments, p is 1, 2, 3 or 4.

Examples of an ionizable compound include the following compound D8:
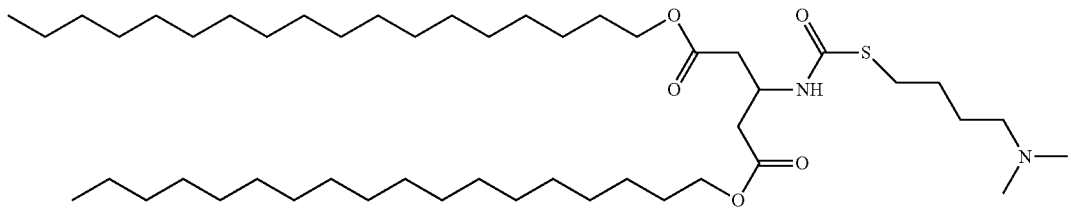 [SMILES: CCCCCCCCCCCCCCCCCCOC(=O)CC(CC(=O)OCCCCCCCCCCCCCCCCCC)NC(=O)SCCCCN(C)C]
Examples of an ionizable compound include the following compound D9:
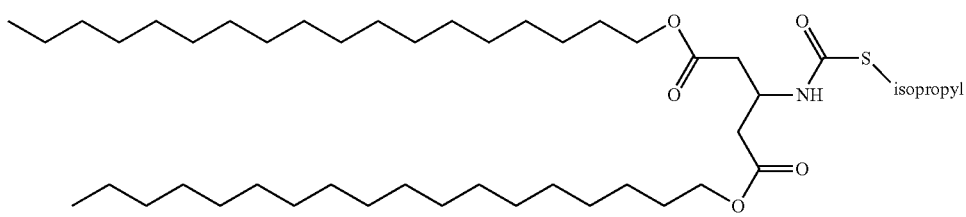
Examples of an ionizable compound include the following compound DA:
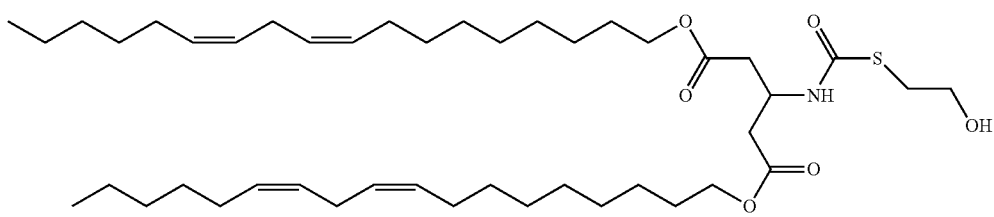 [SMILES: CCCCC/C=C\C/C=C\CCCCCCCCOC(=O)CC(CC(=O)OCCCCCCCC/C=C\C/C=C\CCCCC)NC(=O)SCCO]
Examples of an ionizable compound include the following compound DB:
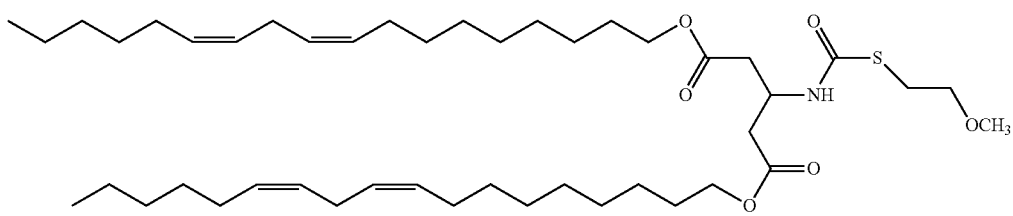 [SMILES: CCCCC/C=C\C/C=C\CCCCCCCCOC(=O)CC(CC(=O)OCCCCCCCC/C=C\C/C=C\CCCCC)NC(=O)SCCOC]
Examples of an ionizable compound include the following compound DC:
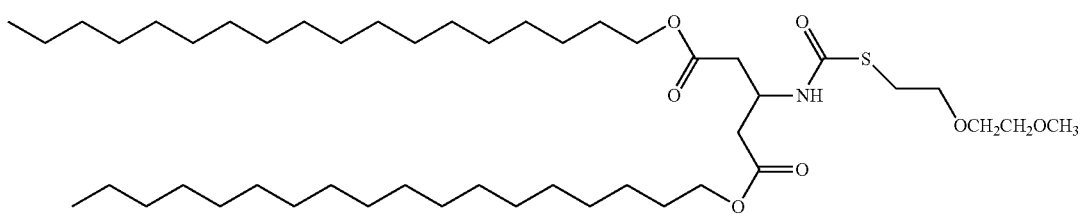

Examples of an ionizable compound include the following compound DD:

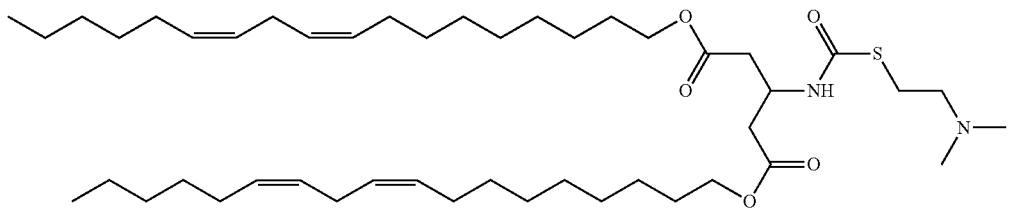 [SMILES: CCCCC/C=C\C/C=C\CCCCCCCCOC(=O)CC(CC(=O)OCCCCCCCC/C=C\C/C=C\CCCCC)NC(=O)SCCN(C)C]

which is di((9Z,12Z)-octadeca-9,12-dien-1-yl) 3-((((2-(dimethylamino)ethyl)thio)carbonyl)amino)pentanedioate.

Examples of an ionizable compound include the following compound DE:

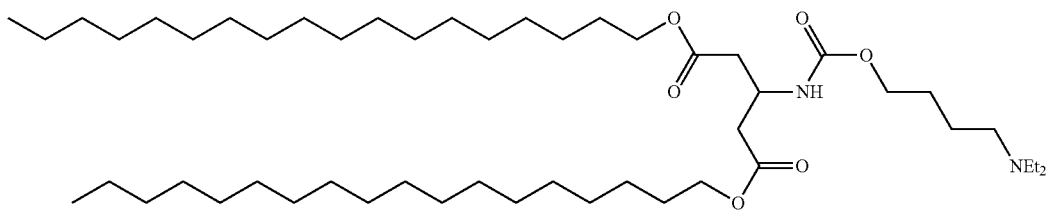

Examples of an ionizable compound include the following compound DF:

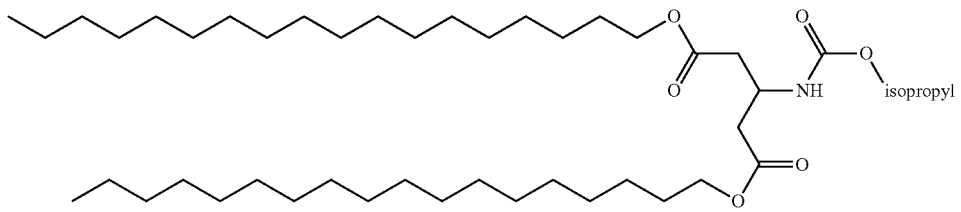

Examples of an ionizable compound include the following compound E1:

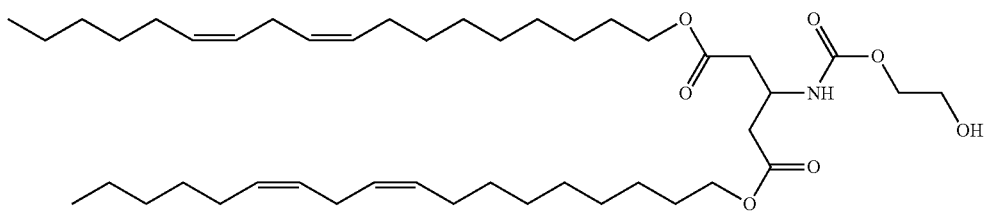 [SMILES: CCCCC/C=C\C/C=C\CCCCCCCCOC(=O)CC(CC(=O)OCCCCCCCC/C=C\C/C=C\CCCCC)NC(=O)OCCO]

Examples of an ionizable compound include the following compound E2:

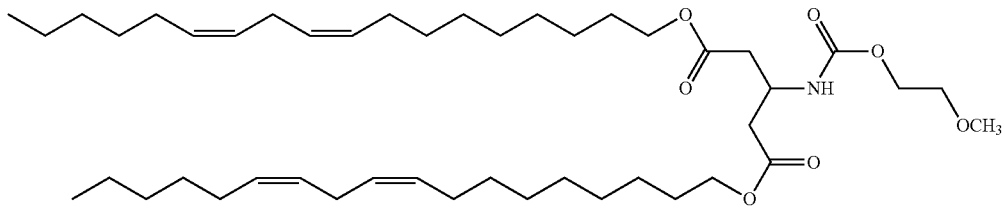 [SMILES: CCCCC/C=C\C/C=C\CCCCCCCCOC(=O)CC(CC(=O)OCCCCCCCC/C=C\C/C=C\CCCCC)NC(=O)OCCOC]

Examples of an ionizable compound include the following compound E3:

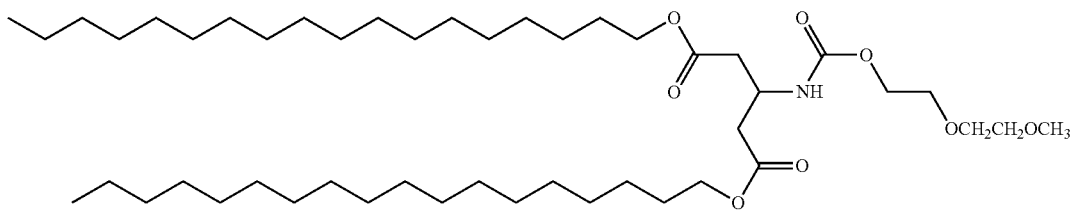

Examples of an ionizable compound include the following compound E4:

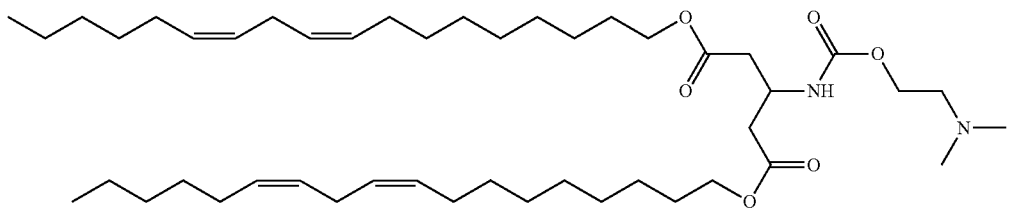 [SMILES: CCCCC/C=C\C/C=C\CCCCCCCCOC(=O)CC(CC(=O)OCCCCCCCC/C=C\C/C=C\CCCCC)NC(=O)OCCN(C)C]

which is di((9Z,12Z)-octadeca-9,12-dien-1-yl) 3-(((2-(dimethylamino)ethoxy)carbonyl)amino)pentanedioate.

Embodiments of this invention include compounds having the structure shown in Formula V

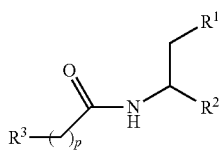

Formula V wherein $R^1$ and $R^2$ are

$R^1 = NHC(=O)R^4$

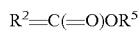

$R^2 = C(=O)OR^5$ wherein $R^4$ and $R^5$ are independently for each occurrence a C(12-20) alkyl group, or a C(12-20) alkenyl group;

wherein p is from 1 to 4;

wherein $R^3$ is selected from 1-azetidines, 1-pyrrolidines, 1-piperidines, 4-morpholines, and 1,4-piperazines wherein the rings can be substituted at any carbon atom position,

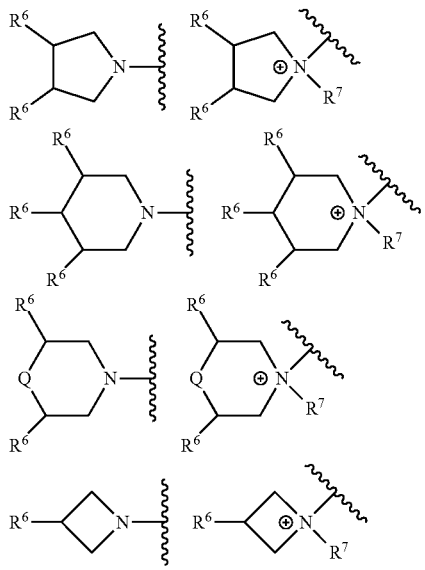

and can also be selected from amino and aminoalkyl groups which can be substituted,

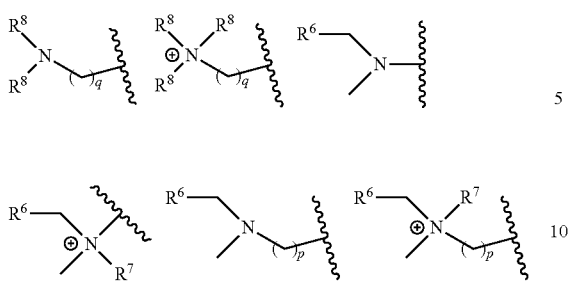

wherein
each R⁶ is independently selected from H, alkyl, hydroxyl, hydroxyalkyl, alkoxy, alkoxyalkoxy, aminoalkyl;

each R⁷ is independently selected from H, alkyl, hydroxyalkyl;

each R⁸ is independently selected from H, alkyl, hydroxyalkyl, and aminoalkyl, and any two R⁸ may form a ring;

q is from zero to four;

Q is O or NR⁷.

In some embodiments, each of the alkenyl groups can have from one to two double bonds.

In some embodiments, R⁴ and R⁵ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, R⁴ and R⁵ are independently for each occurrence a C(16-18) alkyl group, or a C(16-18) alkenyl group.

In some embodiments, p is 1, 2, 3 or 4.

In some embodiments, q is 0, 1, 2, 3 or 4.

Embodiments of this invention include compounds having the structure shown in Formula V

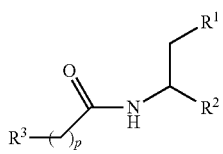

Formula V wherein R¹ and R² are

R¹=NHC(=O)R⁴

R²=C(=O)OR⁵ wherein R⁴ and R⁵ are independently for each occurrence a C(12-20) alkyl group, or a C(12-20) alkenyl group;
wherein p is from 1 to 4;
wherein R³ is selected from

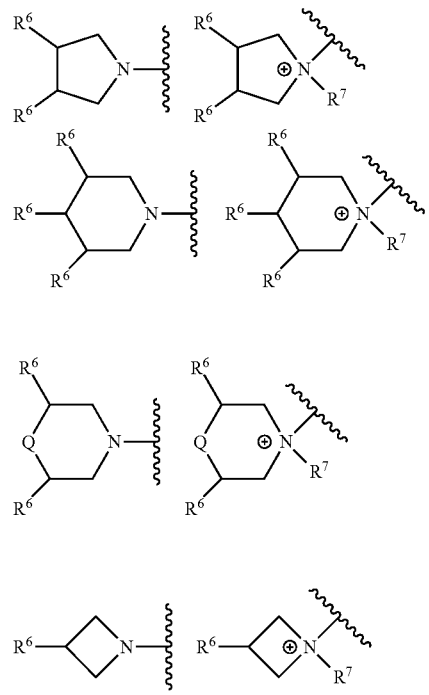

wherein
each R⁶ is independently selected from H, alkyl, hydroxyl, hydroxyalkyl, alkoxy, alkoxyalkoxy, aminoalkyl;
each R⁷ is independently selected from H, alkyl, hydroxyalkyl, and aminoalkyl;
Q is O or NR⁷.

In some embodiments, each of the alkenyl groups can have from one to two double bonds.

In some embodiments, R⁴ and R⁵ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include the following compound E5:

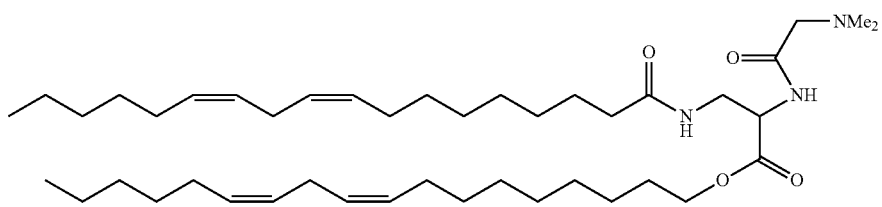 [SMILES: CCCCC/C=C\C/C=C\CCCCCCCCOC(=O)C(CNC(=O)CCCCCCC/C=C\C/C=C\CCCCC)NC(=O)CN(C)C]

Examples of an ionizable compound include the following compound E6:
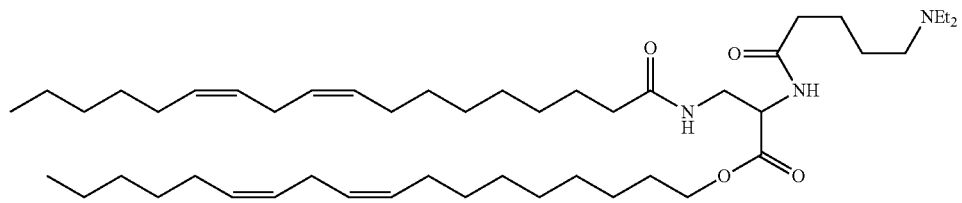
Examples of an ionizable compound include the following compound E7:
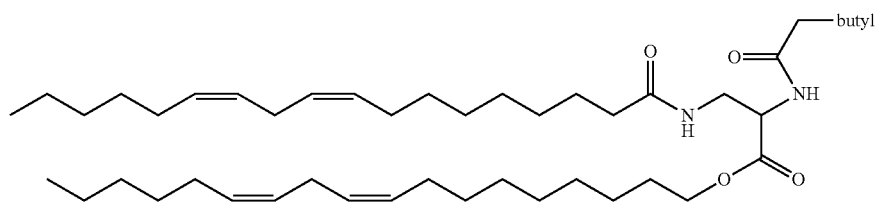
Examples of an ionizable compound include the following compound E8:
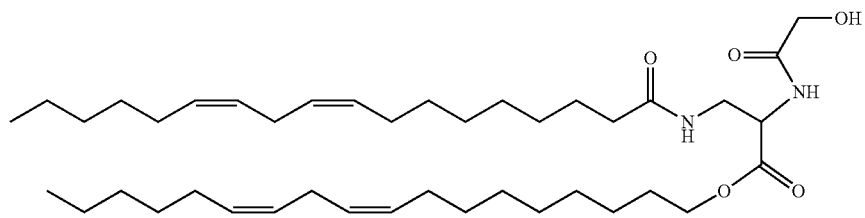 [SMILES: CCCCC/C=C\C/C=C\CCCCCCCCOC(=O)C(CNC(=O)CCCCCCC/C=C\C/C=C\CCCCC)NC(=O)CO]
Examples of an ionizable compound include the following compound E9:
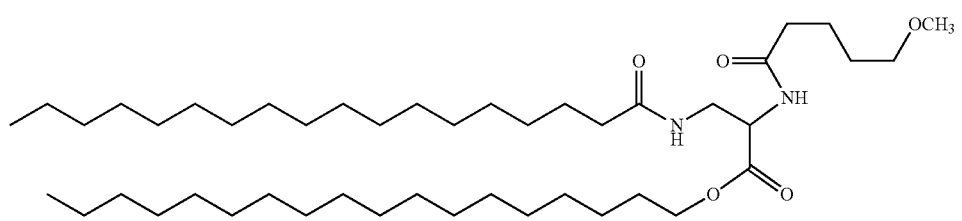 [SMILES: CCCCCCCCCCCCCCCCCCOC(=O)C(CNC(=O)CCCCCCCCCCCCCCCCC)NC(=O)CCCCOC]
Examples of an ionizable compound include the following compound EA:
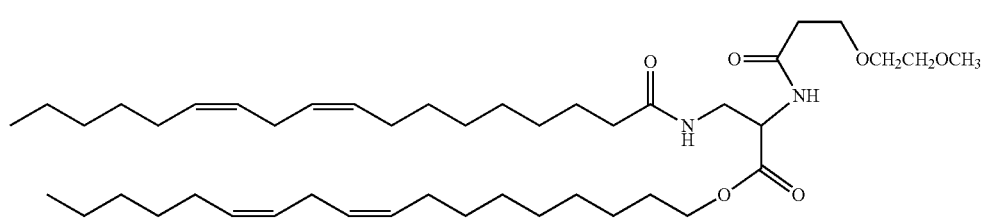

Examples of an ionizable compound include the following compound EB:
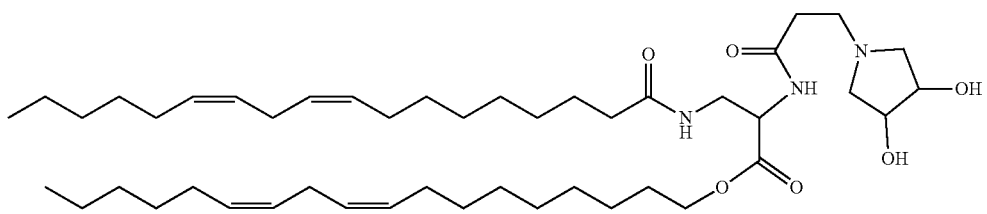 [SMILES: CCCCC/C=C\C/C=C\CCCCCCCCOC(=O)C(CNC(=O)CCCCCCC/C=C\C/C=C\CCCCC)NC(=O)CCN1CC(O)C(O)C1]
Examples of an ionizable compound include the following compound EC:
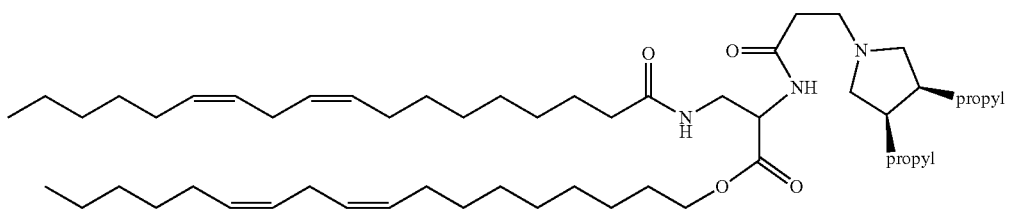
Examples of an ionizable compound include the following compound ED:
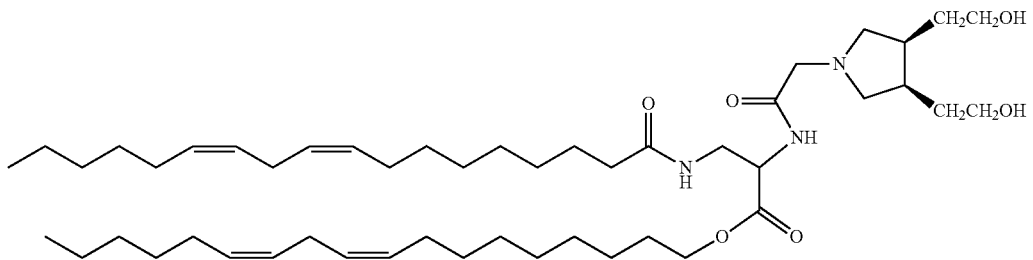
Examples of an ionizable compound include the following compound EE:
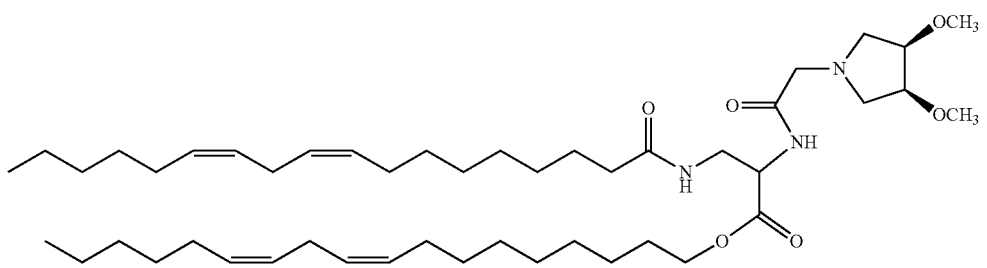 [SMILES: CCCCC/C=C\C/C=C\CCCCCCCCOC(=O)C(CNC(=O)CCCCCCC/C=C\C/C=C\CCCCC)NC(=O)CN1C[C@H](OC)[C@H](OC)C1]

Examples of an ionizable compound include the following compound EF:
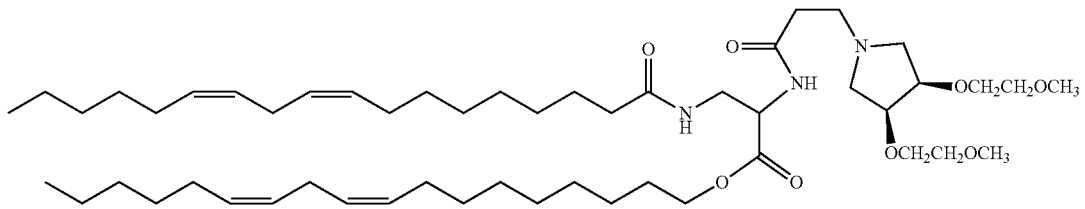
Examples of an ionizable compound include the following compound F1:
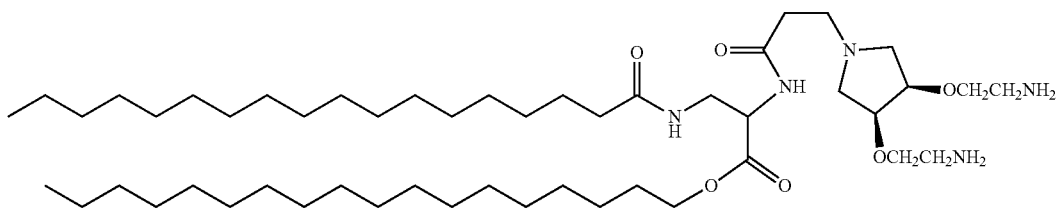
Examples of an ionizable compound include the following compound F2:
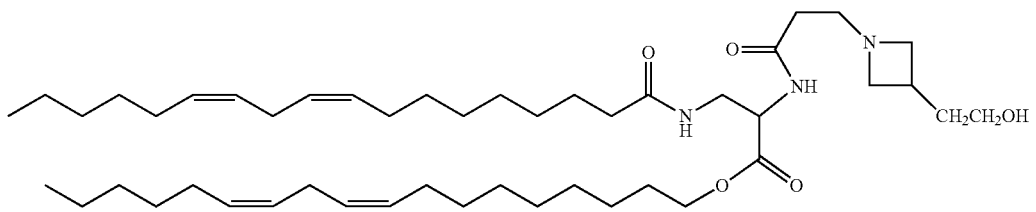
Examples of an ionizable compound include the following compound F3:
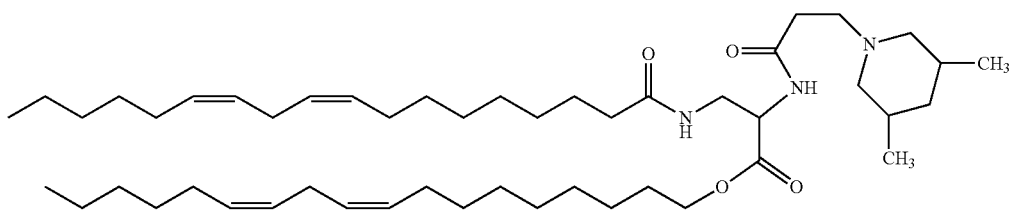 [SMILES: CCCCC/C=C\C/C=C\CCCCCCCCOC(=O)C(CNC(=O)CCCCCCC/C=C\C/C=C\CCCCC)NC(=O)CCN1CC(C)CC(C)C1]
Examples of an ionizable compound include the following compound F4:
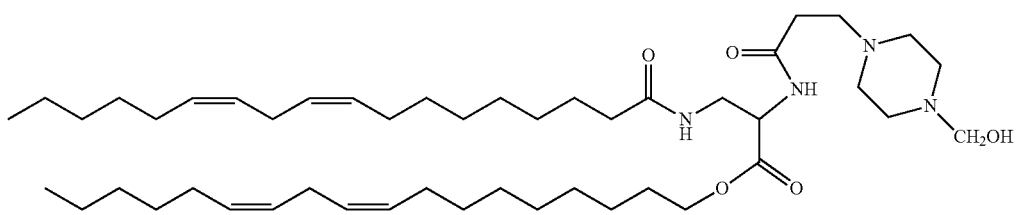 [SMILES: CCCCC/C=C\C/C=C\CCCCCCCCOC(=O)C(CNC(=O)CCCCCCC/C=C\C/C=C\CCCCC)NC(=O)CCN1CCN(CO)CC1]

Examples of an ionizable compound include compounds having the structure shown in Formula VI

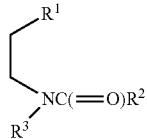

Formula VI wherein $R^1$ is

$R^1$=OC(=O)$R^4$ wherein $R^2$ and $R^4$ are independently for each occurrence a C(12-20) alkyl group, or a C(12-20) alkenyl group;
wherein $R^3$ is selected from aminoalkyl, quaternary aminoalkyl.

In some embodiments, each of the alkenyl groups can have from one to two double bonds.

In some embodiments, $R^2$ and $R^4$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include the following compound F5:

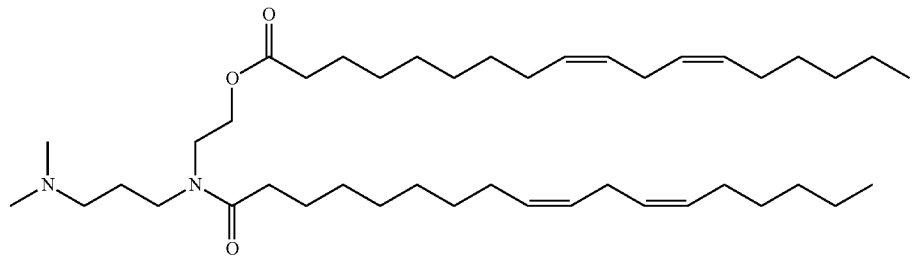 [SMILES: CCCCC/C=C\C/C=C\CCCCCCCC(=O)OCCN(CCCN(C)C)C(=O)CCCCCCC/C=C\C/C=C\CCCCC]

which is 2-((9Z,12Z)—N-(3-(dimethylamino)propyl)octadeca-9,12-dienamido)ethyl (9Z,12Z)-octadeca-9,12-dienoate.

Examples of an ionizable compound include the following compound F6:

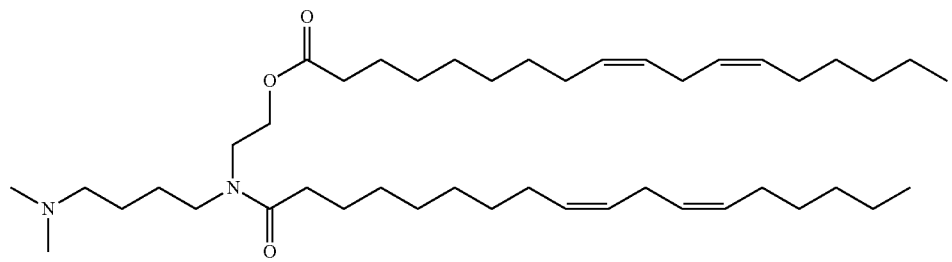 [SMILES: CCCCC/C=C\C/C=C\CCCCCCCC(=O)OCCN(CCCCN(C)C)C(=O)CCCCCCC/C=C\C/C=C\CCCCC]

which is 2-((9Z,12Z)—N-(4-(dimethylamino)butyl)octadeca-9,12-dienamido)ethyl (9Z,12Z)-octadeca-9,12-dienoate.

Examples of an ionizable compound include the following compound F7:

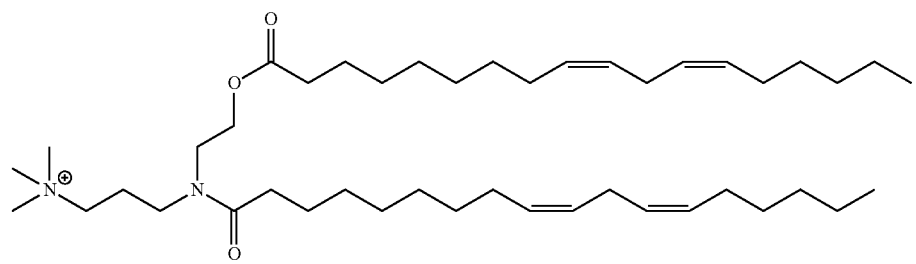 [SMILES: CCCCC/C=C\C/C=C\CCCCCCCC(=O)OCCN(CCC[N+](C)(C)C)C(=O)CCCCCCC/C=C\C/C=C\CCCCC]

which is N,N,N-trimethyl-3-((9Z,12Z)—N-(2-(((9Z,12Z)-octadeca-9,12-dienoyl)oxy)ethyl)octadeca-9,12-dienamido)propan-1-aminium.

Examples of an ionizable compound include the following compound F8:

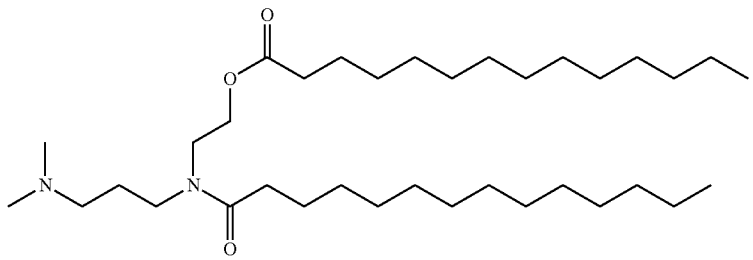 [SMILES: CCCCCCCCCCCCCC(=O)OCCN(CCCN(C)C)C(=O)CCCCCCCCCCCCC]

which is 2-(N-(3-(dimethylamino)propyl)tetradecanamido)ethyl tetradecanoate.

Examples of an ionizable compound include the following compound F9:

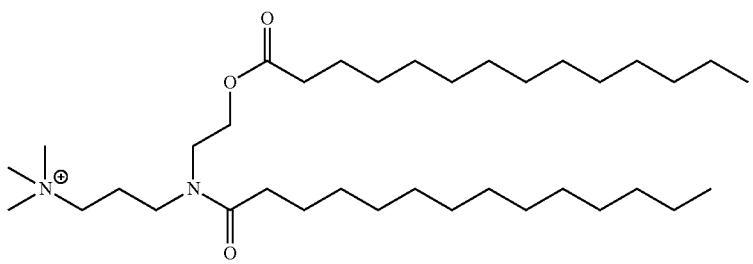 [SMILES: CCCCCCCCCCCCCC(=O)OCCN(CCC[N+](C)(C)C)C(=O)CCCCCCCCCCCCC]

which is N,N,N-trimethyl-3-(N-(2-(tetradecanoyloxy)ethyl)tetradecanamido)propan-1-aminium.

Examples of an ionizable compound include compounds having the structure shown in Formula VII Formula VII

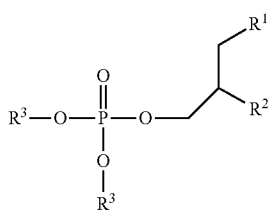

wherein $R^1$ and $R^2$ are

 $R^1$=OC(=O)$R^4$

 $R^2$=OC(=O)$R^5$ wherein n and m are each independently from 1 to 2; and $R^4$ and $R^5$ are independently for each occurrence a C(12-20) alkyl group, or a C(12-20) alkenyl group;

wherein $R^3$ is selected from H, alkyl, aminoalkyl, quaternary aminoalkyl, hydroxyalkyl, alkoxyalkyl, alkoxyalkoxyalkyl.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include the following compound FA:

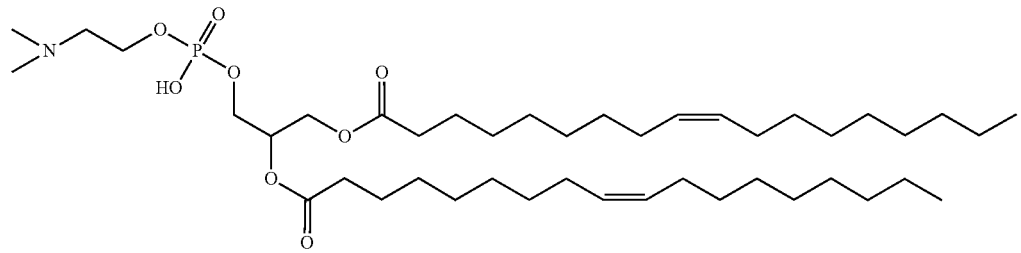

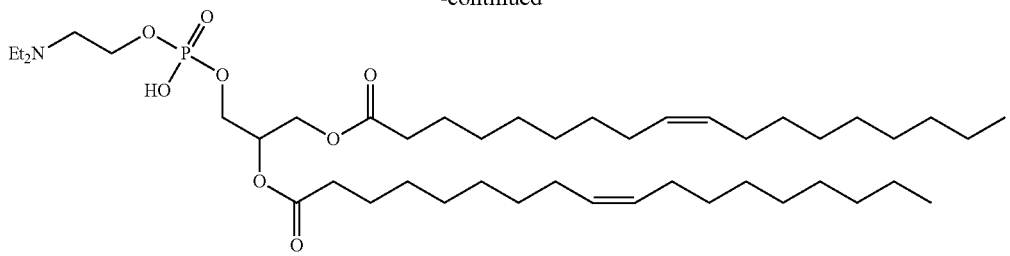

Examples of an ionizable compound include the following compound FB:

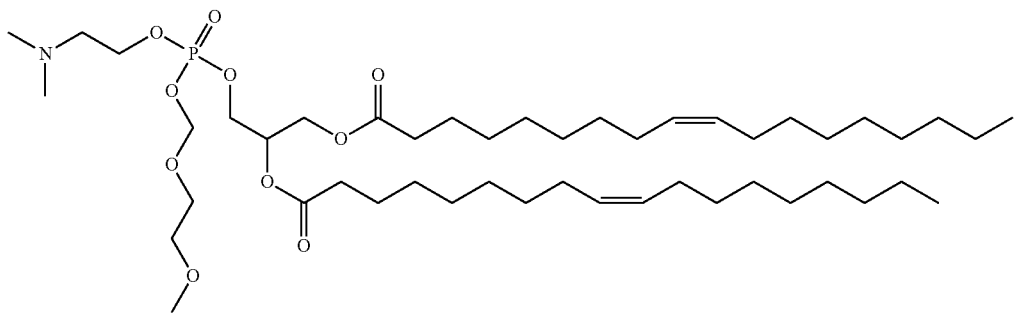 [SMILES: CCCCCCCC/C=C\CCCCCCCC(=O)OCC(COP(=O)(OCCN(C)C)OCOCCOC)OC(=O)CCCCCCC/C=C\CCCCCCCC]

Examples of an ionizable compound include the following compound FC:

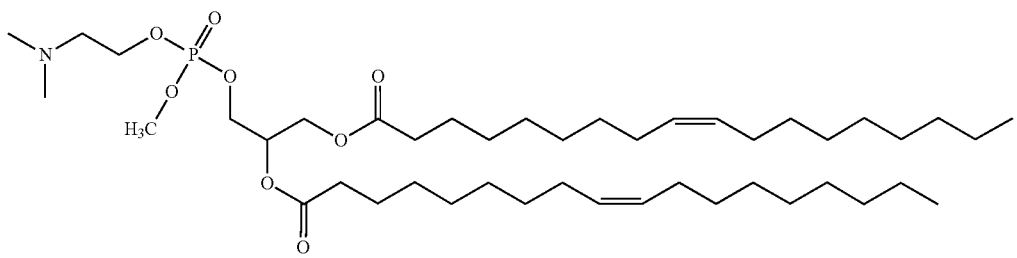

In some embodiments, each of the alkenyl groups can have from one to two double bonds.

In certain embodiments, a compound can have the structure shown in Formula VIII

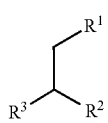

Formula VIII wherein $R^1$ and $R^2$ are

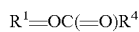

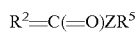

wherein Z is NH or O,
wherein $R^4$ and $R^5$ are independently for each occurrence a C(12-20) alkyl group, or a C(12-20) alkenyl group;

wherein $R^3$ is selected from
  amino;
  quaternary amino;
  aminoalkyl;
  quaternary aminoalkyl;

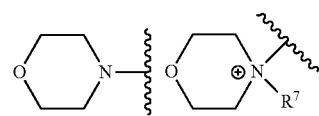

$NHC(=O)(CH_2)_pR^{10}$;
$NHC(=O)SR^9$;

wherein $R^{10}$ is selected from 1-azetidines, 1-pyrrolidines, 1-piperidines, 4-morpholines, and 1,4-piperazines wherein the rings can be substituted at any carbon atom position,

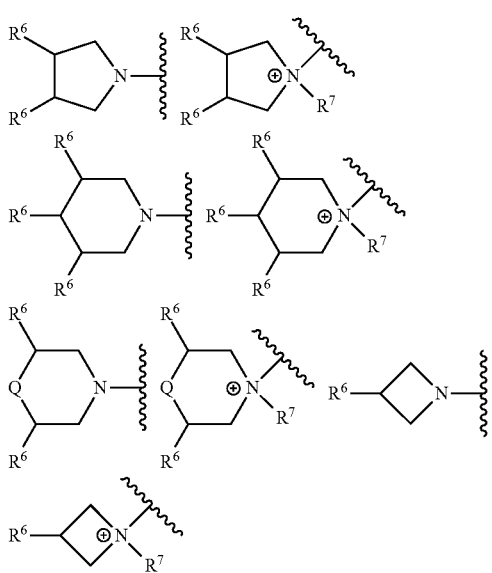

and can also be selected from amino and aminoalkyl groups which can be substituted

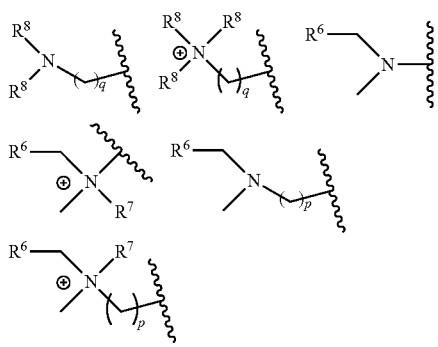

carboxyalkyl;
aminoalkyl;

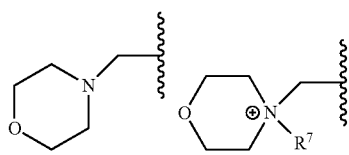

wherein R⁹ is selected from
  alkyl, hydroxyalkyl, alkoxy, alkoxyalkoxy, aminoalkyl;
and wherein
  each R⁶ is independently selected from H, alkyl, hydroxyl, hydroxyalkyl, alkoxy, alkoxyalkoxy, aminoalkyl;
  each R⁷ is independently selected from H, alkyl, hydroxyalkyl, and aminoalkyl;
  each R⁸ is independently selected from H, alkyl, hydroxyalkyl, and aminoalkyl, and any two R⁸ may form a ring;
  q is from zero to four;
  p is from 1 to 4;
  Q is O or NR⁷.
In some embodiments, each of the alkenyl groups can have from one to two double bonds.

In some embodiments, R⁴ and R⁵ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, R⁴ and R⁵ are independently for each occurrence a C(16-18) alkyl group, or a C(16-18) alkenyl group.

In some embodiments, p is 1, 2, 3 or 4.
In some embodiments, q is 0, 1, 2, 3 or 4.
In certain embodiments, a compound can have the structure shown in Formula VIII Formula VIII

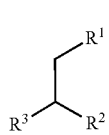

wherein R¹ and R² are
  R¹=OC(=O)R⁴
  R²=C(=O)ZR⁵
wherein Z is NH or O,
wherein R⁴ and R⁵ are independently for each occurrence a C(12-20) alkyl group, or a C(12-20) alkenyl group;
wherein R³ is selected from

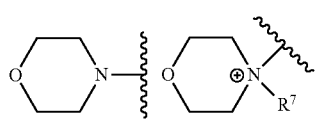

NHC(=O)(CH₂)ₚR¹⁰;
NHC(=O)SR⁹;
wherein R¹⁰ is selected from

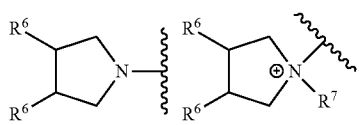

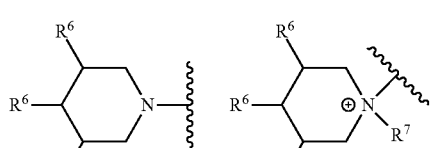

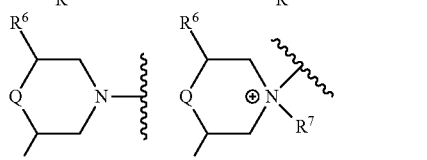

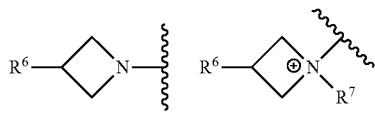

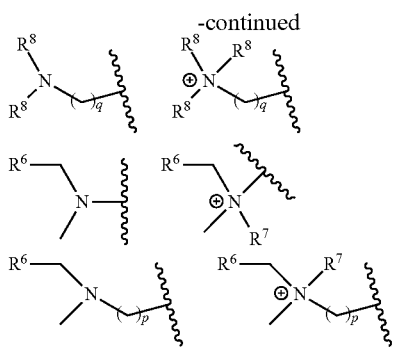

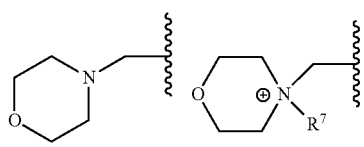

carboxyalkyl;
aminoalkyl;

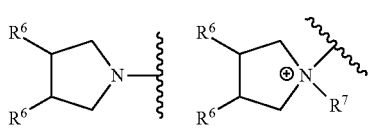

wherein $R^9$ is selected from
alkyl, hydroxyalkyl, alkoxy, alkoxyalkoxy, aminoalkyl;
and wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl;
each $R^8$ is independently selected from H, alkyl, hydroxyalkyl, and aminoalkyl, and any two $R^8$ may form a ring;
p is from 1 to 4;
q is from zero to four;
Q is O or $NR^7$.

In certain embodiments, a compound can have the structure shown in Formula VIII

Formula VIII

wherein $R^1$ and $R^2$ are $R^1 = OC(=O)R^4$ $R^2 = C(=O)ZR^5$ wherein Z is NH or O,
wherein $R^4$ and $R^5$ are independently for each occurrence a C(12-20) alkyl group, or a C(12-20) alkenyl group;
wherein $R^3$ is selected from
$NHC(=O)(CH_2)_pR^{10}$;
$NHC(=O)SR^9$;
wherein $R^{10}$ is selected from

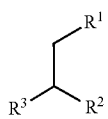

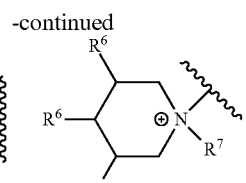

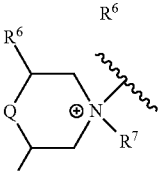

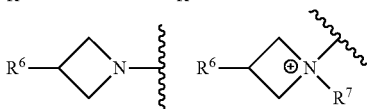

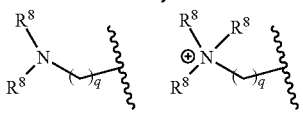

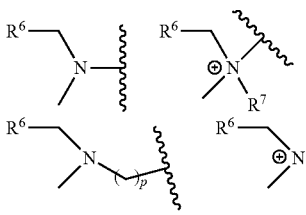

carboxyalkyl;
aminoalkyl;

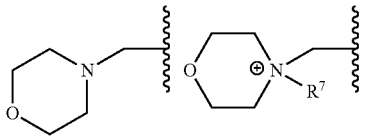

wherein $R^9$ is selected from
alkyl, hydroxyalkyl, alkoxy, alkoxyalkoxy, aminoalkyl;
and wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl;
each $R^8$ is independently selected from H, alkyl, hydroxyalkyl, and aminoalkyl, and any two $R^8$ may form a ring;
p is from 1 to 4;
q is from zero to four;
Q is O or $NR^7$.

In certain embodiments, a compound can have the structure shown in Formula VIII

Formula VIII

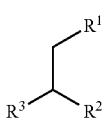

wherein $R^1$ and $R^2$ are

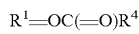

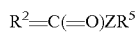

wherein Z is NH or O,
wherein $R^4$ and $R^5$ are independently for each occurrence a C(12-20) alkyl group, or a C(12-20) alkenyl group;
wherein $R^3$ is selected from
$NHC(=O)(CH_2)_pR^{10}$;
$NHC(=O)SR^9$;
wherein $R^{10}$ is selected from

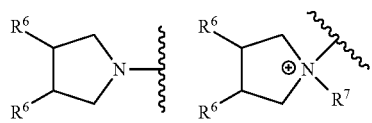

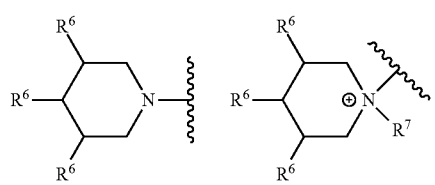

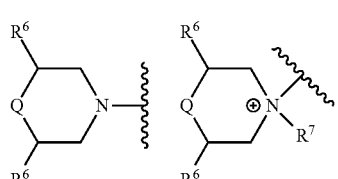

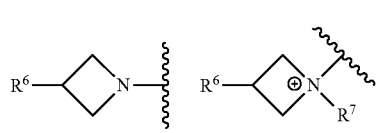

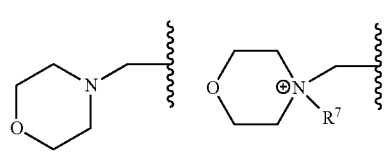

wherein $R^9$ is selected from
alkyl, hydroxyalkyl, alkoxy, alkoxyalkoxy, aminoalkyl;
and wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl;
Q is O or $NR^7$.

In certain embodiments, a compound can have the structure shown in Formula VIII

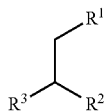

Formula VIII wherein $R^1$ and $R^2$ are

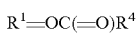

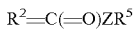

wherein Z is NH,
wherein $R^4$ and $R^5$ are independently for each occurrence a C(12-20) alkyl group, or a C(12-20) alkenyl group;
wherein $R^3$ is selected from
$NHC(=O)(CH_2)_pR^{11}$;
$NHC(=O)SR^9$;
wherein $R^{10}$ is selected from

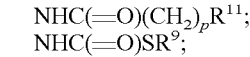

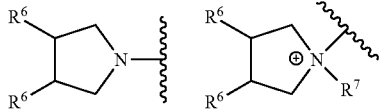

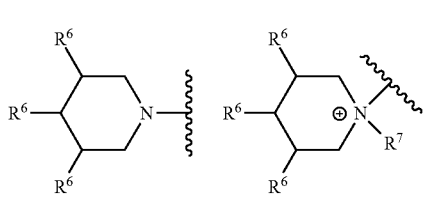

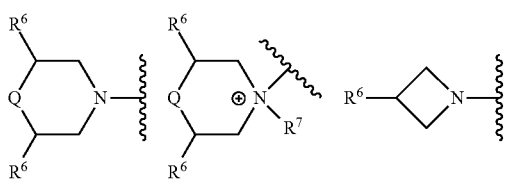

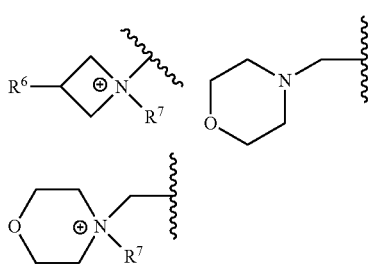

wherein $R^9$ is selected from
alkyl, hydroxyalkyl, alkoxy, alkoxyalkoxy, aminoalkyl;
and wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl;
Q is O or $NR^7$.

Examples of an ionizable compound include the following compound FD:
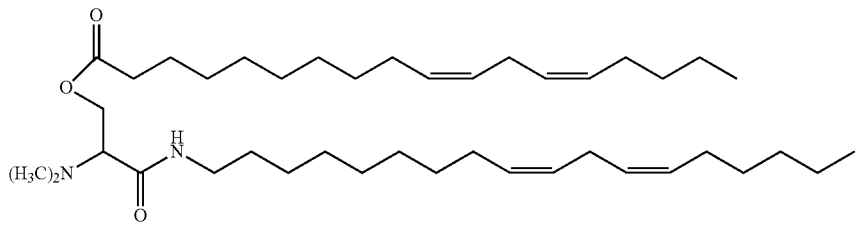
Examples of an ionizable compound include the following compound FE:
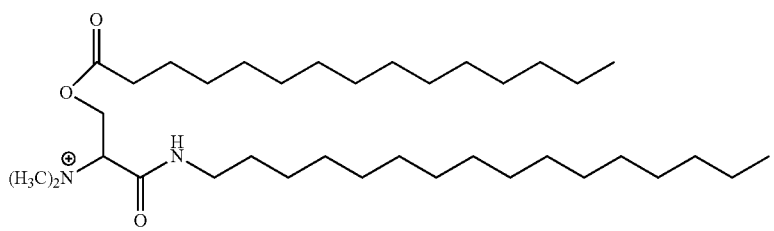
Examples of an ionizable compound include the following compound FF:
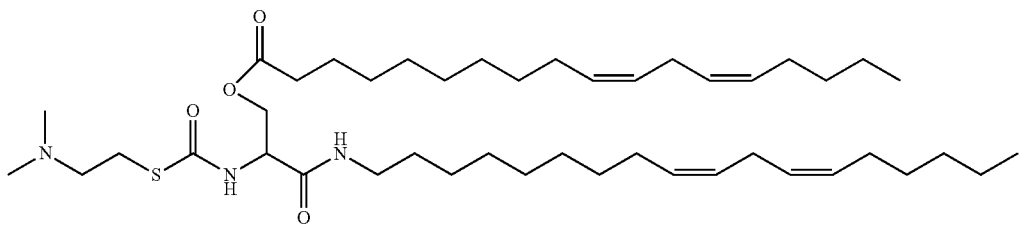 [SMILES: CCCC/C=C\C/C=C\CCCCCCCCC(=O)OCC(NC(=O)SCCN(C)C)C(=O)NCCCCCCCC/C=C\C/C=C\CCCCC]
Examples of an ionizable compound include the following compound A11:
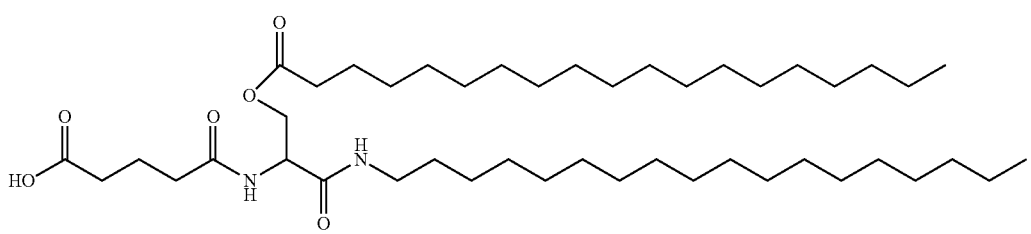 [SMILES: CCCCCCCCCCCCCCCCCCNC(=O)C(COC(=O)CCCCCCCCCCCCCCCCCC)NC(=O)CCCC(=O)O]

Examples of an ionizable compound include the following compound A12:
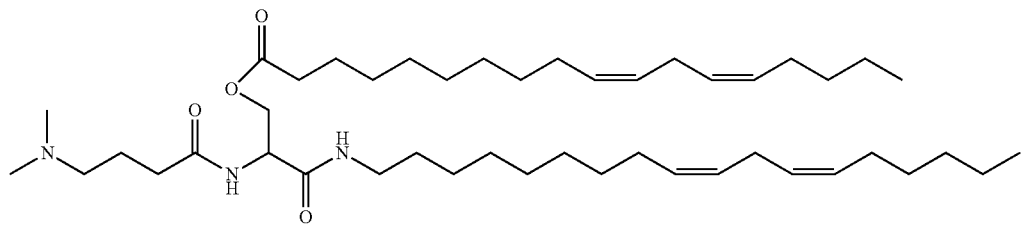 [SMILES: CCCC/C=C\C/C=C\CCCCCCCCC(=O)OCC(NC(=O)CCCN(C)C)C(=O)NCCCCCCCC/C=C\C/C=C\CCCCC]
Examples of an ionizable compound include the following compound A13:
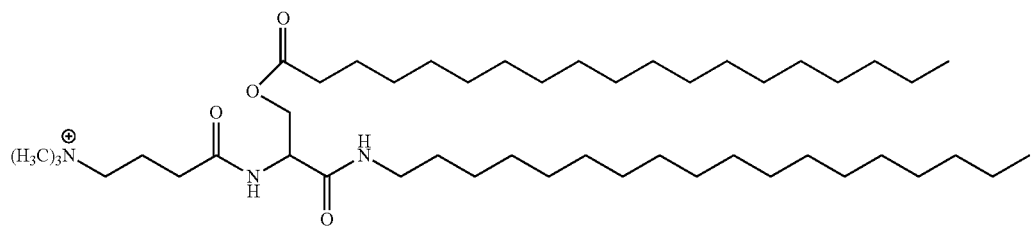
Examples of an ionizable compound include the following compound A14:
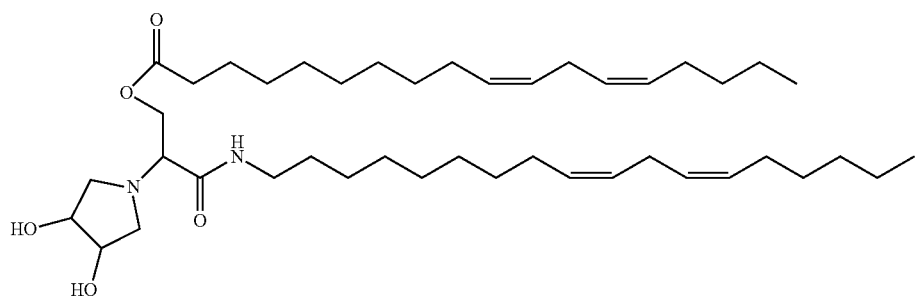 [SMILES: CCCC/C=C\C/C=C\CCCCCCCCC(=O)OCC(C(=O)NCCCCCCCC/C=C\C/C=C\CCCCC)N1CC(O)C(O)C1]
Examples of an ionizable compound include the following compound A15:
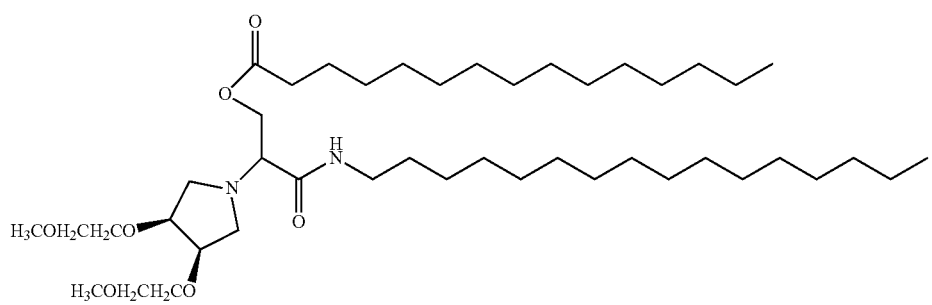

Examples of an ionizable compound include the following compound A16:
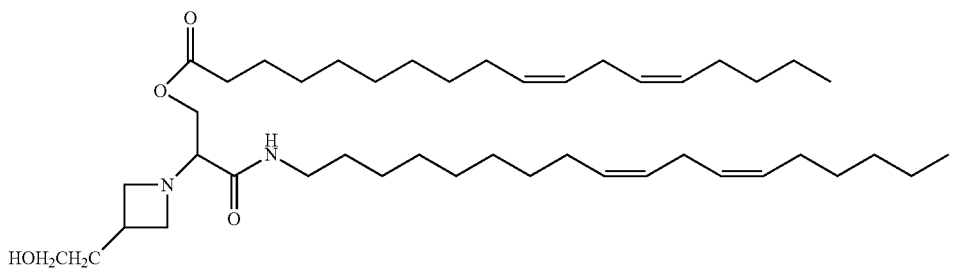
Examples of an ionizable compound include the following compound A17:
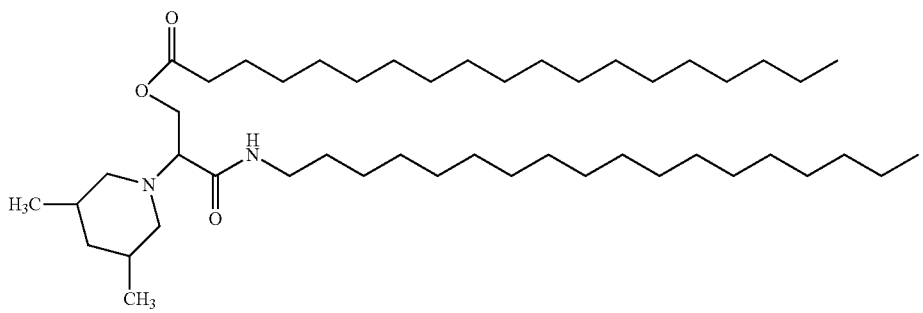 [SMILES: CCCCCCCCCCCCCCCCCCNC(=O)C(COC(=O)CCCCCCCCCCCCCCCCCC)N1CC(C)CC(C)C1]
Examples of an ionizable compound include the following compound A18:
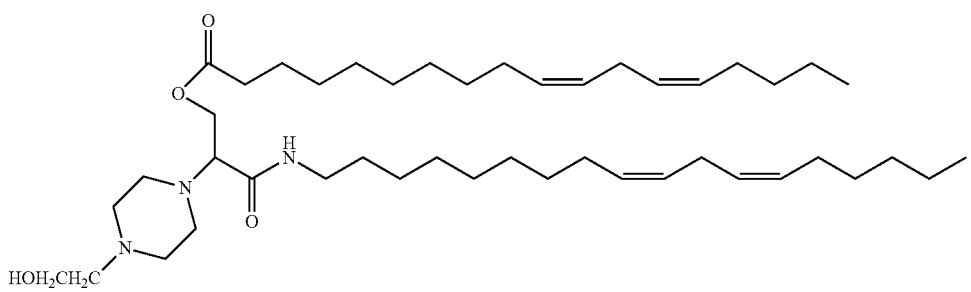
Examples of an ionizable compound include the following compound A19:
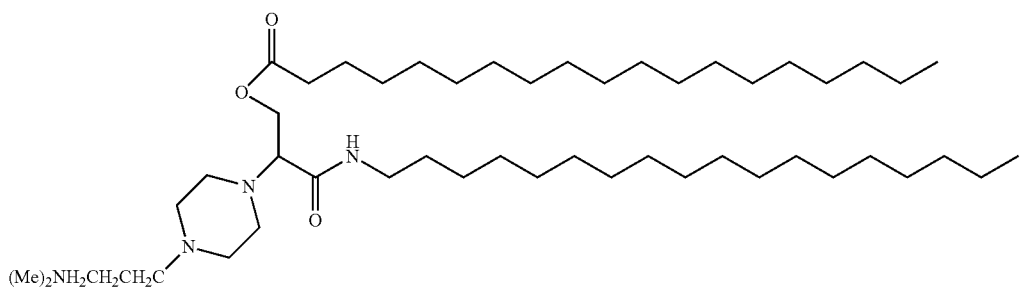

Examples of an ionizable compound include the following compound A20:
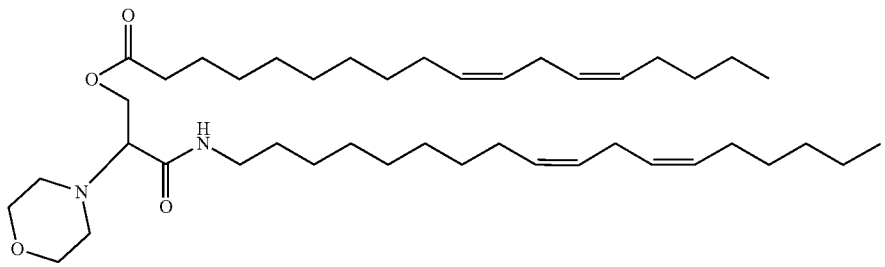 [SMILES: CCCCC/C=C\C/C=C\CCCCCCCCNC(=O)C(COC(=O)CCCCCCCC/C=C\C/C=C(/C)CCCC)N1CCOCC1]
Examples of an ionizable compound include the following compound A21:
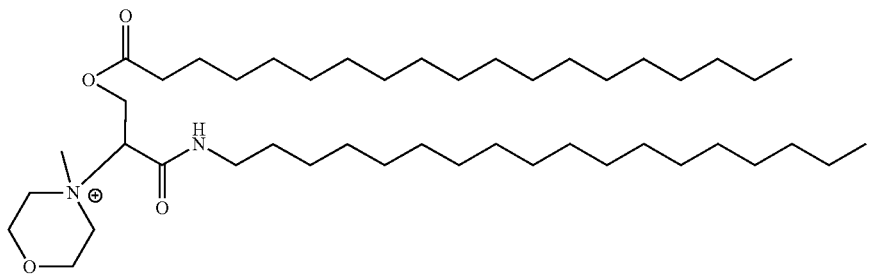 [SMILES: CCCCCCCCCCCCCCCCCCNC(=O)C(COC(=O)CCCCCCCCCCCCCCCCCC)[N+]1(C)CCOCC1]
Examples of an ionizable compound include the following compound A22:
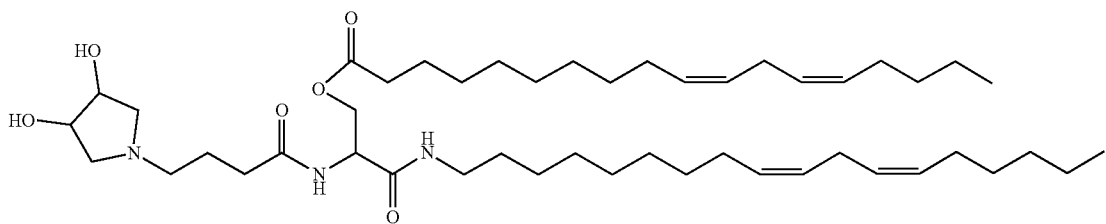 [SMILES: CCCC/C=C\C/C=C\CCCCCCCCC(=O)OCC(NC(=O)CCCN1CC(O)C(O)C1)C(=O)NCCCCCCCC/C=C\C/C=C\CCCCC]
Examples of an ionizable compound include the following compound A23:
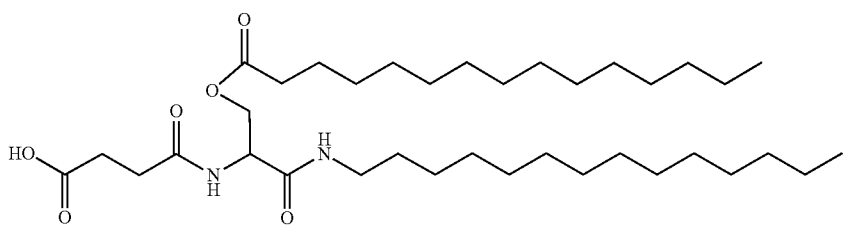 [SMILES: CCCCCCCCCCCCCCNC(=O)C(COC(=O)CCCCCCCCCCCCCC)NC(=O)CCC(=O)O]
which is (S)-4-oxo-4-((1-oxo-3-(tetradecanoyloxy)-1-(tetradecylamino)propan-2-yl)amino)butanoic acid.

Examples of an ionizable compound include the following compound A24:

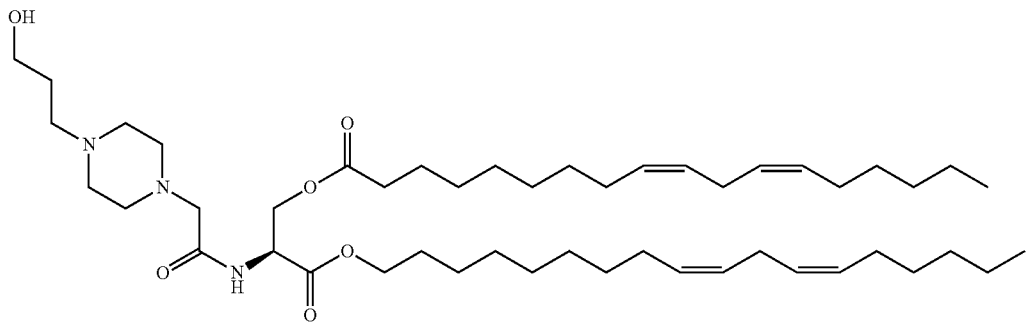 [SMILES: CCCCC/C=C\C/C=C\CCCCCCCCOC(=O)[C@H](COC(=O)CCCCCCC/C=C\C/C=C\CCCCC)NC(=O)CN1CCN(CCCO)CC1]

which is (S)-2-(2-(4-(3-hydroxypropyl)piperazin-1-yl)acetamido)-3-(((9Z,12Z)-octadeca-9,12-dien-1-yl)oxy)-3-oxopropyl (9Z,12Z)-octadeca-9,12-dienoate.

Examples of an ionizable compound include the following compound A25:

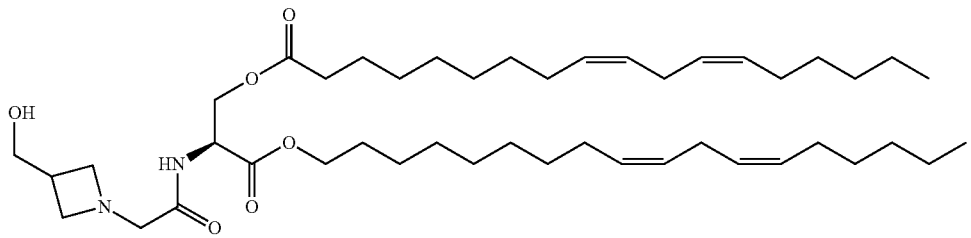 [SMILES: CCCCC/C=C\C/C=C\CCCCCCCCOC(=O)[C@H](COC(=O)CCCCCCC/C=C\C/C=C\CCCCC)NC(=O)CN1CC(CO)C1]

In some embodiments, each of the alkenyl groups can have from one to two double bonds.

In further embodiments, a compound can have the structure shown in Formula VIII-B

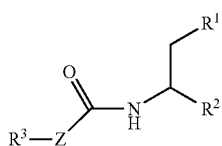

Formula VIII-B wherein $R^1$ and $R^2$ are

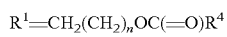

$R^1=CH_2(CH_2)_nOC(=O)R^4$

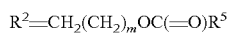

$R^2=CH_2(CH_2)_mOC(=O)R^5$ wherein n and m are each independently from 1 to 2;
$R^4$ and $R^5$ are independently for each occurrence a C(12-20) alkyl group, or a C(12-20) alkenyl group;
wherein Z is N, O;
wherein $R^3$ is selected from
alkyl, hydroxyalkyl, alkoxy, alkoxyalkoxy, aminoalkyl;

wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl, and aminoalkyl;
p is from 1 to 4.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include the following compound B11:

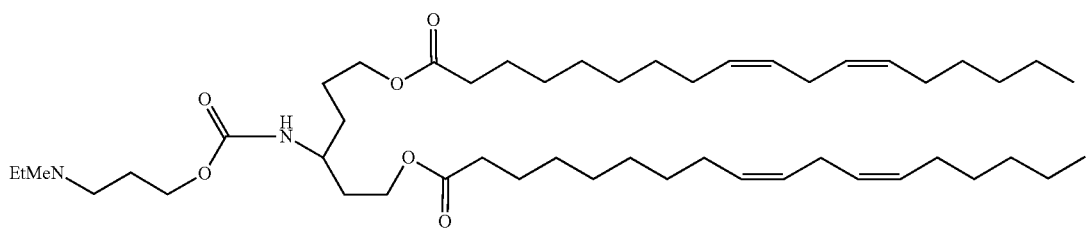

Examples of an ionizable compound include the following compound B12:

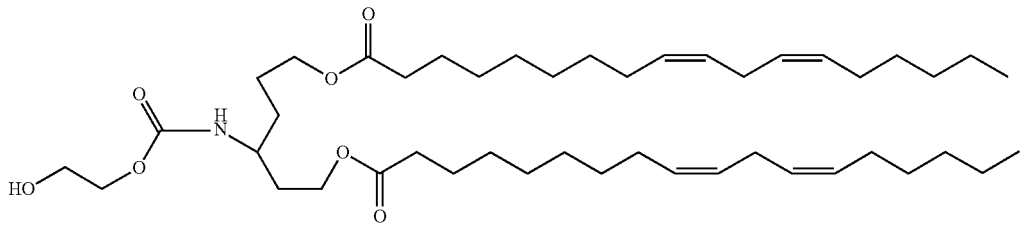 [SMILES: CCCCC/C=C\C/C=C\CCCCCCCC(=O)OCCCC(CCOC(=O)CCCCCCC/C=C\C/C=C\CCCCC)NC(=O)OCCO]

Examples of an ionizable compound include the following compound B13:

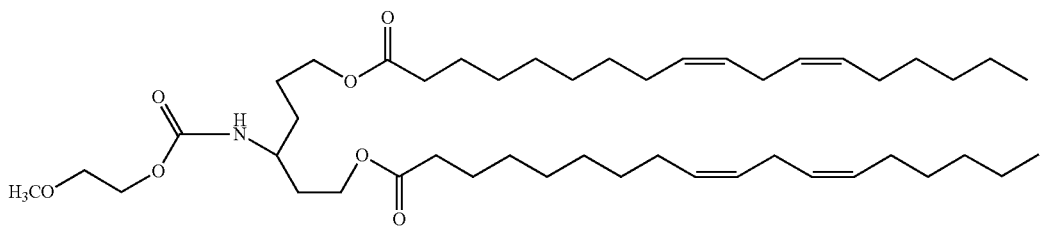 [SMILES: CCCCC/C=C\C/C=C\CCCCCCCC(=O)OCCCC(CCOC(=O)CCCCCCC/C=C\C/C=C\CCCCC)NC(=O)OCCOC]

Examples of an ionizable compound include the following compound B14:

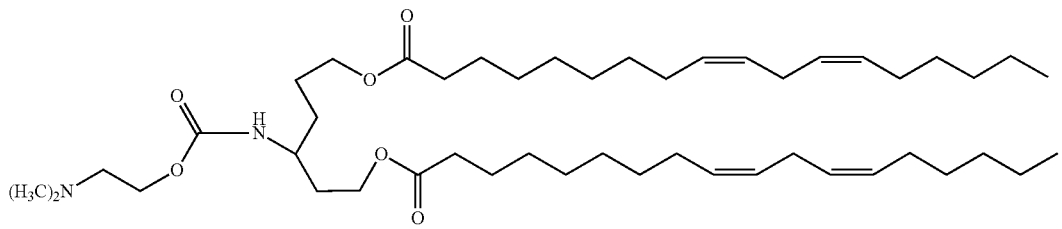

In additional embodiments, a compound can have the structure shown in Formula IX

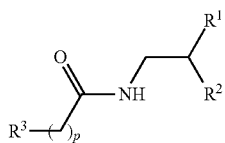

Formula IX wherein $R^1$ and $R^2$ are

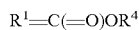

$R^1 = C(=O)OR^4$

$R^2 = NHC(=O)R^5$ wherein $R^4$ and $R^5$ are independently for each occurrence a C(12-20) alkyl group, or a C(12-20) alkenyl group;
wherein p is from 1 to 4;
wherein $R^3$ is selected from 1-azetidines, 1-pyrrolidines, 1-piperidines, 4-morpholines, and 1,4-piperazines wherein the rings can be substituted at any carbon atom position,

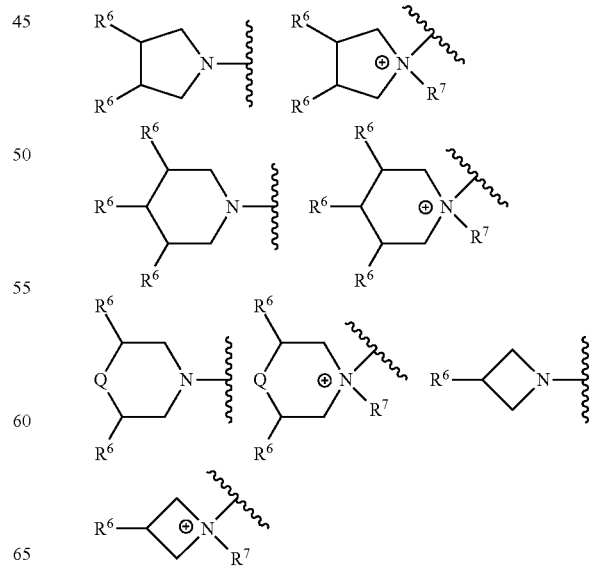

and can also be selected from amino and aminoalkyl groups which can be substituted,

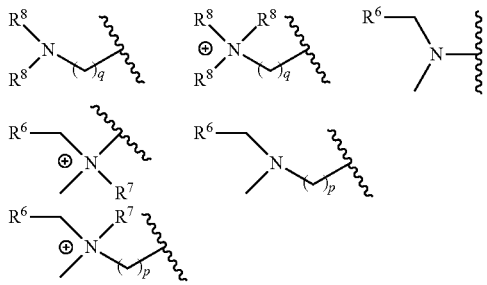

wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl, and aminoalkyl;
each $R^8$ is independently selected from H, alkyl, hydroxyalkyl, and aminoalkyl, and any two $R^8$ may form a ring;
q is from zero to four;
Q is or $NR^7$.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, $R^4$ and $R^5$ are independently for each occurrence a C(16-18) alkyl group, or a C(16-18) alkenyl group.

In some embodiments, p is 1, 2, 3 or 4.
In some embodiments, q is 0, 1, 2, 3 or 4.

In additional embodiments, a compound can have the structure shown in Formula IX

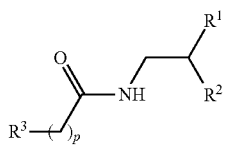

Formula IX wherein $R^1$ and $R^2$ are $R^1$=C(=O)OR$^4$ $R^2$=NHC(=O)R$^5$ wherein $R^4$ and $R^5$ are independently for each occurrence a C(12-20) alkyl group, or a C(12-20) alkenyl group;
wherein p is from 1 to 4;
wherein $R^3$ is selected from

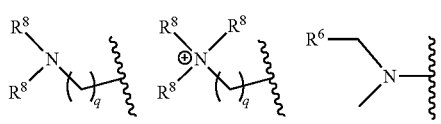

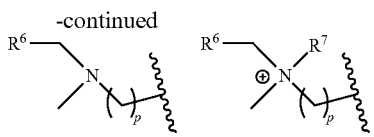

wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl;
each $R^8$ is independently selected from H, alkyl, hydroxyalkyl, and aminoalkyl, and any two $R^8$ may form a ring;
q is from zero to four.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In additional embodiments, a compound can have the structure shown in Formula IX

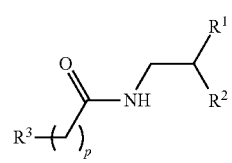

Formula IX wherein $R^1$ and $R^2$ are $R^1$=C(=O)OR$^4$ $R^2$=NHC(=O)R$^5$ wherein $R^4$ and $R^5$ are independently for each occurrence a C(12-20) alkyl group, or a C(12-20) alkenyl group;
wherein p is from 1 to 4;
wherein $R^3$ is selected from

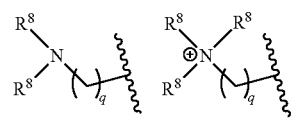

wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl;
each $R^8$ is independently selected from H, alkyl, hydroxyalkyl, and aminoalkyl, and any two $R^8$ may form a ring;
q is from zero to four.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include the following compound C11:
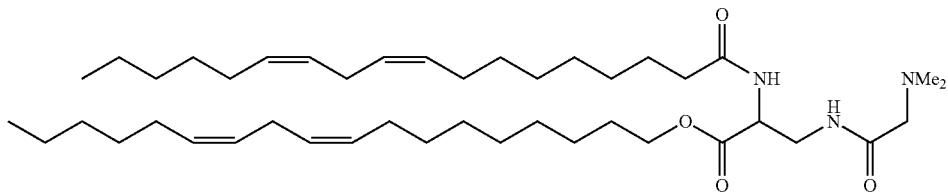 [SMILES: CCCCC/C=C\C/C=C\CCCCCCCCOC(=O)C(CNC(=O)CN(C)C)NC(=O)CCCCCCC/C=C\C/C=C\CCCCC]
Examples of an ionizable compound include the following compound C12:
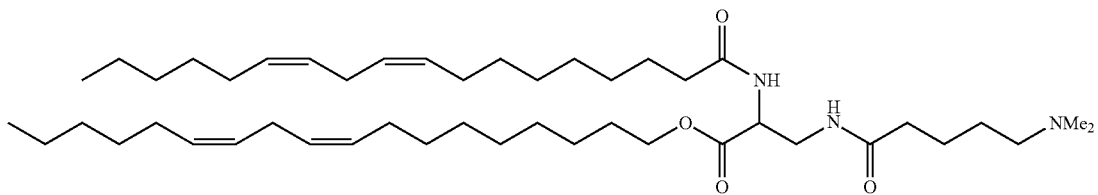
Examples of an ionizable compound include the following compound C13:
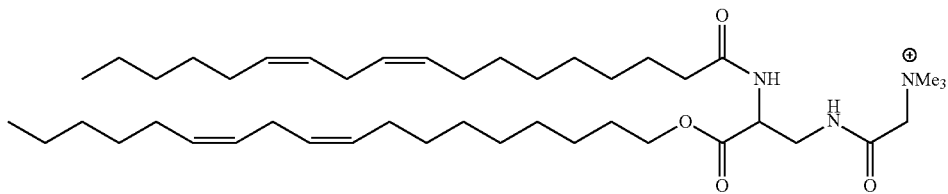
Examples of an ionizable compound include the following compound C14:
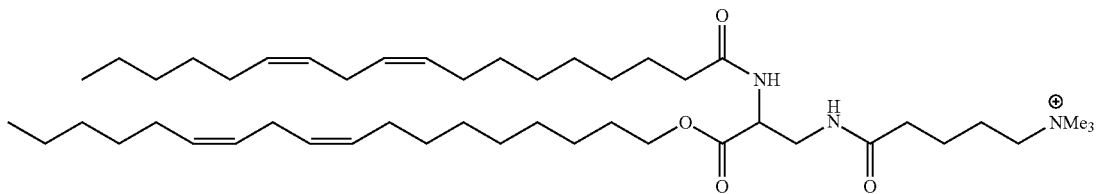
Examples of an ionizable compound include the following compound C15:
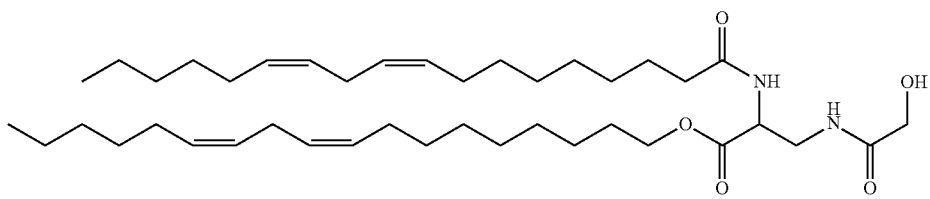 [SMILES: CCCCC/C=C\C/C=C\CCCCCCCCOC(=O)C(CNC(=O)CO)NC(=O)CCCCCCC/C=C\C/C=C\CCCCC]

Examples of an ionizable compound include the following compound C16:
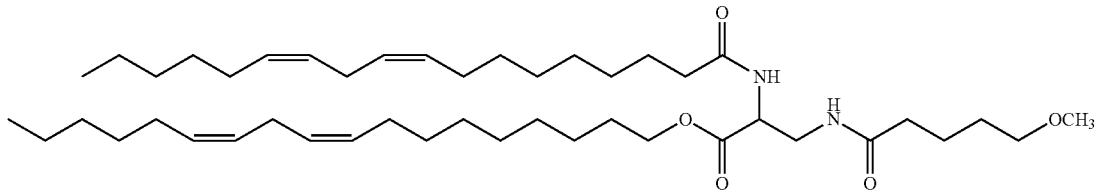 [SMILES: CCCCC/C=C\C/C=C\CCCCCCCCOC(=O)C(CNC(=O)CCCCOC)NC(=O)CCCCCCC/C=C\C/C=C\CCCCC]
Examples of an ionizable compound include the following compound C17:
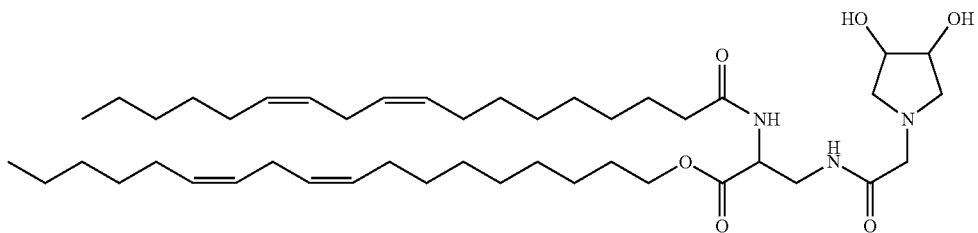 [SMILES: CCCCC/C=C\C/C=C\CCCCCCCCOC(=O)C(CNC(=O)CN1CC(O)C(O)C1)NC(=O)CCCCCCC/C=C\C/C=C\CCCCC]
Examples of an ionizable compound include the following compound C18:
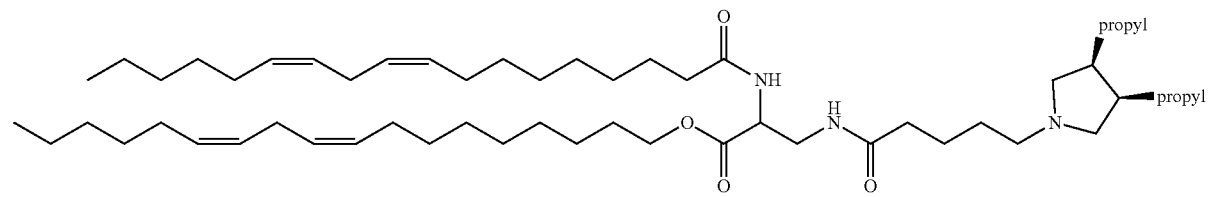
Examples of an ionizable compound include the following compound C19:
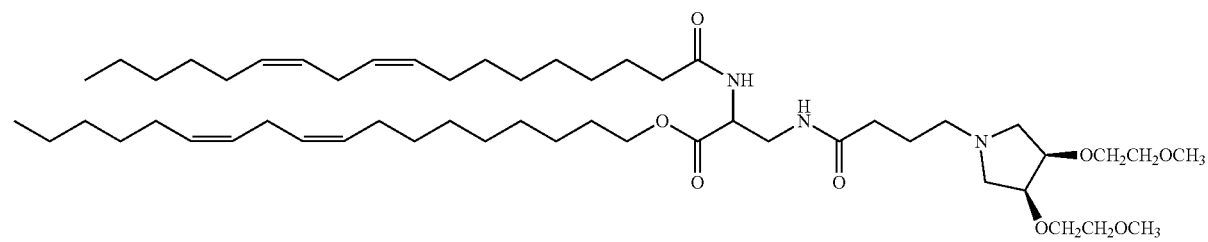
Examples of an ionizable compound include the following compound C20:
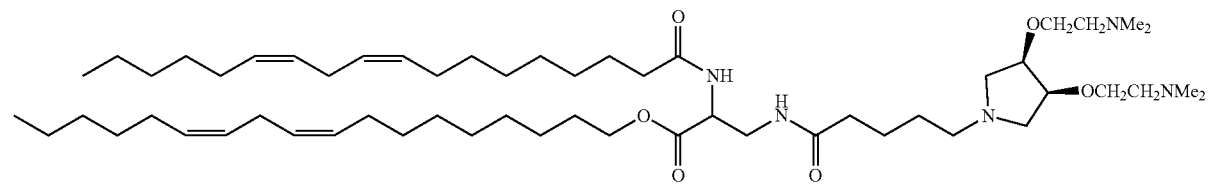

Examples of an ionizable compound include the following compound C21:

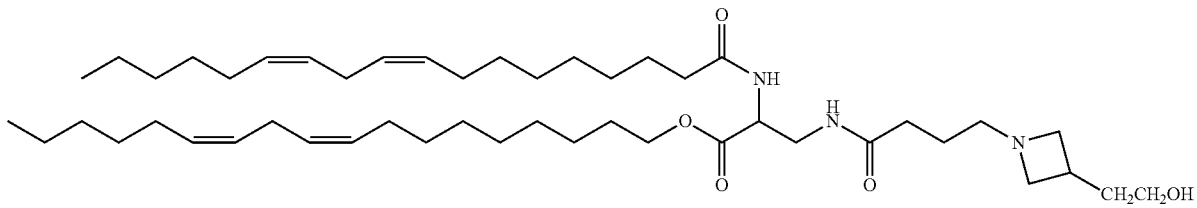

Examples of an ionizable compound include the following compound C22:

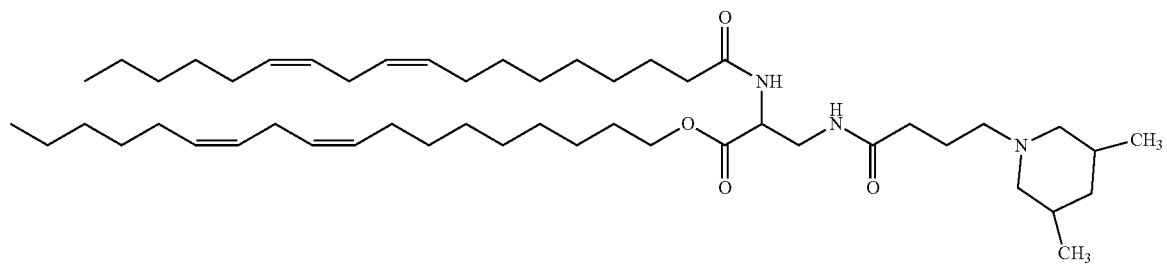 [SMILES: CCCCC/C=C\C/C=C\CCCCCCCCOC(=O)C(CNC(=O)CCCN1CC(C)CC(C)C1)NC(=O)CCCCCCC/C=C\C/C=C\CCCCC]

Examples of an ionizable compound include the following compound C23:

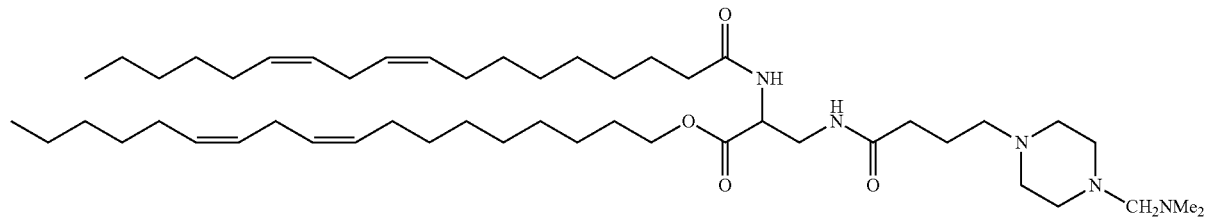

Examples of an ionizable compound include the following compound C24:

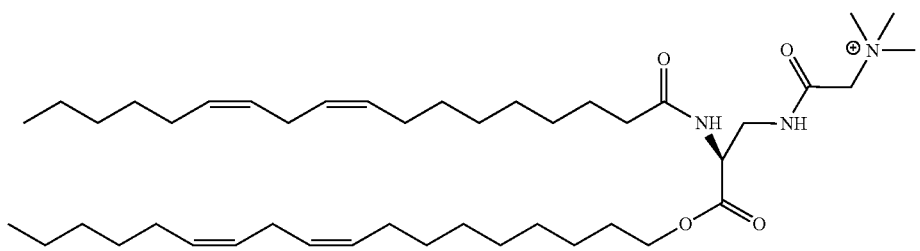 [SMILES: CCCCC/C=C\C/C=C\CCCCCCCCOC(=O)[C@H](CNC(=O)C[N+](C)(C)C)NC(=O)CCCCCCC/C=C\C/C=C\CCCCC]

which is N,N,N-trimethyl-2-(((S)-3-(((9Z,12Z)-octadeca-9,12-dien-1-yl)oxy)-2-((9Z,12Z)-octadeca-9,12-dienamido)-3-oxopropyl)amino)-2-oxoethan-1l-aminium.

Examples of an ionizable compound include the following compound C25:

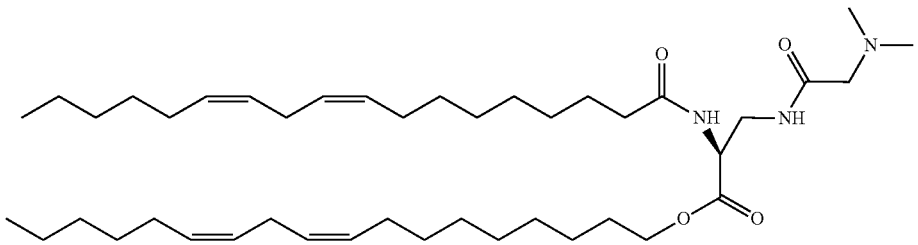 [SMILES: CCCCC/C=C\C/C=C\CCCCCCCCOC(=O)[C@H](CNC(=O)CN(C)C)NC(=O)CCCCCCC/C=C\C/C=C\CCCCC]

which is (9Z,12Z)-octadeca-9,12-dien-1-yl (S)-3-(2-(dimethylamino)acetamido)-2-((9Z,12Z)-octadeca-9,12-dienamido)propanoate.

In some embodiments, a compound can have the structure shown in Formula X

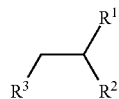

Formula X wherein $R^1$ and $R^2$ are

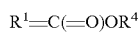

wherein $R^4$ and $R^5$ are independently for each occurrence a C(12-20) alkyl group, or a C(12-20) alkenyl group;
wherein $R^3$ is selected from
  amino;
  quaternary amino;
  aminoalkyl;
  quaternary aminoalkyl;
  hydroxyalkylamino.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include the following compound D11:

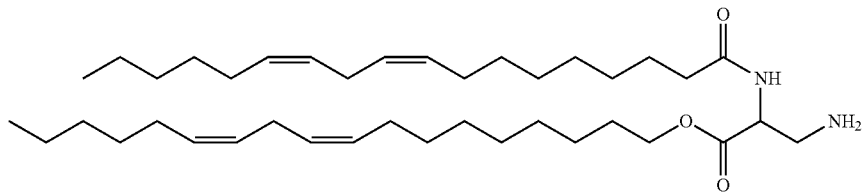 [SMILES: CCCCC/C=C\C/C=C\CCCCCCCCOC(=O)C(CN)NC(=O)CCCCCCC/C=C\C/C=C\CCCCC]

Examples of an ionizable compound include the following compound D12:

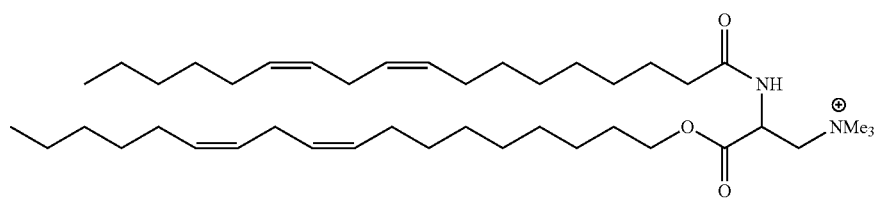

Examples of an ionizable compound include the following compound D13:

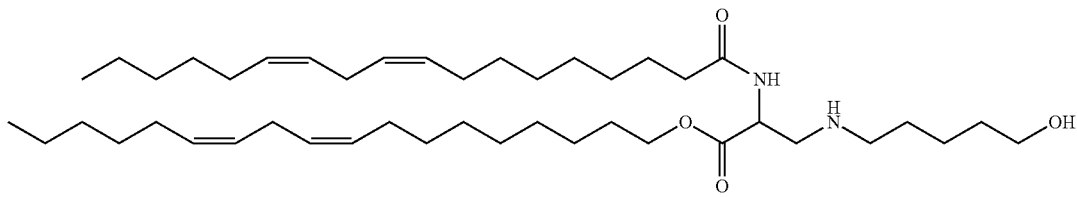 [SMILES: CCCCC/C=C\C/C=C\CCCCCCCCOC(=O)C(CNCCCCCO)NC(=O)CCCCCCC/C=C\C/C=C\CCCCC]

Examples of an ionizable compound include the following compound D14:

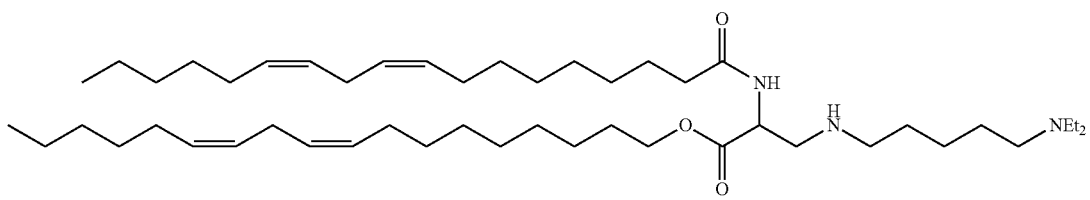

Embodiments of this invention include compounds having the structure shown in Formula XI

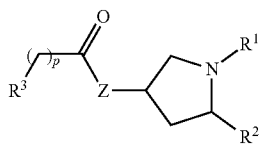

Formula XI wherein $R^1$ and $R^2$ are

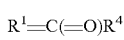

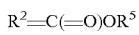

wherein $R^4$ and $R^5$ are independently for each occurrence a C(12-20) alkyl group, or a C(12-20) alkenyl group;

wherein Z is O or NH;

wherein p is from 1 to 4;

wherein $R^3$ is selected from 1-azetidines, 1-pyrrolidines, 1-piperidines, 4-morpholines, and 1,4-piperazines wherein the rings can be substituted at any carbon atom position,

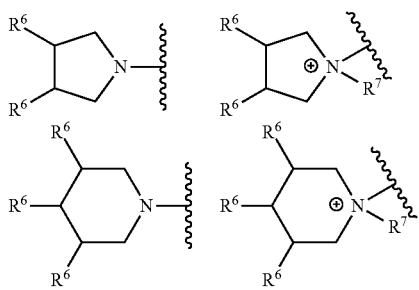

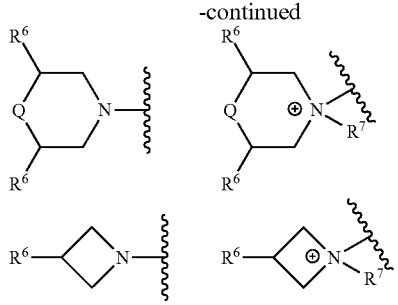

and can also be selected from amino and aminoalkyl groups which can be substituted,

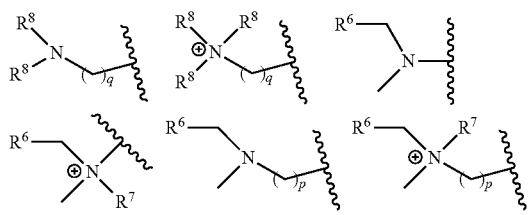

wherein
each $R^6$ is independently selected from H, alkyl, hydroxyl, hydroxyalkyl, alkoxy, alkoxyalkoxy, aminoalkyl;
each $R^7$ is independently selected from H, alkyl, hydroxyalkyl, and aminoalkyl;
each $R^8$ is independently selected from H, alkyl, hydroxyalkyl, and aminoalkyl, and any two $R^8$ may form a ring;
q is from zero to four;
Q is O or $NR^7$.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

In some embodiments, $R^4$ and $R^5$ are independently for each occurrence a C(16-18) alkyl group, or a C(16-18) alkenyl group.

In some embodiments, p is 1, 2, 3 or 4.

In some embodiments, q is 0, 1, 2, 3 or 4.

Embodiments of this invention include compounds having the structure shown in Formula XI

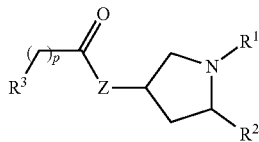

Formula XI wherein $R^1$ and $R^2$ are

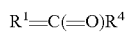

$R^1$=C(=O)$R^4$

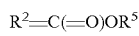

$R^2$=C(=O)O$R^5$ wherein $R^4$ and $R^5$ are independently for each occurrence a C(12-20) alkyl group, or a C(12-20) alkenyl group;
wherein Z is O or NH;
wherein p is from 1 to 4;

wherein $R^3$ is selected from

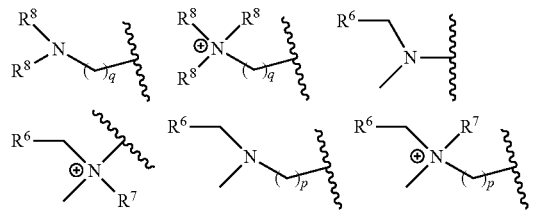

wherein
each $R^6$ is independently selected from H, alkyl, hydroxyl, hydroxyalkyl, alkoxy, alkoxyalkoxy, aminoalkyl;
each $R^7$ is independently selected from H, alkyl;
each $R^8$ is independently selected from H, alkyl, hydroxyalkyl, and aminoalkyl, and any two $R^8$ may form a ring;
q is from zero to four.

In some embodiments, each of the alkenyl groups can have from one to two double bonds.

In some embodiments, $R^4$ and $R^5$ are independently for each occurrence a C(14-18) alkyl group, or a C(14-18) alkenyl group.

In some embodiments, the terms alkyl, hydroxyalkyl, and aminoalkyl refer to C(1-6)alkyl, hydroxyl[C(1-6)alkyl], and amino[C(1-6)alkyl].

Examples of an ionizable compound include the following compound E11:

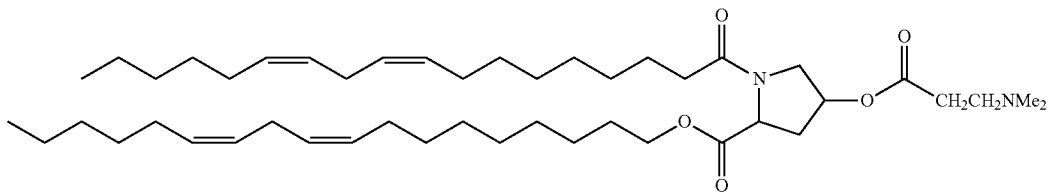

Examples of an ionizable compound include the following compound E12:

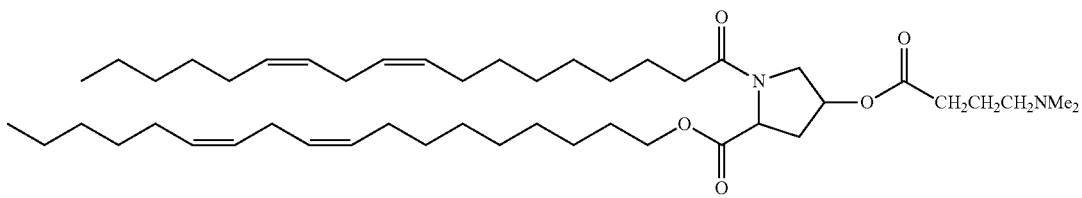

Examples of an ionizable compound include the following compound E13:

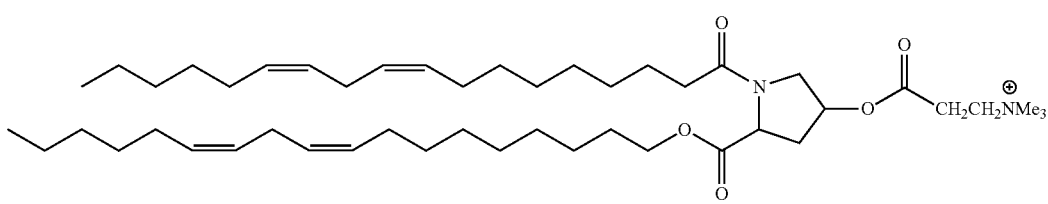

Examples of an ionizable compound include the following compound E14:
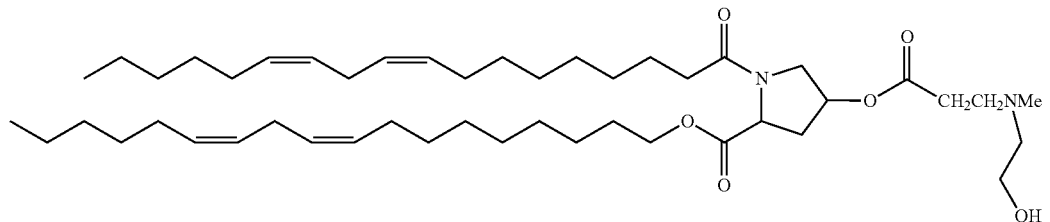
Examples of an ionizable compound include the following compound E15:
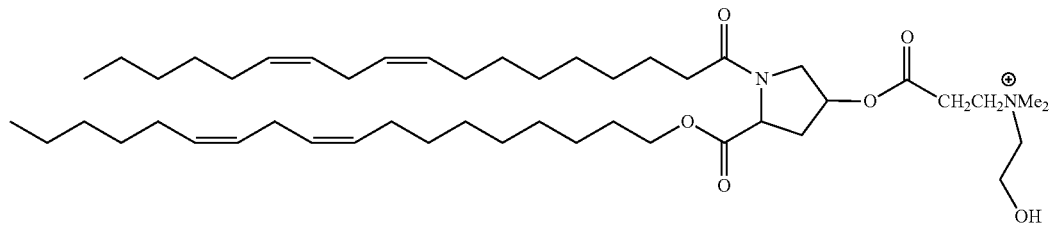
Examples of an ionizable compound include the following compound E16:
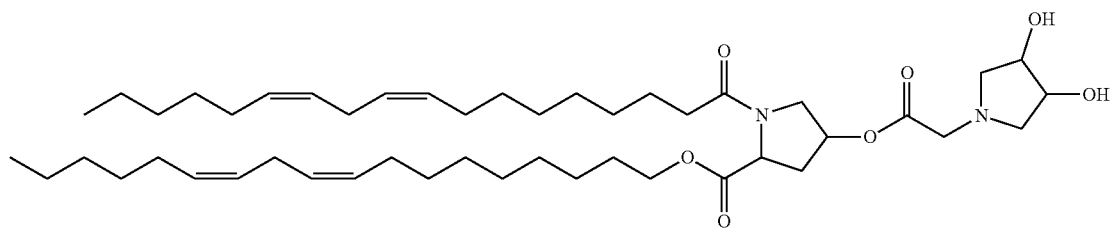 [SMILES: CCCCC/C=C\C/C=C\CCCCCCCCOC(=O)C1CC(OC(=O)CN2CC(O)C(O)C2)CN1C(=O)CCCCCCC/C=C\C/C=C\CCCCC]
Examples of an ionizable compound include the following compound E17:
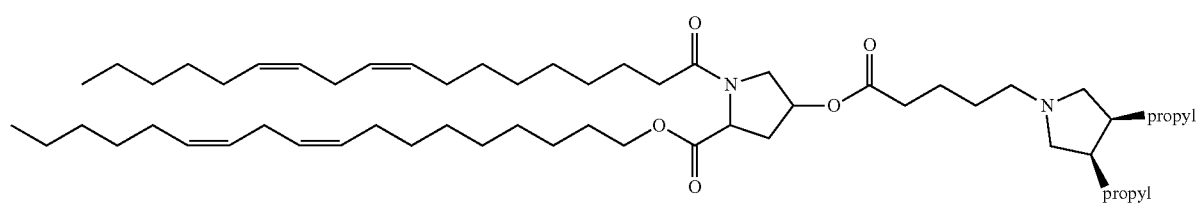

Examples of an ionizable compound include the following compound E18:
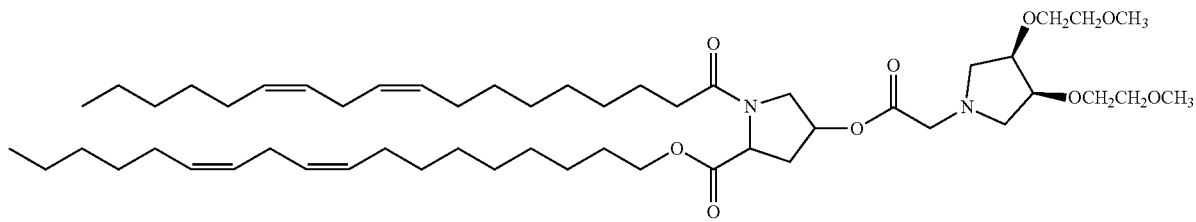
Examples of an ionizable compound include the following compound E19:
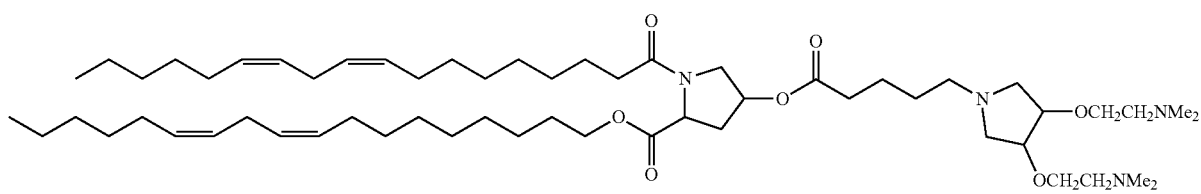
Examples of an ionizable compound include the following compound E20:
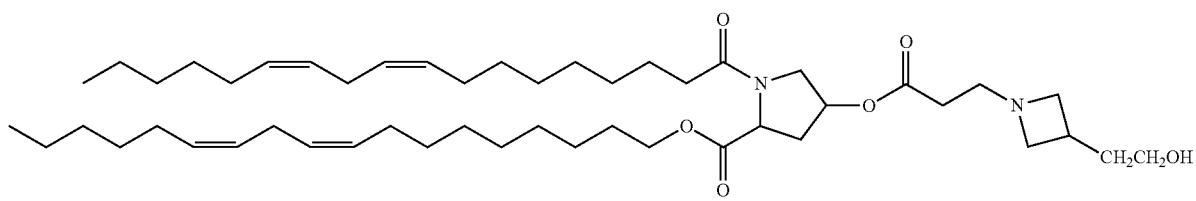
Examples of an ionizable compound include the following compound E21:
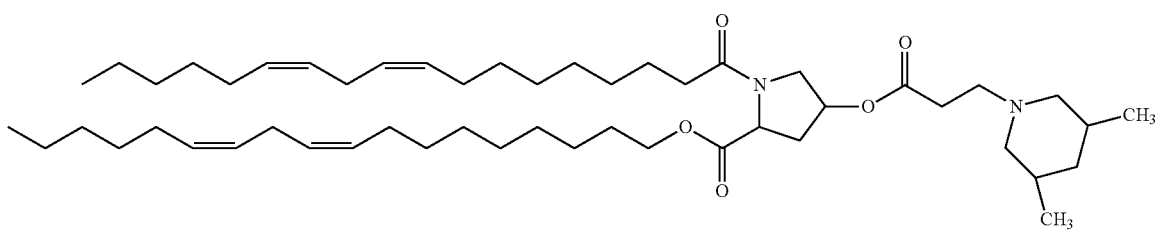 [SMILES: CCCCC/C=C\C/C=C\CCCCCCCCOC(=O)C1CC(OC(=O)CCN2CC(C)CC(C)C2)CN1C(=O)CCCCCCC/C=C\C/C=C\CCCCC]
Examples of an ionizable compound include the following compound E22:
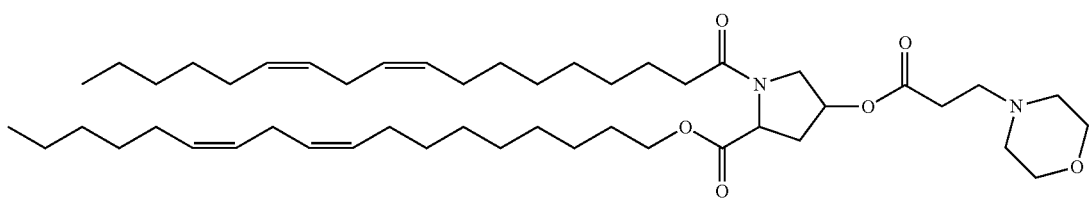 [SMILES: CCCCC/C=C\C/C=C\CCCCCCCCOC(=O)C1CC(OC(=O)CCN2CCOCC2)CN1C(=O)CCCCCCC/C=C\C/C=C\CCCCC]

Examples of an ionizable compound include the following compound E23:
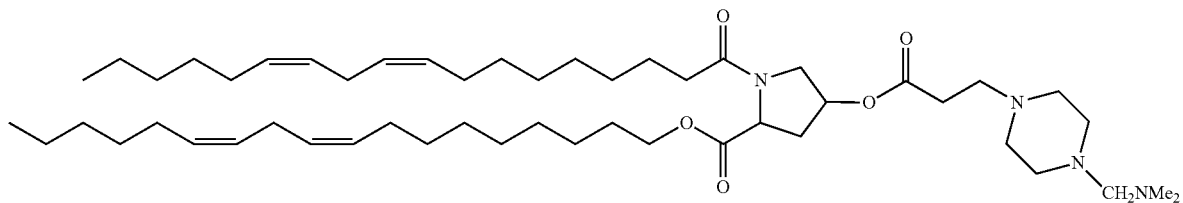
Examples of an ionizable compound include the following compound E24;
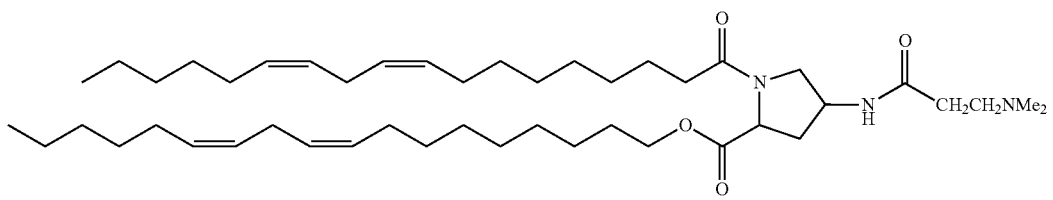
Examples of an ionizable compound include the following compound E25;
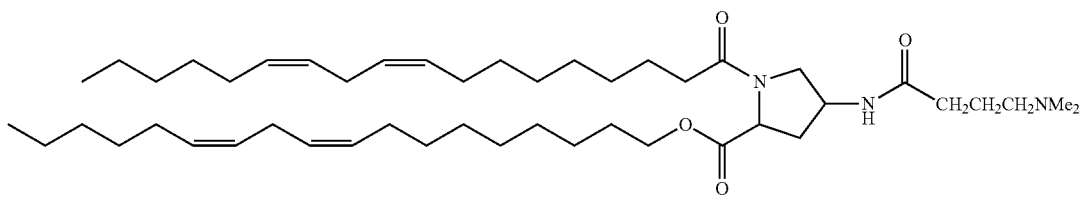
Examples of an ionizable compound include the following compound E26:
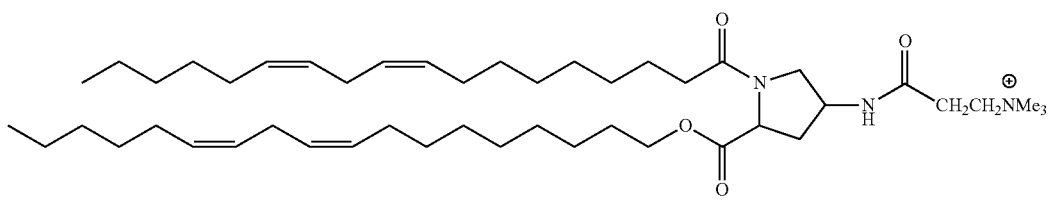
Examples of an ionizable compound include the following compound
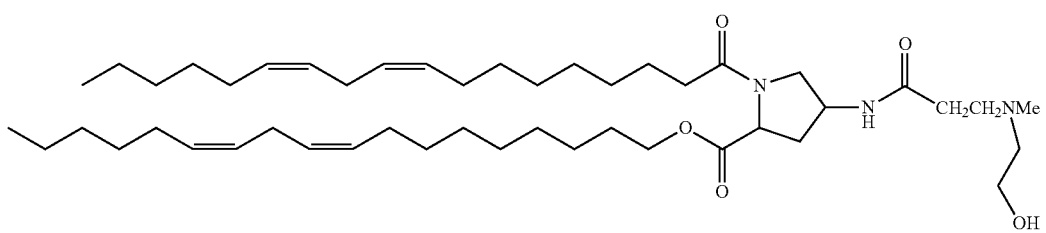

Examples of an ionizable compound include the following compound E28:
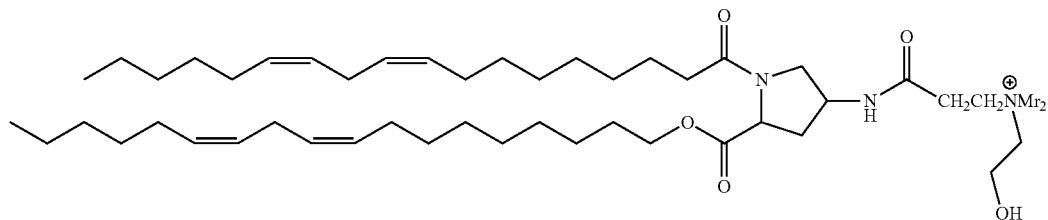
Examples of an ionizable compound include the following compound E29:
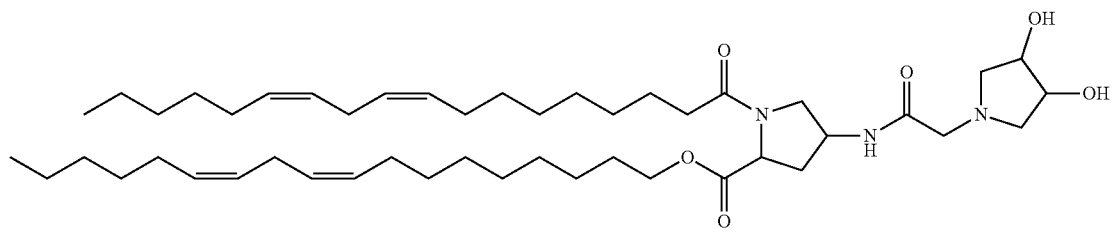
Examples of an ionizable compound include the following compound E30:
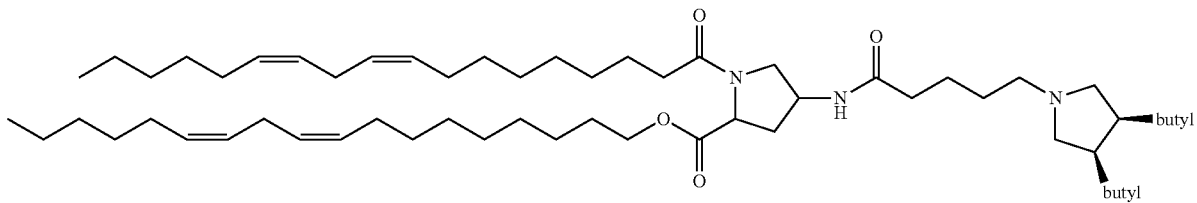
Examples of an ionizable compound include the following compound E31:
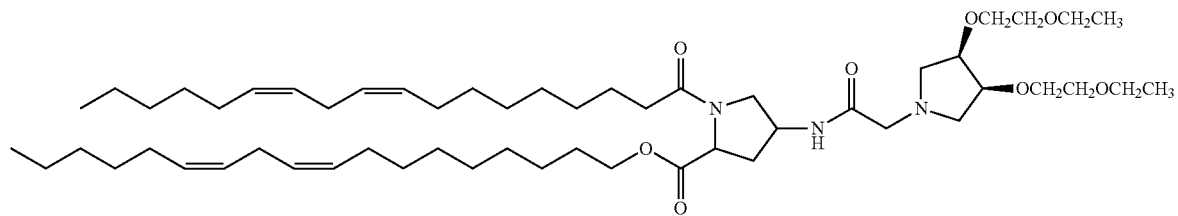

Examples of an ionizable compound include the following compound E33:
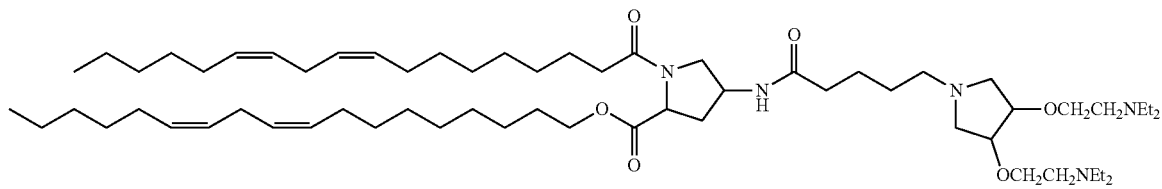
Examples of an ionizable compound include the following compound E33:
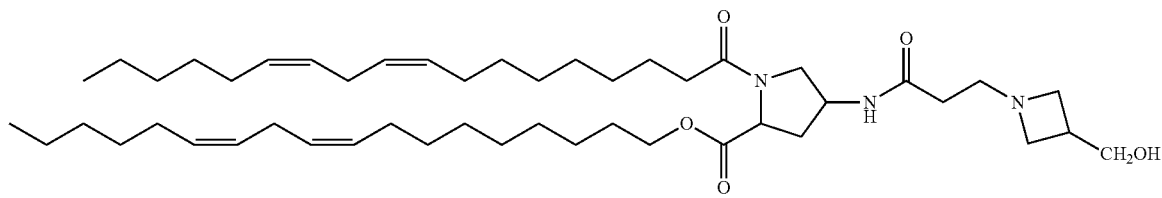 [SMILES: CCCCC/C=C\C/C=C\CCCCCCCCOC(=O)C1CC(NC(=O)CCN2CC(CO)C2)CN1C(=O)CCCCCCC/C=C\C/C=C\CCCCC]
Examples of an ionizable compound include the following compound E34:
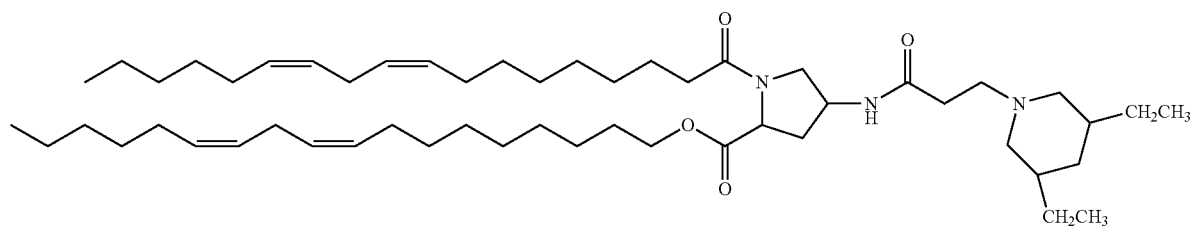 [SMILES: CCCCC/C=C\C/C=C\CCCCCCCCOC(=O)C1CC(NC(=O)CCN2CC(CC)CC(CC)C2)CN1C(=O)CCCCCCC/C=C\C/C=C\CCCCC]
Examples of an ionizable compound include the following compound E35:
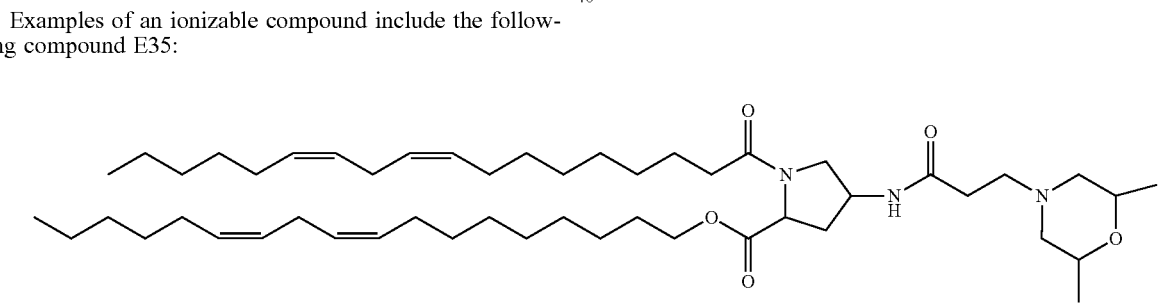
Examples of an ionizable compound include the following compound E36:
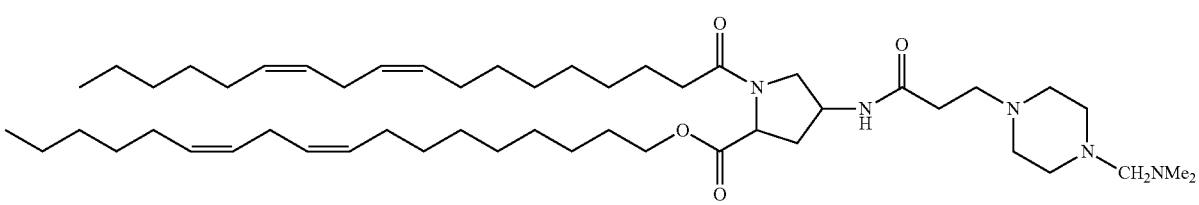

Examples of an ionizable compound include the following compound E37:

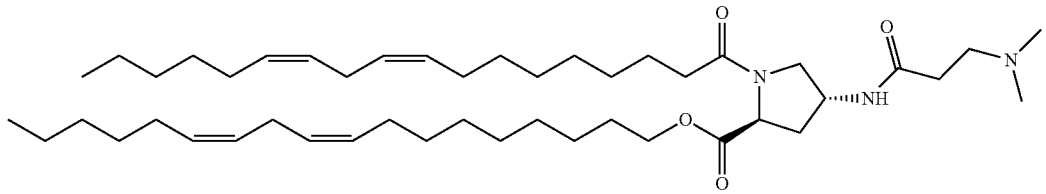 [SMILES: CCCCC/C=C\C/C=C\CCCCCCCCOC(=O)[C@@H]1C[C@@H](NC(=O)CCN(C)C)CN1C(=O)CCCCCCC/C=C\C/C=C\CCCCC]

which is (9Z,12Z)-octadeca-9,12-dien-1-yl (2S,4R)-4-(3-(dimethylamino)propanamido)-1-((9Z,12Z)-octadeca-9,12-dienoyl)pyrrolidine-2-carboxylate.

Examples of an ionizable compound include the following compound E38;

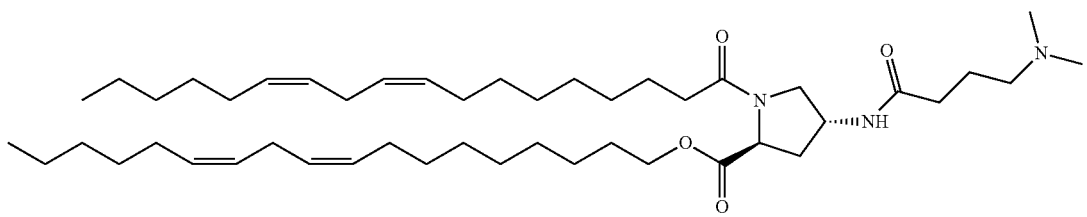 [SMILES: CCCCC/C=C\C/C=C\CCCCCCCCOC(=O)[C@@H]1C[C@@H](NC(=O)CCCN(C)C)CN1C(=O)CCCCCCC/C=C\C/C=C\CCCCC]

which is (9Z,12Z)-octadeca-9,12-dien-1-yl (2S,4R)-4-(4-(dimethylamino)butanamido)-1-((9Z,12Z)-octadeca-9,12-dienoyl)pyrrolidine-2-carboxylate.

Examples of an ionizable compound include the following compound E39.

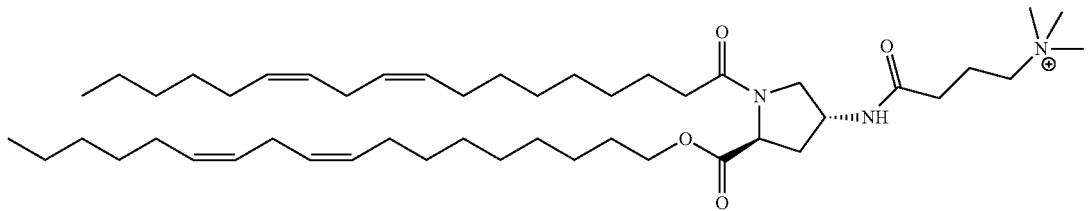 [SMILES: CCCCC/C=C\C/C=C\CCCCCCCCOC(=O)[C@@H]1C[C@@H](NC(=O)CCC[N+](C)(C)C)CN1C(=O)CCCCCCC/C=C\C/C=C\CCCCC]

which is N,N,N-trimethyl-4-(((3R,5S)-5-(((((9Z,12Z)-octadeca-9,12-dien-1-yl)oxy)carbonyl)-1-((9Z,12Z)-octadeca-9,12-dienoyl)pyrrolidin-3-yl)amino)-4-oxobutan-1-aminium.

Examples of an ionizable compound include the following compound E40:

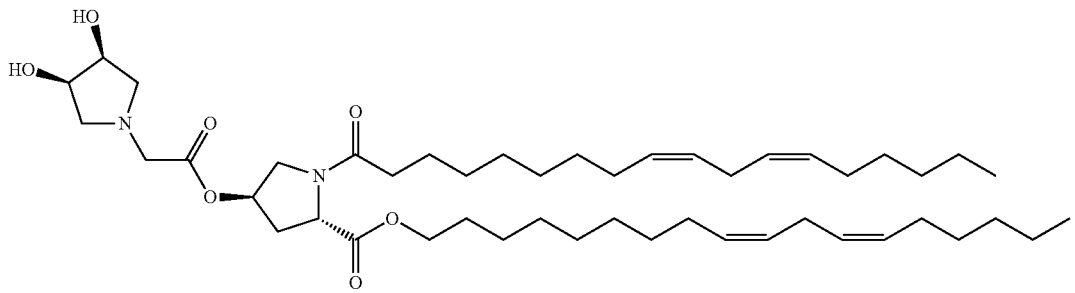 [SMILES: CCCCC/C=C\C/C=C\CCCCCCCCOC(=O)[C@@H]1C[C@@H](OC(=O)CN2C[C@@H](O)[C@@H](O)C2)CN1C(=O)CCCCCCC/C=C\C/C=C\CCCCC]

Structural Lipids

Examples of structural lipids include cholesterols, sterols, and steroids.

Examples of structural lipids include cholanes, cholestanes, ergostanes, campestanes, poriferastanes, stigmastanes, gorgostanes, lanostanes, gonanes, estranes, androstanes, pregnanes, and cycloartanes.

Examples of structural lipids include sterols and zoosterols such as cholesterol, lanosterol, zymosterol, zymostenol, desmosterol, stigmastanol, dihydrolanosterol, and 7-dehydrocholesterol.

Examples of structural lipids include pegylated cholesterols, and cholestane 3-oxo-(C1-22)acyl compounds, for example, cholesteryl acetate, cholesteryl arachidonate, cholesteryl butyrate, cholesteryl hexanoate, cholesteryl myristate, cholesteryl palmitate, cholesteryl behenate, cholesteryl stearate, cholesteryl caprylate, cholesteryl n-decanoate, cholesteryl dodecanoate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, and cholesteryl linoleate.

Examples of structural lipids include sterols such as phytosterols, beta-sitosterol, campesterol, ergosterol, brassicasterol, delta-7-stigmasterol, and delta-7-avenasterol.

Stabilizer Lipids

Examples of stabilizer lipids include zwitterionic lipids.

Examples of stabilizer lipids include compounds such as phospholipids.

Examples of phospholipids include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine and ordilinoleoylphosphatidylcholine.

Examples of stabilizer lipids include phosphatidyl ethanolamine compounds and phosphatidyl choline compounds.

Examples of stabilizer lipids include 1,2-dioleoyl-sn-Glycero-3-Phosphocholine (DOPC).

Examples of stabilizer lipids include diphytanoyl phosphatidyl ethanolamine (DPhPE) and 1,2-Diphytanoyl-sn-Glycero-3-Phosphocholine (DPhPC).

Examples of stabilizer lipids include 1,2-distearoyl-sn-glycero-3-phosphocholine (DSPC), 1,2-dipalmitoyl-sn-glycero-3-phosphocholine (DPPC), 1,2-dipalmitoyl-sn-glycero-3-phosphoethanolamine (DPPE), and 1,2-dioleoyl-sn-glycero-3-phosphoethanolamine (DOPE).

Examples of stabilizer lipids include 1,2-dilauroyl-sn-glycerol (DLG); 1,2-dimyristoyl-sn-glycerol (DMG); 1,2-dipalmitoyl-sn-glycerol (DPG); 1,2-distearoyl-sn-glycerol (DSG); 1,2-diarachidoyl-sn-glycero-3-phosphocholine (DAPC); 1,2-dilauroyl-sn-glycero-3-phosphocholine (DLPC); 1,2-dimyristoyl-sn-glycero-3-phosphocholine (DMPC); 1,2-dipalmitoyl-sn-glycero-O-ethyl-3-phosphocholine (DPePC); 1,2-dilauroyl-sn-glycero-3-phosphoethanolamine (DLPE); 1,2-dimyristoyl-sn-glycero-3-phosphoethanolamine (DMPE); 1,2-distearoyl-sn-glycero-3-phosphoethanolamine (DSPE); 1-palmitoyl-2-linoleoyl-sn-glycero-3-phosphocholine; 1-palmitoyl-2-oleoyl-sn-glycero-3-phosphocholine (POPC); 1-palmitoyl-2-lyso-sn-glycero-3-phosphocholine (P-Lyso-PC); and 1-Stearoyl-2-lyso-sn-glycero-3-phosphocholine (S-Lyso-PC)

Lipids for Reducing Immunogenicity

Examples of lipids for reducing immunogenicity include polymeric compounds and polymer-lipid conjugates.

Examples of lipids for reducing immunogenicity include pegylated lipids having polyethyleneglycol (PEG) regions.

The PEG regions can be of any molecular mass. In some embodiments, a PEG region can have a molecular mass of 200, 300, 350, 400, 500, 550, 750, 1000, 1500, 2000, 3000, 3500, 4000 or 5000 Da.

Examples of lipids for reducing immunogenicity include compounds having a methoxypolyethyleneglycol region.

Examples of lipids for reducing immunogenicity include compounds having a carbonyl-methoxypolyethyleneglycol region.

Examples of lipids for reducing immunogenicity include compounds having a multi-branched PEG region.

Examples of lipids for reducing immunogenicity include compounds having a polyglycerine region.

Examples of lipids for reducing immunogenicity include polymeric lipids such as DSPE-mPEG, DMPE-mPEG, DPPE-mPEG, and DOPE-mPEG.

Examples of lipids for reducing immunogenicity include PEG-phospholipids and PEG-ceramides.

Cationic Lipids

Examples of cationic lipids include cationic HEDC compounds as described in US 2013/0330401 A1. Some examples of cationic lipids are given in US 2013/0115274 A1.

Lipid Compositions

In some embodiments, a composition can contain the ionizable compound A6, the structural lipid cholesterol, the stabilizer lipids DOPC and DOPE, and the lipid for reducing immunogenicity DPPE-mPEG. In certain embodiments, compound A6 can be 15 to 25 mol % of the composition; the cholesterol, DOPC, and DOPE combined can be 75 to 85 mol % of the composition; and DPPE-mPEG can be 5 mol % of the composition.

In one embodiment, compound A6 can be 25 mol % of the composition; cholesterol can be 30 mol % of the composition, DOPC can be 20 mol % of the composition, DOPE can be 20 mol % of the composition; and DPPE-mPEG(2000) can be 5 mol % of the composition.

Nanoparticles

Embodiments of this invention can provide liposome nanoparticle compositions. The ionizable molecules of this invention can be used to form liposome compositions, which can have one or more bilayer structures of lipid-like molecules.

A nanoparticle composition can have one or more of the ionizable molecules of this invention in a liposomal structure, a bilayer structure, a micelle, a lamellar structure, or a mixture thereof.

In some embodiments, a composition can include one or more liquid vehicle components. A liquid vehicle suitable for delivery of active agents of this invention can be a pharmaceutically acceptable liquid vehicle. A liquid vehicle can include an organic solvent, or a combination of water and an organic solvent.

Embodiments of this invention can provide lipid nanoparticles having a size of from 10 to 1000 nm. In some embodiments, the liposome nanoparticles can have a size of from 10 to 150 nm.

Pharmaceutical Compositions

This invention further contemplates methods for distributing an active agent to an organ of a subject for treating fibrosis by administering to the subject a composition of this invention. Organs that can be treated include lung, liver, pancreas, kidney, colon, heart, bone marrow, skin, intestine, brain and eye.

In some embodiments, this invention provides methods for treating a lung fibrosis disease by administering to the subject a composition of this invention.

Examples of fibrosis disease include idiopathic lung fibrosis and liver cirrhosis.

In further aspects, this invention provides a range of pharmaceutical formulations.

A pharmaceutical formulation herein can include an active agent, as well as a drug carrier, or a lipid of this invention, along with a pharmaceutically acceptable carrier or diluent. In general, active agents of this description include siRNAs, active agents for fibrosis, as well as any small molecule drug.

A pharmaceutical formulation of this invention may contain one or more of each of the following: a surface active agent, a diluent, an excipient, a preservative, a stabilizer, a dye, and a suspension agent.

Some pharmaceutical carriers, diluents and components for a pharmaceutical formulation, as well as methods for formulating and administering the compounds and compositions of this invention are described in Remington's Pharmaceutical Sciences, 18th Ed., Mack Publishing Co., Easton, Penn. (1990).

Examples of preservatives include sodium benzoate, ascorbic acid, and esters of p-hydroxybenzoic acid.

Examples of surface active agents include alcohols, esters, sulfated aliphatic alcohols.

Examples of excipients include sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, and calcium carboxymethyl cellulose.

Examples of suspension agents include coconut oil, olive oil, sesame oil, peanut oil, soya, cellulose acetate phthalate, methylacetate-methacrylate copolymer, and ester phthalates.

Structures of Molecular Tails

A compound of this invention may have one or more lipophilic tails that contain one or more alkyl or alkenyl groups. Examples of lipophilic tails having alkenyl groups include C(14:1(5))alkenyl, C(14:1(9))alkenyl, C(16:1(7))alkenyl, C(16:1(9))alkenyl, C(18:1(3))alkenyl, C(18:1(5))alkenyl, C(18:1(7))alkenyl, C(18:1(9))alkenyl, C(18:1(11))alkenyl, C(18:1(12))alkenyl, C(18:2(9,12))alkenyl, C(18:2(9,11))alkenyl, C(18:3(9,12,15))alkenyl, C(18:3(6,9,12))alkenyl, C(18:3(9,11,13))alkenyl, C(18:4(6,9,12,15))alkenyl, C(18:4(9,11,13,15))alkenyl, C(20:1(9))alkenyl, C(20:1(11))alkenyl, C(20:2(8,11))alkenyl, C(20:2(5,8))alkenyl, C(20:2(11,14))alkenyl, C(20:3(5,8,11))alkenyl, C(20:4(5,8,11,14))alkenyl, C(20:4(7,10,13,16))alkenyl, C(20:5(5,8,11,14,17))alkenyl, C(20:6(4,7,10,13,16,19))alkenyl, C(22:1(9))alkenyl, C(22:1(13))alkenyl, and C(24:1(9))alkenyl. Some examples of tail structures are found at Donald Voet and Judith Voet, *Biochemistry*, 3rd Edition (2005), p. 383.

Some examples of lipophilic tails include the following structures:

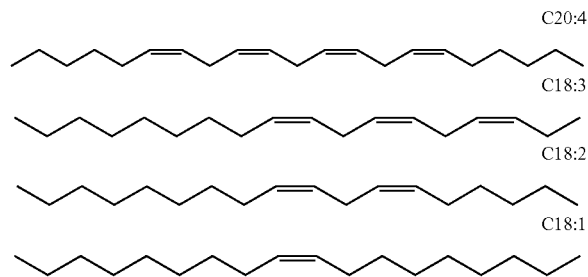

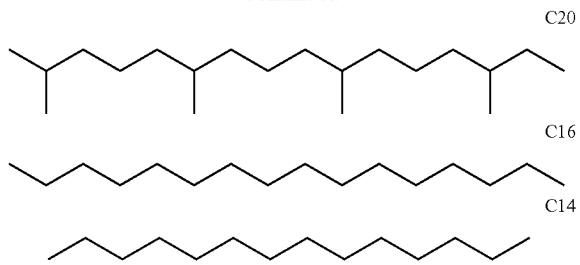

Any of these example structures of lipophilic tails may have one or more additional chemical branches.

Chemical Definitions

The term "alkyl" as used herein refers to a hydrocarbyl radical of a saturated aliphatic group, which can be of any length. An alkyl group can be a branched or unbranched, substituted or unsubstituted aliphatic group containing from 1 to 22 carbon atoms. This definition also applies to the alkyl portion of other groups such as, for example, cycloalkyl, alkoxy, alkanoyl, and aralkyl, for example.

As used herein, for example, a term such as "C(1-5)alkyl" includes C(1)alkyl, C(2)alkyl, C(3)alkyl, C(4)alkyl, and C(5)alkyl. Likewise, for example, the term "C(3-22)alkyl" includes C(1)alkyl, C(2)alkyl, C(3)alkyl, C(4)alkyl, C(5)alkyl, C(6)alkyl, C(7)alkyl, C(8)alkyl, C(9)alkyl, C(10)alkyl, C(11)alkyl, C(12)alkyl, C(13)alkyl, C(14)alkyl, C(15)alkyl, C(16)alkyl, C(17)alkyl, C(18)alkyl, C(19)alkyl, C(20)alkyl, C(21)alkyl, and C(22)alkyl.

As used herein, an alkyl group may be designated by a term such as Me (methyl, —$CH_3$), Et (ethyl, —$CH_2CH_3$), Pr (any propyl group), $^n$Pr (n-Pr, n-propyl), $^i$Pr (i-Pr, isopropyl), Bu (any butyl group), $^n$Bu (n-Bu, n-butyl), $^i$Bu (i-Bu, isobutyl), $^s$Bu (s-Bu, sec-butyl), and $^t$Bu (t-Bu, tert-butyl).

The term "alkenyl" as used herein refers to hydrocarbyl radical having at least one carbon-carbon double bond. An alkenyl group can be branched or unbranched, substituted or unsubstituted hydrocarbyl radical having 2 to 22 carbon atoms and at least one carbon-carbon double bond. An "alkenyl" group has one or more carbon-carbon double bonds.

The term "substituted" as used herein refers to an atom having one or more substitutions or substituents which can be the same or different and may include a hydrogen substituent. Thus, the terms alkyl, cycloalkyl, alkenyl, alkoxy, alkanoyl, and aryl, for example, refer to groups which can include substituted variations. Substituted variations include linear, branched, and cyclic variations, and groups having a substituent or substituents replacing one or more hydrogens attached to any carbon atom of the group.

In general, a compound may contain one or more chiral centers. Compounds containing one or more chiral centers may include those described as an "isomer," a "stereoisomer," a "diastereomer," an "enantiomer," an "optical isomer," or as a "racemic mixture." Conventions for stereochemical nomenclature, for example the stereoisomer naming rules of Cahn, Ingold and Prelog, as well as methods for the determination of stereochemistry and the separation of stereoisomers are known in the art. See, for example, Michael B. Smith and Jerry March, March's Advanced Organic Chemistry, 5th edition, 2001. The compounds and structures of this disclosure are meant to encompass all possible isomers, stereoisomers, diastereomers, enantiomers, and/or optical isomers that would be understood to exist for the specified compound or structure, including any mixture, racemic or otherwise, thereof.

This invention encompasses any and all tautomeric, solvated or unsolvated, hydrated or unhydrated forms, as well as any atom isotope forms of the compounds and compositions disclosed herein.

This invention encompasses any and all crystalline polymorphs or different crystalline forms of the compounds and compositions disclosed herein.

Abbreviations Used

DMAP—4-N,N-Dimethylaminopyridine
DCM—Dichloromethane
TEA—Triethylamine
EDC—1-(3-Dimethylaminopropyl)-3-ethylcarbodimimde hydrochloride
$Na_2SO_4$—Sodium sulphate
EtOAc—Ethyl acetate
DMF—N,N-Dimethylformide
ELSD—Evaporating Light Scattering Detector
NaCl—Sodium chloride
$K_2CO_3$—Potassium carbonate
MeOH—Methanol
TFA—Trifluoroacetic acid
DIEA—N,N-Diisopropylethylamine
$MgSO_4$—Magnesium sulphate
LCMS—Liquid chromatography-mass spectrometry
$NaHCO_3$—Sodium bicarbonate
$H_2O$—Water
HCl—Hydrochloride
KI—Potassium iodide
DMSO—Dimethyl sulfoxide
TBAF—tetra-N-Butylammonium fluoride
$NaBH_4$—Sodium borohydride
THF—Tetrahydrofuran
TBDMS—tert-Butyldimethylsilyl
LiOH—Lithium hydroxide
MeI—Methyl iodide
BOC—tert-Butyloxycarbonyl
Fmoc—Fluorenylmethyloxycarbonyl

EXAMPLES

Example 1: A Scheme for the Preparation of Compound A6 is Shown in FIG. 1

Intermediate 1: Linoleic acid (50.0 g, 178.30 mmol), N-Boc-diethanolamine (18.3 g, 89.10 mmol), and DMAP (1.1 g, 8.90 mmol) in an oven-dried flask (1 L) with a magnetic bar was added anhydrous DCM (400 mL). The mixture was stirred at ambient temperature for 2 minutes to a clear solution. EDC (35.9 g, 187.20 mmol) was then added and the mixture was stirred at room temperature overnight (17 hours). The reaction was finally quenched with saturated NaCl aqueous solution (400 mL) and extracted with DCM twice (400 mL, 100 mL). Organic layers were combined, dried over $Na_2SO_4$ (20 g), and filtered. The filtrate was concentrated under reduced pressure. The crude was dissolved in 50 mL DCM and purified by flash chromatography purification system (330 g silica gel column) using a gradient of hexane for 5 min, then 0-20% EtOAc/hexane for 40 min under the flow rate at 100 mL/min. The product fractions were collected and concentrated to yield Intermediate 1 (59 g, 91% yield) as a clear liquid. $^1$H nmr (400 MHz, $CDCl_3$) δ: 5.32-5.33 (8H, m, CH=), 4.13-4.17 (4H, m, $OCH_2$), 3.43-3.49 (4H, m, $NCH_2$), 2.73-2.74 (4H, m, =CH$CH_2$CH=), 2.03-2.28 (4H, m, $CH_2$CO), 2.00-2.01 (8H, m, =CH$CH_2$), 1.60-1.70 (4H, m, $CH_2CH_2$CO), 1.43 (9H, S, $C(CH_3)_3$), 1.28-1.31 (28H, m, $CH_2$), 0.85-0.86 (6H, m, $CH_3$).

Intermediate 2: Intermediate 1 (50.0 g, 68.50 mmol) in an oven-dried flask (1000 mL) with a magnetic bar was added anhydrous DCM (100 mL). The mixture was stirred for 2 minutes to a clear solution. TFA (100 mL) was then added and the mixture was stirred at ambient temperature for 2 hours. During stirring, the solution color turned from clear to red. Next, the reaction mixture was first concentrated using a rotavapor and washed with saturated $NaHCO_3$ aqueous solution (300 mL). The mixture was then extracted with DCM (2×200 mL) and the organic layers were combined, dried over $Na_2SO_4$ (20 g), filtered, and concentrated under reduced pressure to give an oily intermediate, which was then dissolved in anhydrous DCM (300 mL) and cooled down to 0° C. with an ice-water bath. Chloroacetyl chloride (6.0 mL, 75.30 mmol) followed by DIEA (14.3 mL, 82.20 mmol) were then added slowly at 0° C. After the addition was completed, the ice-water bath was removed and the mixture was stirred at ambient temperature for 2 hours. Next, the reaction mixture was concentrated using a rotavapor, washed with saturated $NaHCO_3$ aqueous solution (300 mL), and extracted with DCM (300 mL, 200 mL). The combined organic layers were then dried over $Na_2SO_4$ (20 g), filtered, and concentrated under reduced pressure. The crude was dissolved in 20 mL DCM and purified with a 330 g silica column using a gradient of hexane for 5 min, then 10% EtOAc/hexane for 20 min followed by 20% EtOAc/hexane for 20 min under the flow rate at 60 mL/min. The product fractions were collected and concentrated to yield Intermediate 2 (41.4 g, 82% yield) as a clear yellow liquid. $^1$H nmr (400 MHz, $CDCl_3$) δ: 5.35-5.33 (8H, m, CH=), 4.24-4.22 (4H, m, $OCH_2$), 4.14 (2H, s, $CH_2$Cl), 3.67-3.63 (4H, m, $NCH_2$), 2.78-2.75 (4H, m, =CH$CH_2$CH=), 2.30-2.29 (4H, m, $CH_2$CO), 2.03-2.05 (8H, m, =CH$CH_2$), 1.60-1.56 (4H, m, $CH_2CH_2$CO), 1.33-1.29 (28H, m, $CH_2$), 0.90-0.86 (6H, m, $CH_3$).

Compound A6: Intermediate 2 (5.0 g, 7.07 mmol), KI (1.2 g, 7.07 mmol) and cis-3,4-dihydroxy-pyrrolidine hydrochloride (1.3 g, 9.20 mmol) in an oven-dried vial (200 mL) with a magnetic bar was added anhydrous DMF (20 mL). The mixture was stirred at ambient temperature for 2 minutes to a clear solution. DIEA (3.0 mL, 9.91 mmol) was then added and the mixture was stirred at 30° C. for 2.5 hours. After removed the solvent by rotavapor under high vacuum, the residue was added with saturated $NaHCO_3$ solution (100 mL) and extracted with DCM (100 mL, 50 mL). The organic layers were then combined, dried over $Na_2SO_4$ (20 g), filtered, and concentrated under reduced pressure. The crude was dissolved in 5 mL DCM and purified with a 120 g silica column using a gradient of hexane for 5 min, then 0-50% EtOAc/hexane for 10 min followed by 50% EtOAc/hexane for 10 min, then with DCM for 5 min and followed by 5% MeOH/DCM for 30 min under the flow rate at 60 mL/min. The product fractions were collected and concentrated to yield Compound A6 (3.5 g, 64% yield) as a yellow liquid. $^1$H nmr (400 MHz, $CDCl_3$) δ: 5.34-5.29 (8H, m, CH=), 4.22-4.20

(6H, m, OCH$_2$, OCH), 3.59-3.49 (6H, m, NCH$_2$, COCH$_2$N), 2.95-2.74 (6H, m, =CHCH$_2$CH=, NCH$_2$), 2.30-2.29 (4H, m, CH$_2$CO), 2.05-2.03 (8H, m, =CHCH$_2$), 1.60 (4H, m, CH$_2$CH$_2$CO), 1.33-1.29 (28H, m, CH$_2$), 0.90-0.88 (6H, m, CH$_3$).

Figure 2:
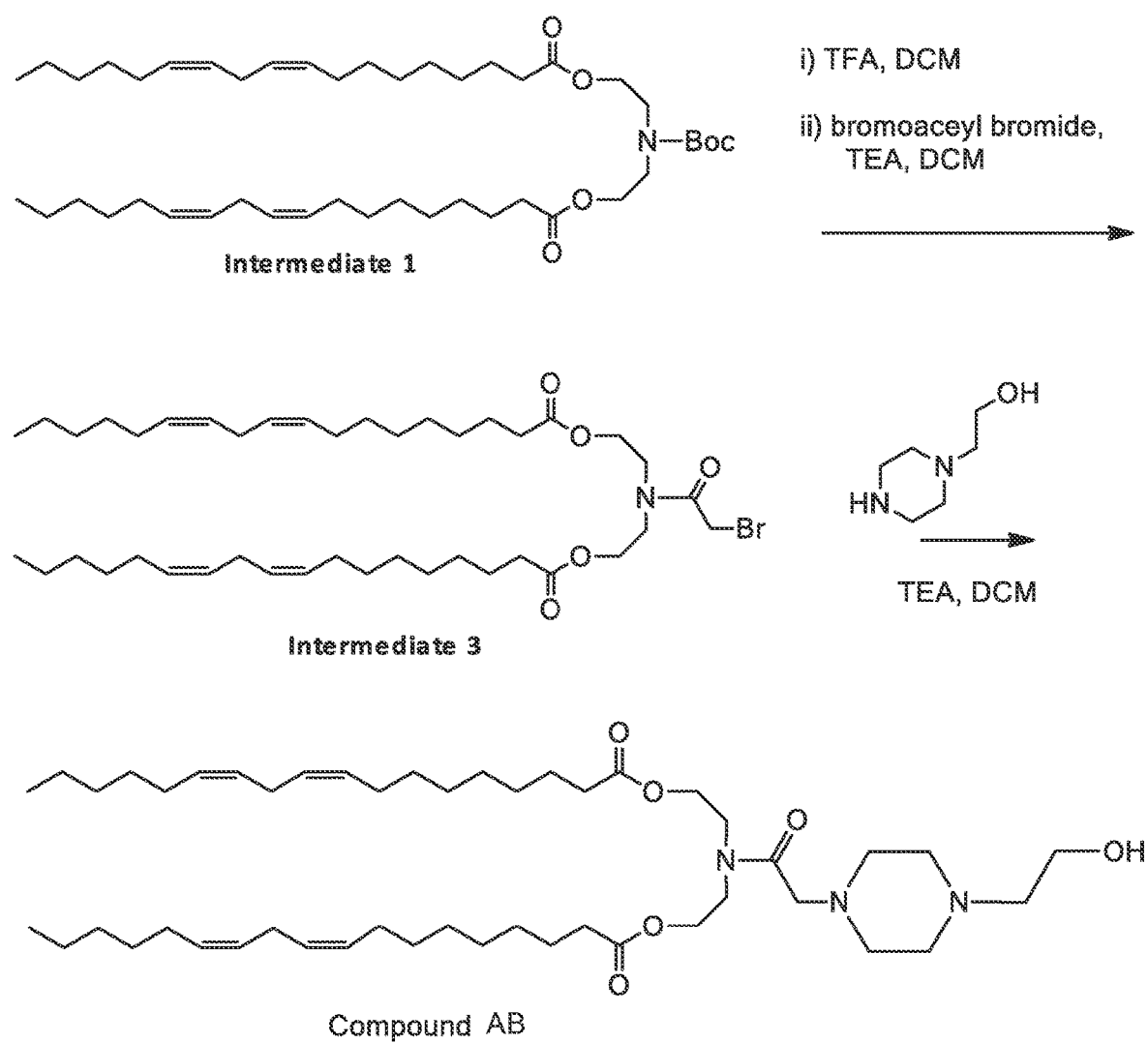
FIG. 2 shows a scheme for the preparation of Compound AB.

Example 2: A Scheme for the Preparation of Compound AB is Shown in FIG. 2

Intermediate 3: Intermediate 1 (10.0 g, 13.70 mmol) in an oven-dried flask (200 mL) with a magnetic bar was added anhydrous DCM (15 mL). The mixture was stirred for 2 minutes to a clear solution. TFA (15 mL) was then added and the mixture was stirred at ambient temperature for 2 hours. During stirring, the solution color turned from clear to red. Next, the reaction mixture was first concentrated using a rotavapor. Residue was diluted with DCM (~50 mL) and 10% K$_2$CO$_3$ (15 mL) was added and stirred for 10-15 minutes in an ice bath. pH of aqueous layer was checked to ensure pH>8. Mixture was then transferred to a separatory funnel & extracting with DCM (50 mL, 25 mL), dried over MgSO$_4$, filtered, and concentrated under reduced pressure to give an oily intermediate, which was then dissolved in anhydrous DCM (30 mL) and bromoacetyl bromide (1.2 mL, 13.70 mmol) followed by TEA (2.1 mL, 15.07 mmol) were then added slowly. After the addition was completed, the mixture was stirred at ambient temperature overnight. The reaction mixture was then concentrated using a rotavapor, washed with water (30 mL), and extracted with DCM (30 mL, 20 mL). The combined organic layers were then dried over MgSO$_4$, filtered, and concentrated under reduced pressure. The crude was dissolved in 20 mL DCM and purified with a 330 g silica column using a gradient of hexane for 0.5 min, then 0-20% EtOAc/hexane 30 min gradient followed by 30% EtOAc/hexane for 5 min under the flow rate at 130 mL/min. The product fractions were collected and concentrated to yield Intermediate 3 (8.1 g, 79% yield) as a clear yellow liquid. $^1$H nmr (400 MHz, CDCl$_3$) δ: 5.35-5.33 (8H, m, CH=), 4.24-422 (4H, m, OCH$_2$), 3.93 (2H, s, CH$_2$Br), 3.69-3.61 (4H, m, NCH$_2$), 2.78-2.74 (4H, m, =CHCH$_2$CH=), 2.32-2.28 (4H, m, CH$_2$CO), 2.06-2.02 (8H, m, =CHCH$_2$), 1.62-1.60 (4H, m, CH$_2$CH$_2$CO), 1.36-1.26 (28H, m, CH$_2$), 0.90-0.86 (6H, m, CH$_3$).

Compound AB: Intermediate 3 (460 mg, 0.61 mmol) and 1-piperazine-propanol (89 mg, 0.61 mmol) in an oven-dried vial (100 mL) with a magnetic bar was added anhydrous DCM (10 mL). The mixture was stirred at ambient temperature for 2 minutes to a clear solution. TEA (103 µL, 0.74 mmol) was then added and the mixture was stirred at ambient temperature overnight. After removed the solvent by a rotavapor under high vacuum, the residue was added with saturated 10% K$_2$CO$_3$ solution (50 mL) and extracted with DCM (50 mL, 25 mL). The organic layers were then combined, dried over MgSO$_4$, filtered, and concentrated under reduced pressure. The crude was purified by flash chromatography purification system. Material directly loaded onto a 24 g silica column and using a gradient of DCM for 3 min, then 0-8% MeOH/DCM for 7 min followed by 8% MeOH/DCM for 20 min under the flow rate at 25 mL/min. The product fractions were collected and concentrated to yield Compound AB (379 mg, 76% yield) as a yellow liquid. $^1$H nmr (400 MHz, CDCl$_3$) δ: 5.39-5.29 (8H, m, CH=), 4.22-4.21 (4H, m, OCH$_2$), 3.74-3.71 (2H, m, CH$_2$OH), 3.59-3.49 (4H, m, NCH$_2$), 3.23 (2H, s, COCH$_2$), 2.78-2.75 (2H, m, CH$_2$CH$_2$OH), 2.59-2.57 (8H, m, NCH$_2$CH$_2$N), 2.32-2.27 (4H, m, CHCH$_2$CH), 2.05-2.03 (8H, m, =CHCH$_2$CH$_2$), 1.60 (4H, m, CH$_2$CH$_2$CO), 1.33-1.29 (28H, m, CH$_2$), 0.90-0.88 (6H, m, CH$_3$).

Figure 3:
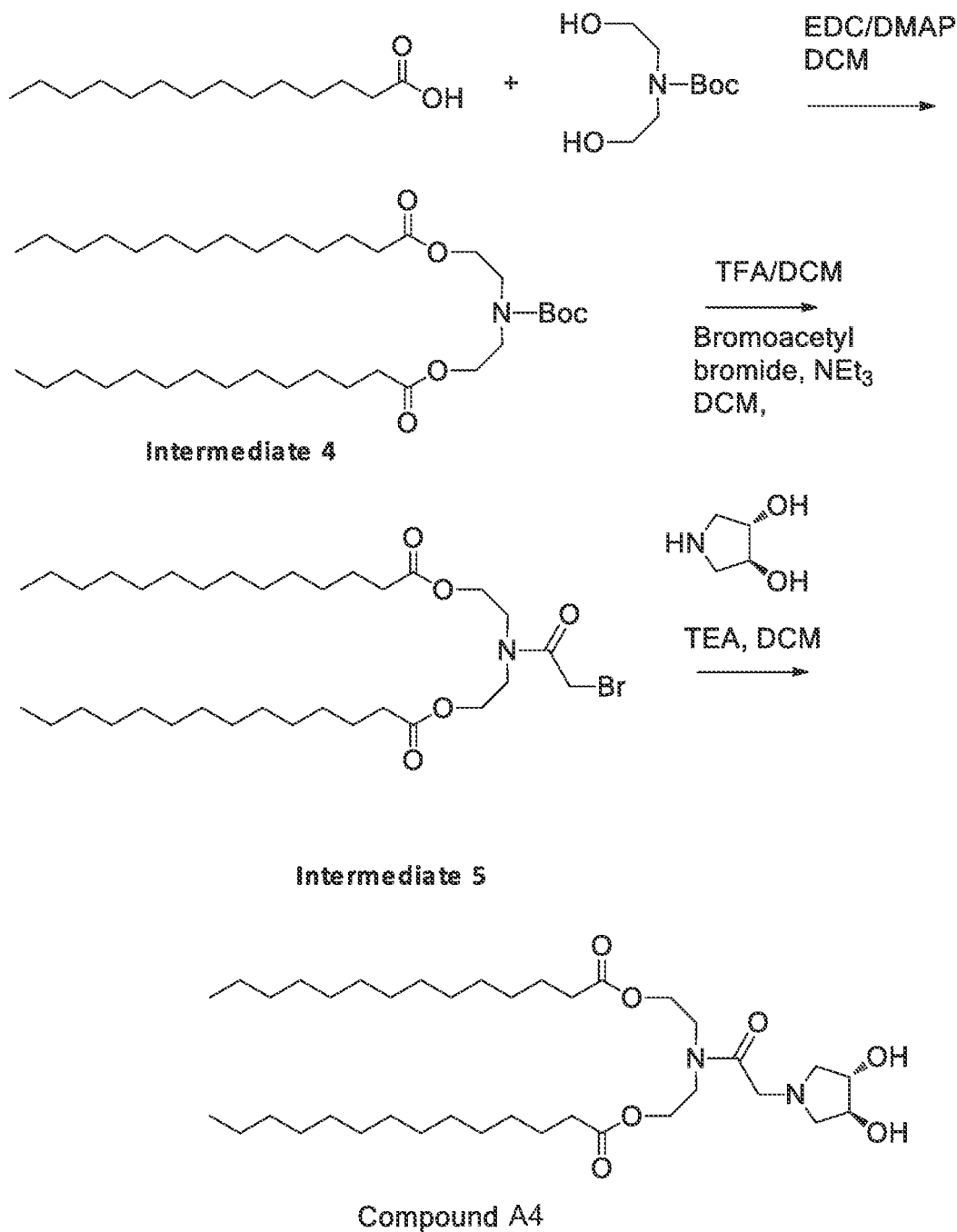
FIG. 3 shows a scheme for the preparation of Compound A4.

Example 3: A Scheme for the Preparation of Compound A4 is Shown in FIG. 3

Intermediate 4: Myristic acid (50.0 g, 218.90 mmol), N-Boc-diethanolamine (21.4 g, 218.90 mmol), and DMAP (3.8 g, 65.70 mmol) in an oven-dried flask (1 L) with a magnetic bar was added anhydrous DCM (300 mL). The mixture was stirred at ambient temperature for 2 minutes to a clear solution. EDC (44.0 g, 481.70 mmol) was then added and the mixture was stirred at room temperature overnight (17 hours). The reaction was finally quenched with saturated NaCl solution (400 mL) and extracted with DCM twice (400 mL, 100 mL). Organic layers were combined, dried over Na$_2$SO$_4$ (20 g), and filtered. The filtrate was concentrated under reduced pressure. The crude was dissolved in 50 mL DCM and purified by flash chromatography purification system (330 g silica gel column) using a gradient of 5-50% EtOAc/hexane for 40 min under the flow rate at 100 mL/min. The product fractions were collected and concentrated to yield Intermediate 4 (50.0 g, 71% yield) as a white solid. $^1$H nmr (400 MHz, CDCl$_3$) δ: 4.14-4.17 (4H, m, OCH$_2$), 3.44-3.50 (4H, m, NCH$_2$), 2.27-2.30 (4H, m, CH$_2$CO), 1.60-1.70 (4H, m, CH$_2$CH$_2$CO), 1.45 (9H, S, C(CH$_3$)), 1.20-1.25 (40H, m, CH$_2$), 0.81-0.88 (6H, m, CH$_3$).

Intermediate 5: Intermediate 4 (10.0 g, 16.00 mmol) in an oven-dried flask (200 mL) with a magnetic bar was added anhydrous DCM (15 mL). The mixture was stirred for 2 minutes to a clear solution. TFA (15.0 mL) was then added and the mixture was stirred at ambient temperature for 2 hours. The reaction mixture was first concentrated using a rotavapor and washed with 10% K$_2$CO$_3$ aqueous solution (100 mL). The mixture was then extracted with DCM (2×100 mL) and the organic layers were combined, dried over Na$_2$SO$_4$ (20 g), filtered, and concentrated under reduced pressure to give a residue, which was then dissolved in anhydrous DCM (50 mL) and cooled down to 0° C. with an ice-water bath. Triethylamine (2.5 mL, 17.60 mmol) followed by bromoacetyl bromide (1.4 mL, 16.00 mmol) were then added slowly at 0° C. After the addition was completed, the ice-water bath was removed and the mixture was stirred at ambient temperature for 2 hours. Next, the reaction mixture was concentrated using a rotavapor. The crude was dissolved in 10 mL DCM and purified with a 220 g silica column using a gradient of 0-50% EtOAc/hexane for 40 min under the flow rate at 60 mL/min. The product fractions were collected and concentrated to yield Intermediate 5 (8.2 g, 79% yield) as a pale yellow solid. $^1$H nmr (400 MHz, CDCl$_3$) δ: 4.23-4.24 (4H, m, OCH$_2$), 3.93 (2H, s, ClCH$_2$), 3.60-3.69 (4H, m, NCH$_2$), 2.28-2.30 (4H, m, CH$_2$CO), 1.57-1.59 (4H, m, CH$_2$CH$_2$CO), 1.24-1.27 (40H, m, CH$_2$), 0.85-0.89 (6H, m, CH$_3$).

Compound A4: Intermediate 5 (1.7 g, 2.57 mmol), (3S, 4S)-dihydroxypyrrolidine (0.3 g, 2.57 mmol) in an oven-dried vial (40 mL) with a magnetic bar was added anhydrous DCM (20 mL). The mixture was stirred at ambient temperature for 2 minutes to a clear solution. Triethylamine (0.4 mL, 2.57 mmol) was then added and the mixture was stirred at ambient temperature overnight (17 hours). After removed the solvent by rotavapor under high vacuum, the residue was added with 10% $K_2CO_3$ solution (50 mL) and extracted with DCM (2×50 mL). The organic layers were then combined, dried over $Na_2SO_4$ (20 g), filtered, and concentrated under reduced pressure. The crude was dissolved in 5 mL DCM and purified with a 24 g silica column using a gradient of 0-20% MeOH/DCM for 30 min under the flow rate at 20 mL/min. The product fractions were collected and concentrated to yield Compound A4 (870 mg, 51% yield) as a white solid. $^1$H nmr (400 MHz, $CDCl_3$) δ: 4.09-4.21 (6H, m, $OCH_2$, OCH), 3.56-3.63 (6H, m, $NCH_2$, $COCH_2N$), 3.28-3.29 (2H, m, $NCH_2CH$), 2.74-2.76 (2H, m, $NCH_2CH$), 2.26-2.30 (4H, m, $CH_2CO$), 1.59-1.60 (4H, m, $CH_2CH_2CO$), 1.24-1.27 (40H, m, $CH_2$), 0.85-0.88 (6H, m, $CH_3$).

Figure 4:
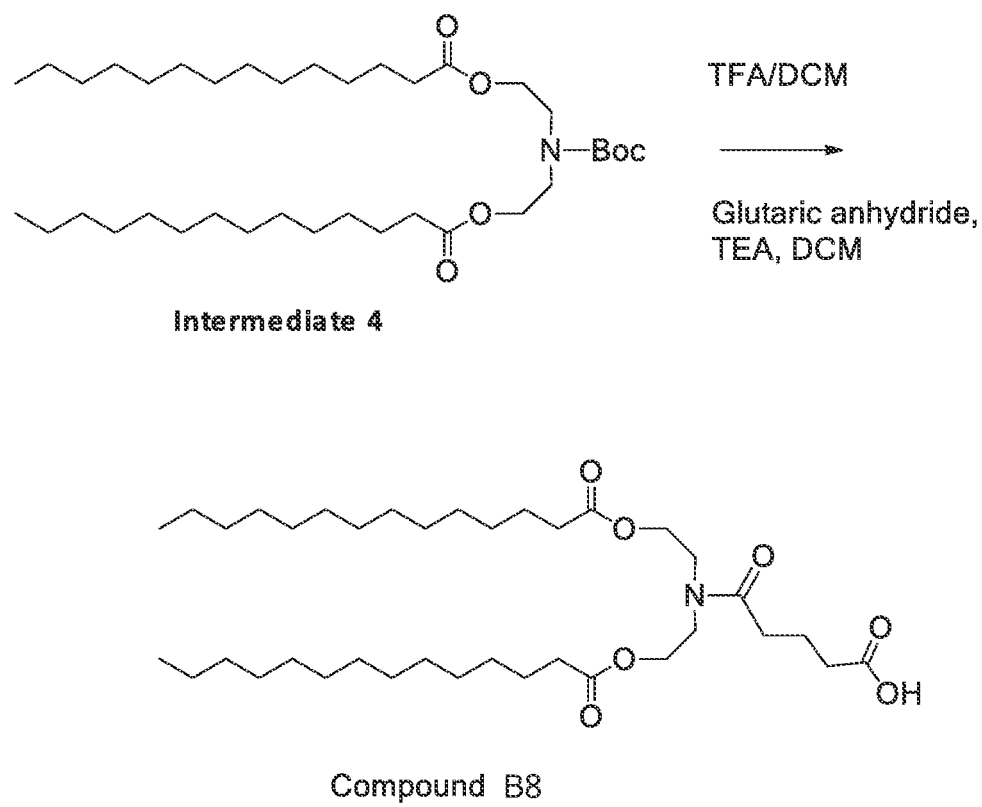
FIG. 4 shows a scheme for the preparation of Compound B8.

Example 4: A Scheme for the Preparation of Compound B8 is Shown in FIG. 4

Compound B8: Intermediate 4 (1.0 g, 1.60 mmol) in an oven-dried vial (20 mL) with a magnetic bar was added anhydrous DCM (3 mL). The mixture was stirred for 2 minutes to a clear solution. TFA (3 mL) was then added and the mixture was stirred at ambient temperature for 2 hours. The reaction mixture was first concentrated using a rotavapor and washed with 10% $K_2CO_3$ aqueous solution (20 mL). The mixture was then extracted with DCM (2×20 mL) and the organic layers were combined, dried over $Na_2SO_4$ (2 g), filtered, and concentrated under reduced pressure to give an intermediate, which was then dissolved in anhydrous DCM (7 mL). Glutaric anhydride (0.3 g, 2.40 mmol) followed by triethylamine (0.3 mL, 2.40 mmol) were then added at ambient temperature. The mixture was stirred at ambient temperature overnight (17 hours). Next, the reaction mixture was concentrated using a rotavapor. The crude was dissolved in 2 mL DCM and purified with a 24 g silica column using a gradient of 0-10% MeOH/DCM for 20 min under the flow rate at 25 mL/min. The product fractions were collected and concentrated to yield Compound B8 (667 mg, 65% yield) as a white solid. $^1$H nmr (400 MHz, $CDCl_3$) δ: 4.18-4.23 (4H, m, $OCH_2$), 3.59-3.62 (4H, m, $NCH_2$), 2.44-2.49 (4H, m, $CH_2CO$), 2.29-2.31 (4H, m, $CH_2CO$), 1.97-2.00 (4H, m, $CH_2CO$), 1.57-1.62 (8H, m, $CH_2CH_2CO$, $CH_2$), 1.26-1.31 (40H, m, $CH_2$), 0.87-0.89 (6H, m, $CH_3$).

Figure 5:
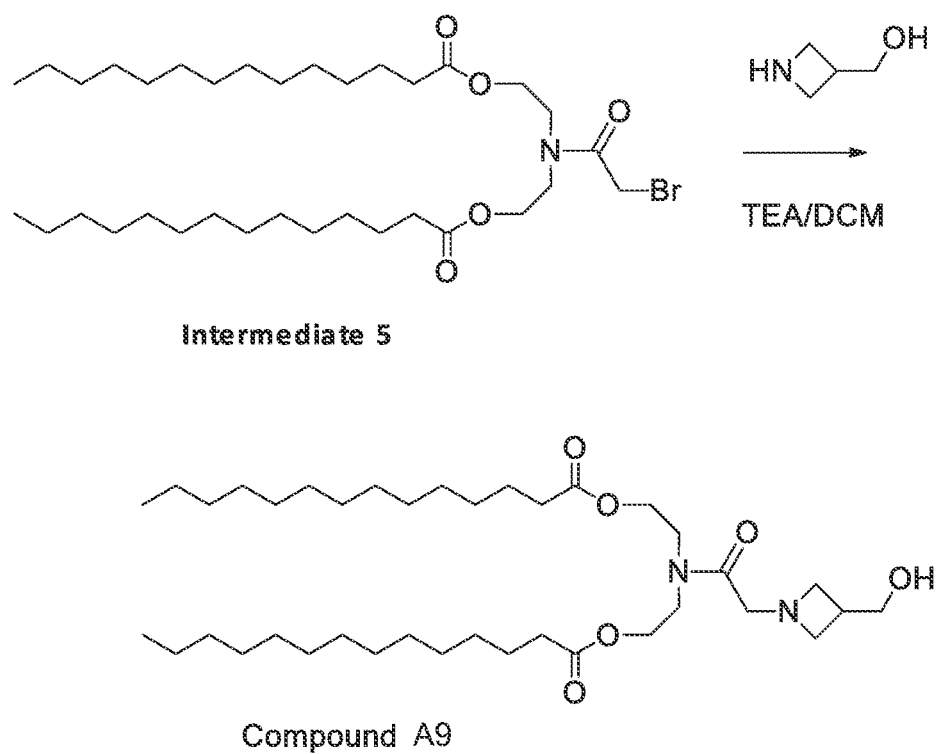
FIG. 5 shows a scheme for the preparation of Compound A9.

Example 5: A Scheme for the Preparation of Compound A9 is Shown in FIG. 5

Compound A9: Intermediate 5 (2.4 g, 3.72 mmol), 3-azetidineethanol hydrochloride (1.0 g, 8.09 mmol) in an oven-dried vial (40 mL) with a magnetic bar was added anhydrous DCM (20 mL) and DMSO (2 mL). The mixture was stirred at ambient temperature for 2 minutes to a clear solution. Triethylamine (1.6 mL, 11.12 mmol) was then added and the mixture was stirred at ambient temperature for 1 hours. The reaction was quenched with saturated 10% $K_2CO_3$ solution (100 mL) and extracted with DCM (2×50 mL). The organic layers were then combined, dried over $Na_2SO_4$ (20 g), filtered, and concentrated under reduced pressure. The crude was dissolved in 5 mL DCM and purified with a 40 g silica column using a gradient of 0-15% MeOH/DCM for 30 min under the flow rate at 20 mL/min. The product fractions were collected and concentrated to yield Compound A9 (1.2 g, 49% yield) as a pale yellow solid. $^1$H nmr (400 MHz, $CDCl_3$) δ: 4.18-4.21 (4H, m, $OCH_2$), 3.76-3.77 (2H, m, $CH_2OH$), 3.60-3.50 (4H, m, $NCH_2$), 3.46-3.47 (2H, m, $NCH_2$), 3.38 (2H, s, $COCH_2N$), 3.25-3.26 (2H, m, $NCH_2$), 2.64-2.70 (OH, m, CH), 2.28-2.31 (4H, m, $CH_2CO$), 1.59 (4H, m, $CH_2CH_2CO$), 1.24-1.26 (40H, m, $CH_2$), 0.85-0.87 (6H, m, $CH_3$).

Figure 6:
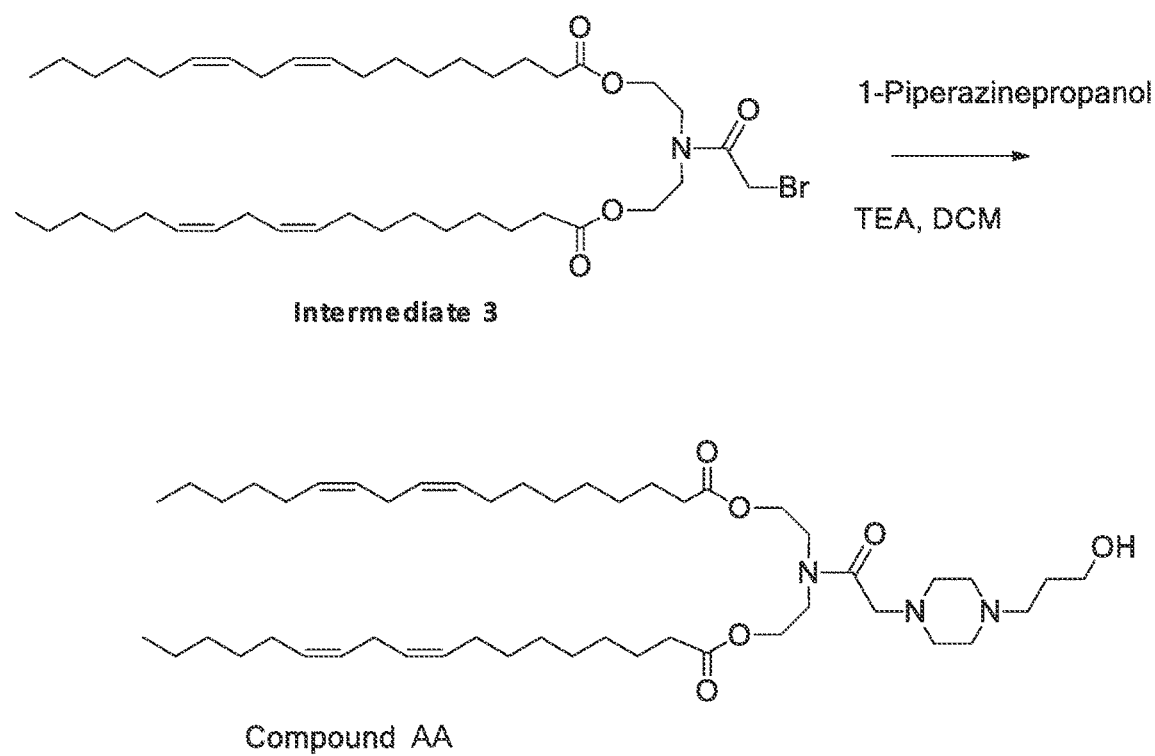
FIG. 6 shows a scheme for the preparation of Compound AA.

Example 6: A Scheme for the Preparation of Compound AA is Shown in FIG. 6

Compound AA: Intermediate 3 (460 mg, 0.61 mmol), 1-piperazinepropanol (88.5 m g, 0.61 mmol) in an oven-dried vial (40 mL) with a magnetic bar was added anhydrous DCM (10 mL). The mixture was stirred at ambient temperature for 2 minutes to a clear solution. Triethylamine (0.1 mL, 0.74 mmol) was then added and the mixture was stirred at ambient temperature overnight (17 hours). The reaction was quenched with 10% $K_2CO_3$ solution (50 mL) and extracted with DCM (2×50 mL). The organic layers were then combined, dried over $MgSO_4$ (5 g), filtered, and concentrated under reduced pressure. The crude was dissolved in 5 mL DCM and purified with a 12 g silica column using a gradient of 0-20% MeOH/DCM for 30 min under the flow rate at 20 mL/min. The product fractions were collected and concentrated to yield Compound AA (389 mg, 78% yield) as a colorless oil. $^1$H nmr (400 MHz, $CDCl_3$) δ: 5.29-5.34 (8H, m, CH=), 4.20-4.23 (4H, m, $OCH_2$), 3.58-3.80 (6H, m, $CH_2OH$ $NCH_2$), 3.21 (2H, s, $COCH_2N$), 2.75-2.78 (4H, m, =$CHCH_2CH$=), 2.35-2.65 (8H, m, $NCH_2$), 2.27-2.31 (4H, m, $CH_2CO$), 2.02-2.06 (8H, m, =$CHCH_2$), 1.70-1.73 (4H, m, $CH_2$), 1.59-1.61 (4H, m, $CH_2CH_2CO$), 1.25-1.36 (28H, m, $CH_2$), 0.87-0.90 (6H, m, $CH_3$).

Figure 7:
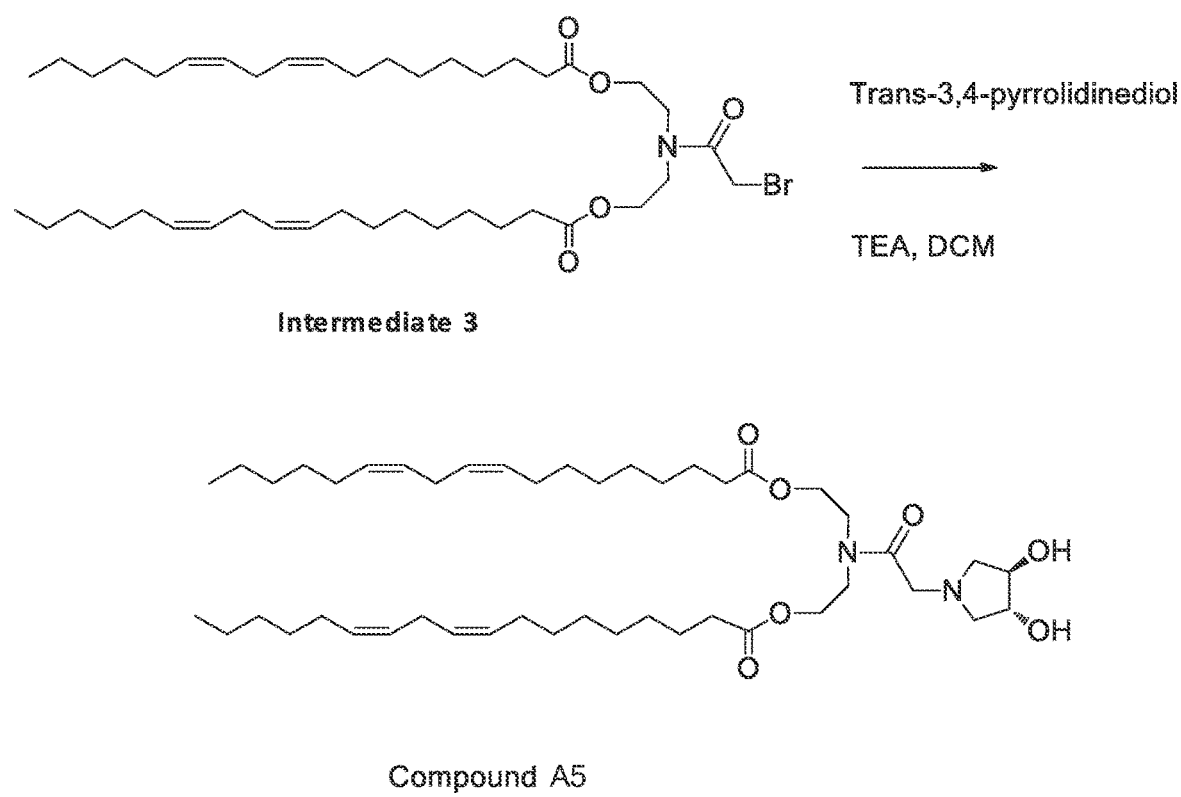
FIG. 7 shows a scheme for the preparation of Compound A5.

Example 7: A Scheme for the Preparation of Compound A5 is Shown in FIG. 7

Compound A5: Intermediate 3 (200 mg, 0.27 mmol), trans-3,4-pyrrolidinediol (28 mg, 0.27 mmol) in an oven-dried vial (40 mL) with a magnetic bar was added anhydrous DCM (10 mL) and DMSO (1 mL). The mixture was stirred at ambient temperature for 2 minutes to a clear solution. Triethylamine (50 mL, 0.32 mmol) was then added and the mixture was stirred at ambient temperature overnight (17 hours). The reaction was quenched with 10% $K_2CO_3$ solution (50 mL) and extracted with DCM (2×50 mL). The organic layers were then combined, dried over $MgSO_4$ (5 g), filtered, and concentrated under reduced pressure. The crude was dissolved in 5 mL DCM and purified with a 12 g silica column using a gradient of EtOAc for 5 min and 0-30% MeOH/DCM for 30 min under the flow rate at 20 mL/min. The product fractions were collected and concentrated to yield Compound A5 (389 mg, 78% yield) as a colorless liquid. $^1$H nmr (400 MHz, $CDCl_3$) δ: 5.29-5.39 (8H, m, CH=), 4.20-4.25 (4H, m, $OCH_2$), 4.10-4.11 (2H, m, CHOH), 3.55-3.62 (4H, m, $NCH_2$, $COCH_2N$), 3.28-3.31 (2H, m, $NCH_2$), 2.75-2.76 (6H, m, $NCH_2$, =$CHCH_2CH$=), 2.60 (2H, m, $NCH_2$), 2.27-2.32 (4H, m, $CH_2CO$), 2.02-2.06 (8H, m, =CHCH$_2$), 1.60-1.61 (4H, m, CH$_2$CH$_2$CO), 1.25-1.36 (28H, m, CH$_2$), 0.87-0.90 (6H, m, CH$_3$).

Figure 8:
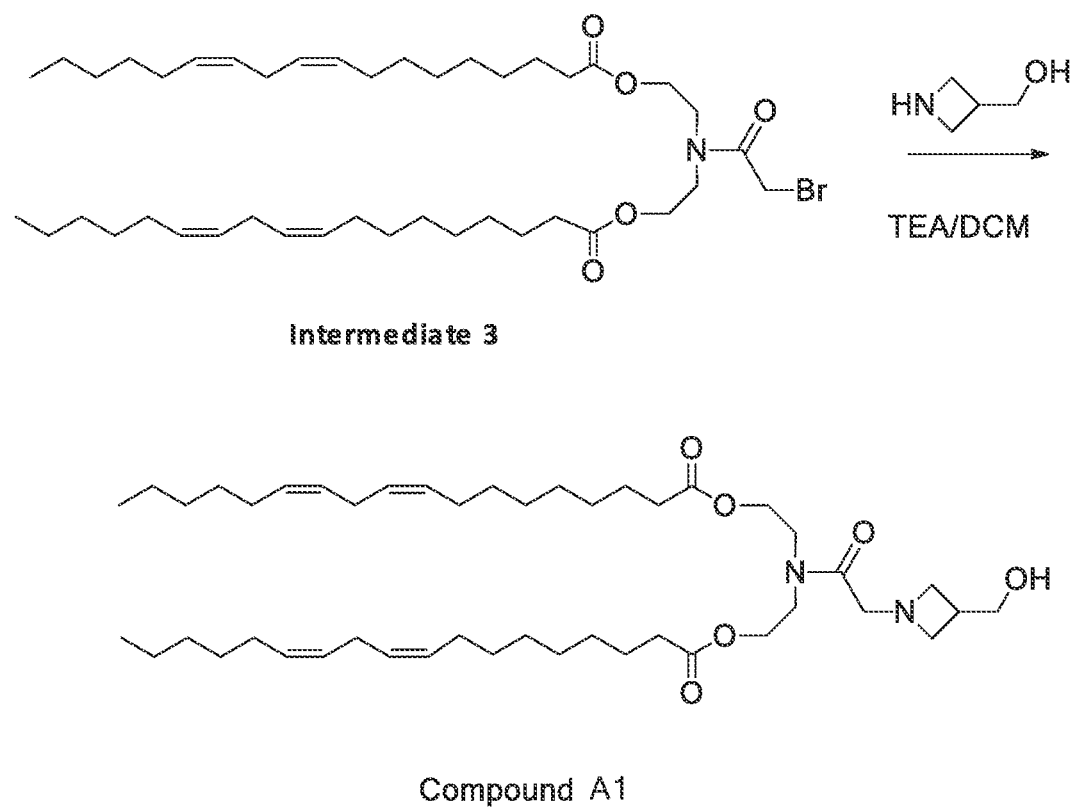
FIG. 8 shows a scheme for the preparation of Compound A1.

Example 8: A Scheme for the Preparation of Compound A1 is Shown in FIG. 8

Compound A1: Intermediate 3 (1.0 g, 1.33 mmol), 3-azetidinemethanol hydrochloride (0.3 g, 2.66 mmol) in an oven-dried vial (40 mL) with a magnetic bar was added anhydrous DCM (20 mL) and DMSO (2 mL). The mixture was stirred at ambient temperature for 2 minutes to a clear solution. Triethylamine (0.7 mL, 5.32 mmol) was then added and the mixture was stirred at ambient temperature overnight (17 hours). The reaction was quenched with 10% K$_2$CO$_3$ solution (50 mL) and extracted with DCM (2×50 mL). The organic layers were then combined, dried over Na$_2$SO$_4$ (5 g), filtered, and concentrated under reduced pressure. The crude was dissolved in 5 mL DCM and purified with a 24 g silica column using a gradient of 0-50% EtOAc/hexane for 10 min and 0-15% MeOH/DCM for 20 min under the flow rate at 20 mL/min. The product fractions were collected and concentrated to yield Compound A1 (130 mg, 13% yield) as a pale yellow liquid. $^1$H nmr (400 MHz, CDCl$_3$) δ: 5.29-5.35 (8H, m, CH=), 4.18-4.21 (4H, m, OCH$_2$), 3.40-3.77 (12H, m, CH$_2$OH, CONCH$_2$, NCH$_2$, NCH$_2$CO), 2.74-2.77 (5H, m, CH, =CHCH$_2$CH=), 2.28-2.30 (4H, m, CH$_2$CO), 2.04-2.05 (8H, m, =CHCH$_2$), 1.60 (4H, m, CH$_2$CH$_2$CO), 1.24-1.26 (40H, m, CH$_2$), 0.85-0.87 (6H, m, CH$_3$).

Figure 9:
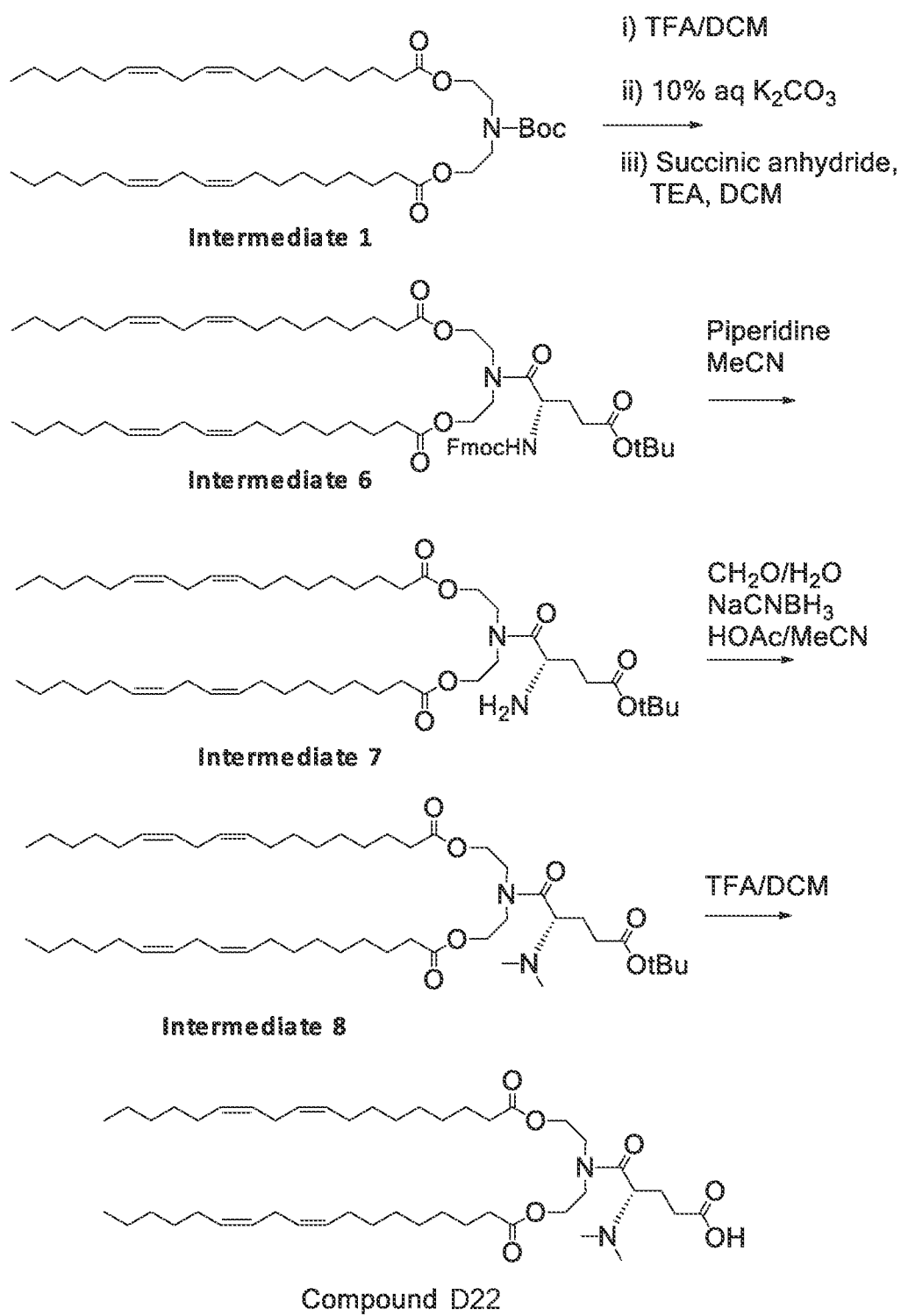
FIG. 9 shows a scheme for the preparation of Compound D22.

Example 9: A Scheme for the Preparation of Compound D22 is Shown in FIG. 9

Intermediate 6: Intermediate 1 (11.4 g, 15.6 mol) in an oven-dried flask (100 mL) with a magnetic bar was added anhydrous DCM (10 mL). The mixture was stirred for 2 minutes to a clear solution. TFA (10.0 mL) was then added and the mixture was stirred at ambient temperature for 2 hours. During stirring, the solution color turned from clear to red. Next, the reaction mixture was first concentrated using a rotavapor and washed with 10% K$_2$CO$_3$ aqueous solution (50 mL). The mixture was then extracted with DCM (2×50 mL) and the organic layers were combined, dried over Na$_2$SO$_4$ (5 g), filtered, and concentrated under reduced pressure to give an oily residue, which was then dissolved in anhydrous DCM (100 mL) and added Fmoc-Glu(OtBu)-OH (6.6 g, 15.60 mmol), EDC (4.5 g, 23.40 mmol) and DMAP (0.4 g, 3.10 mmol) in sequence. The mixture was stirred at ambient temperature overnight (17 hours). Next day, the reaction mixture was washed with brine (100 mL), extracted with DCM (2×50 mL), dried over Na$_2$SO$_4$, filtered, and concentrated by rotavapor. The crude was dissolved in 5 mL DCM and purified with a 220 g silica column using a gradient of 0-50% EtOAc/hexane for 30 min under the flow rate at 50 mL/min. The product fractions were collected and concentrated to yield Intermediate 6 (8.3 g, 47% yield) as a clear liquid. $^1$H nmr (400 MHz, CDCl$_3$) δ: 7.75-7.76 (2H, d, J=6.4 Hz, ArH), 7.59 (2H, t, J=4.8 Hz, ArH), 7.38-7.41 (2H, m, ArH), 7.26-7.33 (2H, m, ArH), 5.62-5.64 (1H, d, J=6.8 Hz, COCH$_2$), 5.30-5.39 (8H, m, OCH$_2$, =CH), 4.76-4.79 (1H, m, COCH$_2$), 4.11-4.41 (6H, m, CH, OCH$_2$), 3.35-3.98 (6H, m, NCH$_2$), 2.74-2.78 (4H, m, =CHCH$_2$CH=), 2.25-2.36 (8H, m, CH$_2$, CH$_2$CO), 2.00-2.06 (8H, m, =CHCH$_2$), 1.54-1.77 (4H, m, CH$_2$CH$_2$CO), 1.45 (9H, s, O(CH$_3$)$_3$), 1.24-1.37 (28H, m, CH$_2$), 0.87-0.90 (6H, m, CH$_3$).

Intermediate 7: Intermediate 6 (4.3 g, 4.14 mmol) was dissolved in acetonitrile (18 mL) in an oven-dried vial (100 mL) with a magnetic bar, followed by adding piperidine (2 mL). The mixture was stirred at ambient temperature for 2 hours. Then solvent was removed under vacuum. The crude was dissolved in 5 mL DCM and purified with a 80 g silica column using a gradient of 0-5% MeOH/DCM for 30 min under the flow rate at 40 mL/min. The product fractions were collected and concentrated to yield Intermediate 7 (2.1 g, 64% yield) as a clear liquid. LC-MS analysis has confirmed the product—m/z of [M+H]$^+$=816.17.

Intermediate 8: To Intermediate 7 (2.1 g, 2.58 mol) in an oven-dried flask (100 mL) with a magnetic bar were added anhydrous acetonitrile (30 mL), sodium cyanoborohydride (0.9 g, 1.48 mmol), formaldehyde (37% in water, 50 mL) and acetic acid (2 mL) in sequence. The mixture was stirred for 2 hours. The reaction mixture was then treated with 10% K$_2$CO$_3$ aqueous solution (50 mL) and extracted with DCM (2×50 mL). The organic layers were combined, dried over Na$_2$SO$_4$ (5 g), filtered, and concentrated under reduce pressure. The crude was dissolved in 2 mL DCM and purified with a 40 g silica column using a gradient of 0-10% MeOH/DCM for 30 min under the flow rate at 30 mL/min. The product fractions were collected and concentrated to yield Intermediate 8 (1.4 g, 64% yield) as a clear liquid. LC-MS analysis has confirmed the product—m/z of [M+H]$^+$=844.22.

Compound D22: Intermediate 8 (1.4 g, 1.66 mmol) in an oven-dried flask (100 mL) with a magnetic bar was added anhydrous DCM (10 mL). The mixture was stirred for 2 minutes to a clear solution. TFA (10.0 mL) was then added and the mixture was stirred at ambient temperature for 4 hours. Then the reaction mixture was concentrated with a rotavapor. The crude was dissolved in 5 mL DCM and purified with a 24 g silica column using a gradient of 0-15% MeOH/DCM for 25 min under the flow rate at 25 mL/min. The product fractions were collected and concentrated to yield Lp09 (200 mg, 15% yield) as a clear liquid. $^1$H nmr (400 MHz, CDCl$_3$) δ: 5.30-5.39 (8H, m, OCH$_2$, =CH), 4.59-4.61 (1H, m, COCHN), 4.23-4.34 (4H, m, OCH$_2$), 3.54-3.77 (4H, m, NCH$_2$), 2.90 (6H, s, NCH$_3$), 2.76 (4H, t, J=5.2 Hz, =CHCH$_2$CH=), 2.50-2.55 (2H, m, CH$_2$CO), 2.31-2.34 (4H, m, CH$_2$CO), 2.22-2.27 (2H, m, CH$_2$), 2.03-2.07 (8H, m, =CHCH$_2$), 1.59-1.60 (4H, m, CH$_2$CH$_2$CO), 1.26-1.37 (28H, m, CH$_2$), 0.88-0.90 (6H, m, CH$_3$).

Figure 10:
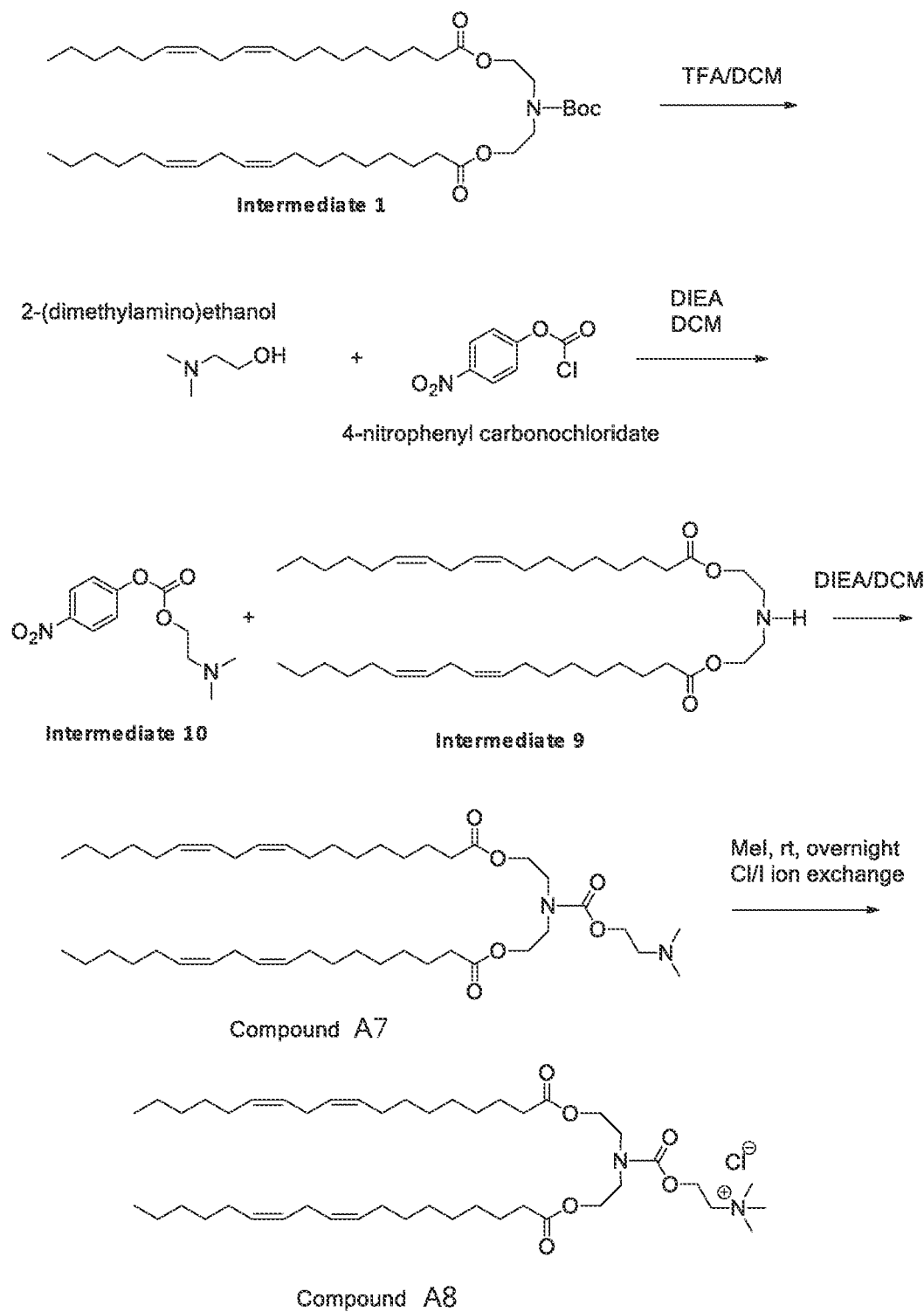
FIG. 10 shows a scheme for the preparation of Compounds A7 and A8.

Example 10: A Scheme for the Preparation of Compounds A7 and A8 is Shown in FIG. 10

Intermediate 9: Intermediate 1 (1.0 g, 1.37 mmol) in an oven-dried flask (100 mL) with a magnetic bar was added anhydrous DCM (10 mL). The mixture was stirred for 2 minutes to a clear solution. TFA (10.0 mL) was then added and the mixture was stirred at ambient temperature for 2 hours. During stirring, the solution color turned from clear to red. Next, the reaction mixture was first concentrated using a rotavapor and washed with 10% K$_2$CO$_3$ aqueous solution (50 mL). The mixture was then extracted with DCM (2×50 mL) and the organic layers were combined, dried over Na$_2$SO$_4$ (5 g), filtered, and concentrated under reduced pressure to give Intermediate 9 as an oil, which was then used without further purification.

Intermediate 10: To 2-(dimethylamino)ethan-1-ol (0.1 mL, 1.39 mmol) in anhydrous DCM (10 mL) was added 4-nitrophenyl carbonochloridate (0.3 g, 1.39 mmol) followed by DIEA (0.5 mL, 2.76 mmol). The mixture was stirred at ambient temperature overnight (17 hours) to give the Intermediate 10 solution, which was used directly without further purification.

Compound A7: Intermediate 9 was dissolved in DCM (10 mL) and transferred into solution of Intermediate 10 in a flask. The mixture was stirred at ambient temperature overnight (17 hours). Next day, the reaction mixture was concentrated using a rotavapor. The crude was dissolved in 2 mL of DCM and purified with a 24 g silica column using a gradient of 0-50% EtOAc/hexane for 10 min, 2-20% MeOH/DCM for 20 min under the flow rate at 25 mL/min. The product fractions were collected and concentrated to yield Compound A7 (540 mg, 54% yield) as a clear yellow liquid. $^1$H nmr (400 MHz, CDCl$_3$) δ: 5.30-5.40 (8H, m, CH=), 4.20-4.40 (6H, m, OCH$_2$), 3.45-3.55 (6H, m, NCH$_2$), 2.75-2.78 (4H, m, =CHCH$_2$CH=), 2.25-2.30 (10H, m, NCH$_3$, CH$_2$CO), 2.03-2.05 (8H, m, =CHCH$_2$), 1.56-1.60 (4H, m, CH$_2$CH$_2$CO), 1.29-1.33 (28H, m, CH$_2$), 0.86-0.90 (6H, m, CH$_3$).

Compound A8: Compound A7 (160 mg, 0.22 mmol) was added to methyl iodide (2 mL) in an oven-dried vial (20 mL) with a magnetic bar. The mixture was stirred at ambient temperature for 2 hours. Next, methyl iodide was removed under vacuum. The crude was dissolved in 1 mL DCM and purified with a 12 g silica column using a gradient of 2-20% MeOH/DCM for 30 min under the flow rate at 20 mL/min. The product fractions were collected and performed iodide to chloride anion exchange using resin Amberst 26. The resulting solution was finally concentrated under reduced pressure to give Compound A8 (100 mg, 59% yield) as a clear liquid. $^1$H nmr (400 MHz, CDCl$_3$) δ: 5.29-5.34 (8H, m, CH=), 4.60-4.65 (2H, m, OCH$_2$), 4.10-4.20 (6H, m, NCH$_2$, OCH$_2$), 3.50-3.55 (13H, m, NCH$_3$, NCH$_2$), 2.75-2.78 (4H, m, =CHCH$_2$CH=), 2.25-2.30 (4H, m, CH$_2$CO), 2.02-2.06 (8H, m, =CHCH$_2$), 1.59-1.61 (4H, m, CH$_2$CH$_2$CO), 1.25-1.36 (28H, m, CH$_2$), 0.87-0.90 (6H, m, CH$_3$).

Figure 11:
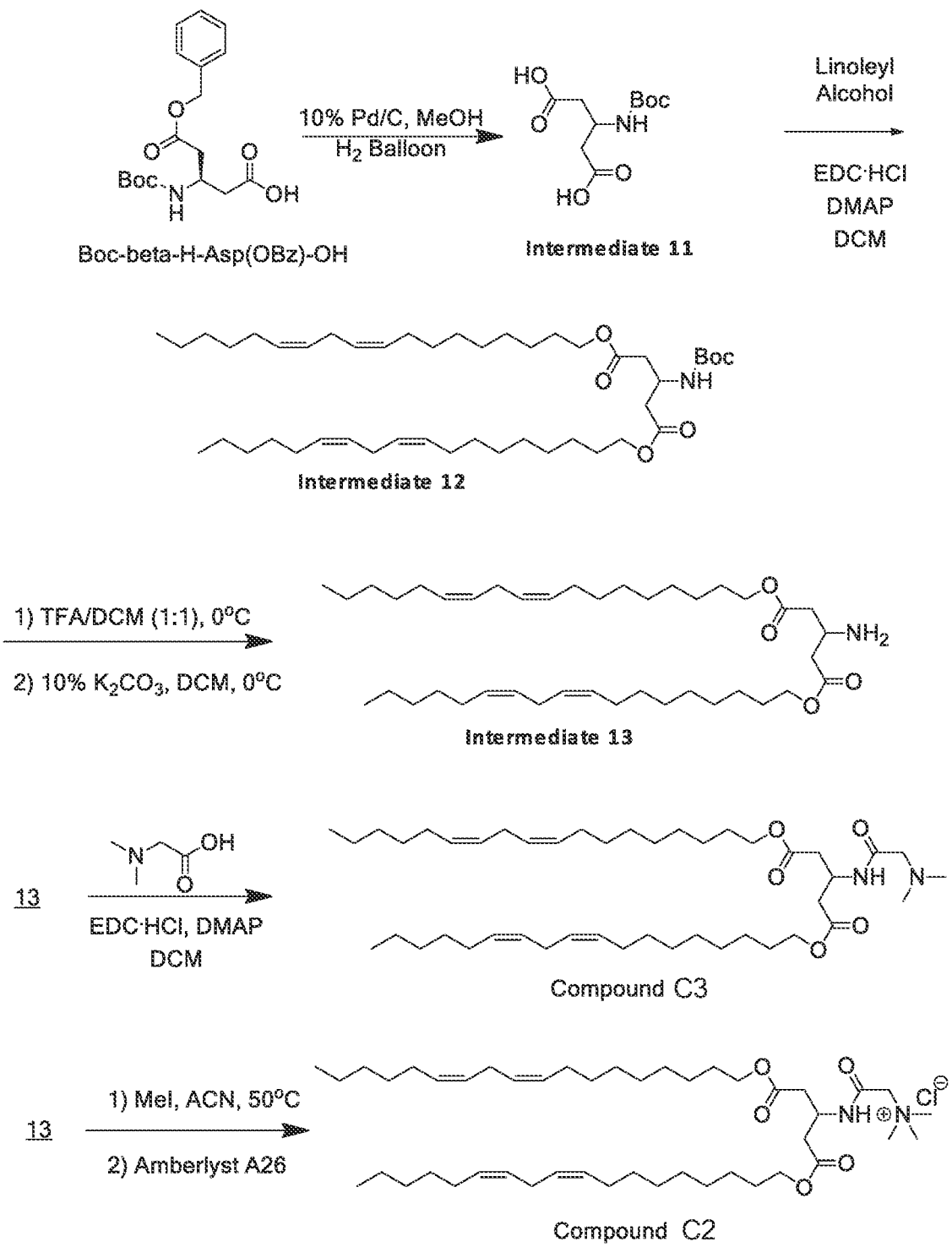
FIG. 11 shows a scheme for the preparation of Compounds C3 and C2.

Example 11: A Scheme for the Preparation of Compounds C3 and C2 is Shown in FIG. 11

Intermediate 11: Boc-beta-H-Asp(OBz)-OH (35.0 g, 10.20 mmol) was dissolved in MeOH (45 mL) in a round-bottomed flask flushed with Argon gas. 10% Pd/C (350 mg) was added and the flask was flushed with Argon gas once again. Next, all air was removed via vacuum pump and a balloon filled with hydrogen gas was attached. Reaction mixture was allowed to stir for ~2 hours at ambient temperature. The hydrogen balloon was removed and the mixture was then filtered out Pd/C catalyst through a pad of celite, followed by rinsing with copious amounts of MeOH. The filtrate was finally concentrated by a rotavap to yield Intermediate 11 (2.5 g, 100% yield), which was used without further purification.

Intermediate 12: Intermediate 11 (2.5 g, 10.11 mmol), EDC (5.8 g, 30.30 mmol), and DMAP (494 mg, 4.04 mmol) in an oven-dried flask (200 mL) with a magnetic bar was added anhydrous DCM (50 mL). The mixture was stirred at ambient temperature for ~5 minutes to a clear solution. Linoleyl alcohol (6.5 g, 24.20 mmol) was then added and the mixture was stirred at room temperature overnight. The reaction was finally quenched with H$_2$O (50 mL) and extracted with DCM twice (2×50 mL). Organic layers were combined, dried over MgSO$_4$, and filtered. The filtrate was concentrated under reduced pressure. The crude purified by flash chromatography purification system (80 g silica gel column) using a gradient of hexane for 2 min, then 0-25% EtOAc/hexane for 15 min, then 25% EtOAc/hexane for 5 min, then 75% EtOAc/hexane for 5 min under the flow rate at 60 mL/min. The product fractions were collected and concentrated to yield Intermediate 12 (7.0 g, 93% yield) as a clear liquid. $^1$H nmr (400 MHz, CDCl$_3$) δ: 5.38-5.31 (8H, m, CH=), 4.28 (1H, bs, NH), 4.08-4.05 (4H, m, OCH$_2$), 2.78-2.75 (4H, m, =CHCH$_2$CH=), 2.69-2.59 (4H, m, COCH$_2$N), 2.06-2.02 (4H, m, CH$_2$CH$_2$CH), 1.62-1.58 (4H, m, CH$_2$CH$_2$O), 1.43 (9H, s, C(CH$_3$)$_3$), 1.35-1.26 (36H, m, CH$_2$), 0.90-0.86 (6H, m, CH$_3$).

Intermediate 13: Intermediate 12 (2.3 g, 3.09 mmol) was dissolved in DCM (20 mL) and cooled in an ice-bath. TFA (20 mL) was added and the mixture was allowed to stir for ~1 hour under a blanket of argon gas. Afterwards, material was concentrated in vacuo. The residue was dissolved in DCM (20 mL) and then 10% K$_2$CO$_3$ (20 mL) was added. After stirred the mixture in an ice bath for ~½ hour, it was partitioned, checking the pH of the aqueous to ensure it was basic. The turbid aqueous layer was extracted with DCM (3×20 mL). The combined organic layers was added MgSO$_4$, stirred once again in the ice bath for ~20 minutes, and filtered. The filtrate, Intermediate 13, was then carried forward without any further refinement (2.0 g, assumed quantitative yield).

Compound C3: N,N-Dimethyl glycine HCl salt (260 mg, 1.86 mmol), EDC (447 mg, 2.33 mmol), and DMAP (38 mg, 0.31 mmol) in an oven-dried flask (50 mL) with a magnetic bar was added anhydrous DCM (15 mL). The mixture was stirred at ambient temperature for ~5 minutes. Intermediate 13 (1.0 g, 1.55 mmol) was then added and the mixture was stirred at room temperature overnight. The reaction was finally quenched with H$_2$O (50 mL) and extracted with DCM twice (2×50 mL). Organic layers were combined, dried over MgSO$_4$, and filtered. The filtrate was concentrated under reduced pressure. The crude purified by flash chromatography purification system (40 g silica gel column) using a gradient of hexane for 1 min, then 0-50% EtOAc/hexane for 25 min, then 50% EtOAc/hexane for 5 min under the flow rate at 40 mL/min. The product fractions were collected and concentrated to yield Lp12 (890 mg, 79% yield) as a clear liquid. $^1$H nmr (400 MHz, CDCl$_3$) δ: 7.76-7.74 (1H, d, NH), 5.40-5.30 (8H, m, CH=), 4.28 (OH, m, CHN), 4.08-4.05 (4H, m, OCH$_2$), 2.92 (2H, s, COCH$_2$N), 2.78-2.75 (4H, m, =CHCH$_2$CH=), 2.73-2.62 (4H, m, COCH$_2$N), 2.27 (6H, s, N(CH$_3$)$_2$), 2.06-2.02 (4H, m, CH$_2$CH$_2$CH), 1.62-1.58 (4H, m, CH$_2$CH$_2$O), 1.43 (9H, s, C(CH$_3$)$_3$), 1.35-1.26 (36H, m, CH$_2$), 0.90-0.86 (6H, m, CH$_3$).

Compound C2: Compound C3 (890 mg, 1.22 mmol) was dissolved in acetonitrile (9 mL) and iodomethane (1 mL) was added. Vial was flushed with argon gas and allowed to stir at 50° C. overnight. Next day, the reaction mixture was concentrated in vacuo and purified by flash chromatography purification system (40 g silica gel column) using a gradient of DCM for 2 min, then 0-8% MeOH/DCM for 20 min, then 8% MeOH/DCM for 5 min under the flow rate at 40 mL/min. The product fractions were collected and concentrated and subjected to Amberlyst A26 Anion Exchange resin to yield Compound C2 (623 mg, 66% yield) as oil. $^1$H nmr (400 MHz, CDCl$_3$) δ: 9.69-9.66 (1H, d, NH), 5.40-5.30 (8H, m, CH=), 4.67 (1H, m, CHN), 4.57 (2H, s, COCH$_2$N), 4.08-4.05 (4H, m, OCH$_2$), 3.43 (9H, s, N(CH$_3$)$_3$), 2.78-2.75 (4H, m, =CHCH$_2$CH=), 2.73-2.62 (4H, m, COCH$_2$N), 2.06-2.02 (4H, m, CH$_2$CH$_2$CH), 1.62-1.58 (4H, m. CH$_2$CH$_2$O), 1.43 (9H, s, C(CH$_3$)$_3$), 1.35-1.26 (36H, m, CH$_2$), 0.90-0.86 (6H, m, CH$_3$).

Figure 12:
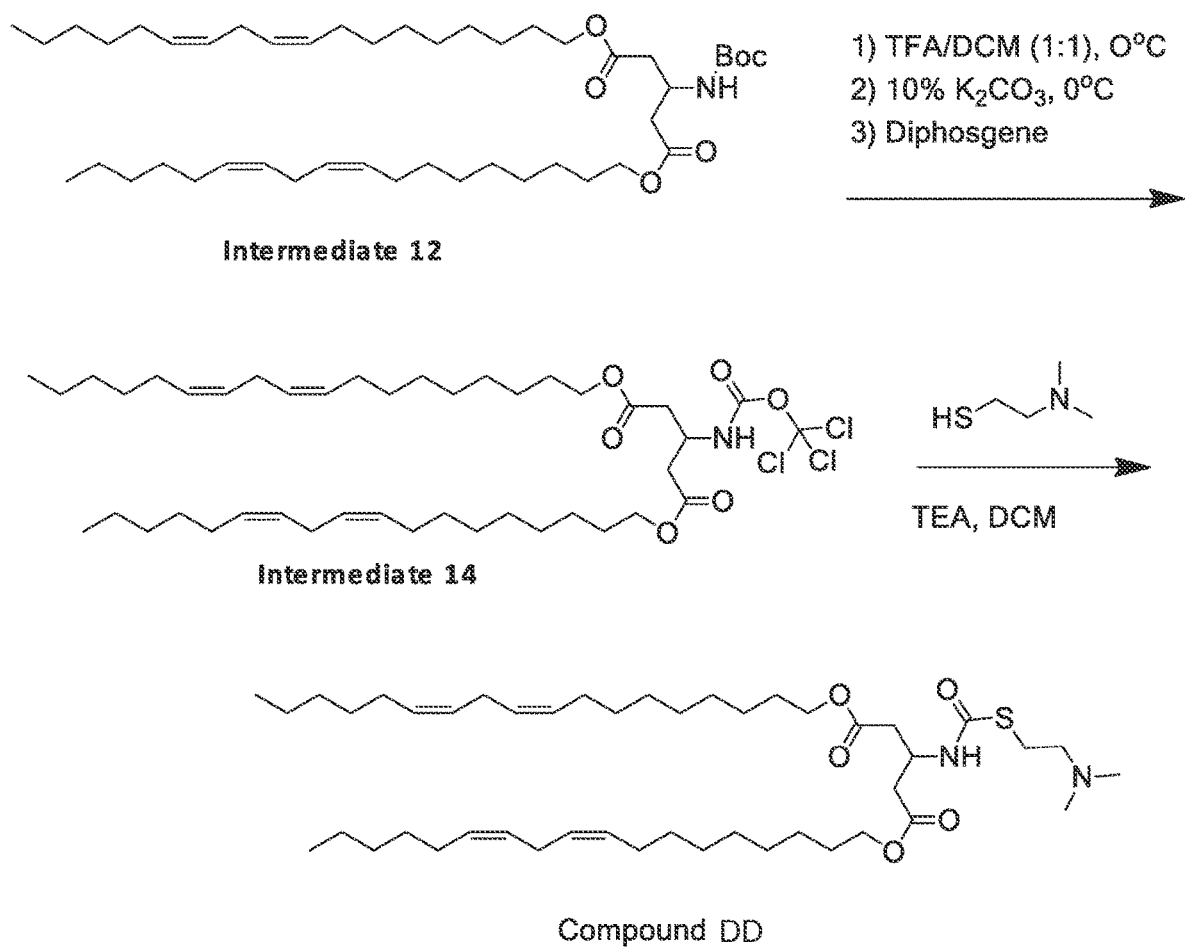
FIG. 12 shows a scheme for the preparation of Compound DD.

Example 12: A Scheme for the Preparation of Compound DD is Shown in FIG. 12

Intermediate 14: Intermediate 12 (4.4 g, 5.93 mmol) was dissolved in DCM (20 mL) and cooled in an ice-bath. TFA (20 mL) was added and the mixture was allowed to stir for ~1 hour under a blanket of Argon gas. The reaction mixture was then concentrated in vacuo. The residue was dissolved in DCM (20 mL) and then 10% K$_2$CO$_3$ (20 mL) was added. After stirred the mixture in an ice bath for ~½ hour, it was partitioned, checking the pH of the aqueous to ensure it was basic. The turbid aqueous layer was extracted with DCM (3×20 mL). The combined organic layers was added MgSO$_4$, stirred once again in the ice bath for ~20 minutes, and filtered. The filtrate was then added diphosgene (1.1 mL, 8.90 mmol). The reaction mixture was allowed to stir overnight at ambient temperatures under a blanket of argon gas. Next day, DCM and excess diphosgene were removed in vacuo. The residue, Intermediate 14, was dried fully before carrying forward without any further refinement (4.6 g, assumed quantitative yield).

Compound DD: 2-(Dimethylamino) ethanethiol HCl salt (2.1 g, 14.90 mmol) was suspended in DCM (25 mL) and added to Intermediate 14 (2.3 g, 2.97 mmol) in DCM (25 mL). TEA (2.7 mL, 19.30 mmol) was added slowly to the mixture. Reaction was allowed to stir overnight at ambient temperature under a blanket of argon gas. Next day, the reaction mixture was diluted with DCM (100 mL) and washed with H$_2$O (100 mL) followed by 10% K$_2$CO$_3$ (100 mL). Back-extraction was performed for both aqueous washes with DCM (2×40 mL). The organic layers were combined, dried with MgSO$_4$, filtered, and concentrated in vacuo. The crude was purified by flash chromatography purification system (80 g silica gel column) using a gradient of 10% EtOAc/hexane for 3 min, then 10-100% EtOAc/hexane for 15 min, then EtOAc for 5 minutes under the flow rate at 60 mL/min. The product fractions were collected and concentrated to yield Compound DD (300 mg, 39% yield) as a clear liquid. $^1$H nmr (400 MHz, CDCl$_1$) δ: 6.53-6.51 (1H, d, NH), 5.34-5.30 (8H, m, CH=), 4.57 (1H, m, CHN), 4.08-4.05 (4H, m, OCH$_2$), 2.75-2.68 (2H, m, SCH$_2$CH$_2$), 2.78-2.75 (4H, m, =CH—CH$_2$CH=), 2.73-2.62 (4H, m, COCH$_2$N), 2.30-2.25 (2H, m, SCH$_2$CH$_2$) 2.15 (6H, s, N(CH$_3$)$_2$), 2.06-2.02 (4H, m, CH$_2$CH$_2$CH), 1.62-1.58 (4H, m, CH$_2$CH$_2$O), 1.43 (9H, s, C(CH$_3$)$_3$), 1.35-1.26 (36H, m, CH$_2$), 0.90-0.86 (6H, m, CH$_3$).

Figure 13:
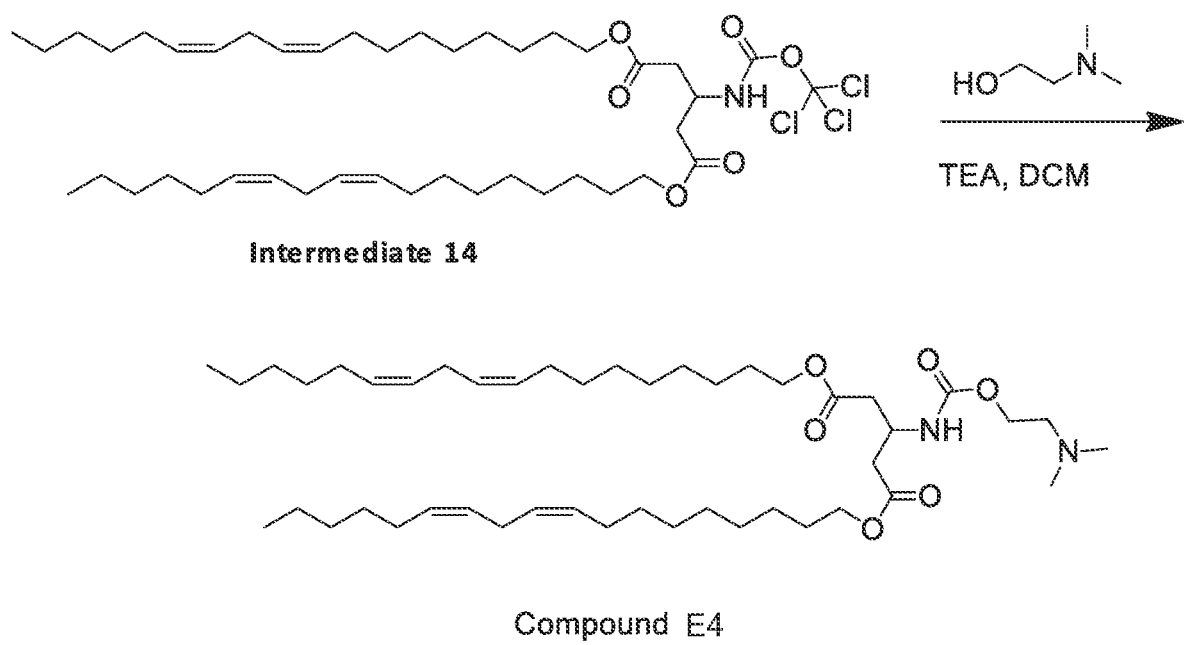
FIG. 13 shows a scheme for the preparation of Compound E4.

Example 13: A Scheme for the Preparation of Compound E4 is Shown in FIG. 13

Compound E4: Intermediate 14 (6.4 g, 8.22 mmol) was suspended in DCM (75 mL) in a round bottom flask (500 mL) with a magnetic stir bar. 2-(Dimethylamino) ethanol (4.1 mL, 41.1 mmol) followed by TEA (7.4 mL, 53.4 mmol) was added slowly to the mixture. Reaction was allowed to stir overnight at ambient temperature under a blanket of argon gas. Next day, the reaction mixture was diluted with DCM (100 mL) and washed with H$_2$O (100 mL) followed by 10% K$_2$CO$_3$ (100 mL). Back-extraction was performed for both aqueous washes with DCM (2×40 mL). The organic layers were combined, dried with MgSO$_4$, filtered, and concentrated in vacuo. The crude was purified by flash chromatography purification system (80 g silica gel column) using a gradient of 10% EtOAc/hexane for 3 min, then 10-100% EtOAc/hexane for 15 min, then EtOAc for 5 minutes under the flow rate at 60 mL/min. The product fractions were collected and concentrated to yield Compound E4 (3.3 g, 53% yield) as a clear liquid. $^1$H nmr (400 MHz, CDCl$_3$) δ: 6.53-6.51 (1H, bs, NH), 5.40-5.20 (8H, m, CH=), 4.35 (1H, m, CHN), 4.20-4.10 (2H, m, COOCH$_2$), 4.10-4.00 (4H, m, COOCH$_2$), 2.78-2.75 (4H, m, =CHCH$_2$CH=), 2.73-2.62 (4H, m, COCH$_2$N), 2.60-2.50 (2H, m, OCH$_2$CH$_2$) 2.25 (6H, s, N(CH$_3$)$_2$), 2.06-2.02 (4H, m, CH$_2$CH$_2$CH), 1.62-1.58 (4H, m, CH$_2$CH$_2$O), 1.43 (9H, s, C(CH$_3$)$_3$), 1.35-1.26 (36H, m, CH$_2$), 0.90-0.86 (6H, m, CH$_3$).

Figure 14:
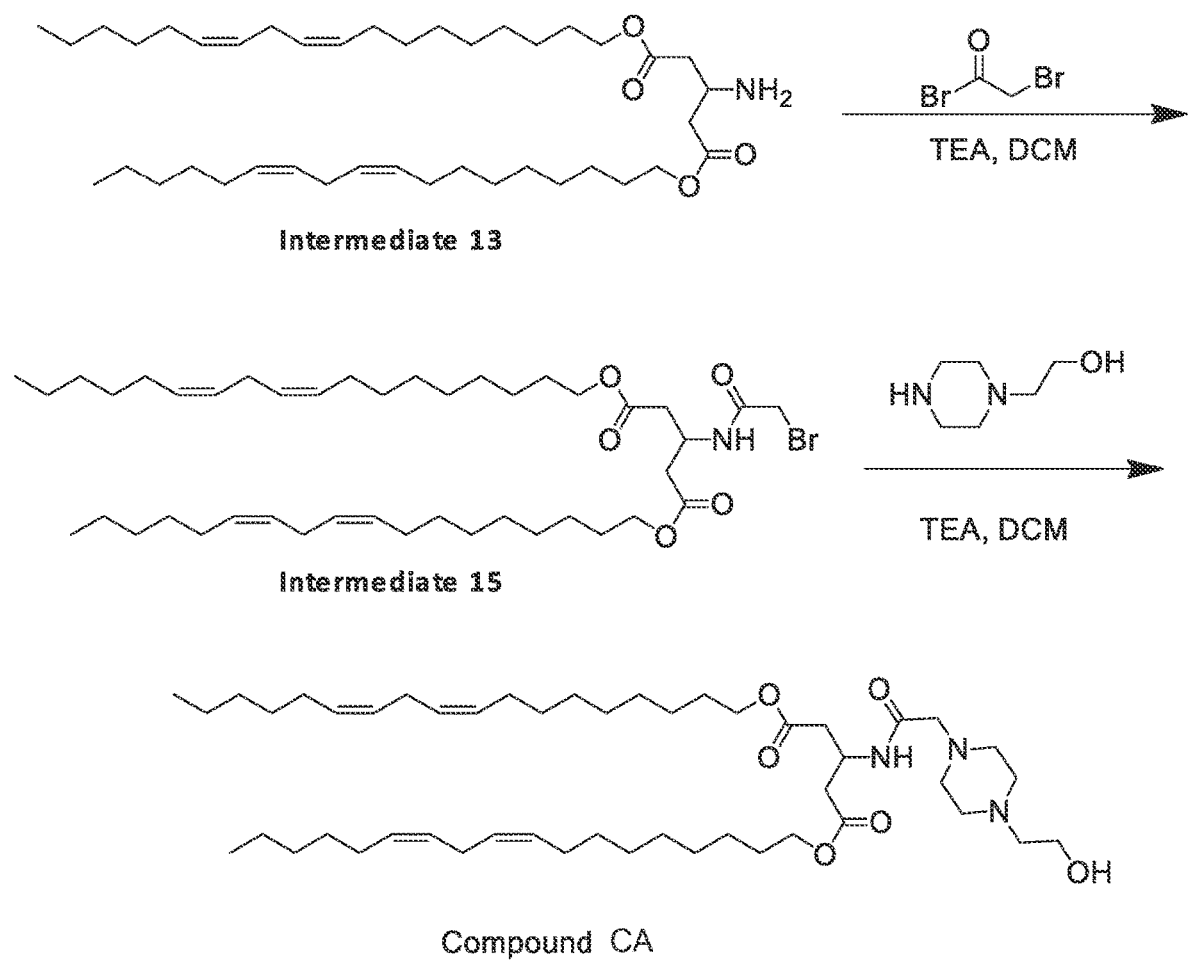
FIG. 14 shows a scheme for the preparation of Compound CA.

Example 14: A Scheme for the Preparation of Compound CA is Shown in FIG. 14

Intermediate 15: Intermediate 13 (1.0 g, 1.55 mmol) was dissolved in anhydrous DCM (15 mL) and bromoacetyl bromide (135 µL, 1.55 mmol) followed by TEA (238 µL, 1.71 mmol) were then added slowly. After the addition was completed, the mixture was stirred at ambient temperature overnight. Next day, the mixture was diluted with DCM (50 mL) and washed with H$_2$O (50 mL) and 10% K$_2$CO$_3$ (50 mL). Back-extraction was performed for both aqueous washes with DCM (2×25 mL). The organic layers were combined, dried with MgSO$_4$, filtered, and concentrated in vacuo. The crude was purified with a 40 g silica column on flash chromatography system equipped with ESLD detector using a gradient of hexane for 0.5 min, then 0-50% EtOAc/hexane 30 min gradient followed by 50% EtOAc/hexane for 5 min under the flow rate at 40 mL/min. The product fractions were collected and concentrated to yield Intermediate 15 (950 mg, 80% yield) as a colorless liquid. $^1$H nmr (400 MHz, CDCl$_3$) δ: 7.44-7.42 (OH, bs, NH), 5.40-5.32 (8H, m, CH=), 4.62-4.57 (1H, m, CHN), 4.10-4.07 (4H, m, COOCH$_2$), 3.83 (2H, s, CH$_2$Br), 2.78-2.75 (4H, m, =CH—CH$_2$CH=), 2.73-2.62 (4H, m, COCH$_2$N), 2.60-2.50 (2H, m, OCH$_2$CH$_2$) 2.25 (6H, s, N(CH$_3$)$_2$), 2.06-2.02 (4H, m, CH$_2$CH$_2$CH), 1.62-1.58 (4H, m, CH$_2$CH$_2$O), 1.43 (9H, s, C(CH$_3$)$_3$), 1.35-1.26 (36H, m, CH$_2$), 0.90-0.86 (6H, m, CH$_3$).

Compound CA: Intermediate 16 (400 mg, 0.52 mmol) was suspended in DCM (10 mL) in a round bottom flask (50 mL) with a magnetic stir bar and 1-(2-hydroxyethyl)piperazine (70 µL, 0.58 mmol) followed by TEA (91 µL, 0.65 mmol) was added. Mixture was stirred overnight at ambient temperature under a blanket of argon gas. Next day, the mixture was diluted with DCM (25 mL) and washed with H₂O (25 mL) followed by 10% K₂CO₃ (25 mL). Back-extraction was performed for both aqueous washes with DCM (2×25 mL). The organic layers were combined, dried with MgSO₄, filtered, and concentrated in vacuo. The crude purified by flash chromatography purification system (40 g silica gel column) using a DCM for 1 min, then 10% MeOH/DCM for 15 min under the flow rate at 40 mL/min. The product fractions were collected and concentrated to yield Compound CA (400 mg, 94% yield) as a clear liquid. ¹H nmr (400 MHz, CDCl₃) δ: 7.82-7.80 (1H, bs, NH), 5.40-5.29 (8H, m, CH═), 4.61-4.57 (1H, m, CHN), 4.07-4.04 (4H, m, COOCH₂), 3.63-3.61 (2H, m, CH₂CH₂OH), 2.97 (2H, s, COCH₂N), 2.78-2.75 (4H, m, ═CHCH₂CH═), 2.73-2.62 (4H, m, COCH₂N), 2.62-2.59 (2H, m, NCH₂CH₂OH), 2.59-2.50 (8H, m, N(CH₃)₂N), 2.06-2.02 (8H, m, CH₂CH₂CH), 1.62-1.58 (4H, m, CH₂CH₂O), 1.35-1.26 (32H, m, CH₂), 0.90-0.86 (6H, m, CH₃).

Figure 15:
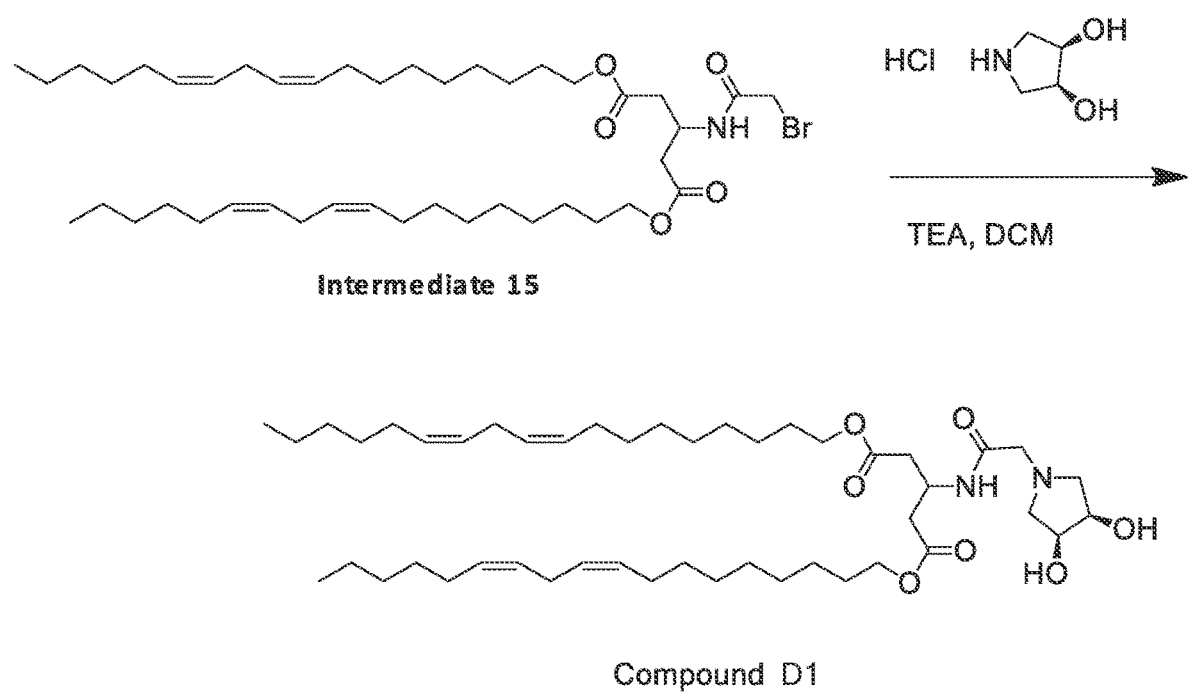
FIG. 15 shows a scheme for the preparation of Compound D1.

Example 15: A Scheme for the Preparation of Compound D1 is Shown in FIG. 15

Compound D1: Intermediate 15 (500 mg, 0.653 mmol) was suspended in DCM (8.5 mL) in a scintillation vial with a magnetic stir bar. Cis-pyrrolidine-3,4-diol HCl salt (100 mg, 0.72 mmol) in DMSO (1 mL) was added followed by TEA (229 µL, 1.64 mmol). The mixture was stirred overnight at ambient temperature under a blanket of argon gas. Next day, the mixture was diluted with DCM (25 mL) and washed with H₂O (25 mL) followed by 10% K₂CO₃ (25 mL). Back-extraction was performed for both aqueous washes with DCM (2×10 mL). The organic layers were combined, dried with MgSO₄, filtered, and concentrated in vacuo. The crude was purified by flash chromatography purification system (40 g silica gel column) using a DCM for 1 min, then 10% MeOH/DCM for 15 min under the flow rate at 40 mL/min. The product fractions were collected and concentrated to yield Compound D1 (437 mg, 87% yield) as a clear liquid. ¹H nmr (400 MHz, CDCl₃) δ: 7.82-7.80 (OH, bs, NH), 5.40-5.29 (8H, m, CH═), 4.61-4.57 (1H, m, CHN), 4.07-4.04 (4H, m, COOCH₂), 3.63-3.61 (2H, m, CH₂CH₂OH), 3.10 (2H, s, CH₂CHOH), 2.78-2.75 (4H, m, ═CHCH₂CH═), 2.73-2.62 (4H, m, COCH₂N), 2.62-2.58 (4H, m, N(CH₂)₂CHOH), 2.06-2.02 (8H, m, CH₂CH₂CH), 1.62-1.58 (4H, m, CH₂CH₂O), 1.35-1.29 (32H, m, CH₂), 0.90-0.86 (6H, m, CH₃).

Figure 16:
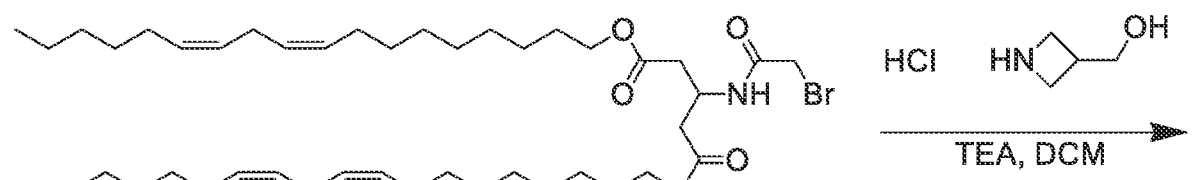
FIG. 16 shows a scheme for the preparation of Compound D7.
Figure 16:
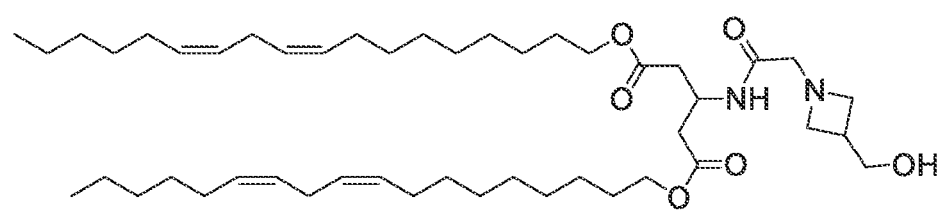

Example 16: A Scheme for the Preparation of Compound D7 is Shown in FIG. 16

Compound D7: Intermediate 15 (750 mg, 0.98 mmol) was suspended in DCM (10 mL) in a round bottom flask (50 mL) with a magnetic stir bar and Azetidine-3-yl-methanol HCl salt (149 mg, 1.18 mmol) was added followed by TEA (341 ILL, 2.45 mmol). The mixture was stirred overnight at ambient temperature under a blanket of argon gas. Next day, the mixture was diluted with DCM (25 mL) and washed with H₂O (25 mL) followed by 10% K₂CO₃ (25 mL). Back-extraction was performed for both aqueous washes with DCM (2×10 mL). The organic layers were combined, dried with MgSO₄, filtered, and concentrated in vacuo. The crude purified by flash chromatography purification system (40 g silica gel column) using a DCM for 2 min, then 10% MeOH/DCM for 20 min under the flow rate at 40 mL/min. The product fractions were collected and concentrated to yield Compound D7 (350 mg, 46% yield) as a clear liquid. ¹H nmr (400 MHz, CDCl₃) δ: 7.71-7.68 (1H, bs, NH), 5.35-5.33 (8H, m, CH═), 4.57-4.55 (1H, m, CHN), 4.07-4.04 (4H, m, COOCH₂), 3.77 (2H, s, COCH₂N), 3.38-3.35 (2H, m, CHCH₂OH), 3.20-3.00 (4H, m, N(CH₃)₂CH), 2.78-2.75 (4H, m, ═CHCH₂CH═), 2.73-2.62 (4H, m, COCH₂N), 2.06-2.02 (8H, m, CH₂CH₂CH), 1.62-1.58 (4H, m, CH₂CH₂O), 1.35-1.26 (32H, m, CH₂), 0.90-0.86 (6H, m, CH₃).

Figure 17:
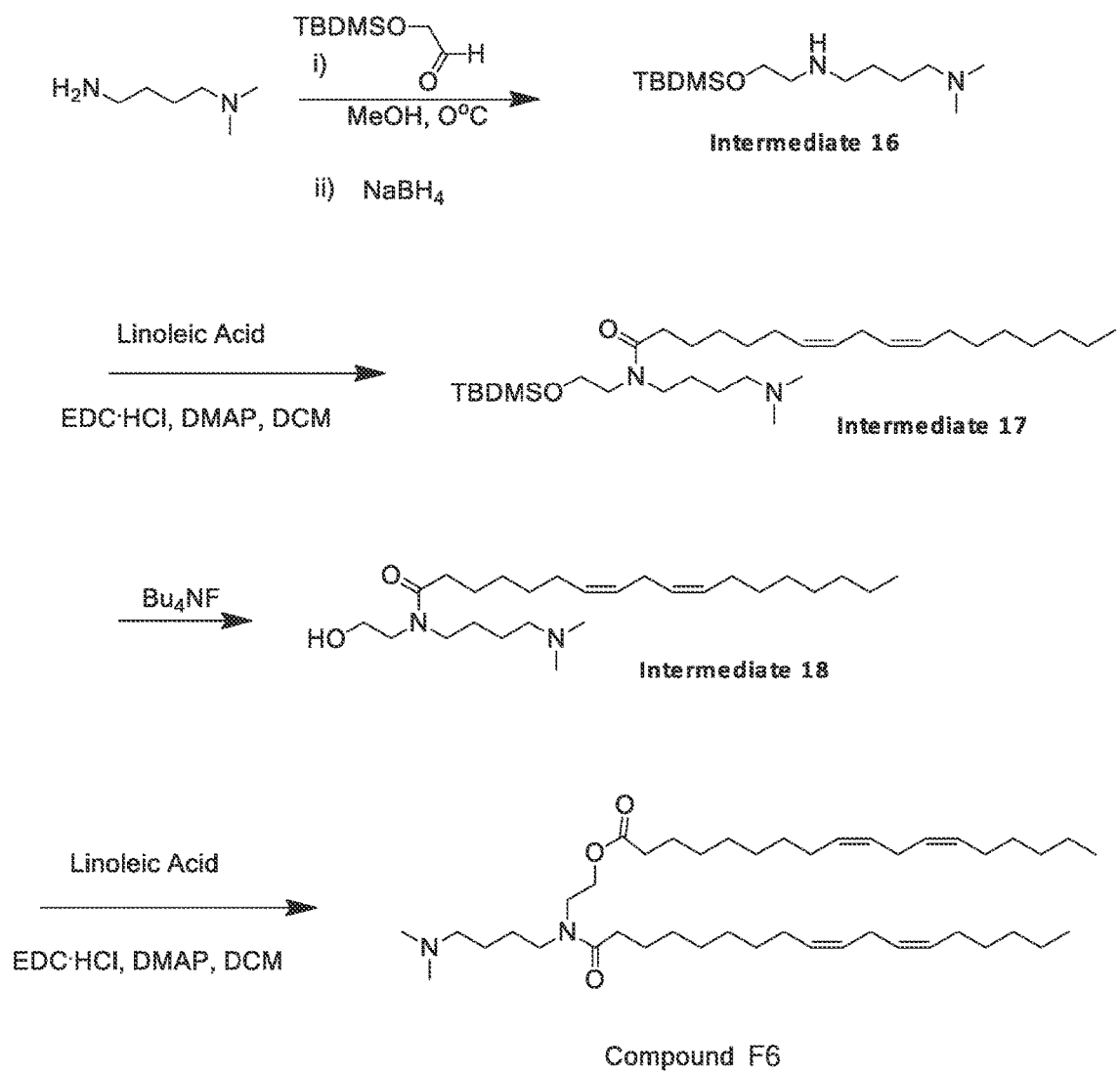
FIG. 17 shows a scheme for the preparation of Compound F6.

Example 17: A Scheme for the Preparation of Compound F6 is Shown in FIG. 17

Intermediate 16: N,N-Dimethyl-1,4-butane-diamine (1.0 g, 8.60 mmol) was dissolved in MeOH (15 mL). Mixture was placed in an ice-bath and (tert-butyl)-dimetholsiloxy)-acetaldehyde (1.7 mL, 9.03 mmol) was added and stirred for 1 hour. NaBH₄ (522 mg, 13.8 mmol) was then added and the mixture was stirred for another hour 0° C. Next, the reaction was quenched with H₂O (1 mL) and concentrated in vacuo to yield Intermediate 16. The material was carried forward with any further refinement (2.4 g, assumed quantitative yield).

Intermediate 17: Linoleic acid (1.2 g, 4.37 mmol), EDC (1.1 g, 5.46 mmol), and DMAP (89 mg, 0.73 mmol) in an oven-dried flask (50 mL) with a magnetic bar was added anhydrous DCM (15 mL). The mixture was stirred at ambient temperature for ~5 minutes to a clear solution. Intermediate 16 (1.0 g, 3.64 mmol) was then added and the mixture was stirred at room temperature overnight. The reaction was finally quenched with H₂O (50 mL) and extracted with DCM twice (2×50 mL). Organic layers were combined, dried over MgSO₄, and filtered. The filtrate was concentrated under reduced pressure. The crude was purified by flash chromatography purification system (24 g silica gel column) using a gradient of DCM for 1 min, then 0-10% MeOH/DCM for 2 min, then 10% MeOH/DCM for 7 min, then 10-30% MeOH/DCM for 2 min, then 30% MeOH/DCM for 7 min under the flow rate at 35 mL/min. The product fractions were collected and concentrated to yield Intermediate 17 (460 mg, 24% yield) as a clear liquid. The product was verified with LC-MS prior to executing the next step.

Intermediate 18: LOM TBAF/THF (2.6 mL, 2.57 mmol) was added to Intermediate 17 (460 mg, 0.86 mmol) dissolved in THF (5 mL) in an oven-dried flask (50 mL) with a magnetic bar and the mixture was allowed to stir at ambient temperature overnight under a blanket of argon gas. Next day, the mixture was concentrated in vacuo and carried forward without any further purification (361 mg, assumed quantitative yield). The product was verified with LC-MS prior to executing the next step.

Compound F6: Linoleic acid (289 mg, 1.0 mmol), EDC (247 mg, 1.29 mmol), and DMAP (21 mg, 0.171 mmol) in an oven-dried flask (50 mL) with a magnetic bar was added anhydrous DCM (20 mL). The mixture was stirred at ambient temperature for ~5 minutes to a clear solution. Intermediate 18 (361 mg, 0.86 mmol) was then added and the mixture was stirred at room temperature overnight. Next day, the mixture was diluted with DCM (50 mL) and washed with H$_2$O (50 mL) followed by 10% K$_2$CO$_3$ (50 mL). Back-extraction was performed for both aqueous washes with DCM (2×20 mL). The organic layers were combined, dried with MgSO$_4$, filtered, and concentrated in vacuo. The crude was purified by flash chromatography purification system (80 g silica gel column) using a gradient of hexane for 2 min, then 0-25% EtOAc/hexane for 15 min, then 25% EtOAc/hexane for 5 min, then 75% EtOAc/hexane for 5 min under the flow rate at 60 mL/min. The product fractions were collected and concentrated to yield Compound F6 (385 mg, 65% yield) as a clear liquid. $^1$H nmr (400 MHz, CDCl$_3$) δ: 5.40-5.30 (8H, m, CH═), 4.20-4.17 (2H, m, NCH$_2$CH$_2$O), 3.56-3.50 (2H, m, NCH$_2$CH$_2$O), 3.38-3.27 (2H, m, CO NCH$_2$), 2.77-2.75 (2H, m, ═CHCH$_2$CH═), 2.66-2.56 (4H, m, N(CH$_3$)$_2$CH$_f$), 2.40-2.27 (10H, m, COCH$_2$, & N(CH$_3$)$_2$), 2.06-2.02 (8H, m, CH$_2$CH$_2$CH), 1.85-1.58 (8H, m, CH$_2$CH$_2$CO & NCH$_2$(CH$_2$)$_2$CH$_2$N), 1.36-1.26 (28H, m, CH$_2$), 0.90-0.86 (6H, m, CH$_3$).

Figure 18:
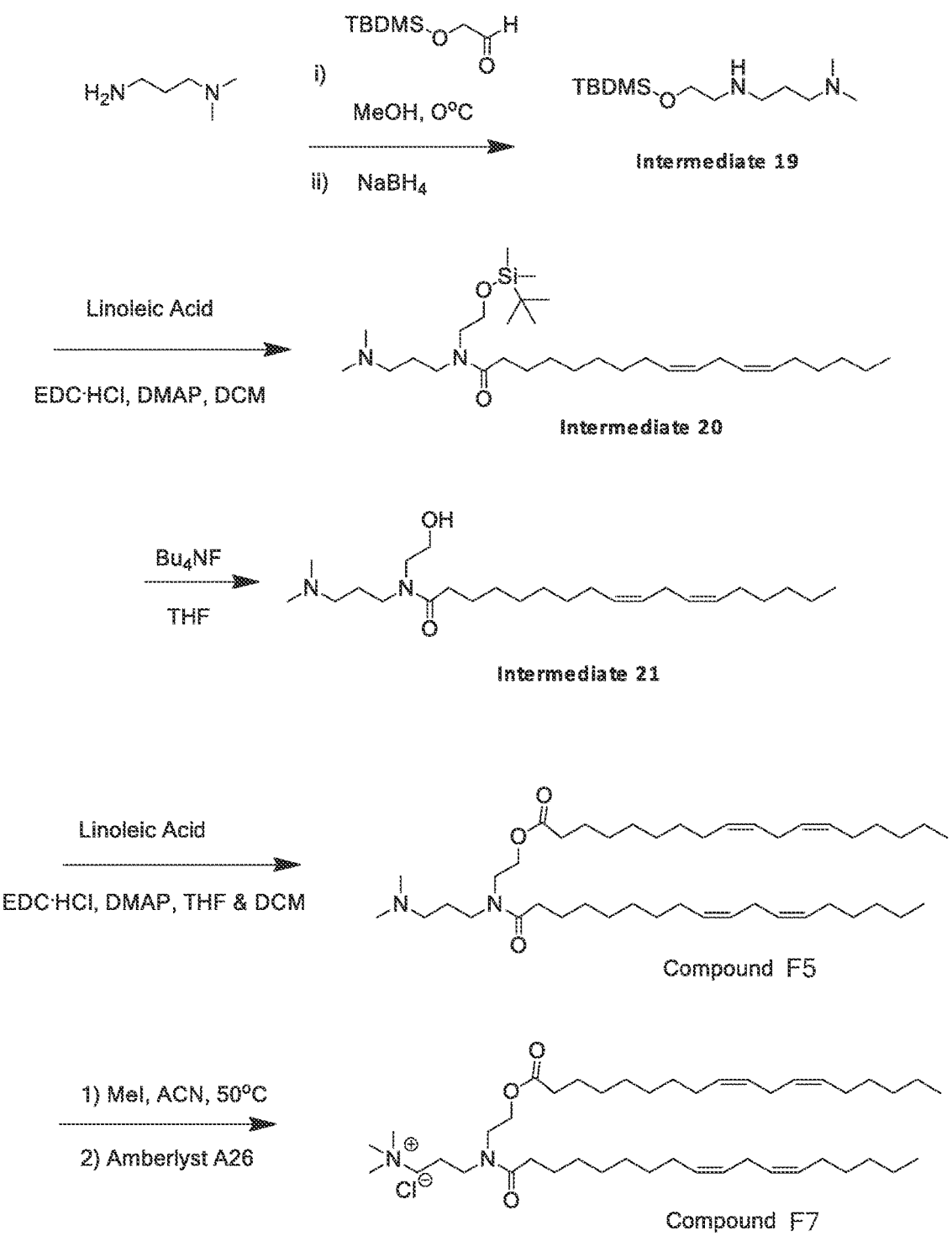
FIG. 18 shows a scheme for the preparation of Compounds F5 and F7.

Example 18: A Scheme for the Preparation of Compounds F5 and F7 is Shown in FIG. 18

Intermediate 19: 3-(Dimethylamino)-1-propylamine (4.4 mL, 30.50 mmol) was dissolved in MeOH (20 mL). Mixture was placed in an ice-bath and (tert-butyldimethylsilyl)acetaldehyde (6.1 mL, 32.00 mmol) was added allowed to stir for 1 hour. NaBH$_4$ (1.9 g, 48.79 mmol) was then added and the mixture was stirred for another hour at 0° C. Next, the reaction was quenched with H$_2$O (5 mL), filtered out precipitate, and concentrated in vacuo to yield Intermediate 19. Material was carried forward with any further refinement (8.1 g, assumed quantitative yield).

Intermediate 20: Linoleic Acid (10.4 g, 37.10 mmol), EDC (8.9 g, 46.42 mmol), and DMAP (755 mg, 6.22 mmol) in an oven-dried flask (200 mL) with a magnetic bar was added anhydrous DCM (50 mL). The mixture was stirred at ambient temperature for ~5 minutes to a clear solution. Intermediate 19 (8.1 g, 30.91 mmol) was then added and the mixture was stirred at room temperature overnight. Next day, diluted with DCM (50 mL) and washed with H$_2$O (50 mL) followed by 10% K$_2$CO$_3$ (50 mL). Back-extraction was performed for both aqueous washes with DCM (2×25 mL). The organic layers were combined, dried with MgSO$_4$, filtered, and concentrated in vacuo. The crude purified by flash chromatography purification system (330 g silica gel column) using a gradient of DCM for 5 min, then 0-10% MeOH/DCM for 25 min, then 10% MeOH/DCM for 15 min under the flow rate at 200 mL/min. The product fractions were collected and concentrated to yield Intermediate 20 (9.8 g, 60% yield) as a clear liquid. $^1$H nmr (400 MHz, CDCl$_3$) δ: 5.37-5.29 (4H, m, CH═), 3.75-3.67 (2H, m, NCH$_2$CH$_2$O), 3.46-3.35 (4H, m, CONCH$_2$), 2.77-2.74 (2H, m, ═CHCH$_2$CH═), 2.36-2.23 (4H, m, COCH$_2$ & (CH$_3$)$_2$NCH$_2$), 2.21-2.20 (6H, d, (CH$_3$)$_2$N), 2.04-2.00 (4H, m, CH$_2$CH$_2$CH), 1.71-1.59 (2H, m, NCH$_2$CH$_2$CH$_2$N), 1.36-1.26 (14H, m, CH$_2$), 0.89-0.86 (12H, s, SiC(CH$_3$)$_3$ & CH$_3$), 0.36-0.28 (6H, m, Si(CH$_3$)$_2$).

Intermediate 21: 1.0 M TBAF/THF (55.2 mL, 55.21 mmol) was added to Intermediate 20 (9.6 g, 18.43 mmol) in an oven-dried flask (50 mL) with a magnetic bar and allowed to stir for three hours under a blanket of argon gas. Then, the mixture was concentrated in vacuo and carried forward with any further refinement (7.5 g, assumed quantitative yield). The product was verified with LC-MS prior to executing the next step.

Compound F5: Linoleic Acid (6.2 g, 22.13 mmol), EDC (5.3 g, 27.64 mmol), and DMAP (450 mg, 3.68 mmol) in an oven-dried flask (50 mL) with a magnetic bar was added anhydrous DCM (20 mL). The mixture was stirred at ambient temperature for ~5 minutes to a clear solution. Intermediate 21 (7.5 g, 18.42 mmol) was then added and the mixture was stirred at room temperature overnight. Next day, diluted with DCM (50 mL) and washed with H$_2$O (50 mL) flowed by 10% K$_2$CO$_3$ (50 mL). Back-extraction was performed for both aqueous washes with DCM (2×40 mL). The organic layers were combined, dried with MgSO$_4$, filtered, and concentrated in vacuo. The crude purified by flash chromatography purification system (330 g silica gel column) using a gradient of DCM for 10 min, then 0-5% MeOH/DCM for 5 min, then 5% MeOH/DCM for 15 min, then 5-20% MeOH/DCM for 10 min, then 20% MeOH/DCM for 2 minutes under the flow rate at 200 mL/min. The product fractions were collected and concentrated to yield Compound F5 (8.0 g, 65% yield) as a clear liquid. $^1$H nmr (400 MHz, CDCl$_3$) δ: 5.40-5.20 (8H, m, CH═), 4.20-4.17 (2H, m, NCH$_2$CH$_2$O), 3.90-4.10 (2H, m, NCH$_2$CH$_2$O), 3.50-3.60 (2H, m, CONCH$_2$), 2.77-2.75 (4H, m, ═CHCH$_2$CH═), 2.40-2.10 (14H, m, CH$_2$CH$_2$CH & N(CH$_3$)$_2$), 2.10-1.90 (8H, m, COCH$_2$, & N(CH$_2$)& OCOCH$_2$CH$_2$), 2.06-2.02 (4H, m, CH$_2$CH$_2$CH), 1.80-1.50 (4H, m, NCH$_2$CH$_2$CH$_2$N & NCOCH$_2$CH$_2$), 1.40-1.00 (28H, m, CH$_2$), 0.99-0.71 (6H, m, CH$_3$).

Compound F7: Compound F5 (6.1 g, 9.04 mmol) was dissolved in acetonitrile (18 mL) and methyl iodide (2 mL) was added. Vial was flushed with argon gas and the mixture was allowed to stir at 40° C. for 4 hours. Afterwards, the mixture was concentrated in vacuo and purified by flash chromatography with loading the crude oil directly onto 120 g silica gel column and using a gradient of DCM for 2 min, then 0-10% MeOH/DCM for 10 min, then 10% MeOH/DCM for 5 min, then 10-15% MeOH/DCM for 5 min, then 15% MeOH/DCM for 5 min under the flow rate at 85 mL/min. The product fractions were collected, concentrated, and subjected to Amberlyst A26 Anion Exchange resin to yield Compound F7 (3.2 g, 50% yield) as oil. $^1$H nmr (400 MHz, CDCl$_3$) δ: 5.40-5.20 (8H, m, CH═), 4.30-4.20 (2H, m, NCH$_2$CH$_2$O), 3.80-3.60 (4H, m, NCH$_2$CH$_2$O & CONCH$_2$), 3.68-3.39 (9H, m, N(CH$_3$)$_3$), 2.77-2.73 (4H, m, ═CHCH$_2$CH═), 2.40-2.30 (2H, m, COCH$_2$), 2.30-2.20 (2H, m, (CH$_3$)$_2$NCH$_2$), 2.20-1.10 (2H, m, OCOCH$_2$CH$_2$), 2.10-1.90 (8H, m, CH$_2$CH$_2$CH), 1.70-1.50 (4H, m, NCH$_2$CH$_2$CH$_2$N & NCOCH$_2$CH$_2$), 1.40-1.10 (28H, m, CH$_2$), 0.90-0.85 (6H, m, CH$_3$).

Figure 19:
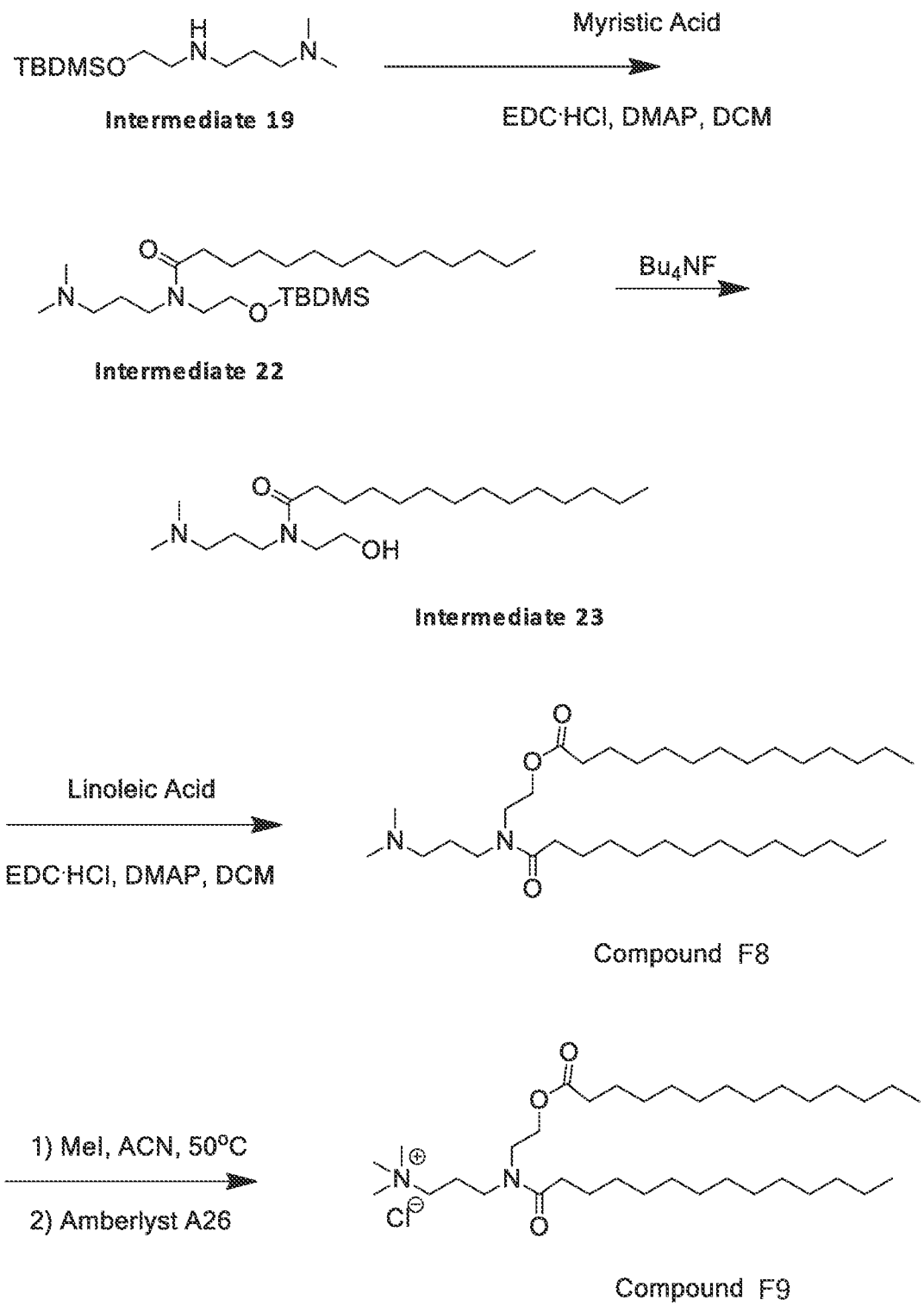
FIG. 19 shows a scheme for the preparation of Compounds F8 and F9.

Example 19: A Scheme for the Preparation of Compounds F8 and F9 is Shown in FIG. 19

Intermediate 22: Myristic Acid (2.0 g, 8.82 mmol), EDC (2.1 g, 11.02 mmol), and DMAP (180 mg, 1.47 mmol) in an oven-dried flask (100 mL) with a magnetic bar was added anhydrous DCM (20 mL). The mixture was stirred at ambient temperature for ~5 minutes to a clear solution. Intermediate 19 (1.9 g, 7.35 mmol) was then added and the mixture was stirred at room temperature overnight. Next day, the reaction mixture was diluted with DCM (50 mL) and washed with H$_2$O (50 mL) flowed by 10% K$_2$CO$_3$ (50 mL). Back-extraction was performed for both aqueous washes with DCM (2×25 mL). The organic layers were combined, dried with MgSO$_4$, filtered, and concentrated in vacuo. The crude was purified by flash chromatography purification system (80 g silica gel column) using a gradient of DCM for 1 min, then 0-10% MeOH/DCM for 15 min, then 10% MeOH/DCM for 5 min, then 30% MeOH/DCM for 5 min under the flow rate at 60 mL/min. The product fractions were collected and concentrated to yield Intermediate 22 (1.5 g, 39% yield) as a clear liquid. $^1$H nmr (400 MHz, CDCl$_3$) δ: 3.75-3.67 (2H, m, NCH$_2$CH$_2$O), 3.44-3.35 (4H, m, CONCH$_2$), 2.36-2.21 (4H, m, COCH$_2$ & (CH$_3$)$_2$NCH$_2$), 2.26-2.21 (6H, d, (CH$_3$)$_2$N), 1.71-1.59 (2H, m, NCH$_2$CH$_2$CH$_2$N), 1.63-1.59 (2H, m, COCH$_2$CH$_2$), 1.28-1.24 (20H, m, CH$_2$), 0.88-0.85 (12H, m, SiC(CH$_3$)$_3$ & CH$_3$), 0.38-0.30 (6H, m, Si(CH$_3$)$_2$).

Intermediate 23: 1.0 M TBAF/THF (6.4 mL, 6.36 mmol) was added to Intermediate 22 (1.0 g, 2.12 mmol) dissolved in THF (5 mL) in an oven-dried flask (25 mL) with a magnetic bar and allowed to stir for three hours under a blanket of argon gas. Then, the mixture was concentrated in vacuo and carried forward with any further refinement (728 mg, assumed quantitative yield). The product was verified with LC-MS prior to executing the next step.

Compound F8: Linoleic Acid (659 mg, 2.35 mmol), EDC (631 mg, 3.29 mmol), and DMAP (54 mg, 0.44 mmol) in an oven-dried flask (25 mL) with a magnetic bar was added anhydrous DCM (5 mL). The mixture was stirred at ambient temperature for ~5 minutes to a clear solution. Intermediate 23 (781 mg, 2.19 mmol) was then added and the mixture was stirred at room temperature overnight. Next day, diluted with DCM (50 mL) and washed with H$_2$O (50 mL) followed by 10% K$_2$CO$_3$ (50 mL). Back-extraction was performed for both aqueous washes with DCM (2×40 mL). The organic layers were combined, dried with MgSO$_4$, filtered, and concentrated in vacuo. The crude was purified by flash chromatography purification system (80 g silica gel column) using a gradient of DCM for 1 min, then 0-30% MeOH/DCM for 30 min under the flow rate at 60 mL/min. The product fractions were collected and concentrated to yield Compound F8 (225 mg, 68% yield) as a clear liquid. $^1$H nmr (400 MHz, CDCl$_3$) δ: 4.20-4.15 (2H, m, NCH$_2$CH$_2$O), 3.57-3.54 (2H, m, NCH$_2$CH$_2$O), 3.40-3.33 (4H, m, CONCH$_2$), 2.42-2.21(12H, m, CH$_2$CH$_2$CH & CH$_2$N(CH$_3$)$_2$), 1.80-1.71 (2H, m, NCH$_2$CH$_2$CH$_2$N), 1.70-1.58 (4H, m, COCH$_2$CH$_2$), 1.29-1.15 (20H, m, CH$_2$), 0.93-0.86 (6H, m, CH$_3$).

Compound F9: Compound F8 (620 mg, 1.09 mmol) was dissolved in acetonitrile (9 mL) and methyl iodide (1 mL) was added. The vial was flushed with argon gas and allowed to stir at 40° C. for 4 hours. Afterwards, the mixture was concentrated in vacuo and purified by flash chromatography with loading the crude oil directly onto 24 g silica gel column and using a gradient of DCM for 1 min, then 0-25% MeOH/DCM for 25 min under the flow rate at 32 mL/min. The product fractions were combined, concentrated, and subjected to Amberlyst A26 Anion Exchange resin to yield Compound F9 (325 mg, 48% yield) as a clear oil. $^1$H nmr (400 MHz, CDCl$_3$) δ: 4.21-4.19 (2H, m, NCH$_2$CH$_2$O), 3.86-3.81 (2H, m, NCH$_2$CH$_2$O), 3.47-3.44 (2H, m, CONCH$_2$), 3.41 (9H, s, N(CH$_3$)), 2.38-2.35 (2H, m, CH$_2$N(CH$_3$)$_3$), 2.28-2.25 (2H, m, NCH$_2$CH$_2$CH$_2$N), 2.13-2.08 (2H, m, NCOCH$_2$CH$_2$N), 1.58-1.56 (4H, m, COCH$_2$CH$_2$), 1.29-1.17 (44H, m, CH$_2$), 0.87-0.85 (6H, m, CH$_3$).

Figure 20:
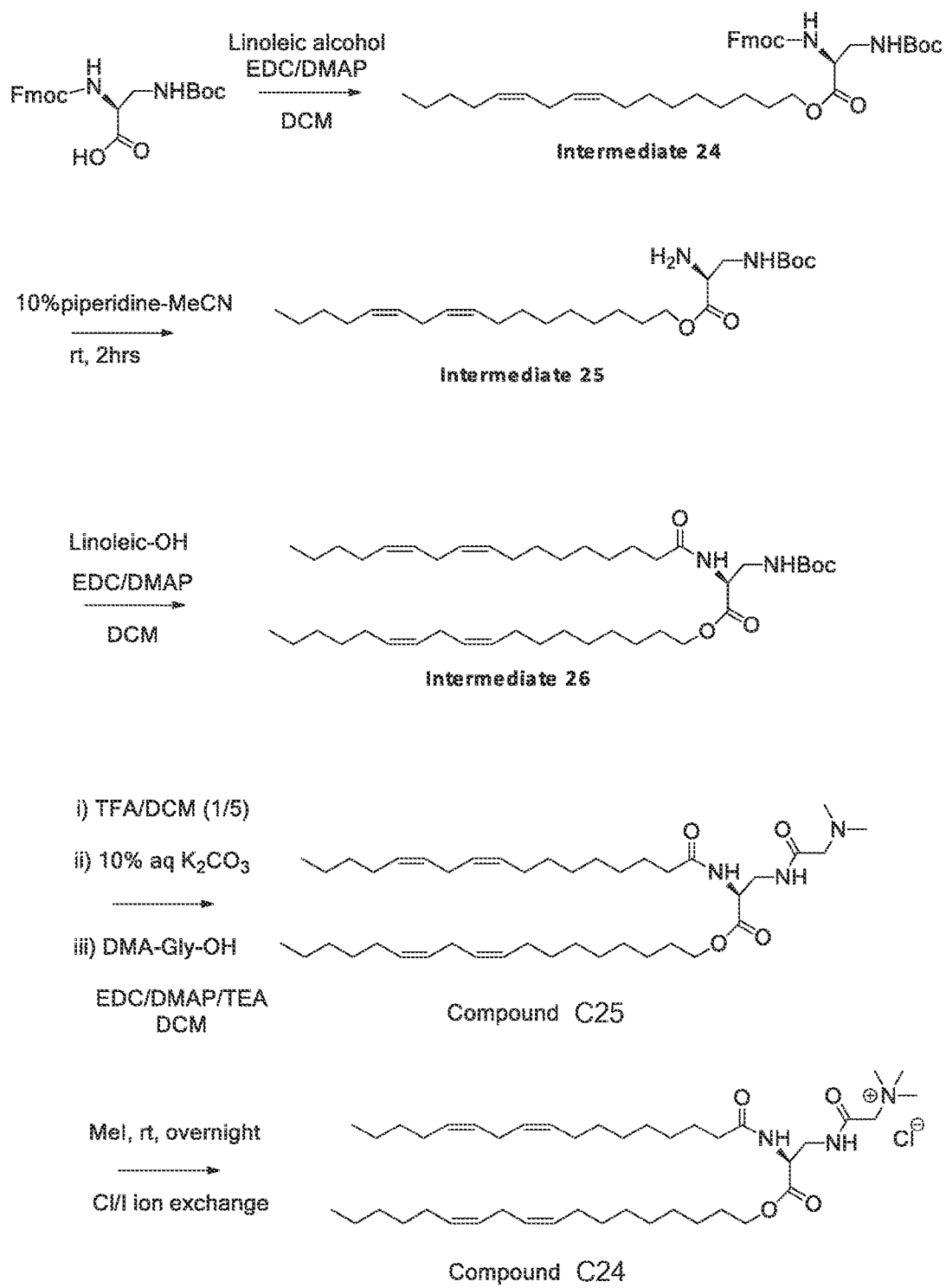
FIG. 20 shows a scheme for the preparation of Compounds C25 and C24.

Example 20: A Scheme for the Preparation of Compounds C25 and C24 is Shown in FIG. 20

Intermediate 24: To Fmoc-Dap(Boc)·H$_2$O (10.0 g, 22.50 mmol) in an oven-dried flask (250 mL) with a magnetic bar were added anhydrous DCM (100 mL), linoleic acid (7.7 mL, 24.79 mmol), EDC (6.5 g, 33.80 mmol), and DMAP (0.6 g, 4.52 mmol) in sequence. The mixture was stirred at ambient temperature stirred overnight (17 hours). The reaction mixture was concentrated under reduced pressure, dissolved in 5 mL DCM and purified by flash chromatography purification system (220 g silica gel column) using a gradient of 0-50% EtOAc/hexane for 30 min under the flow rate at 60 mL/min. The product fractions were collected and concentrated to yield Intermediate 24 (15.2 g, 100% yield) as a clear liquid. The product was verified with LC-MS prior to executing the next step—m/z of [M+H]$^+$=675.98.

Intermediate 25: To intermediate 24 (3.0 g, 4.44 mmol) in an oven-dried flask (100 mL) with a magnetic bar were added anhydrous acetonitrile (20 mL) and piperidine (2 mL). The mixture was stirred at ambient temperature for 2 hours. The reaction mixture was concentrated, dissolved in 2 mL DCM and purified with a 40 g silica column using a gradient of 0-50% EtOAc/hexane for 10 min, 0-15% MeOH/DCM for 20 min under the flow rate at 40 mL/min. The product fractions were collected and concentrated to yield Intermediate 25 (1.3 g, 65% yield) as a clear yellow liquid. The product was verified with LC-MS prior to executing the next step—m/z of [M+H]$^+$=453.82.

Intermediate 26: To intermediate 25 (1.3 g, 2.87 mmol) in an oven-dried flask (100 mL) with a magnetic bar were added anhydrous DCM (30 mL), linoleic acid (0.9 mL, 2.87 mmol), EDC (0.7 g, 3.44 mmol), and DMAP (0.1 g, 0.57 mmol) in sequence. The mixture was stirred at ambient temperature stirred overnight (17 hours). The reaction mixture was then concentrated under reduced pressure, dissolved in 2 mL DCM, and purified by flash chromatography purification system (24 g silica gel column) using a gradient of 0-20% EtOAc/hexane for 30 min under the flow rate at 25 mL/min. The product fractions were collected and concentrated to yield Intermediate 26 (2.0 g, 97% yield) as a clear liquid. The product was verified with LC-MS prior to executing the next step—m/z of [M+H]$^+$=716.16.

Compound C25: To Intermediate 26 (2.0 g, 2.80 mmol) in an oven-dried flask (100 mL) with a magnetic bar were added anhydrous DCM (20 mL) and TFA (4 mL) in sequence. The mixture was stirred at ambient temperature stirred for 2 hours. During stirring, the solution color turned from clear to red. Next, the reaction mixture was first concentrated using a rotavapor and washed with 10% K$_2$CO$_3$ aqueous solution (50 mL). The mixture was then extracted with DCM (2×50 mL) and the organic layers were combined, dried over Na$_2$SO$_4$ (5 g), filtered, and concentrated under reduced pressure to give an oily residue, which was dissolved in anhydrous DCM (20 mL) and added DMA-Gly-OH·HCl (0.5 g, 3.37 mmol), EDC·HCL (0.8 g, 4.22 mmol), DMAP (0.2 g, 1.64 mmol), and TEA (0.2 mL, 1.50 mmol) in sequence. The mixture was stirred at ambient temperature for 2.5 hours. Next, the reaction mixture was washed with 10% aqueous $K_2CO_3$ solution (50 mL), extracted with DCM (2×50 mL), dried over $Na_2SO_4$ and concentrated by rotavapor. The crude was dissolved in 2 mL DCM and purified with a 40 g silica column using a gradient of 0-15% MeOH/DCM for 30 min under the flow rate at 40 mL/min. The product fractions were collected and concentrated to yield Compound C25 (1.5 g, 76.6% yield) as a clear liquid. $^1$H nmr (400 MHz, $CDCl_3$) δ: 7.50 (OH, bs, NH), 6.75 (1H, bs, NH), 5.33-5.35 (8H, m, CH=), 4.60-4.65 (1H, m, COCHN), 4.10-4.15 (2H, m, $OCH_2$), 3.70-3.75 (2H, m, $NCH_2$), 2.90 (2H, s, $NCH_2$), 2.74-2.76 (4H, m, =$CHCH_2CH$=), 2.25 (6H, s, $NCH_3$), 2.23-2.24 (2H, m, $CH_2CO$), 2.03-2.04 (8H, m, =$CHCH_2$), 1.65-1.66 (4H, m, $CH_2CH_2CO$), 1.29-1.31 (30H, m, $CH_2$), 0.86-0.88 (6H, m, $CH_3$).

Compound C24: Compound C25 (1.5 g, 2.14 mmol) was added to methyl iodide (2 mL) in an oven-dried vial (20 mL) with a magnetic bar. The mixture was stirred at ambient temperature overnight (17 hours). Next, the excess reagent was removed under vacuum. The crude was dissolved in 1 mL DCM and purified with a 40 g silica column using a gradient of 0-15% MeOH/DCM for 30 min under the flow rate at 30 mL/min. The product fractions were combined, concentrated, and subjected to Amberlyst A26 Anion Exchange resin to yield Compound C24 (1.6 g, 96% yield) as a clear liquid. $^1$H nmr (400 MHz, $CDCl_3$) δ: 8.80 (1H, bs, NH), 6.90 (OH, bs, NH), 5.33-5.35 (8H, m, CH=), 4.80-4.85 (2H, m, $COCH_2N$), 4.25-4.26 (1H, m, COCHN), 4.10-4.18 (2H, m, $OCH_2$), 3.80-3.81 (1H, m, $NCH_2$), 3.60-3.61 (1H, m, $NCH_2$), 3.45 (9H, s, $NCH_3$), 2.74-2.76 (4H, m, =$CHCH_2CH$=), 2.37-2.38 (2H, m, $CH_2CO$), 2.03-2.04 (8H, m, =$CHCH_2$), 1.65-1.66 (4H, m, $CH_2CH_2CO$), 1.29-1.31 (30H, m, $CH_2$), 0.86-0.88 (6H, m, $CH_3$).

Figure 21:
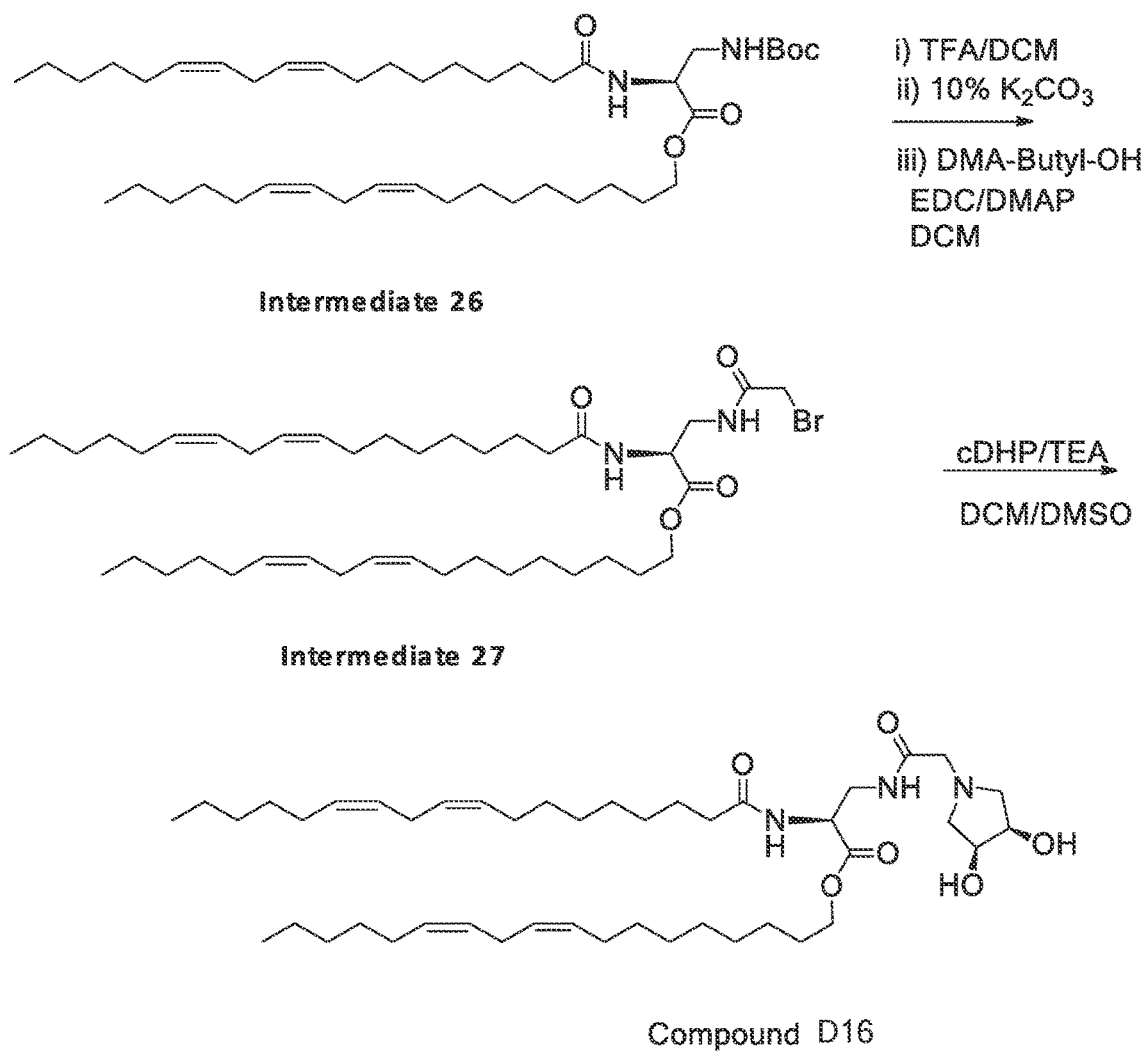
FIG. 21 shows a scheme for the preparation of Compound D16.

Example 21: A Scheme for the Preparation of Compound D16 is Shown in FIG. 21

Intermediate 27: To intermediate 26 (10.3 g, 14.44 mmol) in an oven-dried flask (100 mL) with a magnetic bar were added anhydrous DCM (20 mL) and TFA (4 mL) in sequence. The mixture was stirred at ambient temperature stirred for 2 hours. During stirring, the solution color turned from clear to red. Next, the reaction mixture was first concentrated using a rotavapor and washed with 10% $K_2CO_3$ aqueous solution (50 mL). The mixture was then extracted with DCM (2×50 mL) and the organic layers were combined, dried over $Na_2SO_4$ (5 g), filtered, and concentrated under reduced pressure to give an oily residue, which was then dissolved in anhydrous DCM (30 mL) and added bromoacetyl bromide (1.3 mL, 14.44 mmol), and TEA (2.2 mL, 15.85 mmol) slowly in sequence. The mixture was stirred at ambient temperature for 2.5 hours. Next, the reaction mixture was concentrated by rotavapor. The crude was dissolved in 10 mL DCM and purified with a 220 g silica column using a gradient of 0-50% EtOAc/hexane for 30 min under the flow rate at 60 mL/min. The product fractions were collected and concentrated to yield Intermediate 27 (8.0 g, 76% yield) as a clear liquid. The product was verified with LC-MS prior to executing the next step—m/z of $[M+H]^+$=736.03.

Compound D16: Intermediate 27 (1.0 g, 1.36 mmol) was added to anhydrous DCM (20 mL) with DMSO (1 mL) in an oven-dried vial (40 mL) with a magnetic bar. Then were added cis-pyrrolidine-3,4-diol hydrochloride (cDHP·HCL) (0.3 g, 2.03 mmol) and TEA (0.5 mL, 3.41 mmol). The mixture was stirred at ambient temperature for 2 hours. After removed the solvent by rotavapor under vacuum, the residue was treated with 10% $K_2CO_3$ solution (50 mL) and extracted with DCM (2×50 mL). The organic layers were then combined, dried over $Na_2SO_4$ (10 g), filtered, and concentrated under reduced pressure. The crude was dissolved in 2 mL DCM and purified with a 24 g silica column using a gradient of 0-15% MeOH/DCM for 30 min under the flow rate at 25 mL/min. The product fractions were collected and concentrated to yield Compound D16 (0.8 g, 78% yield) as a yellow liquid. $^1$H nmr (400 MHz, $CDCl_3$) δ: 8.264 (1H, bs, NH), 6.71 (1H, d, J=5.2 Hz, NH), 5.34-5.37 (8H, m, CH=), 4.60-4.70 (1H, m, COCHN), 4.15-4.24 (4H, m, $OCH_2$, OCH), 3.83-3.86 (1H, m, $COCH_2N$), 3.36-3.40 (1H, m, $COCH_2N$), 3.16 (2H, bs, $COCH_2N$), 3.09 (1H, d, J=8.4 Hz, $NCH_2$), 2.92 (1H, d, J=8.4 Hz, $NCH_2$), 2.77-2.93 (4H, m, =$CHCH_2CH$=), 2.61 (2H, bs, $NCH_2$), 2.28-2.31 (2H, m, $CH_2CO$), 2.03-2.07 (8H, m, =$CHCH_2$), 1.64-1.67 (4H, m, $CH_2CH_2CO$), 1.30-1.37 (30H, m, $CH_2$), 0.87-0.90 (6H, m, $CH_3$).

Figure 22:
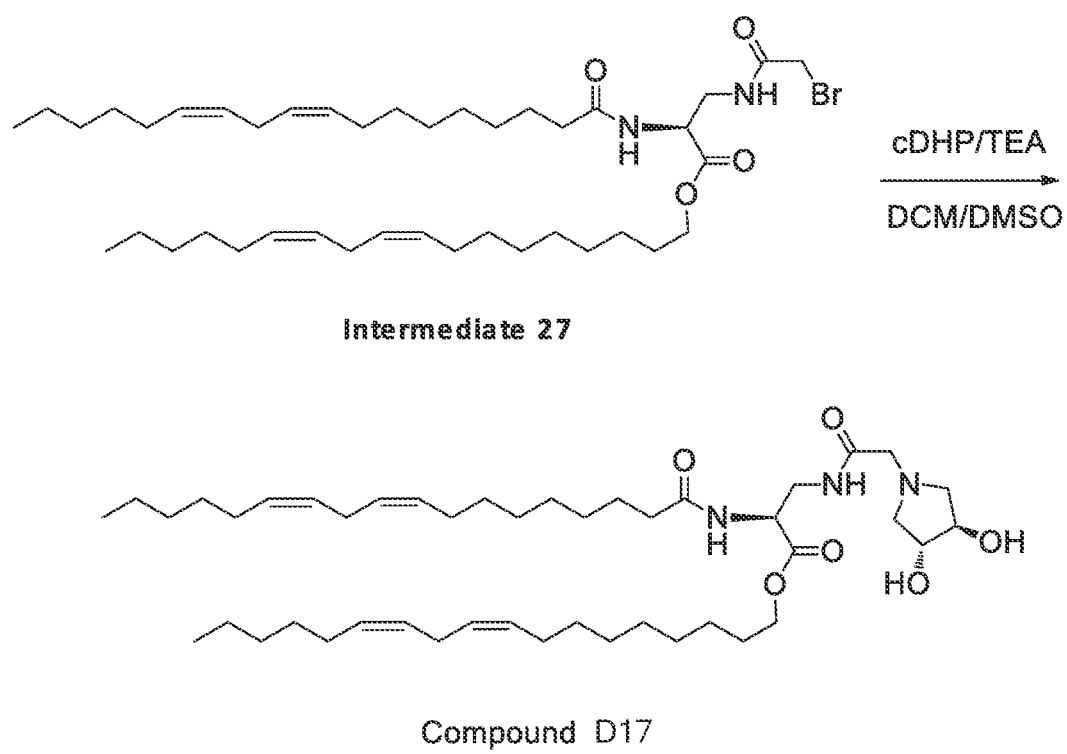
FIG. 22 shows a scheme for the preparation of Compound D17.

Example 22: A Scheme for the Preparation of Compound D17 is Shown in FIG. 22

Compound D17: Intermediate 27 (1.0 g, 1.36 mmol) was added to anhydrous DCM (20 mL) with DMSO (1 mL) in an oven-dried vial (40 mL) with a magnetic bar. Then were added trans-pyrrolidine-3,4-diol hydrochloride (tDHP·HCL) (0.3 g, 2.03 mmol), and TEA (0.5 mL, 3.41 mmol). The mixture was stirred at ambient temperature for 2 hours. After removed the solvent by rotavapor under vacuum, the residue was treated with 10% $K_2CO_3$ solution (50 mL) and extracted with DCM (2×50 mL). The organic layers were then combined, dried over $Na_2SO_4$ (10 g), filtered, and concentrated under reduced pressure. The crude was dissolved in 2 mL DCM and purified with a 24 g silica column using a gradient of 0-15% MeOH/DCM for 30 min under the flow rate at 25 mL/min. The product fractions were collected and concentrated to yield Compound D17 (1.1 g, 100% yield) as a yellow liquid. $^1$H nmr (400 MHz, $CDCl_3$) δ: 8.23 (1H, bs, NH), 6.68 (1H, d, J=5.2 Hz, NH), 5.30-5.37 (8H, m, CH=), 4.64-4.67 (1H, m, COCHN), 4.12-4.18 (4H, m, $OCH_2$, OCH), 3.91-3.94 (1H, m, $COCH_2N$), 3.17-3.31 (3H, m, $COCH_2N$), 3.09-3.12 (2H, m, $CH_2OH$), 2.76-2.78 (4H, m, =$CHCH_2CH$=), 2.67-2.71 (2H, m, $CH_2OH$), 2.25-2.28 (2H, m, $CH_2CO$), 2.03-2.07 (8H, m, =$CHCH_2$), 1.63-1.77 (4H, m, $OCH_2CH_2$), $CH_2CH_2CO$), 1.27-1.37 (30H, m, $CH_2$), 0.87-0.90 (6H, m, $CH_3$).

Figure 23:
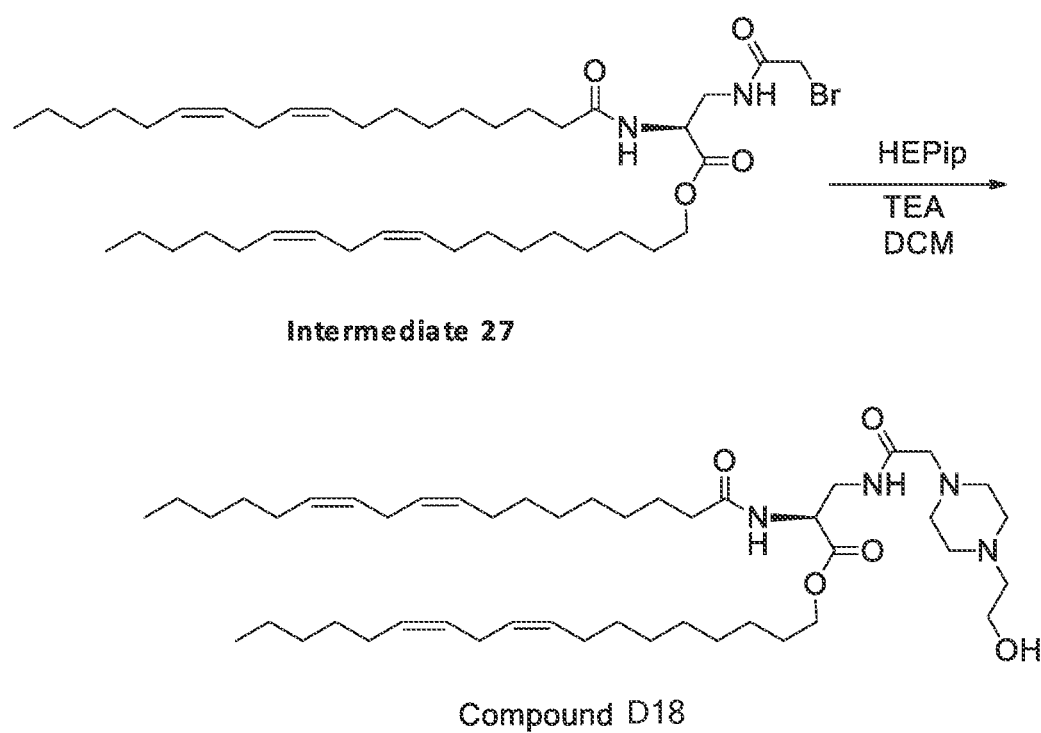
FIG. 23 shows a scheme for the preparation of Compound D18.

Example 23: A Scheme for the Preparation of Compound D18 is Shown in FIG. 23

Compound D18: Intermediate 27 (1.0 g, 1.36 mmol) was added to anhydrous DCM (20 mL) in an oven-dried vial (40 mL) with a magnetic bar. Then were added 1-(2-hydroxy)ethylpiperazine (0.2 mL, 1.63 mmol) and TEA (0.2 mL, 1.5 mmol). The mixture was stirred at ambient temperature for 2 hours. After removed the solvent by rotavapor under vacuum, the residue was treated with 10% $K_2CO_3$ solution (50 mL) and extracted with DCM (2×50 mL). The organic layers were then combined, dried over $Na_2SO_4$ (10 g), filtered, and concentrated under reduced pressure. The crude was dissolved in 2 mL DCM and purified with a 24 g silica column using a gradient of 0-15% MeOH/DCM for 30 min under the flow rate at 25 mL/min. The product fractions were collected and concentrated to yield Compound D18 (0.9 g, 84% yield) as a yellow liquid. $^1$H nmr (400 MHz, CDCl$_3$) δ: 7.48-7.50 (1H, m, NH), 6.68-6.70 (1H, s, NH), 5.29-5.35 (8H, m, CH=), 4.59-4.62 (1H, m, COCHN), 4.10-4.12 (2H, m, OCH$_2$), 3.59-3.66 (4H, m, CH$_2$OH, COCH$_2$N), 2.99 (2H, s, COCH$_2$N), 2.75-2.76 (4H, m, =CHCH$_2$CH=), 2.53-2.55 (10H, m, CH$_2$N), 2.20-2.21 (2H, m, CH$_2$CO), 2.03-2.05 (8H, m, =CH—CH$_2$), 1.61-1.63 (4H, m, OCH$_2$CH$_2$), CH$_2$CH$_2$CO), 1.29-1.30 (30H, m, CH$_2$), 0.86-0.89 (6H, m, CH$_3$).

Figure 24:
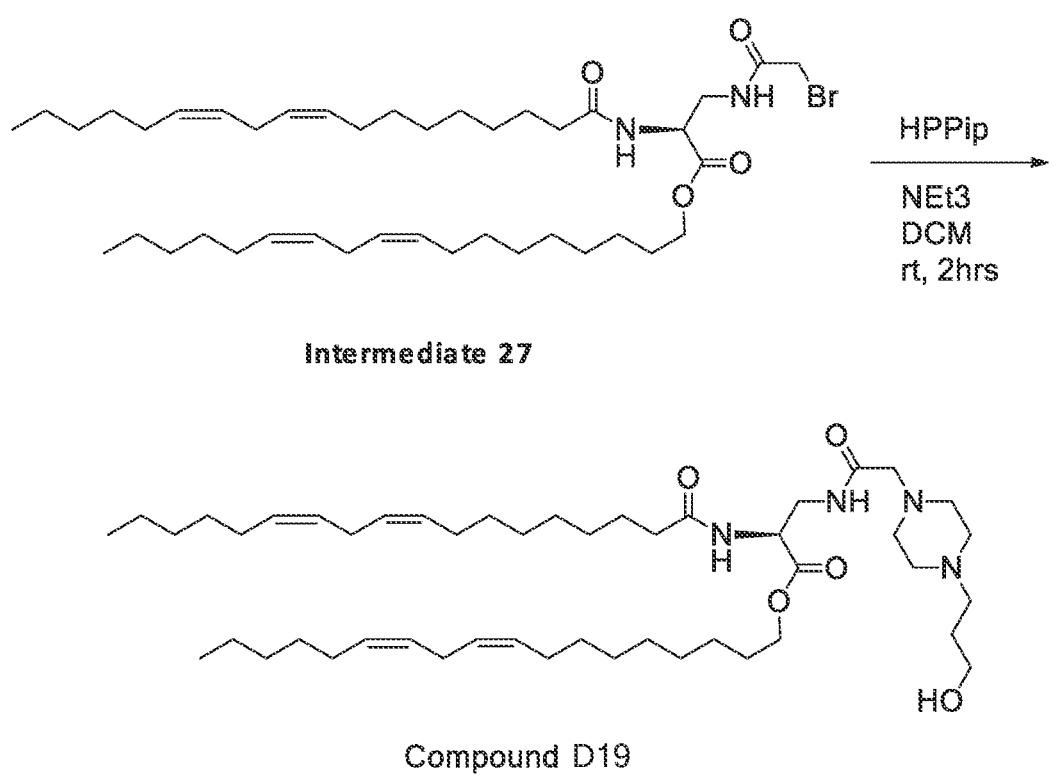
FIG. 24 shows a scheme for the preparation of Compound D19.

Example 24: A Scheme for the Preparation of Compound D19 is Shown in FIG. 24

Compound D19: Intermediate 27 (1.0 g, 1.36 mmol) was added to anhydrous DCM (20 mL) in an oven-dried vial (40 mL) with a magnetic bar. Then were added 1-(2-hydroxy)propylpiperazine (HPPip) (0.2 mL, 1.63 mmol) and TEA (0.2 mL, 1.50 mmol). The mixture was stirred at ambient temperature for 2 hours. After removed the solvent by rotavapor under vacuum, the residue was treated with 10% $K_2CO_3$ solution (50 mL) and extracted with DCM (2×50 mL). The organic layers were then combined, dried over $Na_2SO_4$ (10 g), filtered, and concentrated under reduced pressure. The crude was dissolved in 2 mL DCM and purified with a 24 g silica column using a gradient of 0-15% MeOH/DCM for 30 min under the flow rate at 25 mL/min. The product fractions were collected and concentrated to yield Compound D19 (0.9 g, 84% yield) as a yellow liquid. $^1$H nmr (400 MHz, CDCl$_3$) δ: 7.48-7.50 (1H, m, NH), 6.68-6.70 (1H, s, NH), 5.29-5.35 (8H, m, CH=), 4.59-4.62 (1H, m, COCHN), 4.10-4.12 (2H, m, OCH$_2$), 3.59-3.66 (4H, m, CH$_2$OH, COCH$_2$N), 2.99 (2H, s, COCH$_2$N), 2.75-2.76 (4H, m, =CHCH$_2$CH=), 2.53-2.55 (10H, m, CH$_2$N), 2.20-2.21 (2H, m, CH$_2$CO), 2.03-2.05 (8H, m, =CHCH$_2$), 1.61-1.63 (4H, m, OCH$_2$CH$_2$), CH$_2$CH$_2$CO), 1.29-1.30 (30H, m, CH$_2$), 0.86-0.89 (6H, m, CH$_3$).

Figure 25:
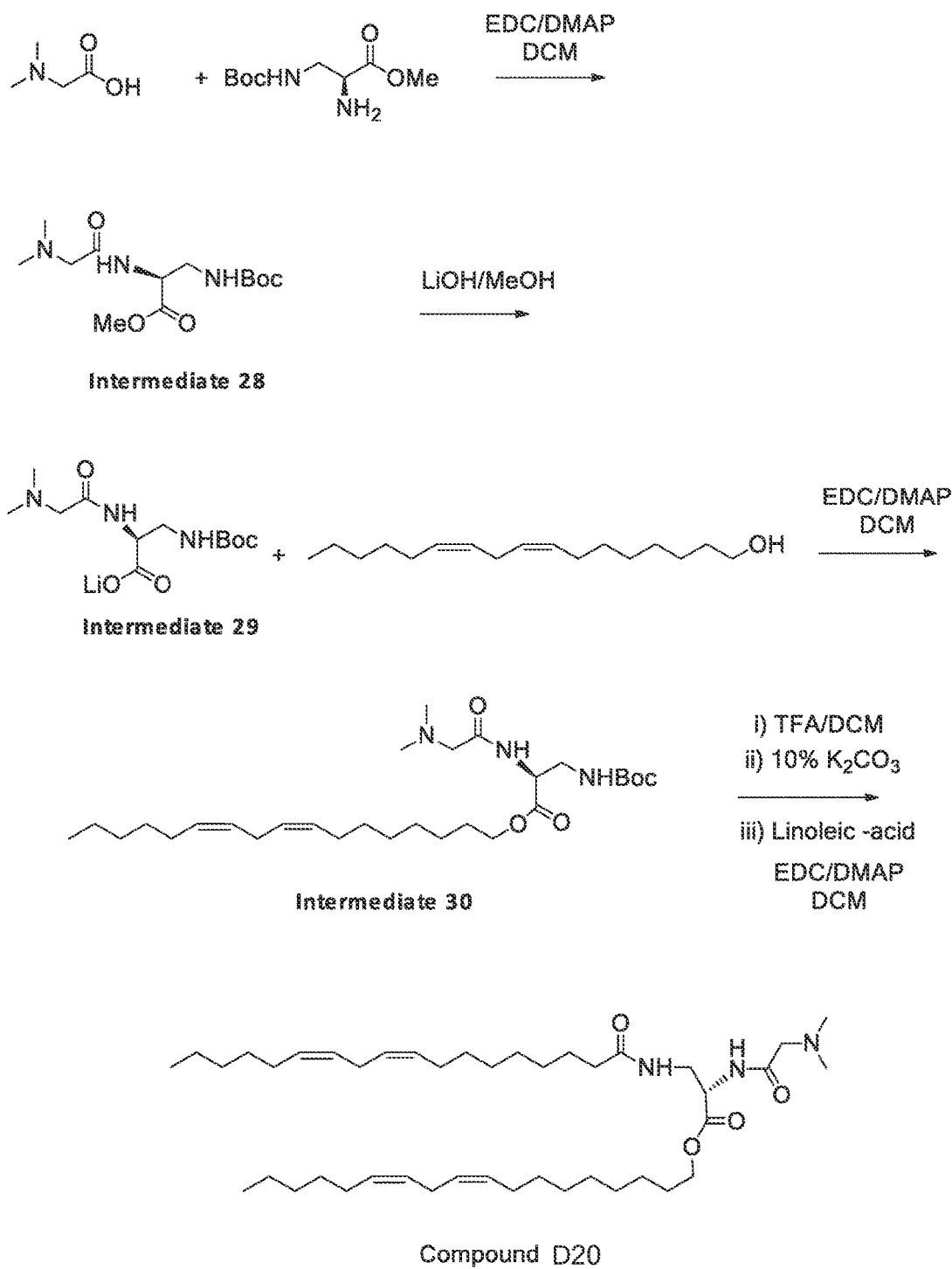
FIG. 25 shows a scheme for the preparation of Compound D20.

Example 25: A Scheme for the Preparation of Compound D20 is Shown in FIG. 25

Intermediate 28: To N,N-dimethylglycine hydrochloride (0.6 g, 3.94 mmol) in an oven-dried flask (100 mL) with a magnetic bar were added anhydrous DCM (20 mL), H-Dap(Boc)-OMe·HCl (1.0 g, 3.94 mmol), EDC (1.0 g, 4.73 mmol), and DMAP (0.1 g, 0.80 mmol) in sequence. The mixture was stirred at ambient temperature stirred overnight (17 hours). The reaction mixture was concentrated under reduced pressure and purified by flash chromatography purification system (24 g silica gel column) using a gradient of 2-20% MeOH/DCM for 30 min under the flow rate at 25 mL/min. The product fractions were collected and concentrated to yield Intermediate 28 (1.0 g, 84% yield) as a white solid. The product was verified with LC-MS prior to executing the next step—m/z of [M+H]$^+$=304.51.

Intermediate 29: To Intermediate 28 (1.0 g, 3.30 mmol) in an oven-dried vial (40 mL) with a magnetic bar were added methanol (10 mL) and LiOH (87 mg, 3.60 mmol). The mixture was stirred at ambient temperature overnight (17 hours). The reaction mixture was concentrated to deliver crude Intermediate 29 for next step without purification. The product was verified with LC-MS prior to executing the next step—m/z of [M+H]$^+$=209.44.

Intermediate 30: To crude Intermediate 29 (~1.1 g, ~2.87 mmol) in an oven-dried flask (100 mL) with a magnetic bar were added anhydrous DCM (20 mL), linoleic acid (1.1 mL, 3.60 mmol), EDC (0.9 g, 4.80 mmol), and DMAP (0.1 g, 0.64 mmol) in sequence. The mixture was stirred at ambient temperature stirred overnight (17 hours). The reaction mixture was concentrated under reduced pressure and purified by flash chromatography purification system (24 g silica gel column) using a gradient of 0-20% MeOH/DCM for 30 min under the flow rate at 25 mL/min. The product fractions were collected and concentrated to yield Intermediate 30 (22 mg, 13% yield) as a clear liquid. The product was verified with LC-MS prior to executing the next step—m/z of [M+H]$^+$=538.84.

Compound D20: To Intermediate 30 (220 mg, 0.41 mmol) in an oven-dried flask (100 mL) with a magnetic bar were added anhydrous DCM (15 mL) and TFA (1 mL) in sequence. The mixture was stirred at ambient temperature stirred for 2 hours. During stirring, the solution color turned from clear to red. Next, the reaction mixture was first concentrated using a rotavapor and washed with 10% $K_2CO_3$ aqueous solution (50 mL). The mixture was then extracted with DCM (2×50 mL) and the organic layers were combined, dried over $Na_2SO_4$ (5 g), filtered, and concentrated under reduced pressure to give an oily residue, which was then dissolved in anhydrous DCM (30 mL) and added anhydrous DCM (20 mL), linoleic acid (0.2 mL, 0.49 mmol), EDC (118 mg, 0.62 mmol), and DMAP (10 mg, 0.08 mmol) in sequence. The mixture was stirred at ambient temperature stirred for 4 hours. The reaction mixture was concentrated using a rotavapor and washed with 10% $K_2CO_3$ aqueous solution (50 mL). The mixture was then extracted with DCM (2×50 mL) and the organic layers were combined, dried over $Na_2SO_4$ (5 g), filtered, and concentrated under reduced pressure. The crude was finally purified with a 12 g silica column using a gradient of 0-15% MeOH/DCM for 30 min under the flow rate at 20 mL/min. The product fractions were collected and concentrated to yield Compound D20 (140 mg, 49% yield) as a clear liquid. $^1$H nmr (400 MHz, CDCl$_3$) δ: 7.90 (1H, bs, NH), 6.10 (1H, bs, NH), 5.60-5.70 (8H, m, CH=), 4.65 (1H, bs, COCHN), 4.20-4.25 (2H, m, OCH$_2$), 3.58-3.71 (2H, m, CH$_2$N), 2.90-2.91 (2H, m, COCH$_2$N), 2.75-2.76 (4H, m, =CHCH$_2$CH$_2$), 2.30 (6H, s, NCH$_3$), 2.10-2.11 (2H, m, COCH$_2$), 2.0-2.1 (8H, m, =CHCH$_2$), 1.54-1.69 (4H, m, OCH$_2$CH$_2$), CH$_2$CH$_2$CO), 1.10-1.30 (30H, m, CH$_2$), 0.80-0.82 (6H, m, CH$_3$).

Figure 26:
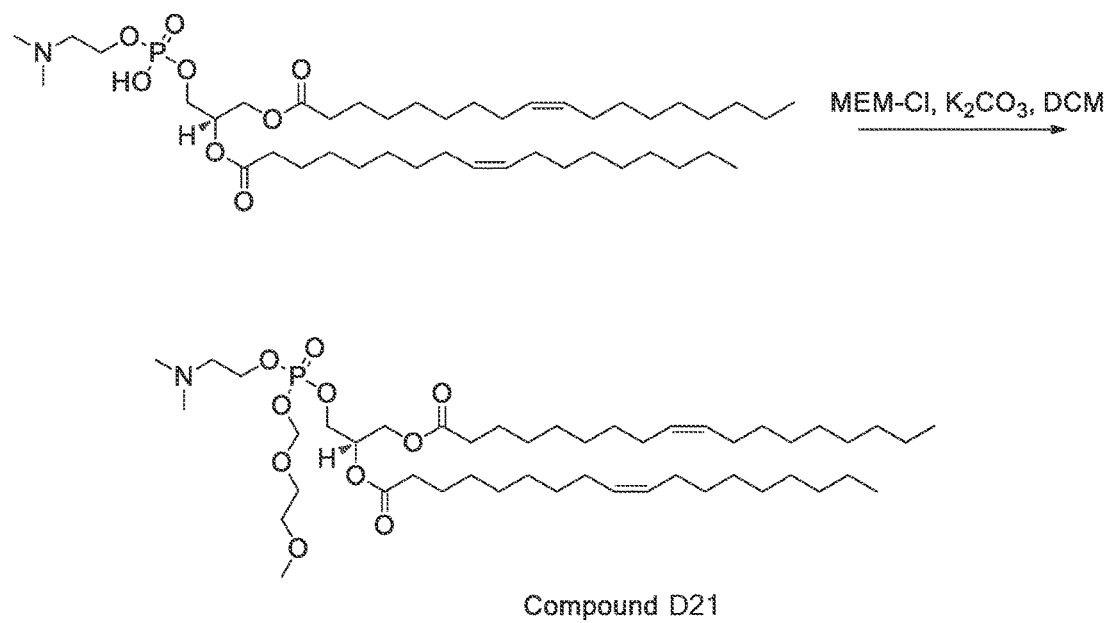
FIG. 26 shows a scheme for the preparation of Compound D21.

Example 26: A Scheme for the Preparation of Compound D21 is Shown in FIG. 26

Compound D21: To (2R)-3-(((2-(dimethylamino)ethoxy) (hydroxy)phosphoryl)oxy)propane-1,2-diyl dioleate (450 mg, 0.58 mmol) in an oven-dried vial (40 mL) with a magnetic bar were added anhydrous DCM (8 mL), 2-Methoxyethoxymethyl chloride (133 mL, 1.16 mmol) and potassium carbonate (332 mg, 2.32 mmol) in sequence. The mixture was stirred at ambient temperature for one week. The reaction mixture was filtered, and concentrated under reduced pressure, which was purified with a 12 g silica column using a gradient of 0-20% MeOH/DCM for 30 min under the flow rate at 20 mL/min. The product fractions were collected and concentrated to yield Compound D21 (150 mg, 30% yield) as a clear liquid. $^1$H nmr (400 MHz, CDCl$_3$) δ: 75.29-5.33 (8H, m, CH=), 5.20 (1H, bs, OCH), 4.92 (2H, s, OCH$_2$O), 4.31-4.40 (2H, m, OCH$_2$), 3.98-4.04 (4H, m, OCH$_2$), 3.70-3.71 (2H, m, OCH$_2$), 3.56-3.57 (2H, m, OCH$_2$), 3.36 (3H, s, OCH$_3$), 3.24 (6H, s, NCH$_3$), 2.27-2.90 (2H, m, COCH$_2$), 1.99-2.00 (8H, m, =CHCH$_2$), 1.54-1.69 (4H, m, COCH$_2$CH$_2$), 1.20-1.30 (40H, m, CH$_2$), 0.85-0.88 (6H, m, CH$_3$).

Figure 27:
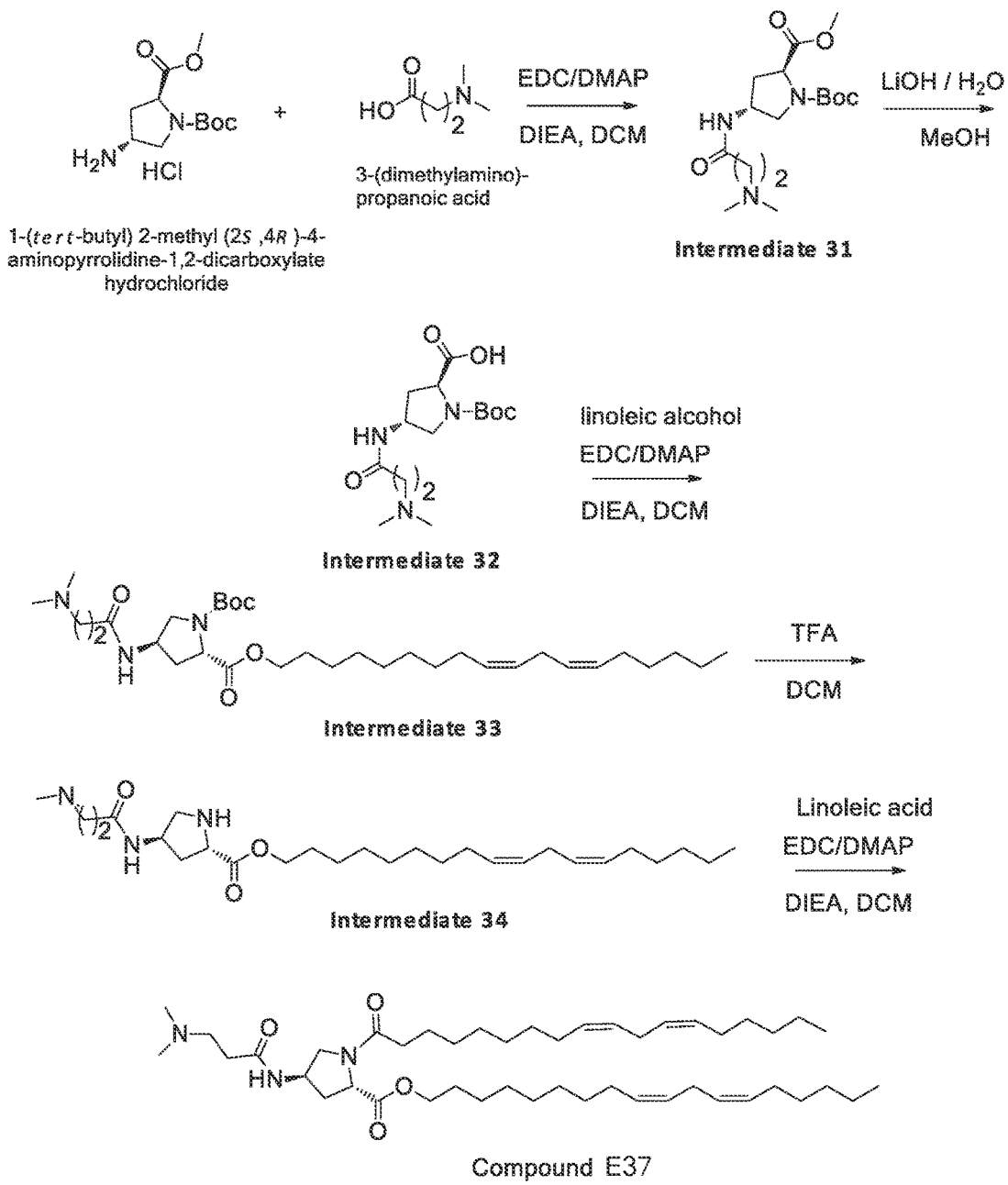
FIG. 27 shows a scheme for the preparation of Compound E37.

Example 27: A Scheme for the Preparation of Compound E37 is Shown in FIG. 27

Intermediate 31: To 1-(tert-butyl)-2-methyl (2S,4R)-4-aminopyrrolidine-1,2-dicarboxylate hydrochloride (2.0 g, 7.12 mmol) in an oven-dried flask (100 mL) with a magnetic bar were added anhydrous DCM (25 mL), 3-(dimethylamino)-propanoic acid (1.3 g, 8.55 mmol), 1-[bis(dimethylamino)methylene]-1H-1,2,3-triazolo[4,5-b]pyridinium-3-oxide-hexafluorophosphate (4.1 g, 10.68 mmol), and DIEA (2.6 mL, 14.96 mmol) in sequence. The mixture was stirred at ambient temperature stirred overnight (17 hours). The reaction mixture was concentrated under reduced pressure and purified by flash chromatography purification system (24 g silica gel column) using a gradient of 0-10% MeOH/DCM for 30 min under the flow rate at 25 mL/min. The product fractions were collected and concentrated to yield Intermediate 31 (1.5 g, 85% yield) as a clear oil. The product was verified with LC-MS prior to executing the next step—m/z of [M+H]$^+$=344.57.

Intermediate 32: To Intermediate 31 (1.5 g, 4.25 mmol) in an oven-dried flask (50 mL) with a magnetic bar were added lithium hydroxide (1.2 mg, 5.10 mmol), water (5 mL) and MeOH (5 mL). The mixture was stirred at ambient temperature overnight. Next solvents were removed under reduced pressure and the wet material was dried via lyophilization to give a crude Intermediate 32 (1.3 g, 95% yield) as a white solid, which was used without further purification. The crude was verified with LC-MS prior to executing the next step—m/z of [M+H]$^+$=330.00.

Intermediate 33: To Intermediate 32 (1.3 g, 3.95 mmol) in an oven-dried flask (100 mL) with a magnetic bar were added anhydrous DMF (20 mL), linoleyl alcohol (1.4 g, 5.14 mmol), EDC (1.5 g, 7.90 mmol), and DMAP (0.5 g, 3.95 mmol) in sequence. The mixture was stirred at ambient temperature stirred overnight (17 hours). The reaction mixture was diluted with DCM (25 mL), washed with sodium bicarbonate (20 mL), dried over Na$_2$SO$_4$ (5 g), filtered, and concentrated under reduced pressure. The crude was purified by flash chromatography purification system (24 g silica gel column) using a gradient of 0-10% MeOH/DCM for 30 min under the flow rate at 25 mL/min. The product fractions were collected and concentrated to yield Intermediate 33 (1.9 g, 85% yield) as a clear oil. The product was verified with LC-MS prior to executing the next step—m/z of [M+H]$^+$=578.91.

Intermediate 34: To Intermediate 33 (1.9 g, 3.33 mmol) in an oven-dried flask (25 mL) with a magnetic bar were added anhydrous DCM (10 mL) and TFA (2 mL) in sequence. The mixture was stirred at ambient temperature stirred for 2 hours. During stirring, the solution color turned from clear to red. Next, the reaction mixture was first concentrated using a rotavapor and washed with 10% Na$_2$CO$_3$ solution (20 mL). The mixture was then extracted with DCM (2×20 mL) and the organic layers were combined, dried over Na$_2$SO$_4$ (5 g), filtered, and concentrated under reduced pressure to give an oily Intermediate 34 (1.5 g, 92% yield) which was used for the next step without further purification. The product was verified with LC-MS prior to executing the next step—m/z of [M+H]$^+$=478.82.

Compound E37: To Intermediate 34 (1.5 g, 3.14 mmol) in an oven-dried flask (100 mL) with a magnetic bar were added anhydrous DMF (10 mL), linoleic acid (1.3 g, 4.71 mmol), and 1-[bis(dimethylamino)methylene]-1H-1,2,3-triazolo[4,5-b]pyridinium 3-oxide-hexafluorophosphate (2.3 g, 6.28 mmol) in sequence. The mixture was stirred at ambient temperature stirred overnight (17 hours). The reaction mixture was concentrated under reduced pressure and purified by flash chromatography purification system (24 g silica gel column) using a gradient of 0-10% MeOH/DCM for 30 min under the flow rate at 25 mL/min. The product fractions were collected and concentrated to yield Compound E37 (2.0 g, 92% yield) as a clear oil. $^1$H nmr (400 MHz, CDCl$_3$) δ: 8.0 (1H, bs, NH) 5.54-5.25 (8H, m, CH=), 4.65-4.29 (2H, m, NHCH, NCHCO), 4.30-3.90 (2H, m, OCH$_2$), 3.80-3.62 (2H, m, NCH$_2$CHNH—), 3.60-3.45 (2H, m, (CH$_3$)$_2$NCH$_2$), 2.84 (6H, s, N(CH$_3$)$_2$), 2.80-2.60 (6H, m, CH$_2$), 2.40-1.90 (12H, m, CH$_2$CONH, CH$_2$CH=), 1.65-1.48 (4H, m, CH$_2$), 1.45-1.20 (30H, m, CH$_2$), 0.86-0.85 (6H, m, CH$_3$).

Figure 28:
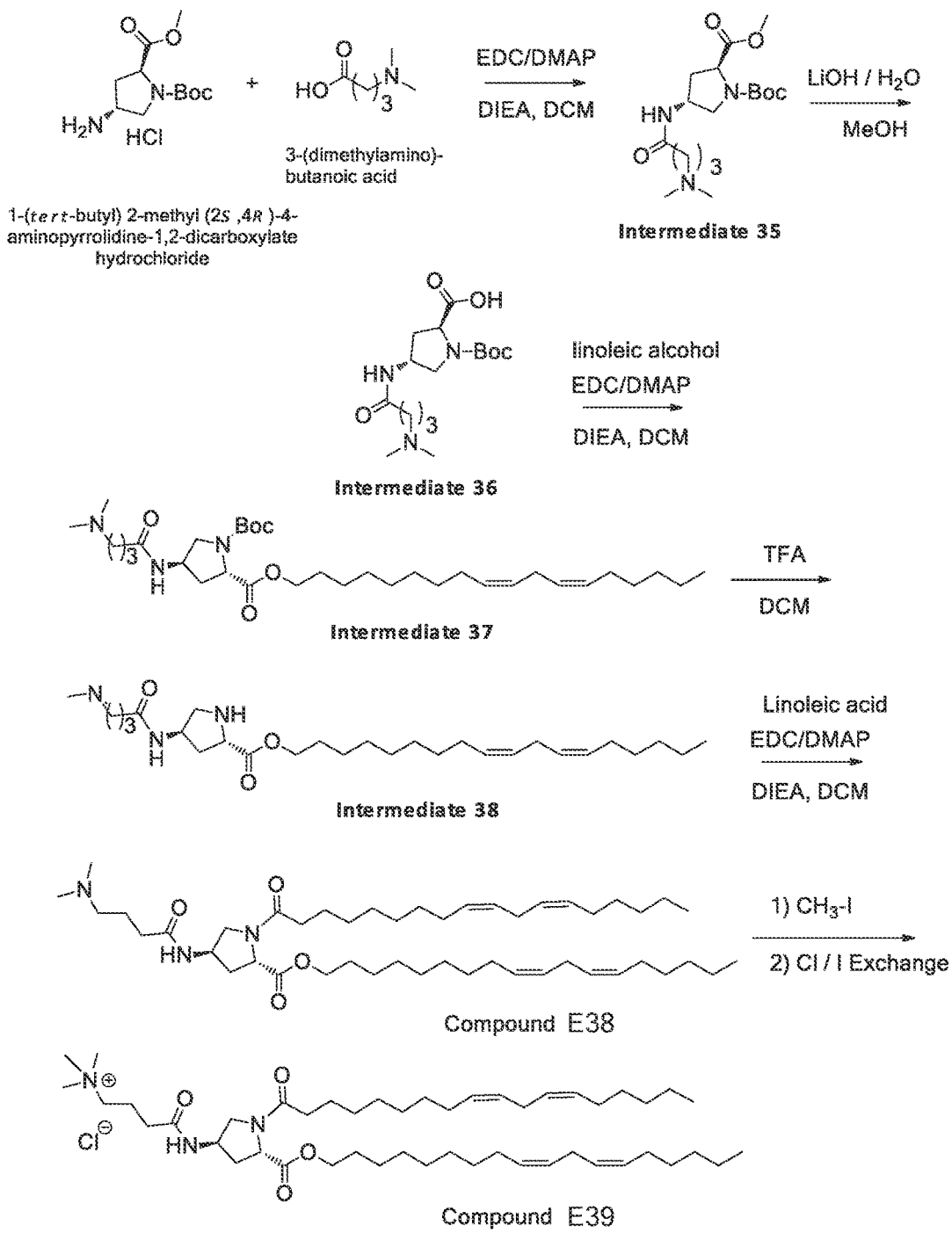
FIG. 28 shows a scheme for the preparation of Compounds E38 and E39.

Example 28: A Scheme for the Preparation of Compounds E38 and E39 is Shown in FIG. 28

Intermediate 35: To 1-(tert-butyl)-2-methyl (2S,4R)-4-aminopyrrolidine-1,2-dicarboxylate hydrochloride (5.0 g, 17.81 mmol) in an oven-dried flask (100 mL) with a magnetic bar were added anhydrous DCM (25 mL), 3-(dimethylamino)butanoic acid (3.6 g, 21.37 mmol), EDC (6.8 g, 35.62 mmol), DMAP (2.2 g, 17.81 mmol), and DIEA (8.1 g, 62.34 mmol) in sequence. The mixture was stirred at ambient temperature stirred overnight (17 hours). The reaction mixture was then diluted with DCM (25 mL), washed with sodium bicarbonate (20 mL), dried over Na$_2$SO$_4$ (5 g), filtered, and concentrated under reduced pressure. The crude was purified by flash chromatography purification system (120 g silica gel column) using a gradient of 0-10% MeOH/DCM for 30 min under the flow rate at 25 mL/min. The product fractions were collected and concentrated to yield Intermediate 35 (6.1 g, 80% yield) as a clear oil. The product was verified with LC-MS prior to executing the next step—m/z of [M+H]$^+$=358.59.

Intermediate 36: To Intermediate 35 (6.1 g, 17.03 mmol) in an oven-dried flask (50 mL) with a magnetic bar were added lithium hydroxide (0.5 g, 20.44 mmol), water (5 mL) and MeOH (20 mL). The mixture was stirred at ambient temperature overnight. Next solvents were removed under reduced pressure and the wet material was dried via lyophilization to give a crude Intermediate 36 (5.6 g, 95% yield) as a white solid, which was used without further purification. The crude was verified with LC-MS prior to executing the next step—m/z of [M+H]$^+$=344.55.

Intermediate 37: To Intermediate 36 (2.8 g, 8.11 mmol) in an oven-dried flask (100 mL) with a magnetic bar were added anhydrous DMF (10 mL), linoleyl alcohol (2.6 g, 9.73 mmol), and 1-[bis(dimethylamino)methylene]-1H-1,2,3-triazolo[4,5-b]pyridinium 3-oxide-hexafluorophosphate (4.6 g, 12.16 mmol) in sequence. The mixture was stirred at ambient temperature stirred overnight (17 hours). The reaction mixture was diluted with DCM (25 mL), washed with sodium bicarbonate (20 mL) dried over $Na_2SO_4$ (5 g), filtered, and concentrated under reduced pressure. The crude was purified by flash chromatography purification system (24 g silica gel column) using a gradient of 0-10% MeOH/DCM for 30 min under the flow rate at 25 mL/min. The product fractions were collected and concentrated to yield Intermediate 37 (3.9 g, 82% yield) as a white solid. The product was verified with LC-MS prior to executing the next step—m/z of [M+H]$^+$=592.91.

Intermediate 38: To Intermediate 37 (1.4 g, 2.31 mmol) in an oven-dried flask (25 mL) with a magnetic bar were added anhydrous DCM (20 mL) and TFA (5 mL) in sequence. The mixture was stirred at ambient temperature stirred for 2 hours. During stirring, the solution color turned from clear to red. Next, the reaction mixture was first concentrated using a rotavapor and washed with 10% $Na_2CO_3$ solution (20 mL). The mixture was then extracted with DCM (2×20 mL) and the organic layers were combined, dried over $Na_2SO_4$ (5 g), filtered, and concentrated under reduced pressure to give a light yellow oily Intermediate 38 (580 mg, 51% yield) which was used for the next step without further purification. The product was verified with LC-MS prior to executing the next step—m/z of [M+H]=492.81.

Compound E38: To Intermediate 38 (580 mg, 1.18 mmol) in an oven-dried flask (100 mL) with a magnetic bar were added anhydrous DMF (5 mL), linoleic acid (460 mg, 1.53 mmol), and 1-[bis(dimethylamino)methylene]-1H-1,2,3-triazolo[4,5-b]pyridinium 3-oxide-hexafluorophosphate (898 mg, 2.36 mmol) in sequence. The mixture was stirred at ambient temperature stirred overnight (17 hours). The reaction mixture was concentrated under reduced pressure and purified by flash chromatography purification system (24 g silica gel column) using a gradient of 0-10% MeOH/DCM for 30 min under the flow rate at 25 mL/min. The product fractions were collected and concentrated to yield Compound E38 (750 mg, 95% yield) as a clear oil. $^1$H nmr (400 MHz, CDCl$_3$) δ: 5.45-5.25 (8H, m, CH=), 4.70-4.29 (2H, m, NHCH, NCHCO), 4.20-4.00 (2H, m, OCH$_2$), 3.90-3.78 (2H, m, NCH$_2$CHNH—), 3.75-3.62 (2H, m, Me$_2$NCH$_2$), 2.84 (6H, s, N(CH$_3$)$_2$), 2.90-2.70 (4H, m, CH$_2$), 2.60-2.55 (2H, m, CH$_2$), 2.10-1.90 (12H, m, CH$_2$CONH, CH$_2$CH=), 1.65-1.40 (6H, m, CH$_2$), 1.40-1.20 (30H, m, CH$_2$), 0.90-0.80 (6H, m, CH$_3$).

Compound E39: Compound E38 (350 mg, 0.46 mmol) was added to methyl iodide (2 mL) in an oven-dried vial (20 mL) with a magnetic bar. The mixture was stirred at ambient temperature overnight (17 hours). Next, the excess reagent was removed under vacuum. The crude was dissolved in 1 mL DCM and purified with a 40 g silica column using a gradient of 0-15% MeOH/DCM for 30 min under the flow rate at 30 mL/min. The product fractions were combined, concentrated, and subjected to Amberlyst A26 Anion Exchange resin to yield Compound E39 (165 mg, 82% yield) as a clear liquid. $^1$H nmr (400 MHz, CDCl$_3$) δ: 5.45-5.25 (8H, m, CH=), 4.70-4.35 (2H, m, NHCH, NCHCO), 4.20-4.00 (2H, m, OCH$_2$), 3.90-3.40 (4H, m, NCH$_2$CH$_2$CH$_2$CO—, NCH$_2$CHNH—), 3.30 (9H, s, N$^+$(CH$_3$)$_3$), 2.85-2.70 (4H, m, CH$_2$), 2.60-2.45 (2H, m, CH$_2$), 2.45-2.10 (8H, m, CH$_2$CH$_2$CH=), 2.10-2.00 (6H, m, CH$_2$), 1.70-1.40 (4H, m, CH$_2$), 1.40-1.20 (30H, m, CH$_2$), 0.90-0.70 (6H, m, CH$_3$).

Figure 29:
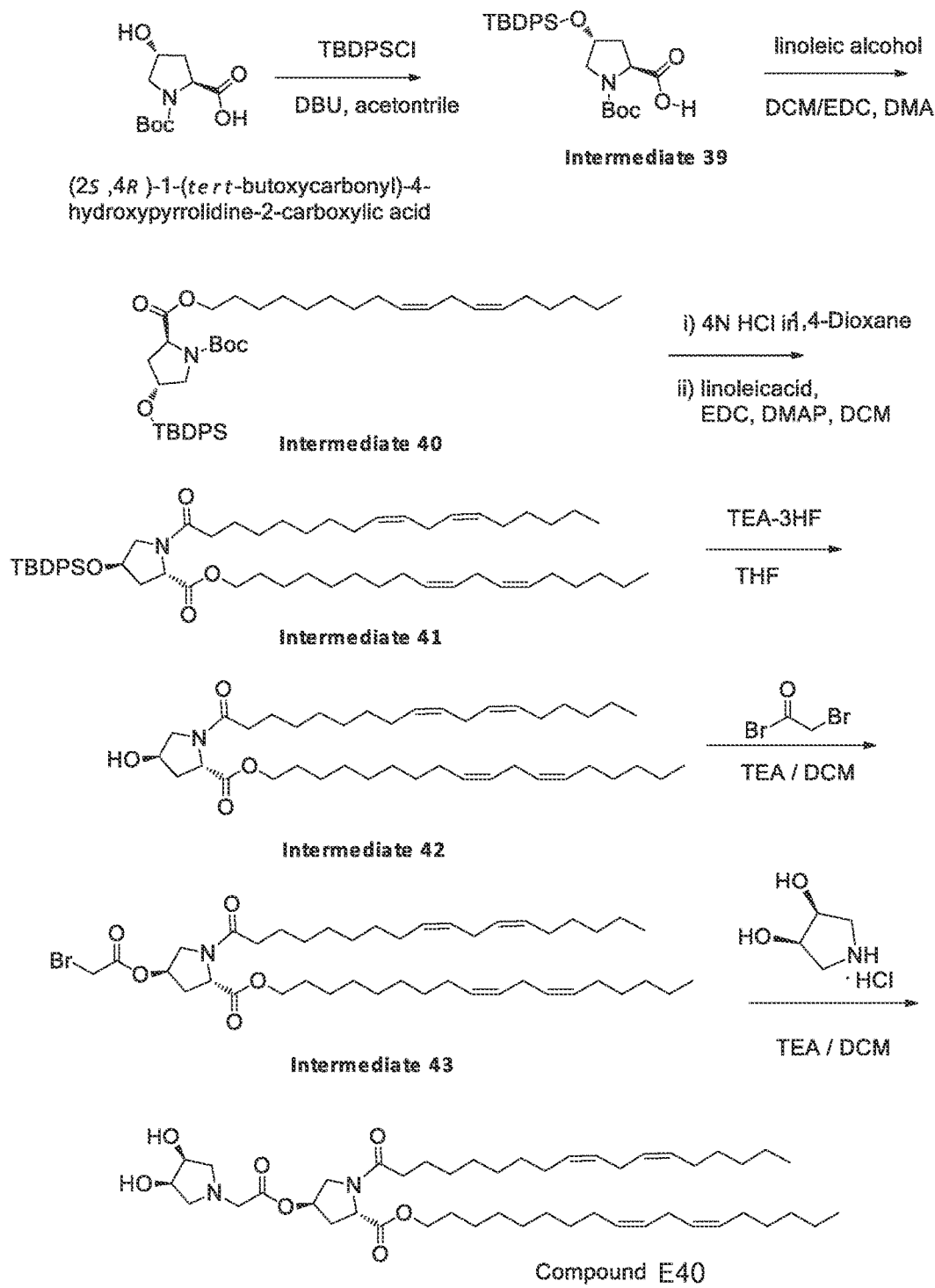
FIG. 29 shows a scheme for the preparation of Compound E40.

Example 29: A Scheme for the Preparation of Compound E40 is Shown in FIG. 29

Intermediate 39: To (2S,4R)-1-(tert-butoxycarbonyl)-4-hydroxypyrrolidine-2-carboxylic acid (5.0 g, 21.62 mmol) in an oven-dried flask (100 mL) with a magnetic bar were added anhydrous acetonitrile (500 mL), TBDPS-Cl (11.9 g, 43.24 mmol) and 1,8-diazabicycloundec-7-ene (11.5 g, 75.67 mmol) in sequence. The mixture was refluxed at 50° C. for 4 hours. Then, the solvent was removed under reduced pressure. The residue was dissolved in 0.2 N HCl (50 mL), extracted with DCM (2×50 mL), dried over $Na_2SO_4$ (5 g), filtered, and concentrated under reduced pressure. The crude was purified by flash chromatography purification system (330 g silica gel column) using a gradient of 0-5% MeOH/DCM for 30 min under the flow rate at 25 mL/min. The product fractions were collected and concentrated to yield Intermediate 39 (9.9 g, 97% yield) as a clear oil. The product was verified with LC-MS prior to executing the next step—m/z of [M+H]$^+$=470.49.

Intermediate 40: To Intermediate 39 (9.9 g, 21.29 mmol) in an oven-dried flask (250 mL) with a magnetic bar were added anhydrous DCM (100 mL), linoleyl alcohol (6.8 g, 25.55 mmol), EDC (8.2 g, 42.58 mmol), and DMAP (1.3 g, 10.65 mmol) in sequence. The mixture was stirred at ambient temperature stirred overnight (17 hours). The reaction mixture was diluted with DCM (25 mL), washed with sodium bicarbonate (20 mL) dried over $Na_2SO_4$ (5 g), filtered, and concentrated under reduced pressure. The crude was purified by flash chromatography purification system (330 g silica gel column) using a gradient of 0-20% MeOH/DCM for 30 min under the flow rate at 25 mL/min. The product fractions were collected and concentrated to yield Intermediate 40 (12.8 g, 98% yield) as a white solid. The product was verified with LC-MS prior to executing the next step—m/z of [M+H]$^+$=718.75.

Intermediate 41: To Intermediate 40 (5.8 g, 6.96 mmol) in an oven-dried flask (50 mL) with a magnetic bar were added 4 N HCl in 1,4-dioxane solution (20 mL). The mixture was then stirred at ambient temperature for 3 hours. Next, the reaction mixture was concentrated under reduced pressure to gain a clear oil, which was then dissolved in anhydrous DCM (20 mL) and added linoleic acid (2.3 g, 8.36 mmol), EDC (2.0 g, 10.45 mmol), and DMAP (0.6 g, 4.87 mmol) in sequence. The mixture was stirred at ambient temperature stirred overnight (17 hours). The reaction mixture was diluted with DCM (25 mL), washed with sodium bicarbonate (20 mL) dried over Na$_2$SO$_4$ (5 g), filtered, and concentrated under reduced pressure. The crude was purified by flash chromatography purification system (330 g silica gel column) using a gradient of 0-20% MeOH/DCM for 30 min under the flow rate at 25 mL/min. The product fractions were collected and concentrated to yield Intermediate 41 (5.8 g, 94% yield) as a colorless oil. The product was verified with LC-MS prior to executing the next step—m/z of [M+H]$^+$=880.91.

Intermediate 42: To Intermediate 41 (5.8 g, 6.58 mmol) in an oven-dried flask (250 mL) with a magnetic bar were added THF (100 mL) and triethylamine trihydrofluoride (10.6 g, 65.8 mmol) sequentially. The mixture was then stirred at ambient temperature for 17 hours. Next, the reaction mixture was concentrated under reduced pressure and purified by flash chromatography purification system (120 g silica gel column) using a gradient of 0-30% EtOAc/hexane for 10 min then 0-10% MeOH/DCM for 20 min under the flow rate at 25 mL/min. The product fractions were collected and concentrated to yield Intermediate 42 (4.3 g, 78% yield) as a colorless oil. The product was verified with LC-MS prior to executing the next step—m/z of [M+H]$^+$=642.91.

Intermediate 43: To Intermediate 42 (2.3 g, 7.16 mmol) in an oven-dried flask (50 mL) with a magnetic bar were added DCM(10 mL), 2-bromoacetyl bromide (0.9 g, 4.66 mmol) and TEA (0.7 g, 7.16 mmol) sequentially. The mixture was then stirred at ambient temperature for 3 hours. Next, the reaction mixture was concentrated under reduced pressure and purified by flash chromatography purification system (120 g silica gel column) using a gradient of 0-30% EtOAc/hexane for 10 min then 0-10% MeOH/DCM for 20 min under the flow rate at 25 mL/min. The product fractions were collected and concentrated to yield Intermediate 43 (2.4 g, 82% yield) as a colorless oil. The product was verified with LC-MS prior to executing the next step—m/z of [M+H]$^+$=764.74.

Compound E40: Intermediate 43 (300 mg, 0.39 mmol) was added to anhydrous DCM (5 mL) in an oven-dried vial (40 mL) with a magnetic bar. Then 3-azetidinemethanol hydrochloride (97 mg, 0.79 mmol) and TEA (0.2 mL, 1.18 mmol) were added in sequence. The mixture was stirred at ambient temperature for 17 hours. After removed the solvent by rotavapor under vacuum, the residue was treated with 10% K$_2$CO$_3$ solution (50 mL) and extracted with DCM (2×50 mL). The organic layers were then combined, dried over Na$_2$SO$_4$ (10 g), filtered, and concentrated under reduced pressure. The crude was dissolved in 2 mL DCM and purified with a 24 g silica column using a gradient of 0-15% MeOH/DCM for 30 min under the flow rate at 25 mL/min. The product fractions were collected and concentrated to yield Compound E40 (196 mg, 65% yield) as a yellow liquid. The lipid's identity was confirmed with LC-MS analysis—m/z of [M+H]$^+$=769.17.

Figure 30:
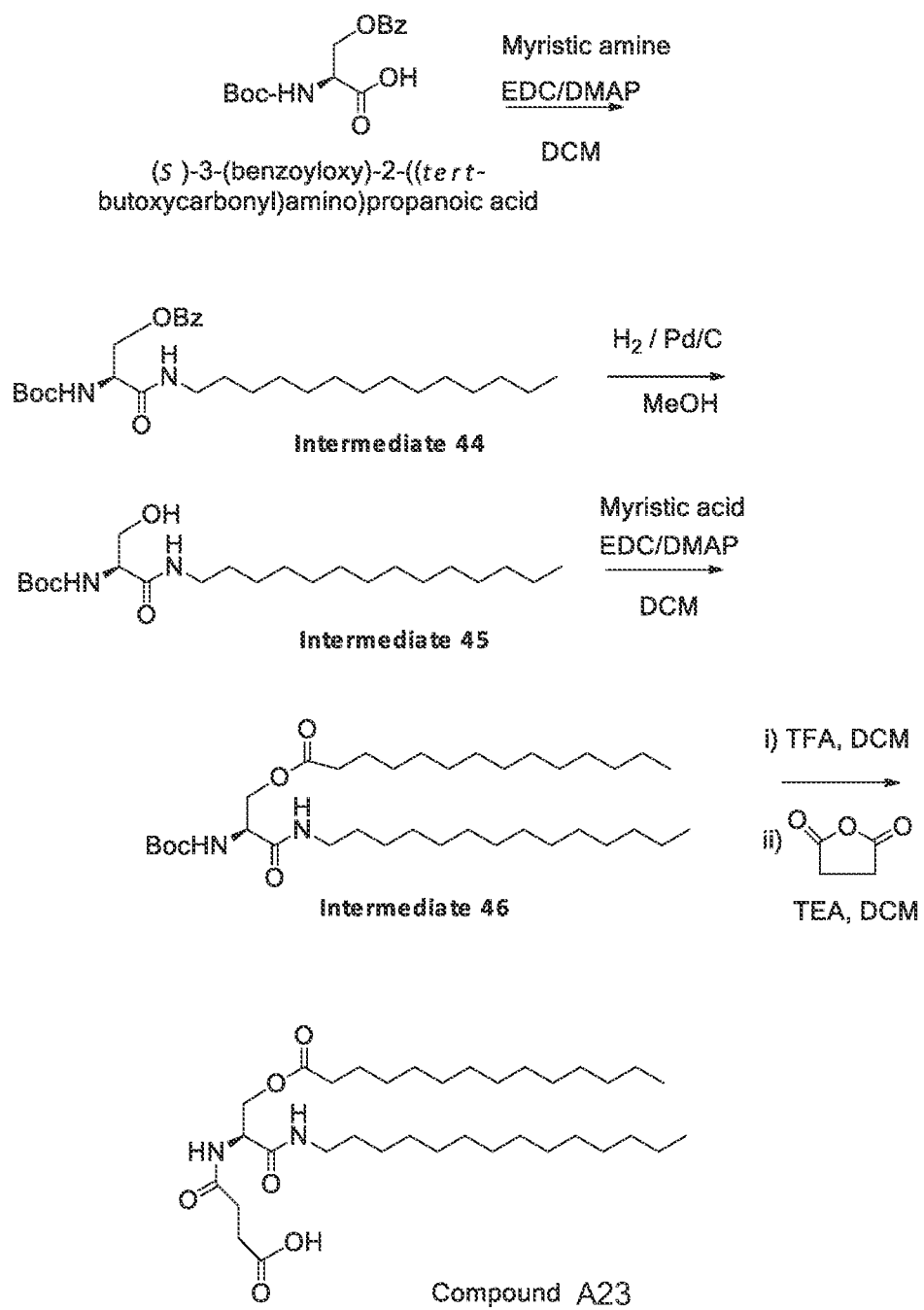
FIG. 30 shows a scheme for the preparation of Compound A23.

Example 30: A Scheme for the Preparation of Compound A23 is Shown in FIG. 30

Intermediate 44: To O-benzoyl-N-(tert-butoxycarbonyl)-L-serine (3.0 g, 10.16 mmol) in an oven-dried flask (100 mL) with a magnetic bar were added anhydrous DCM (40 mL), myristic amine (2.4 g, 11.17 mmol), EDC (2.9 g, 15.24 mmol), and DMAP (0.6 g, 5.08 mmol) in sequence. The mixture was stirred at ambient temperature stirred overnight (17 hours). The reaction mixture was diluted with EtOAc (300 mL), washed with sodium bicarbonate (20 mL) dried over Na$_2$SO$_4$ (5 g), filtered, and concentrated under reduced pressure. The crude was purified by flash chromatography purification system (330 g silica gel column) using 1:2 v/v EtOAc/hexane for 30 min under the flow rate at 25 mL/min. The product fractions were collected and concentrated to yield Intermediate 44 (4.4 g, 89% yield) as a white solid. The product was verified with LC-MS prior to executing the next step—m/z of [M+H]$^+$=491.61.

Intermediate 45: To Intermediate 44 (2.0 g, 4.08 mmol) in an oven-dried flask (50 mL) with a magnetic bar were added MeOH (30 mL) and palladium on carbon (120 mg). The flask was then purge with hydrogen using a hydrogen balloon. The mixture was stirred at ambient temperature for 5 hours and filtered via a bed of celite. The filtrate was then concentrated under reduced pressure to gain Intermediate 45 (1.7 g, 95%) as a white solid, which was used for the next step without further purification. The product was verified with LC-MS prior to executing the next step—m/z of [M+H]$^+$=401.44.

Intermediate 46: To Intermediate 45 (1.7 g, 4.28 mmol) in an oven-dried flask (50 mL) with a magnetic bar were added anhydrous DCM (20 mL), myristic acid (1.3 g, 5.56 mmol), EDC (1.6 g, 8.55 mmol), and DMAP (0.5 g, 4.28 mmol) in sequence. The mixture was stirred at ambient temperature stirred overnight (17 hours). The reaction mixture was diluted with EtOAc (100 mL), washed with 1 N HCl (20 mL) dried over Na$_2$SO$_4$ (5 g), filtered, and concentrated under reduced pressure. The crude was purified by flash chromatography purification system (120 g silica gel column) using 1:2 v/v EtOAc/hexane for 30 min under the flow rate at 25 mL/min. The product fractions were collected and concentrated to yield Intermediate 46 (2.4 g, 94% yield) as a white solid. The product was verified with LC-MS prior to executing the next step—m/z of [M+H]$^+$=612.02.

Compound A23: To Intermediate 46 (435 mg, 0.85 mmol) in an oven-dried flask (25 mL) with a magnetic bar were added anhydrous DCM (20 mL) and TFA (5 mL) in sequence. The mixture was stirred at ambient temperature stirred for 2 hours. During stirring, the solution color turned from clear to red. Next, the reaction mixture was first concentrated using a rotavapor and washed with 10% Na$_2$CO$_3$ solution (20 mL). The mixture was then extracted with DCM (2×20 mL) and the organic layers were combined, dried over Na$_2$SO$_4$ (5 g), filtered, and concentrated to an oily residue, which was then in DCM (10 mL) and added succinic anhydride (118 mg, 1.17 mmol), and TEA (118 mg, 1.17 mmol). The mixture was stirred at ambient temperature stirred overnight (17 hours). The reaction mixture was diluted with DCM (100 mL), washed with sodium bicarbonate (20 mL) dried over Na$_2$SO$_4$ (5 g), filtered, and concentrated under reduced pressure. The crude was purified by flash chromatography purification system (120 g silica gel column) using 0-20% MeOH/DCM for 30 min under the flow rate at 25 mL/min. The product fractions were collected and concentrated to yield Compound A23 (338 mg, 92% yield) as a white solid. $^1$H nmr (400 MHz, CDCl$_3$) δ: 6.76-6.70 (1H, m, CHNHCO), 6.40-6.35 (1H, m, CH$_2$NHCO), 4.70-4.60 (1H, m, NHCHCO), 4.42-4.20 (2H, m, CH$_2$O), 3.26-3.12 (2H, m, NHCH$_2$), 2.80-2.60 (2H, m, CH$_2$CO$_2$H), 2.57-2.50 (2H, m, CH$_2$CONH), 2.30-2.20 (2H, m, CH$_2$CO$_2$), 1.60-1.50 (2H, m, CH$_2$CH$_2$CO$_2$), 1.50-1.40 (2H, CH$_2$CH$_2$NH), 1.35-1.15 (42H, m, NH(CH$_2$)$_2$(CH$_2$)$_{11}$Me, CO(CH$_2$)$_2$(CH$_2$)$_{10}$Me), 0.90-0.83 (6H, m, CH$_3$).

Figure 31:
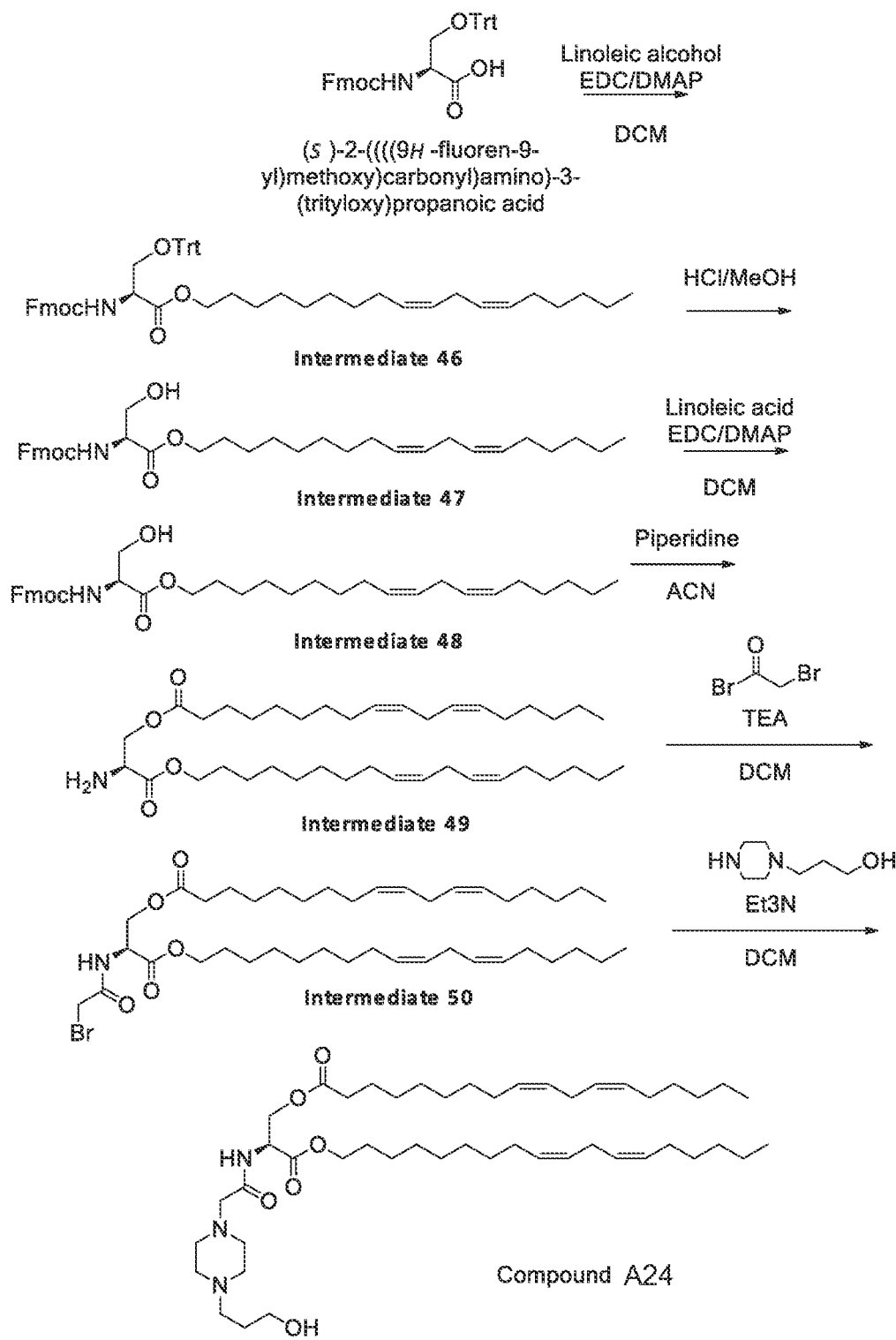
FIG. 31 shows a scheme for the preparation of Compound A24.

Example 31: A Scheme for the Preparation of Compound A24 is Shown in FIG. 31

Intermediate 46: To N-(((9H-fluoren-9-yl)methoxy)carbonyl)-O-trityl-L-serine (3.0 g, 5.27 mmol) in an oven-dried flask (100 mL) with a magnetic bar were added anhydrous DCM (40 mL), linoleyl alcohol (1.5 g, 5.79 mmol), EDC (2.0 g, 10.54 mmol), and DMAP (3.7 g, 0.70 mmol) in sequence. The mixture was stirred at ambient temperature stirred overnight (17 hours). The reaction mixture was diluted with DCM (100 mL), washed with sodium bicarbonate (20 mL) dried over Na$_2$SO$_4$ (5 g), filtered, and concentrated under reduced pressure. The crude was purified by flash chromatography purification system (120 g silica gel column) using 1:2 v/v EtOAc/hexane for 30 min under the flow rate at 25 mL/min. The product fractions were collected and concentrated to yield Intermediate 46 (4.3 g, 90% yield) as a clear oil. The product was verified with LC-MS prior to executing the next step—m/z of [M+NH$_4$]$^+$=835.00.

Intermediate 47: To Intermediate 46 (4.3 g, 5.19 mmol) in an oven-dried flask (50 mL) with a magnetic bar were added 3 N HCl in MeOH solution (40 mL). The mixture was then stirred at ambient temperature for 3 hours. Next, the reaction mixture was concentrated under reduced pressure to gain Intermediate 47 (2.5 g, 86% yield) as a clear oil, which was then used for the next reaction without further purification. The product was verified with LC-MS prior to executing the next step—m/z of [M+H]$^+$=576.68.

Intermediate 48: To Intermediate 47 (2.5 g, 4.34 mmol) in an oven-dried flask (100 mL) with a magnetic bar were added anhydrous DCM (50 mL), linoleic acid (1.3 g, 4.78 mmol), EDC (1.7 g, 8.68 mmol), and DMAP (0.3 g, 2.17 mmol) in sequence. The mixture was stirred at ambient temperature stirred overnight (17 hours). The reaction mixture was diluted with DCM (100 mL), washed with 1 N sodium bicarbonate (20 mL) dried over Na$_2$SO$_4$ (5 g), filtered, and concentrated under reduced pressure. The crude was purified by flash chromatography purification system (120 g silica gel column) using 1:2 v/v EtOAc/hexane for 30 min under the flow rate at 25 mL/min. The product fractions were collected and concentrated to yield Intermediate 48 (2.1 g, 82% yield) as a white solid. The product was verified with LC-MS prior to executing the next step—m/z of [M+NH$_4$]$^+$=856.06.

Intermediate 49: To Intermediate 48 (2.9 g, 3.40 mmol) in an oven-dried flask (50 mL) with a magnetic bar were added anhydrous acetonitrile (20 mL) and piperidine (4 mL). The mixture was stirred at ambient temperature stirred overnight (17 hours), the reaction mixture was concentrated under reduced pressure and purified by flash chromatography purification system (120 g silica gel column) using 0-50% EtOAc/hexane for 30 min under the flow rate at 40 mL/min. The product fractions were collected and concentrated to yield Intermediate 49 (1.3 g, 900% yield) as a clear oil. The product was verified with LC-MS prior to executing the next step—m/z of [M+H]$^+$=617.06.

Intermediate 50: Intermediate 49 (500 mg, 0.81 mmol) was dissolved in anhydrous DCM (10 mL) and bromoacetyl bromide (0.1 mL, 0.81 mmol) followed by TEA (0.1 mL, 0.89 mmol) were then added slowly. After the addition was completed, the mixture was stirred at ambient temperature overnight. Next day, the mixture was diluted with DCM (50 mL) and washed with H$_2$O (50 mL) and 10% K$_2$CO$_3$ (50 mL). Back-extraction was performed for both aqueous washes with DCM (2×25 mL). The organic layers were combined, dried with MgSO$_4$, filtered, and concentrated in vacuo. The crude was purified with a 40 g silica column on flash chromatography system equipped with ESLD detector using a gradient of hexane for 0.5 min, then 0-50% EtOAc/hexane 30 min gradient followed by 50% EtOAc/hexane for 5 min under the flow rate at 40 mL/min. The product fractions were collected and concentrated to yield Intermediate 50 (445 mg, 80% yield) as a colorless liquid. The product was verified with LC-MS prior to executing the next step—m/z of [M+H]$^+$=737.01.

Compound A24: Intermediate 50 (150 mg, 0.20 mmol) was added to anhydrous DCM (5 mL) in an oven-dried vial (40 mL) with a magnetic bar. Then were added 3-(piperazin-1-yl)propan-1-ol (33 mg, 0.22 mmol) and TEA (40 mL, 0.25 mmol). The mixture was stirred at ambient temperature for 4 hours. After removed the solvent by rotavapor under vacuum, the residue was treated with 10% K$_2$CO$_3$ solution (50 mL) and extracted with DCM (2×50 mL). The organic layers were then combined, dried over Na$_2$SO$_4$ (10 g), filtered, and concentrated under reduced pressure. The crude was dissolved in 2 mL DCM and purified with a 24 g silica column using a gradient of 10-15% EtOAc/hexane for 10 min then 0-10% MeOH/DCM for 30 min under the flow rate at 25 mL/min. The product fractions were collected and concentrated to yield Compound A24 (128 mg, 70% yield) as a colorless liquid. $^1$H nmr (400 MHz, CDCl$_3$) δ: 6.50-6.40 (1H, m, NHCO), 5.45-5.20 (8H, m, CH═), 4.90-4.60 (2H, m, NHCHCO, HO) 4.60-4.50 (1H, m, CH$_2$CHOC(O)), 4.45-4.30 (1H, m, CH$_2$CHOC(O)), 4.20-4.10 (2H, m, C(O)OCH$_2$CH$_2$), 3.80-3.70 (2H, m, HOCH$_2$CH$_2$), 3.47 (2H, s, NCH$_2$C(O)NH), 2.85-2.70 (4H, m, ═CHCH$_2$CH═), 2.70-2.45 (8H, m, HOCH$_2$CH$_2$CH$_2$N, CH$_2$NCH$_2$C(O), O(CO)CH$_2$CH$_2$), 2.30-1.90 (12H, m, NCH$_2$CH$_2$NCH$_2$C(O), CH$_2$CH$_2$CH═), 1.60-1.10 (36H, m, CH$_2$), 0.90-0.75 (6H, m, CH$_3$).

Figure 32:
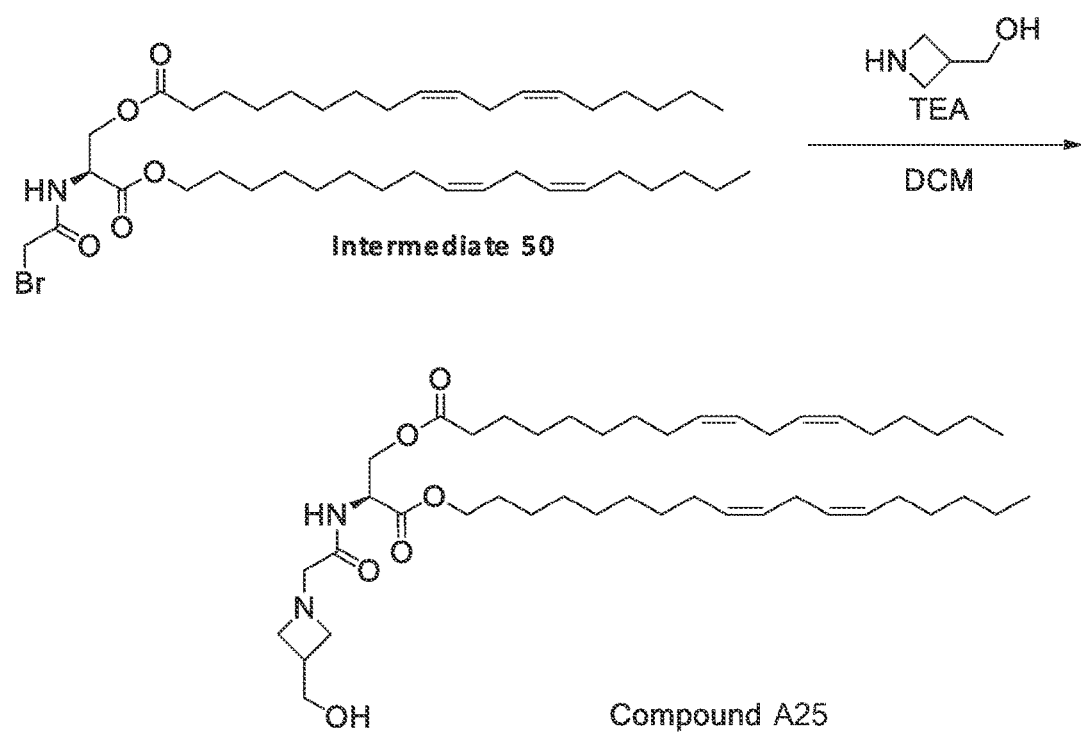
FIG. 32 shows a scheme for the preparation of Compound A25.

Example 32: A Scheme for the Preparation of Compound A25 is Shown in FIG. 32

Compound A25: Intermediate 50 (208 mg, 0.28 mmol) was added to anhydrous DCM (5 mL) in an oven-dried vial (40 mL) with a magnetic bar. Then 3-azetidinemethanol hydrochloride (70 mg, 0.26 mmol) and TEA (120 mL, 0.85 mmol) were added. The mixture was stirred at ambient temperature for 2 hours. After removed the solvent by rotavapor under vacuum, the residue was treated with 10% K$_2$CO$_3$ solution (50 mL) and extracted with DCM (2×50 mL). The organic layers were then combined, dried over Na$_2$SO$_4$ (10 g), filtered, and concentrated under reduced pressure. The crude was dissolved in 2 mL DCM and purified with a 24 g silica column using a gradient of 0-10% MeOH/DCM for 30 min under the flow rate at 25 mL/min. The product fractions were collected and concentrated to yield Compound A25 (66 mg, 31% yield) as a colorless liquid. $^1$H nmr (400 MHz, CDCl$_3$) δ: 6.60-6.50 (1H, m, NHCO), 5.40-5.20 (8H, m, CH=), 4.90-4.80 (2H, m, CH$_2$CH$_2$OC(O)), 4.52-4.45 (1H, m, NHCHCO), 4.13-4.02 (2H, m, CH$_2$OC(O)), 3.60-3.40 (2H, m, CH$_2$OH), 3.70-3.30 (4H, m, CHCH$_2$N), 3.20 (2H, s, CH$_2$N), 2.80-2.65 (5H, m, =CHCH$_2$CH=, —OH), 2.70-2.40 (3H, m, CH$_2$CH$_2$CO(O), HOCH$_2$CH), 2.30-1.90 (8H, m, CH$_2$CH$_2$CH=), 1.60-1.10 (34H, m, CH$_2$), 0.90-0.83 (6H, m, CH$_3$).

Example 33: Example Formulations are Prepared for Encapsulating a Small Interfering Nucleic Acid Agents (siRNA), as Shown in Table 3

TABLE 3

Lipid formulations for siRNA

| No. | Compound C2 (mol %) | Cholesterol (mol %) | DOPE (mol %) | DOPC (mol %) | DPPE-mPEG(2000) (mol %) | EE* (%) |
|---|---|---|---|---|---|---|
| 1 | 25 | 30 | 30 | 10 | 5 | >90 |
| 2 | 25 | 30 | 25 | 15 | 5 | >90 |
| 3 | 25 | 30 | 20 | 20 | 5 | >90 |
| 4 | 25 | 30 | 15 | 25 | 5 | >90 |
| 5 | 25 | 30 | 10 | 30 | 5 | >90 |
| 6 | 25 | 35 | 15 | 20 | 5 | >90 |
| 7 | 25 | 35 | 20 | 15 | 5 | >90 |
| 8 | 30 | 30 | 15 | 20 | 5 | >90 |
| 9 | 30 | 30 | 20 | 15 | 5 | >90 |
| 10 | 35 | 30 | 15 | 15 | 5 | >90 |

*Encapsulation efficiency for siRNA.

Example 34: Example Formulations are Prepared for Encapsulating a Small Interfering Nucleic Acid Agents (siRNA), as Shown in Table 4

TABLE 4

Lipid formulations for siRNA

| No. | Compound A9 (mol %) | Cholesterol (mol %) | DOPE (mol %) | DOPC (mol %) | DPPE-mPEG(2000) (mol %) | EE* (%) |
|---|---|---|---|---|---|---|
| 1 | 25 | 30 | 30 | 10 | 5 | >90 |
| 2 | 25 | 30 | 25 | 15 | 5 | >90 |
| 3 | 25 | 30 | 20 | 20 | 5 | >90 |
| 4 | 25 | 30 | 15 | 25 | 5 | >90 |
| 5 | 25 | 30 | 10 | 30 | 5 | >90 |
| 6 | 25 | 35 | 15 | 20 | 5 | >90 |
| 7 | 25 | 35 | 20 | 15 | 5 | >90 |
| 8 | 30 | 30 | 15 | 20 | 5 | >90 |
| 9 | 30 | 30 | 20 | 15 | 5 | >90 |
| 10 | 35 | 30 | 15 | 15 | 5 | >90 |

*Encapsulation for efficiency siRNA.

Example 35: Example Formulations are Prepared for Encapsulating a Small Interfering Nucleic Acid Agents (siRNA), as Shown in Table 5

TABLE 5

Lipid formulations for siRNA

| No. | Compound AA (mol %) | Cholesterol (mol %) | DOPE (mol %) | DOPC (mol %) | DPPE-mPEG(2000) (mol %) | EE* (%) |
|---|---|---|---|---|---|---|
| 1 | 25 | 30 | 30 | 10 | 5 | >90 |
| 2 | 25 | 30 | 25 | 15 | 5 | >90 |
| 3 | 25 | 30 | 20 | 20 | 5 | >90 |
| 4 | 25 | 30 | 15 | 25 | 5 | >90 |
| 5 | 25 | 30 | 10 | 30 | 5 | >90 |
| 6 | 25 | 35 | 15 | 20 | 5 | >90 |
| 7 | 25 | 35 | 20 | 15 | 5 | >90 |
| 8 | 30 | 30 | 15 | 20 | 5 | >90 |
| 9 | 30 | 30 | 20 | 15 | 5 | >90 |
| 10 | 35 | 30 | 15 | 15 | 5 | >90 |

*Encapsulation efficiency for siRNA.

Example 36: Example Formulations are Prepared for Encapsulating a Small Interfering Nucleic Acid Agents (siRNA), as Shown in Table 6

TABLE 6

Lipid formulations for siRNA

| No. | Compound F5 (mol %) | Cholesterol (mol %) | DOPE (mol %) | DOPC (mol %) | DPPE-mPEG(2000) (mol %) | EE* (%) |
|---|---|---|---|---|---|---|
| 1 | 25 | 30 | 30 | 10 | 5 | >90 |
| 2 | 25 | 30 | 25 | 15 | 5 | >90 |
| 3 | 25 | 30 | 20 | 20 | 5 | >90 |
| 4 | 25 | 30 | 15 | 25 | 5 | >90 |
| 5 | 25 | 30 | 10 | 30 | 5 | >90 |
| 6 | 25 | 35 | 15 | 20 | 5 | >90 |
| 7 | 25 | 35 | 20 | 15 | 5 | >90 |
| 8 | 30 | 30 | 15 | 20 | 5 | >90 |
| 9 | 30 | 30 | 20 | 15 | 5 | >90 |
| 10 | 35 | 30 | 15 | 15 | 5 | >90 |

*Encapsulation efficiency for siRNA.

Example 37: Formulations were Prepared for Encapsulating a Small Interfering Nucleic Acid Agents (siRNA), as Shown in Table 7

TABLE 7

Lipid formulations for siRNA

| No. | Compound A6 (mol %) | Cholesterol (mol %) | DOPE (mol %) | DOPC (mol %) | DPPE-mPEG(2000) (mol %) | EE* (%) |
|---|---|---|---|---|---|---|
| 1 | 25 | 30 | 30 | 10 | 5 | 92 |
| 2 | 25 | 30 | 25 | 15 | 5 | 91 |
| 3 | 25 | 30 | 20 | 20 | 5 | 87 |
| 4 | 75 | 30 | 15 | 25 | 5 | 93 |
| 5 | 25 | 30 | 10 | 30 | 5 | 92 |
| 6 | 25 | 35 | 15 | 20 | 5 | 93 |
| 7 | 25 | 35 | 20 | 15 | 5 | 95 |
| 8 | 30 | 30 | 15 | 20 | 5 | 87 |

TABLE 7-continued

Lipid formulations for siRNA

| No. | Compound A6 (mol %) | Cholesterol (mol %) | DOPE (mol %) | DOPC (mol %) | DPPE-mPEG(2000) (mol %) | EE* (%) |
|---|---|---|---|---|---|---|
| 9 | 30 | 30 | 20 | 15 | 5 | 92 |
| 10 | 35 | 30 | 15 | 15 | 5 | 88 |

*Encapsulation efficiency for siRNA.

Example 38: Formulations were Prepared for Encapsulating a Small Interfering Nucleic Acid Agents (siRNA)

Lipid nanoparticle formulations were prepared with the following compositions:
(Ionizable compound/DOPE/DOPC/Cholesterol/DMPE-PEG) mol %
50/28/0/21/1
50/28/0/20/2
26/21/21/31/1.

Characteristics of the nanoparticle formulations are shown in Table 8. The formulations had superior properties for encapsulating the siRNA, and in having small particle size.

TABLE 8

Lipid formulations for siRNA

| Compound No. | Z (ave) nm | EE* (%) |
|---|---|---|
| C2 | 111 | 95 |
| A6 | 121 | 96 |
| A9 | 97 | 95 |
| D15 | 117 | 96 |
| C24 | 127 | 98 |
| DD | 137 | 92 |
| E4 | 131 | 94 |
| AA | 120 | 90 |

*Encapsulation efficiency for siRNA.

Example 39: Formulations were Prepared for Encapsulating a Small Interfering Nucleic Acid Agents (siRNA)

Lipid nanoparticle formulations were prepared with the following compositions:
(Ionizable compound/DOPE/Cholesterol/DMPE-PEG) mol %
50/28/21/1.

Serum stability and EC50 of nanoparticle formulations were measured and are shown in Table 9. The formulations were capable of encapsulating the siRNA, and retaining stability in human serum.

TABLE 9

Lipid formulations for siRNA

| Compound | pKa | EC50 GFP siRNA (nM) | t(½) (hr) human serum 37 C. |
|---|---|---|---|
| D23 | 4.8 | | 23 |
| D24 | | | >200 |
| D25 | 3.7, 9.5 | | |
| D26 | 5.4 | | |
| D27 | 4.2, 8.9 | | 151 |
| D28 | 4.5, 7.3 | | 118 |
| D29 | 6.7 | | >200 |
| D30 | | | >200 |
| D31 | | | >200 |
| D32 | 5.4 | | 61 |
| D33 | | | |
| D34 | 6.0 | | 91 |
| D35 | 6.1 | | 21 |
| D36 | | | |
| D37 | | | 15 |
| A4 | 5.8 | | 93 |
| D38 | 5.3 | | 33 |
| D39 | | | >200 |
| D40 | | | >200 |
| D41 | | | |
| D42 | | | >200 |
| D43 | 10.1 | | >200 |
| D44 | 3.7, 9.1 | | 26 |
| D45 | | | >200 |
| D46 | | | |
| D47 | | | |
| D48 | | | |
| D49 | | | |
| D50 | | | >200 |
| D51 | 4.1, 9.1 | | 39 |
| D52 | 9.7 | | >200 |
| D53 | | | |
| D54 | 8.2 | | >200 |
| D55 | 4.5 | | 14 |
| D56 | | | >200 |
| D57 | | | 123 |
| D58 | | | |
| D59 | | | |
| D60 | | | |
| D61 | | | |
| D62 | 9.4 | | 92 |
| D63 | | | |
| D64 | 8.8 | | 41 |
| D65 | | | >200 |
| C3 | 6.9 | | >200 |
| D66 | | | >200 |
| D67 | 6.6 | | >200 |
| D68 | 5.7 | | >200 |
| C2 | | 33 | >200 |
| D69 | | | |
| D70 | 3.0 | | 130 |
| D71 | | 42 | |
| D72 | 4.7 | | >200 |
| D73 | 4.3 | | >200 |
| D74 | 4.3 | | 85 |
| F6 | 9.3 | | 97 |
| AA | 7.4 | 22 | 81 |
| D75 | 9.1 | | 108 |
| D76 | 4.5 | | |
| B8 | 4.3 | | |
| D77 | 7.5 | | |
| D78 | 5.6 | | 136 |
| D79 | | | |
| D80 | 5.6 | | >200 |
| D81 | 5.9 | | >200 |
| D82 | | | |
| D83 | 4.8, 7.2 | | 47 |
| D84 | 6.4 | | 80 |
| A23 | | | |
| E37 | 9.2 | | 79 |
| A9 | 7.4 | 31 | 56 |
| D85 | | | >200 |
| D86 | 7.7 | | >200 |
| D87 | | | >200 |
| D88 | | | 82 |
| F5 | 9.4 | 33 | 59 |
| F8 | | | 72 |

TABLE 9-continued

Lipid formulations for siRNA

| Compound | pKa | EC50 GFP siRNA (nM) | t(½) (hr) human serum 37 C. |
|---|---|---|---|
| F7 | | | >200 |
| F9 | | | >200 |
| D89 | | | |
| A6 | 6.3 | 11 | |
| A5 | 6.1 | 6.9 | |
| D90 | | | |
| AB | 6.9 | 7.4 | |
| A7 | 7.6 | 35 | |
| A8 | | | |
| D91 | | | |
| D92 | | | |
| D93 | | | |
| D94 | | | |
| E38 | | | |
| D95 | | | |
| D96 | 6.0 | 5.1 | |
| DD | 5.1 | | |
| E4 | | 2.7 | |
| D97 | | | |
| D98 | | | |
| C25 | | | |
| E39 | | | |
| D99 | | | |
| D9A | | 60 | |
| C24 | | 92 | |
| D9B | | | |
| D9C | | | |
| D9D | | <50 | |
| CA | | <50 | |
| D1 | | | |

Example 40: Example Formulations are Prepared for Encapsulating a Small Interfering Nucleic Acid Agents (siRNA)

Lipid nanoparticle formulations are prepared with the following compositions:
(Ionizable compound/DOPE/Cholesterol/DMPE-PEG) mol %
50/28/21/1.

Serum stability of a nanoparticle formulation is measured and is shown in Table 10. The formulations are capable of encapsulating the siRNA, and retaining stability in human serum.

TABLE 10

Lipid formulations for siRNA

| Compound | t(½) (hr) human serum 37 C. |
|---|---|
| C24 | >50 |
| AB | >50 |
| A6 | >50 |
| B8 | >50 |
| A23 | >50 |
| A5 | >50 |
| A7 | >50 |
| A8 | >50 |
| E38 | >50 |
| DD | >50 |
| E4 | >50 |
| C25 | >50 |
| E39 | >50 |

The embodiments described herein are not limiting and one skilled in the art can readily appreciate that specific combinations of the modifications described herein can be tested without undue experimentation toward identifying nucleic acid molecules with improved RNAi activity.

All publications, patents and literature specifically mentioned herein are incorporated by reference in their entirety for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention. It will be readily apparent to one skilled in the art that varying substitutions and modifications can be made to the description disclosed herein without departing from the scope and spirit of the description, and that those embodiments are within the scope of this description and the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably, and shall be read expansively and without limitation.

Recitation of ranges of values herein are merely intended to serve as a shorthand method of referring individually to each separate value falling within the range, unless otherwise indicated herein, and each separate value is incorporated into the specification as if it were individually recited herein. For Markush groups, those skilled in the art will recognize that this description includes the individual members, as well as subgroups of the members of the Markush group.

A compound, molecule or composition of this invention may have an ionic form for which the corresponding counterion or counterions are not shown. A person of skill in the art will immediately understand that the counterion or counterions will exist as necessary. Examples of counterions include alkali metal ions, Cl⁻, and pharmaceutically acceptable counterions.

For example, when a list of examples or components is given, such as a list of compounds, molecules or compositions suitable for this invention, it will be apparent to those skilled in the art that mixtures of the listed compounds, molecules or compositions may also be suitable.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A compound comprising the structure shown in Formula IV

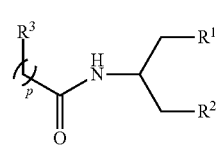

Formula IV wherein $R^1$ and $R^2$ are $R^1 = C(=O)OR^4$ $R^2 = C(=O)OR^5$ wherein $R^4$ and $R^5$ are independently for each occurrence a C(12-20) alkyl group, or a C(12-20) alkenyl group:

wherein $R^3$ is selected from

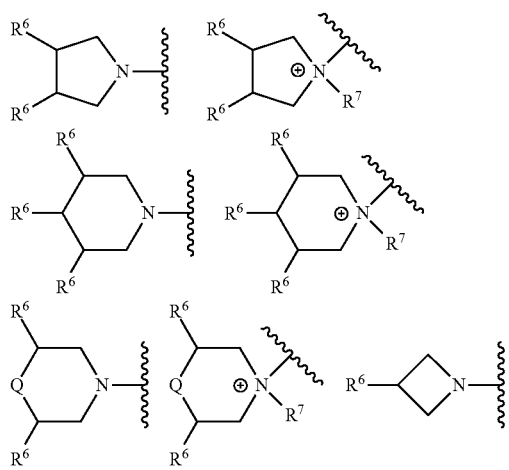

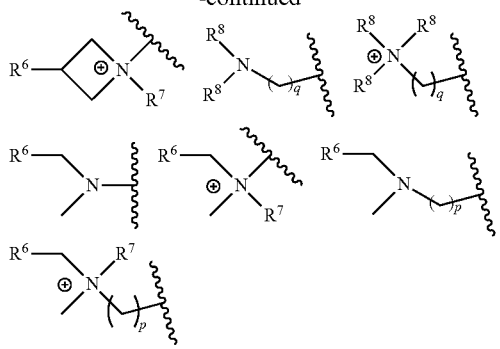

wherein
- each $R^6$ is independently selected from H, alkyl, hydroxyl, hydroxyalkyl, alkoxy, alkoxyalkoxy, and aminoalkyl;
- each $R^7$ is independently selected from H, alkyl, hydroxyalkyl, and aminoalkyl;
- each $R^8$ is independently selected from H, alkyl, hydroxyalkyl, and aminoalkyl, and any two $R^8$ may form a ring;
- q is from zero to four;
- Q is O or $NR^7$;
- p is from 1 to 4.

2. The compound of claim 1, having a structure selected from

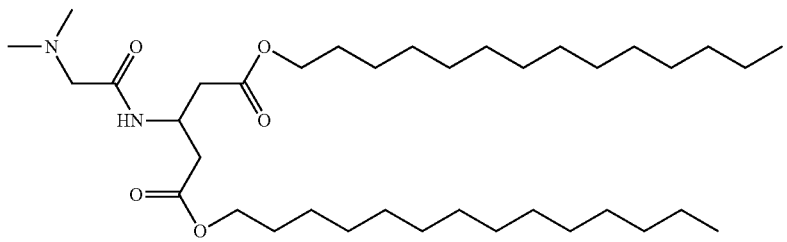

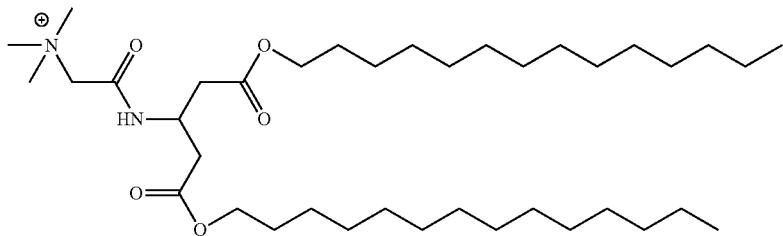

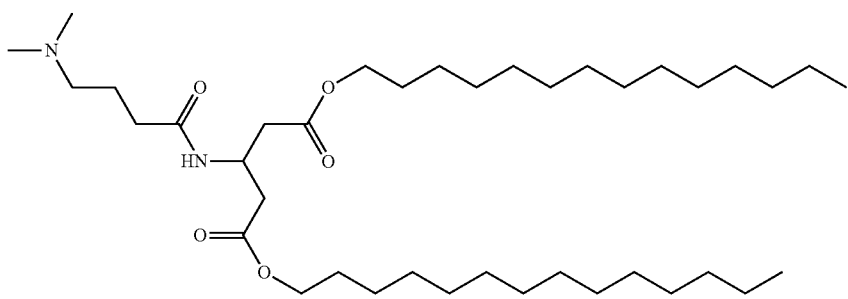

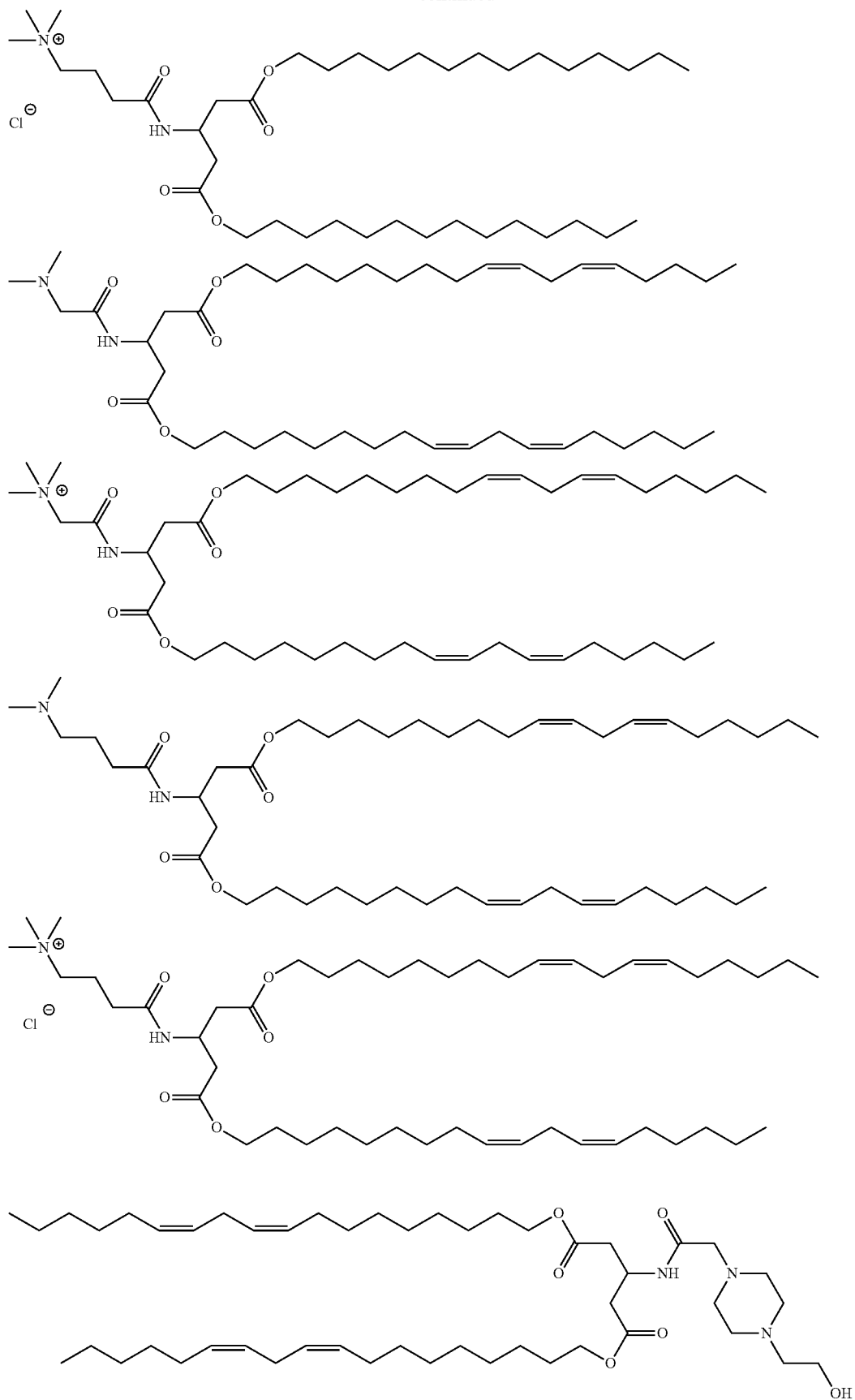

-continued
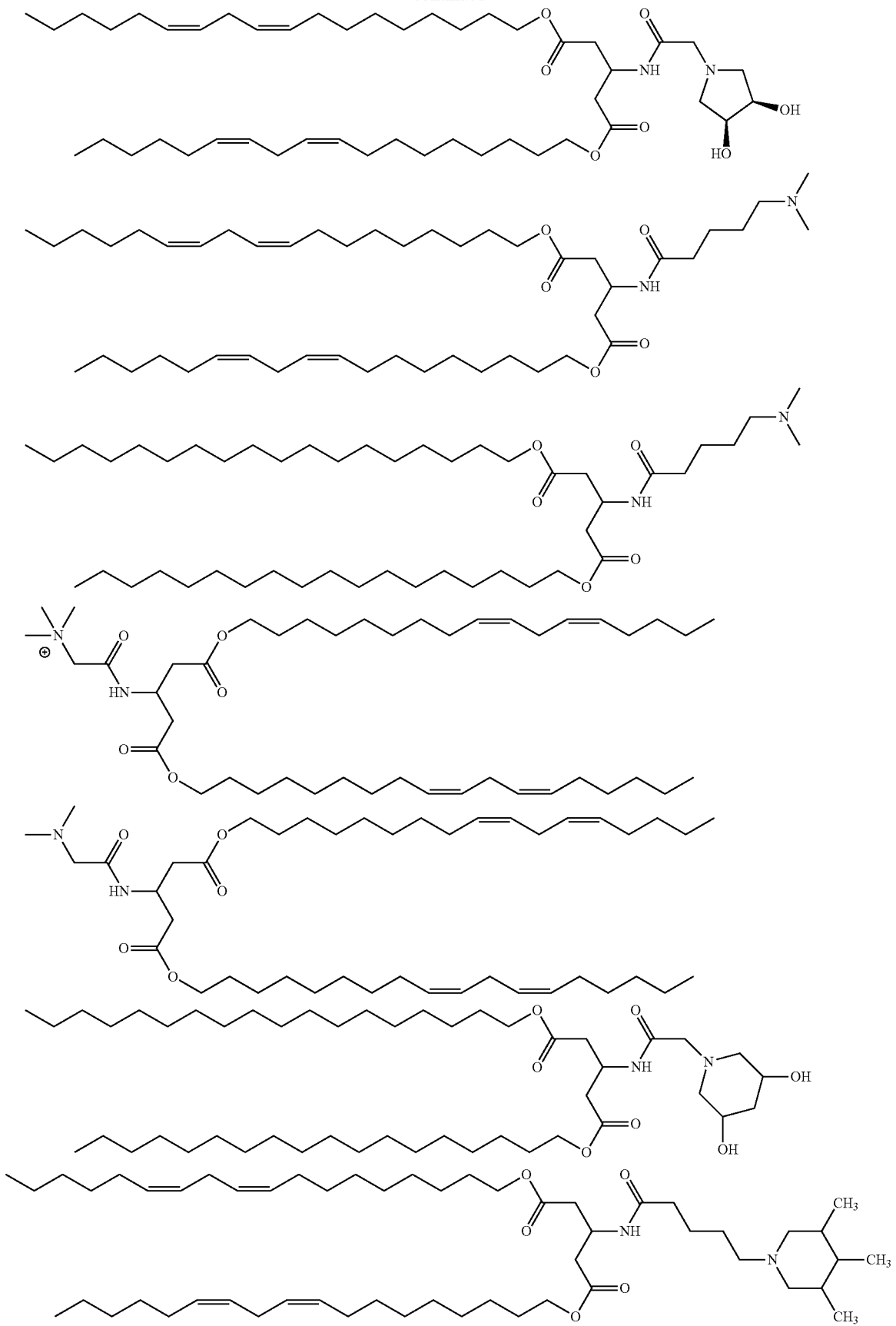

163
164
-continued
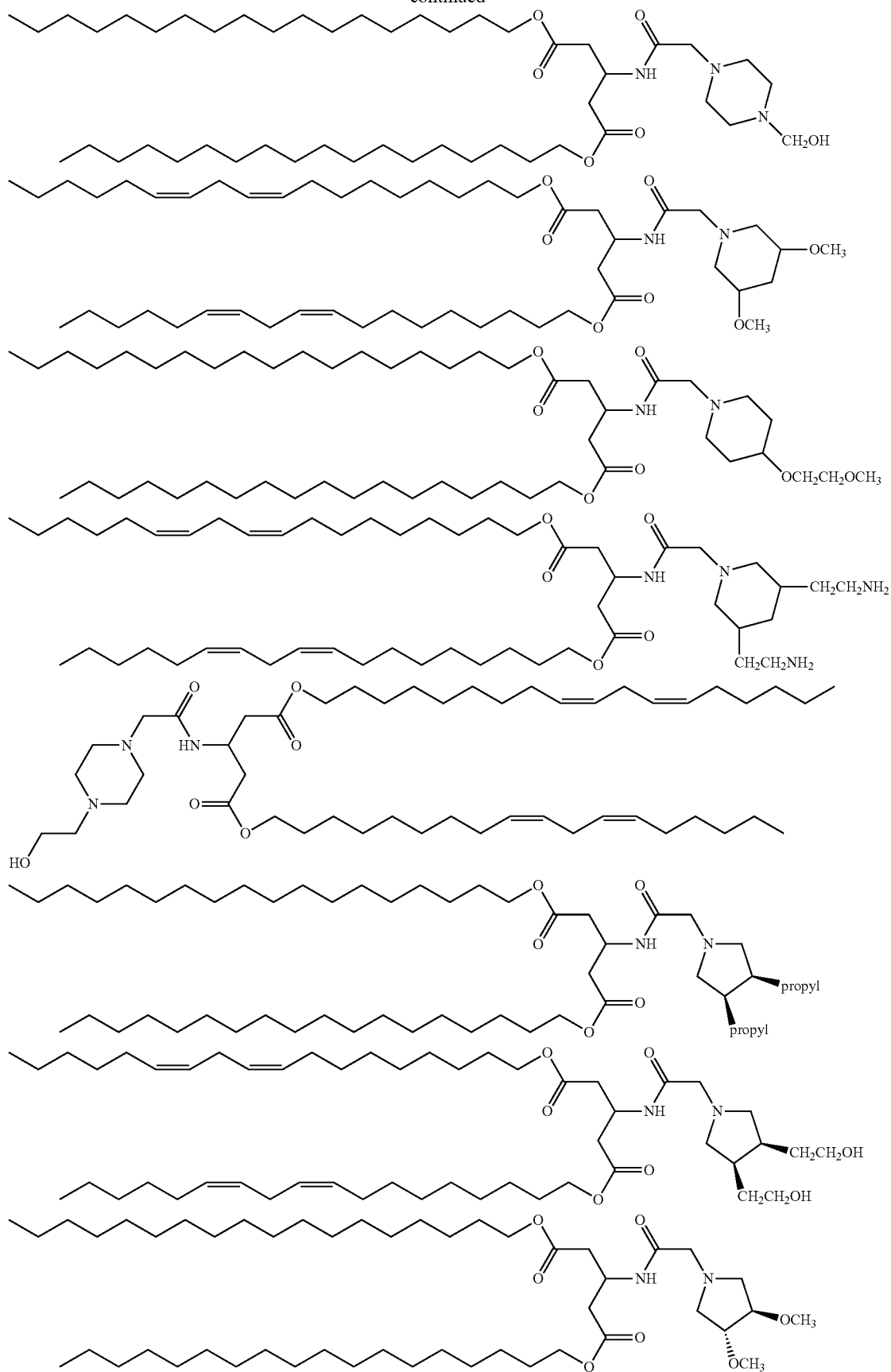

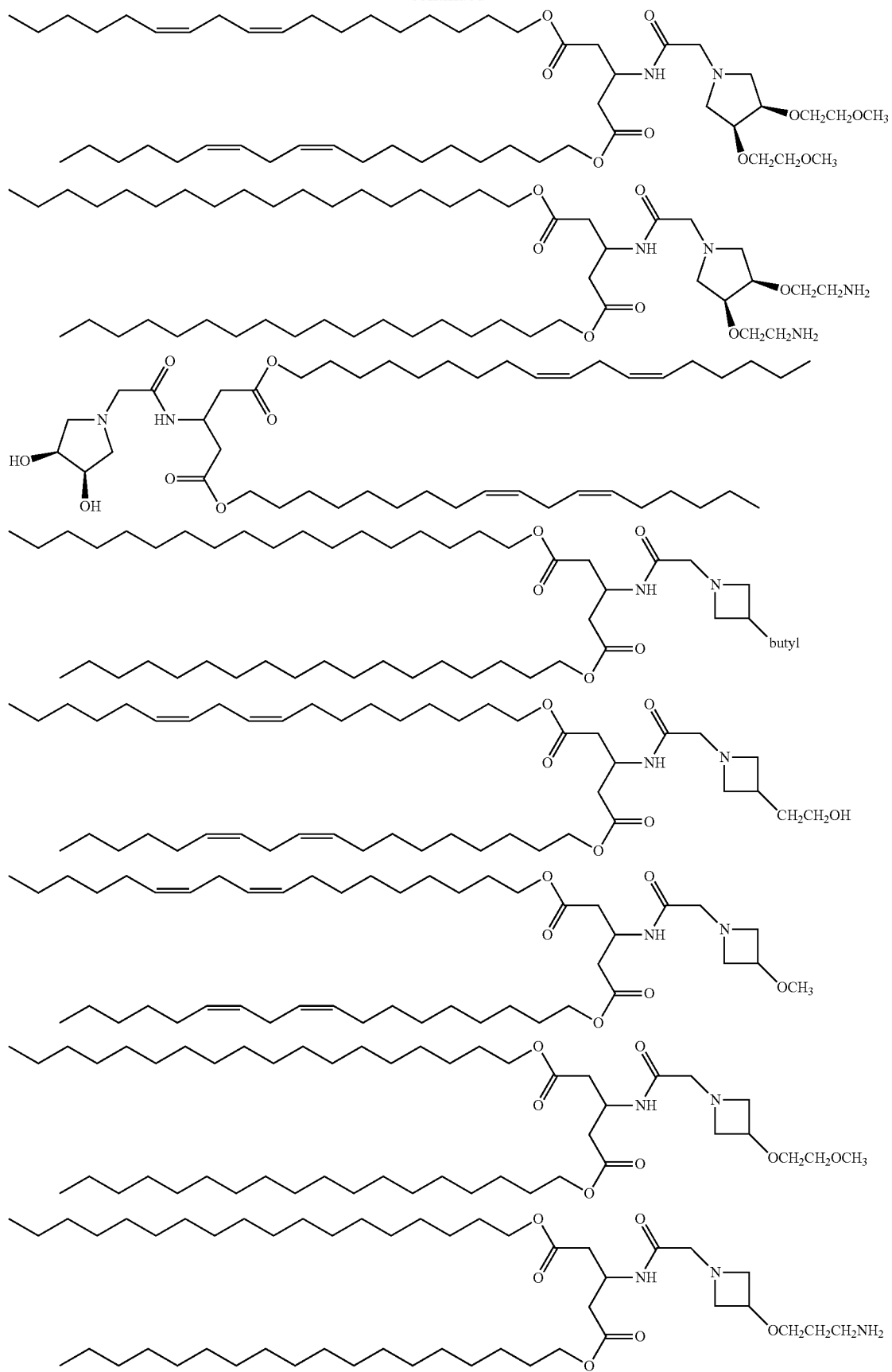

-continued

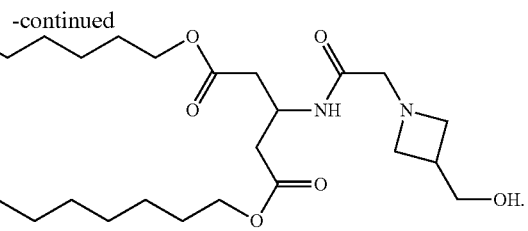

3. A composition comprising an ionizable compound of claim 1 and a pharmaceutically acceptable carrier.

4. The composition of claim 3, wherein the composition comprises nanoparticles.

5. A pharmaceutical composition comprising an ionizable compound of claim 1, an active agent, and a pharmaceutically acceptable carrier.

6. The composition of claim 5, wherein the ionizable compound is from 15 mol % to 40 mol % of the lipids of the composition.

7. The composition of claim 5, wherein the composition comprises nanoparticles.

8. The composition of claim 5, wherein the active agent is one or more RNAi molecules.

9. The composition of claim 5, wherein the active agent is one or more RNAi molecules selected from small interfering RNAs (siRNA), double stranded RNAs (dsRNA) that are Dicer substrates, microRNAs (miRNA), short hairpin RNAs (shRNA), DNA-directed RNAs (ddRNA), Piwi-interacting RNAs (piRNA), repeat associated siRNAs (rasiRNA), and modified forms thereof.

10. A composition for use in distributing an active agent for treating a condition or disease in a subject, the composition comprising an ionizable compound of claim 1, a structural lipid, a stabilizer lipid, and a lipid for reducing immunogenicity of the composition.

11. The composition of claim 10, wherein the active agent is one or more RNAi molecules and the composition comprises nanoparticles that encapsulate the RNAi molecules.

12. The composition of claim 11, wherein the active agent is one or more RNAi molecules selected from small interfering RNAs (siRNA), double stranded RNAs (dsRNA) that are Dicer substrates, microRNAs (miRNA), short hairpin RNAs (shRNA), DNA-directed RNAs (ddRNA), Piwi-interacting RNAs (piRNA), repeat associated siRNAs (rasiRNA), and any modified forms thereof.

* * * * *